US012545670B2

(12) United States Patent
Abbott et al.

(10) Patent No.: US 12,545,670 B2
(45) Date of Patent: Feb. 10, 2026

(54) ANNULATED 2-AMINO-3-CYANO THIOPHENES AND DERIVATIVES FOR THE TREATMENT OF CANCER

(71) Applicants: Boehringer Ingelheim International GmbH, Ingelheim am Rhein (DE); Vanderbilt University, Nashville, TN (US)

(72) Inventors: Jason Abbott, Libertyville, IL (US); Joachim Broeker, Modling (AT); Jianwen Cui, Franklin, TN (US); Steve W. Fesik, Nashville, TN (US); Andreas Gollner, Vienna (AT); Tim Hodges, Chicago, IL (US); Jale Karolyi-Oezguer, Vienna (AT); Andrew Little, Sudbury, MA (US); Andreas Mantoulidis, Vienna (AT); Jason Phan, Nashville, TN (US); Dhruba Sarkar, Karnataka (IN); Christian Alan Paul Smethurst, Vienna (AT); Qi Sun, Libertyville, IL (US); Matthias Treu, Vienna (AT); Alex Waterson, Murfreesboro, TN (US)

(73) Assignees: Boehringer Ingelheim International GmbH, Ingelheim am Rhein (DE); Vanderbilt University, Nashville, TN (US)

( * ) Notice: Subject to any disclaimer, the term of this patent is extended or adjusted under 35 U.S.C. 154(b) by 0 days.

(21) Appl. No.: 18/441,380

(22) Filed: Feb. 14, 2024

(65) Prior Publication Data

US 2025/0002485 A1 Jan. 2, 2025

Related U.S. Application Data

(63) Continuation of application No. 17/335,620, filed on Jun. 1, 2021, now Pat. No. 11,945,812.

(Continued)

(30) Foreign Application Priority Data

Dec. 5, 2020 (EP) .................................... 20212067

(51) Int. Cl.

| | |
|---|---|
| ***C07D 521/00*** | (2006.01) |
| ***A61K 31/506*** | (2006.01) |
| ***A61P 35/00*** | (2006.01) |
| ***C07D 409/14*** | (2006.01) |
| ***C07D 413/14*** | (2006.01) |

(Continued)

(52) U.S. Cl.

CPC .......... *C07D 413/14* (2013.01); *A61K 31/506* (2013.01); *A61P 35/00* (2018.01); *C07D 409/14* (2013.01); *C07D 417/14* (2013.01); *C07D 471/04* (2013.01); *C07D 471/10* (2013.01);

(Continued)

(58) Field of Classification Search

CPC ...... C07D 521/00; A61K 31/381; A61P 35/00

See application file for complete search history.

(56) References Cited

U.S. PATENT DOCUMENTS

| | | | |
|---|---|---|---|
| 2018/0177767 | A1 | 6/2018 | Lanman et al. |
| 2021/0380574 | A1 | 12/2021 | Abbott et al. |
| 2023/0227470 | A1 | 7/2023 | Broeker et al. |

FOREIGN PATENT DOCUMENTS

| | | | |
|---|---|---|---|
| CN | 113683616 | A | 11/2021 |
| WO | 2015054572 | A1 | 4/2015 |

(Continued)

OTHER PUBLICATIONS

Abbas et al., "Abbas and Ahmed: 1-18 New Approaches for the Synthesis and Ctytotoxicity New Approaches for the Synthesis and Ctytotoxicity of Thiazoles Derived from Cyclohexanone", Acta Chim. Slov, vol. 61, 2014, pp. 835-843.

(Continued)

*Primary Examiner* — Bruck Kifle

(74) *Attorney, Agent, or Firm* — Robin L. Teskin; Baker, Donelson, Bearman, Caldwell & Berkowitz PC

(57) ABSTRACT

The present invention encompasses compounds of formula (I)

(I)

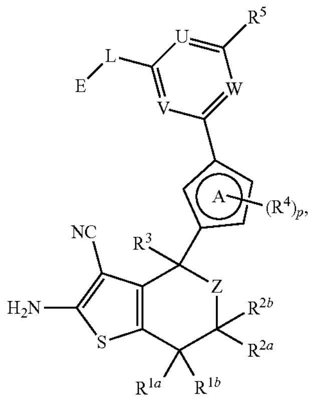

wherein $R^{1a}$, $R^{1b}$, $R^{2a}$, $R^{2b}$, Z, $R^3$ to $R^5$, A, p, U, V, W, L and E have the meanings given in the claims and specification, their use as inhibitors of mutant Ras family proteins, pharmaceutical compositions and preparations containing such compounds and their use as medicaments/medical uses, especially as agents for treatment and/or prevention of oncological diseases.

20 Claims, No Drawings

Related U.S. Application Data

(60) Provisional application No. 63/033,505, filed on Jun. 2, 2020.

(51) Int. Cl.

| | |
|---|---|
| ***C07D 417/14*** | (2006.01) |
| ***C07D 471/04*** | (2006.01) |
| ***C07D 471/10*** | (2006.01) |
| ***C07D 487/04*** | (2006.01) |
| ***C07D 487/08*** | (2006.01) |
| ***C07D 487/10*** | (2006.01) |

(52) U.S. Cl.
CPC ......... *C07D 487/04* (2013.01); *C07D 487/08* (2013.01); *C07D 487/10* (2013.01)

(56) References Cited

FOREIGN PATENT DOCUMENTS

| | | | |
|---|---|---|---|
| WO | 2017201161 | A1 | 11/2017 |
| WO | 2018102453 | A1 | 6/2018 |
| WO | 2018140599 | A1 | 8/2018 |
| WO | 2018217651 | A1 | 11/2018 |
| WO | 2019099524 | A1 | 5/2019 |
| WO | 2020028706 | A1 | 2/2020 |
| WO | 2020102730 | A1 | 5/2020 |
| WO | 2020177629 | A1 | 9/2020 |
| WO | 2020236940 | A1 | 11/2020 |
| WO | 2021118877 | A1 | 6/2021 |
| WO | 2021120890 | A1 | 6/2021 |
| WO | 2021139748 | A1 | 7/2021 |
| WO | 2021150613 | A1 | 7/2021 |
| WO | 2021245051 | A1 | 12/2021 |
| WO | 2021245055 | A1 | 12/2021 |
| WO | 2023099592 | A1 | 6/2023 |
| WO | 2023099608 | A1 | 6/2023 |
| WO | 2023099612 | A1 | 6/2023 |
| WO | 2023099620 | A1 | 6/2023 |
| WO | 2023099623 | A1 | 6/2023 |

OTHER PUBLICATIONS

Abstract in English for CN113683616, dated Nov. 23, 2021.
Awad et al., "Acquired resistance to KRAS(G12C) inhibition in cancer", N Engl J Med, 2021, 384, pp. 2382-2393.
Chardin et al., "Human Sos1: a guanine nucleotide exchange factor for Ras that binds to GRB2", Science, 1993, 260 (5112), pp. 1338-1343.
Cox et al., "Drugging the undruggable RAS: Mission possible", Nat. Rev. Drug Discov., 2014, 13(11), pp. 828-851.
Eberlein et al., "Acquired Resistance to the Mutant-Selective EGFR Inhibitor AZD9291 is Associated with Increased Dependence on RAS Signaling in Preclinical Models", Cancer Res., 2015, 75(12), pp. 2489-2500.
Herdeis et al., "Stopping the beating heart of cancer: KRAS reviewed", Curr Opin Struct Biol., 2021, 71, pp. 136-147.
Hunter et al., "Biochemical and Structural Analysis of Common Cancer-Associated KRAS Mutations", Mol. Cancer Res., 2015, 13(9), pp. 1325-1335.
International Search Report and Written Opinion for corresponding application PCT/EP2021/064612, date of mailing Jul. 2, 2021.
Leto et al., "Primary and acquired resistance to EGFR-targeted therapies in colorectal cancer: impact on future treatment strategies", J. Mol. Med. (Berl). Jul. 2014;92(7), pp. 709-722.
Markó et al., "Efficient and convergent stereocontrolled spiroannulation of ketones, Tetrahedron Letters", 2003, 44, pp. 3333-3336.
Maulide et al., "Connective Synthesis of Spirovetivanes: Total Synthesis of (+−)-Agarospirol, (+−)-Hinesol and (+−)-?-Vetispirene", EurJOC, 2004, 19, pp. 3962-3967.
McCormick et al., "K-Ras protein as a drug target", J. Mol. Med. (Berl)., 2016, 94(3), pp. 253-258.
McCormick et al., "The potential of targeting Ras proteins in lung cancer", Expert Opin. Ther. Targets., 2015, 19(4), pp. 451-454.
Meyers et al., "Computational correction of copy number effect improves specificity of CRISPR-Cas9 essentiality screens in cancer cells", Nat Genet, 2017, 49, pp. 1779-1784.
Nimnual et al., "The Two Hats of SOS", Sci. STKE., 2002, 145, p. 36.
Ortiz-Cuaran et al., "Heterogeneous Mechanisms of Primary and Acquired Resistance to Third-Generation EGFR Inhibitors", Clin. Cancer Res., 2016, 22(19), pp. 4837-4847.
Rodriguez-Viciana et al., "RalGDS comes of age", Cancer Cell. 2005, 7(3), pp. 205-206.
Tanaka et al., "Clinical acquired resistance to KRAS(G12C) 30 inhibition through a novel KRAS switch-II pocket mutation and polyclonal alterations converging on RAS-MAPK reactivation", Cancer Discov, 2021, 11, pp. 1913-1922.
Wong et al., "Targeting wild-type KRAS-amplified gastroesophageal cancer through combined MEK and SHP2 inhibition", Nat Med., 2018, 24(7), pp. 968-977.
Yao et al., "Tumours with class 3 BRAF mutants are sensitive to the inhibition of activated RAS", Nature, 2017, 548, pp. 234-238.
Young et al., "Ras signaling and therapies", Adv. Cancer Res., 2009, 102, pp. 1-17.

ANNULATED 2-AMINO-3-CYANO THIOPHENES AND DERIVATIVES FOR THE TREATMENT OF CANCER

FIELD OF THE INVENTION

The present invention relates to annulated 2-amino-3-cyano thiophenes and derivatives of formula (I)

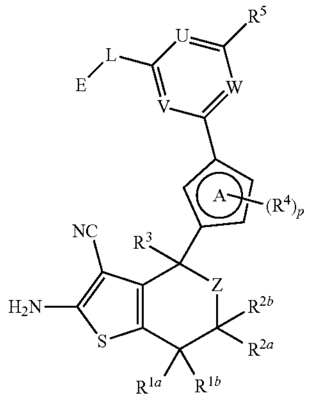

(I)

wherein $R^{1a}$, $R^{1b}$, $R^{2a}$, $R^{2b}$, Z, $R^3$ to $R^5$, A, p, U, V, W, L and E have the meanings given in the claims and specification, their use as inhibitors of mutant Ras family proteins, pharmaceutical compositions and preparations containing such compounds and their use as medicaments/medical uses, especially as agents for treatment and/or prevention of oncological diseases, e.g. cancer.

BACKGROUND OF THE INVENTION

Ras family proteins including KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof are small GTPases that exist in cells in either GTP-bound or GDP-bound states (McCormick et al., J. Mol. Med. (Berl)., 2016, 94 (3): 253-8; Nimnual et al., Sci. STKE., 2002, 2002 (145): pe36). The Ras family proteins have a weak intrinsic GTPase activity and slow nucleotide exchange rates (Hunter et al., Mol. Cancer Res., 2015, 13 (9): 1325-35). Binding of GTPase activating proteins (GAPs) such as NF1 increases the GTPase activity of Ras family proteins. The binding of guanine nucleotide exchange factors (GEFs) such as SOS1 (Son of Sevenless 1) promote release GDP from Ras family proteins, enabling GTP binding (Chardin et al., Science, 1993, 260 (5112): 1338-43). When in the GTP-bound state, Ras family proteins are active and engage effector proteins including C-RAF and phosphoinositide 3-kinase (PI3K) to promote the RAF/mitogen or extracellular signal-regulated kinases (MEK/ERK) pathway, PI3K/AKT/mammalian target of rapamycin (mTOR) pathway and RalGDS (Ral guanine nucleotide dissociation stimulator) pathway (McCormick et al., J. Mol. Med. (Berl)., 2016, 94 (3): 253-8; Rodriguez-Viciana et al., Cancer Cell. 2005, 7 (3): 205-6). These pathways affect diverse cellular processes such as proliferation, survival, metabolism, motility, angiogenesis, immunity and growth (Young et al., Adv. Cancer Res., 2009, 102:1-17; Rodriguez-Viciana et al., Cancer Cell. 2005, 7 (3): 205-6).

Cancer-associated mutations in Ras family proteins suppress their intrinsic and GAP-induced GTPase activity leading to an increased population of GTP-bound/active mutant Ras family proteins (McCormick et al., Expert Opin. Ther. Targets., 2015, 19 (4): 451-4; Hunter et al., Mol. Cancer Res., 2015, 13 (9): 1325-35). This in turn leads to persistent activation of effector pathways (e.g. RAF/MEK/ERK, PI3K/AKT/mTOR, RalGDS pathways) downstream of mutant Ras family proteins. KRAS mutations (e.g. amino acids G12, G13, Q61, A146) are found in a variety of human cancers including lung cancer, colorectal cancer and pancreatic cancer (Cox et al., Nat. Rev. Drug Discov., 2014, 13 (11): 828-51). Mutations in HRAS (e.g. amino acids G12, G13, Q61) and NRAS (e.g. amino acids G12, G13, Q61, A146) are also found in a variety of human cancer types however typically at a lower frequency compared to KRAS mutations (Cox et al., Nat. Rev. Drug Discov., 2014, 13 (11): 828-51). Alterations (e.g. mutation, over-expression, gene amplification) in Ras family proteins/Ras genes have also been described as a resistance mechanism against cancer drugs such as the EGFR antibodies cetuximab and panitumumab (Leto et al., J. Mol. Med. (Berl). 2014 July; 92 (7): 709-22) and the EGFR tyrosine kinase inhibitor osimertinib/AZD9291 (Ortiz-Cuaran et al., Clin. Cancer Res., 2016, 22 (19): 4837-47; Eberlein et al., Cancer Res., 2015, 7 5 (12): 2489-500).

Glycine to cysteine mutations at residue 12 of Ras family proteins (the G12C mutation, e.g. KRAS G12C, NRAS G12C and HRAS G12C) is generated from a G.C to T.A base transversion at codon 12, a mutation commonly found in RAS genes that accounts for 14% of all KRAS, 2% of all NRAS and 2% of all HRAS mutations across cancer types. The G12C mutation is particularly enriched in KRAS mutant non-small cell lung cancer with approximately half carrying this mutation, which has been associated with the DNA adducts formed by tobacco smoke. The G12C mutation is not exclusively associated with lung cancer and is found in other RAS mutant cancer types including, e.g., 3-5% of all KRAS mutant colorectal cancer.

Inhibitors of such G12C mutant Ras family proteins which are capable to covalently bind to these proteins, e.g. covalent binders to KRAS G12C, NRAS G12C and HRAS G12C, are expected to inhibit signaling in cells downstream of Ras family proteins (e.g. ERK phosphorylation). In cancer cells associated with dependence on mutant Ras family proteins (e.g. KRAS mutant cancer cell lines), such binders/inhibitors are expected to deliver anti-cancer efficacy (e.g. inhibition of proliferation, survival, metastasis etc.).

To date there have been no inhibitors of G12C mutant Ras family proteins which have been approved for therapeutic use. Recently the first selective drugs against KRAS G12C have moved into clinical development with sotorasib and adagrasib already in advanced stage for the treatment of KRAS G12C driven lung cancers (see corresponding patent applications WO 2018/217651, WO 2017/201161, WO 2019/099524, WO 2020/102730). There is a need for new or even improved inhibitors of G12C mutant Ras family proteins to be suitable for clinical use.

DETAILED DESCRIPTION OF THE INVENTION

Compounds

It has now been found that, surprisingly, compounds of formula (I) wherein $R^{1a}$, $R^{1b}$, $R^{2a}$, $R^{2b}$, Z, $R^3$ to $R^5$, A, p, U, V, W, L and E have the meanings given hereinafter act as inhibitors of G12C mutant Ras family proteins which are involved in controlling cell proliferation and possess anti-tumor activity, being useful in inhibiting the uncontrolled cellular proliferation which arises from malignant disease. It is believed that this anti-tumor activity is derived from inhibition of G12C mutant Ras family proteins, in particular KRAS G12C, that are key mediators of proliferation and survival in certain tumor cells. It is further believed that the compounds according to the invention interact with, and then covalently bind to, G12C mutant Ras family proteins, in particular KRAS G12C, via an electrophilic moiety (e.g. a MICHAEL acceptor) present in compounds of formula (I) (confirmed by means of crystallography for KRAS G12C). In covalently binding to G12C mutant Ras family proteins, in particular KRAS G12C, which most probably occurs at position 12 of the Ras family proteins, the compounds impair or substantially eliminate the ability of the G12C Ras family proteins to access their active, pro-proliferative/pro-survival conformation.

Indeed, the binding of the compounds of formula (I) according to the invention may lead to selective and very strong antiproliferative cellular effects in G12C mutant KRAS cell lines and large selectivity windows compared to KRAS wild type cells. This excellent potency can potentially lead to lower systemic exposures and/or doses needed for full efficacy in humans and therefore to good/better tolerability (e.g. a lower risk of idiosyncratic toxicities), may allow to hit the pathway harder if necessary and may also turn out to be beneficial and bring increased flexibility in case of combination treatments. The compounds show strong biomarker modulation, e.g. pERK in G12C mutant KRAS cell lines. Selected compounds were tested in selectivity panels and show good selectivity against other human targets, e.g. kinases. Last but not least, selected compounds disclosed herein were tested and show good permeability, excellent solubility and have fine-tuned PK properties.

Thus, in a first aspect, the present invention relates to a compound of formula (I)

(I)

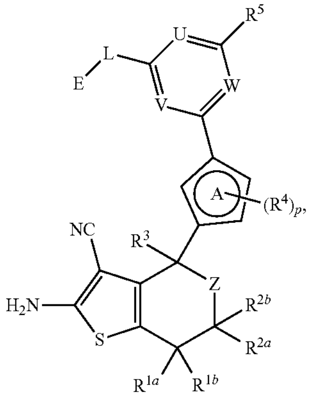

wherein

[A0]

$R^{1a}$ and $R^{1b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

$R^{2a}$ and $R^{2b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

and/or, optionally, one of $R^{1a}$ or $R^{1b}$ and one of $R^{2a}$ or $R^{2b}$ together with the carbon atoms they are attached form a cyclopropane ring;

[B0]

Z is —$(CR^{6a}R^{6b})_n$—;

each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

n is selected from the group consisting 0, 1 and 2;

[C0]

$R^3$ is selected from the group consisting of hydrogen, $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

[D0]

ring A is a ring selected from the group consisting of pyrrole, furan, thiophene, imidazole, pyrazole, oxazole, isoxazole, thiazole, isothiazole and triazole;

[E0]

each $R^4$, if present, is independently selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl; p is selected from the group consisting 0, 1, 2 and 3;

[F0]

U is selected from the group consisting of nitrogen (=N—) and carbon substituted with $R^A$ (=C($R^A$)—);

V is selected from the group consisting of nitrogen (=N—) and carbon substituted with $R^B$ (=C($R^B$)—);

W is selected from the group consisting of nitrogen (=N—) and carbon substituted with $R^C$ (=C($R^C$)—);

$R^A$, $R^B$ and $R^C$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, —S—$C_{1-6}$alkyl, —S(=O)$_2$—$C_{1-6}$alkyl, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$;

[G0]

$R^5$ is selected from the group consisting of $R^{a1}$ and $R^{b1}$;

$R^{a1}$ is selected from the group consisting of $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —CN, $-C(=O)R^{c1}$, $-C(=O)OR^{c1}$, $-C(=O)NR^{c1}R^{c1}$, $-S(=O)_2R^{c1}$, $-S(=O)_2NR^{c1}R^{c1}$, $-NHC(=O)R^{c1}$, $-N(C_{1-4}alkyl)C(=O)R^{c1}$, $-NHS(=O)_2R^{c1}$, $-N(C_{1-4}alkyl)S(=O)_2R^{c1}$, $-NHC(=O)OR^{c1}$, $-N(C_{1-4}alkyl)C(=O)OR^{c1}$ and the bivalent substituent =O;

each $R^{c1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of $-OR^{e1}$, $-NR^{e1}R^{e1}$, halogen, $-CN$, $-C(=O)R^{e1}$, $-C(=O)OR^{e1}$, $-C(=O)NR^{e1}R^{e1}$, $-S(=O)_2R^{e1}$, $-S(=O)_2NR^{e1}R^{e1}$, $-NHC(=O)R^{e1}$, $-N(C_{1-4}alkyl)C(=O)R^{e1}$, $-NHS(=O)_2R^{e1}$, $-N(C_{1-4}alkyl)S(=O)_2R^{e1}$, $-NHC(=O)OR^{e1}$, $-N(C_{1-4}alkyl)C(=O)OR^{e1}$ and the bivalent substituent =O;

each $R^{e1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl optionally substituted with one or more, identical or different $C_{1-4}$alkyl, $C_{6-10}$aryl, 5-10 membered heteroaryl, $-OH$, $C_{1-6}$alkoxy, $C_{1-4}$alkoxy-$C_{1-4}$alkyl, hydroxy-$C_{1-4}$alkyl, halogen, $-CN$, $-NH_2$, $-C(=O)C_{1-4}alkyl$, $-NH(C_{1-4}alkyl)$, $-N(C_{1-4}alkyl)_2$ and the bivalent substituent =O;

[H0]

L is $-L^1-L^2-L^3-$, wherein $L^1$ is linked to E;

$L^1$ is selected from the group consisting of a bond, $-NH-$, $-N(C_{1-4}alkyl)-$, $-O-$, $-C(=O)-$, $-NH-C(=O)-$, $-N(C_{1-4}alkyl)-C(=O)-$, $-C(=O)-NH-$, $-C(=O)-N(C_{1-4}alkyl)-$, $-C(=O)-$, $C_{1-6}$alkylen, $C_{3-7}$cycloalkylene, phenylene, 4-12 membered heterocyclylene and 5-10 membered heteroarylene;

$L^2$ is selected from the group consisting of $C_{1-6}$alkylen, $C_{3-7}$cycloalkylene, phenylene, 4-12 membered heterocyclylene and 5-10 membered heteroarylene;

$L^3$ is selected from the group consisting of a bond, $-NH-$, $-N(C_{1-4}alkyl)-$, $-O-$, $-C(=O)-$, $-NH-C(=O)-$, $-N(C_{1-4}alkyl)-C(=O)-$, $-C(=O)-NH-$, $-C(=O)-N(C_{1-4}alkyl)-$, $-C(=O)-$, $C_{1-6}$alkylen, $C_{3-7}$cycloalkylene, phenylene, 4-12 membered heterocyclylene and 5-10 membered heteroarylene;

wherein each $C_{1-6}$alkylen, $C_{3-7}$cycloalkylene, phenylene, 4-12 membered heterocyclylene and 5-10 membered heteroarylene in $L^1$, $L^2$ and $L^3$ is optionally and independently substituted with one or more, identical or different substituent(s) selected from the group consisting of $C_{2-6}$alkinyl, $C_{1-6}$haloalkyl, $C_{3-7}$cycloalkyl, phenyl, 5-6 membered heteroaryl, halogen, $-OH$, $-CN$, $C_{1-6}$alkoxy, $-NH_2$, $-NH(C_{1-4}alkyl)$, $-N(C_{1-4}alkyl)_2$, $-C(=O)OH$, $-C(=O)-OC_{1-6}alkyl$, $-C(=O)NH_2$, $-C(=O)NH(C_{1-4}alkyl)$, $-C(=O)N(C_{1-4}alkyl)_2$, the bivalent substituent =O and $C_{1-6}$alkyl optionally substituted with one or more, identical or different substituent(s) selected from the group consisting of halogen, $-OH$, $-CN$, $C_{1-4}$alkoxy, $-NH_2$, $-NH(C_{1-4}alkyl)$, $-N(C_{1-4}alkyl)_2$, $-C(=O)OH$, $-C(=O)-OC_{1-6}alkyl$, $-C(=O)NH_2$, $-C(=O)NH(C_{1-4}alkyl)$ and $-C(=O)N(C_{1-4}alkyl)_2$;

[I0]

E is

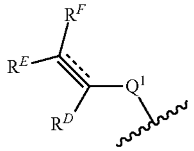

(i)

 represents a double or a triple bond;

$Q^1$ is selected from the group consisting of a bond, $-CH_2-$, $-CH(OH)-$, $-C(=O)-$, $-C(=O)N(R^{G1})-$, $-C(=O)O-$, $-S(=O)_2-$, $-S(=O)_2N(R^{G1})-$ and $-C(=NR^{H1})-$;

each $R^{G1}$ is independently selected from the group consisting of hydrogen, $C_{1-6}$alkyl, $C_{1-6}$haloalkyl, hydroxy-$C_{1-6}$alkyl, $H_2N-C_{1-6}alkyl$, cyano-$C_{1-6}$alkyl, $(C_{1-4}alkyl)HN-C_{1-6}alkyl$, $(C_{1-4}alkyl)_2N-C_{1-6}alkyl$, $C_{1-6}$alkoxy-$C_{1-6}$alkyl, $C_{3-7}$cycloalkyl and 3-11 membered heterocyclyl;

each $R^{H1}$ is independently selected from the group consisting of hydrogen, $-OH$, $C_{1-6}$alkoxy, $-CN$ and $C_{1-6}$alkyl;

if  represents a double bond then $R^D$ is selected from the group consisting of hydrogen, $C_{3-7}$cycloalkyl, phenyl, halogen, $-CN$, $C_{1-6}$alkoxy, $-C(=O)O-C_{1-6}alkyl$, $-NHC(=O)-C_{1-6}alkyl$ and $C_{1-6}$alkyl optionally substituted with one or more, identical or different substituent(s) selected from the group consisting of phenyl, 3-11 membered heterocyclyl, $C_{1-6}$alkoxy, halogen, $-OH$, $-NH_2$, $-NH(C_{1-6}alkyl)$, $-N(C_{1-6}alkyl)_2$, $-C(=O)OH$, $-C(=O)O-C_{1-6}alkyl$, $-C(=O)NH(C_{1-6}alkyl)$, $-NHC(=O)-C_{1-6}alkyl$, $-OC(=O)-C_{1-6}alkyl$ and phenyl-$C_{1-6}$alkoxy;

$R^E$ and $R^F$ is each independently selected from the group consisting of $R^{a2}$ and $R^{b2}$;

$R^{a2}$ is selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of $-OR^{c2}$, $-NR^{c2}R^{c2}$, halogen, $-CN$, $-C(=O)R^{c2}$, $-C(=O)OR^{c2}$, $-C(=O)NR^{c2}R^{c2}$, $—S(═O)_2R^{c2}$, $—S(═O)_2NR^{c2}R^{c2}$, $—NHC(═O)R^{c2}$, $—N(C_{1-4}alkyl)C(═O)R^{c2}$, $—NHC(═O)OR^{c2}$, $—N(C_{1-4}alkyl)C(═O)OR^{c2}$ and the bivalent substituent ═O;

each $R^{c2}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$alkoxy, halogen, —OH, —C(═O)OH, $—C(═O)O—C_{1-6}alkyl$, $—C(═O)C_{1-6}alkyl$, $—C(═O)NH_2$, $—C(═O)NH(C_{1-6}alkyl)$, $—C(═O)N(C_{1-6}alkyl)_2$, and the bivalent substituent ═O;

or $R^D$ and $R^E$ taken together with the carbon atoms they are attached form a 4-7 membered unsaturated alicycle or 4-7 membered unsaturated heterocycle, wherein this 4-7 membered unsaturated alicycle or 4-7 membered unsaturated heterocycle is optionally, in addition to $R^F$, substituted with one or more identical or different substituent(s) selected from the group consisting of $C_{1-6}$alkyl, $C_{1-6}$haloalkyl, —OH, $C_{1-6}$alkoxy, $C_{1-4}$alkoxy-$C_{1-4}$alkyl, $—NH_2$, —CN, $—NH(C_{1-4}alkyl)$, $—N(C_{1-4}alkyl)_2$, halogen, $—C(═O)O—C_{1-6}alkyl$ and the bivalent substituent ═O;

or if $Q^1$ is $—C(═O)N(R^{G1})—$, then $R^{G1}$ of $—C(═O)N(R^{G1})—$ and $R^F$ together form a linker selected from the group consisting of —C(═O)—, $—CH_2—$, $—CH_2—C(═O)—$, $—C(═O)—CH_2—$ and $—C_2H_4—$;

if  represents a triple bond then $R^D$ and $R^E$ are both absent;

$R^F$ is $R^{a2}$;

$R^{a2}$ is selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of $—OR^{c2}$, $—NR^{c2}R^{c2}$, halogen, —CN, $—C(═O)R^{c2}$, $—C(═O)OR^{c2}$, $—C(═O)NR^{c2}R^{c2}$, $—S(═O)_2R^{c2}$, $—S(═O)_2NR^{c2}R^{c2}$, $—NHC(═O)R^{c2}$, $—N(C_{1-4}alkyl)C(═O)R^{c2}$, $—NHC(═O)OR^{c2}$, $—N(C_{1-4}alkyl)C(═O)OR^{c2}$ and the bivalent substituent ═O;

each $R^{c2}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl;

or

E is (ii)

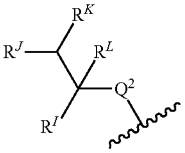

$Q^2$ is selected from the group consisting of a bond, $—CH_2—$, —CH(OH)—, —C(═O)—, $—C(═O)N(R^{G2})—$, —C(═O)O—, $—S(═O)_2—$, $—S(═O)_2N(R^{G2})—$ and $—C(═NR^{H2})$;

each $R^{G2}$ is independently selected from the group consisting of hydrogen, $C_{1-6}$alkyl, $C_{1-6}$haloalkyl, hydroxy-$C_{1-6}$alkyl, $H_2N—C_{1-6}$alkyl, cyano-$C_{1-6}$alkyl, $(C_{1-4}alkyl)HN—C_{1-6}alkyl$, $(C_{1-4}alkyl)_2N—C_{1-6}alkyl$, $C_{1-6}$alkoxy-$C_{1-6}$alkyl, $C_{3-7}$cycloalkyl and 3-11 membered heterocyclyl;

each $R^{H2}$ is independently selected from the group consisting of hydrogen, —OH, $C_{1-6}$alkoxy, —CN and $C_{1-6}$alkyl;

$R^I$ is selected from the group consisting of hydrogen and halogen;

$R^J$ is hydrogen; or $R^I$ and $R^J$ together with the carbon atoms they are attached form a cyclopropane or oxirane ring;

$R^K$ is selected from the group consisting of hydrogen, $C_{1-6}$alkyl, —CN and halogen;

$R^L$ is selected from the group consisting of hydrogen, $C_{1-6}$alkyl, —CN, halogen and $—C(═O)—C_{1-6}alkyl$;

or

E is (iii)

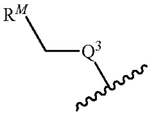

$Q^3$ is selected from the group consisting of —C(═O)—, $—C(═O)N(R^{G3})—$, —C(═O)O—, $—S(═O)_2—$, $—S(═O)_2N(R^{G3})—$ and $—C(═NR^{H3})—$;

each $R^{G3}$ is independently selected from the group consisting of hydrogen, $C_{1-6}$alkyl, $C_{1-6}$haloalkyl, hydroxy-$C_{1-6}$alkyl, $H_2N—C_{1-6}$alkyl, cyano-$C_{1-6}$alkyl, $(C_{1-4}alkyl)HN—C_{1-6}alkyl$, $(C_{1-4}alkyl)_2N—C_{1-6}alkyl$, $C_{1-6}$alkoxy-$C_{1-6}$alkyl, $C_{3-7}$cycloalkyl and 3-11 membered heterocyclyl;

each $R^{H3}$ is independently selected from the group consisting of hydrogen, —OH, $C_{1-6}$alkoxy, —CN and $C_{1-6}$alkyl;

$R^M$ is selected from the group consisting of halogen, —CN and $—O—C(═O)—C_{1-6}alkyl$;

or

E is (iv)

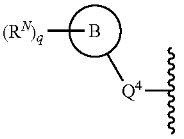

$Q^4$ is selected from the group consisting of a bond, —C(=O)—, —C(=O)O—, —C(=O)NH—, —C(=O)N($C_{1-4}$alkyl)-, —S(=O)$_2$— and —S(=O)$_2$NH—;

ring B is selected from the group consisting of phenyl, pyridyl, pyrimidyl, pyridazinyl, pyrazinyl and 5-membered heteroaryl;

q is selected from the group consisting 1, 2, 3 and 4;

each $R^N$ is independently selected from the group consisting of $C_{1-4}$alkyl, $C_{1-4}$haloalkyl, vinyl, ethinyl, halogen, —CN, nitro and $C_{1-4}$alkoxy;

or a salt thereof.

In a second aspect, the present invention relates to a compound of formula (I*) or a salt thereof (I*)

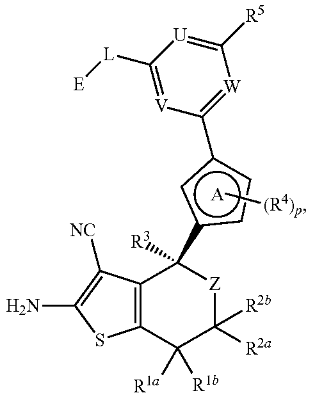

wherein $R^{1a}$, $R^{1b}$, $R^{2a}$, $R^{2b}$, Z, $R^3$, ring A, $R^4$, p, U, V, W, $R^5$, L and E are defined as in formula (I) in the first aspect.

In a third aspect, the present invention relates to a compound of formula (Ib) or a salt thereof (Ib)

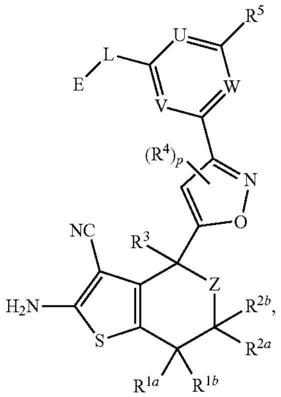

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a fourth aspect, the present invention relates to a compound of formula (Ib*) or a salt thereof (Ib*)

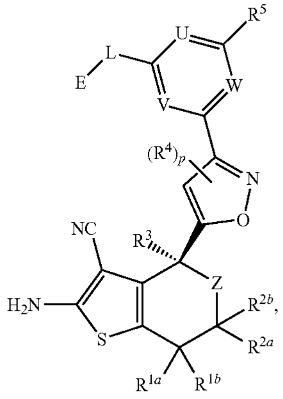

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a fifth aspect, the present invention relates to a compound of formula (Ic) or a salt thereof (Ic)

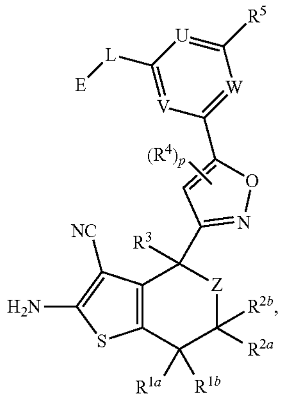

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a sixth aspect, the present invention relates to a compound of formula (Ic*) or a salt (Ic*)

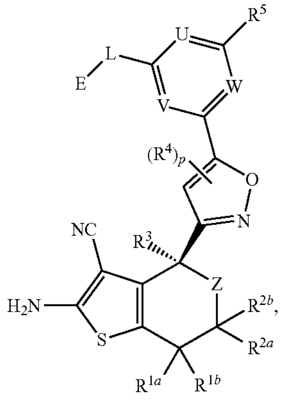

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a seventh aspect, the present invention relates to a compound of formula (Id) or a salt thereof (Id)

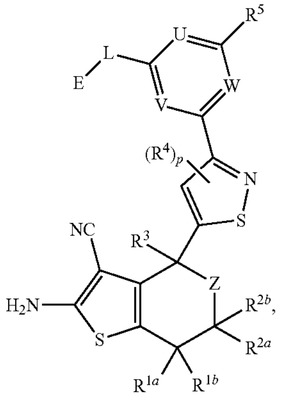

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In an eighth aspect, the present invention relates to a compound of formula (Id*) or a salt thereof (Id*)

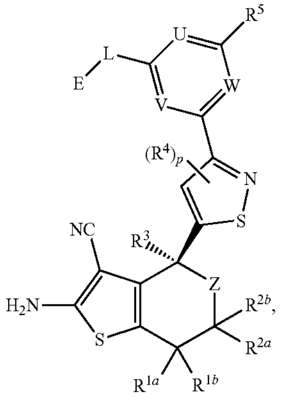

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a ninth aspect, the present invention relates to a compound of formula (Ie) or a salt thereof (Ie)

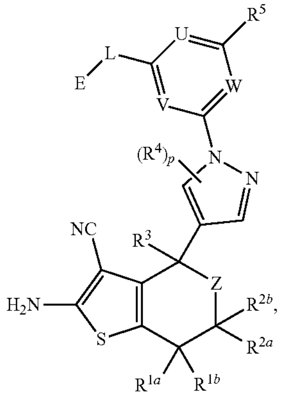

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

In a tenth aspect, the present invention relates to a compound of formula (Ie*) or a salt thereof (Ie*)

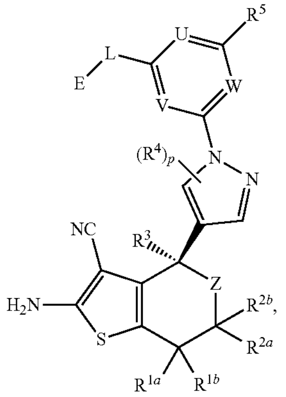

wherein $R^{1a}$, $R^{1b}$, $R^{2a}$, $R^{2b}$, Z, $R^3$, $R^4$, p, U, V, W, $R^5$, L and E are defined as in formula (I) in the first aspect.

It is to be understood that compounds (I*), (Ib), (Ib*), (Ic), (Ic*), (Id), (Id*), (Ie) and (Ie*) each are a subset of compounds (I) and that whenever it is referred to compounds (I) this is meant to also refer to and include compounds (I*), (Ib), (Ib*), (Ic), (Ic*), (Id), (Id*), (Ie) and (Ie*) unless stated otherwise.

It is to be understood that compounds (Ib*), (Ic*), (Id*) and (Ie*) each are a subset of the respective compounds (Ib), (Ic), (Id) and (Ie), and that whenever it is referred to compounds (Ib), (Ic), (Id) and/or (Ie) this is meant to also refer to and include compounds (Ib*), (Ic*), (Id*) and/or (Ie*) unless stated otherwise.

The following structural aspects represent preferred embodiments [A1] to [A3], [B1] to [B5], [C1] to [C5], [D1] to [D6], [E1] to [E4], [F1] to [F9], [G1] to [G8], [H1] to [H3] and [I1] to [I8] of the corresponding structural aspects [A0], [B0], [C0], [D0], [E0], [F0], [G0], [H0], and [I0], respectively.

In one aspect [A1] the invention relates to a compound of formula (I), (I*), (Ib), (Ib*), (Ic), (Ic*), (Id), (Id*), (Ie) or (Ie*) or a salt thereof, wherein $R^{1a}$ and $R^{1b}$ are both independently selected from the group consisting of hydrogen and $C_{1-4}$alkyl;

$R^{2a}$ and $R^{2b}$ are both independently selected from the group consisting of hydrogen and halogen.

In another aspect [A2] the invention relates to a compound of formula (I), (I*), (Ib), (Ib*), (Ic), (Ic*), (Id), (Id*), (Ie) or (Ie*) or a salt thereof, wherein $R^{1a}$ and $R^{1b}$ are both independently selected from the group consisting of hydrogen and methyl;

$R^{2a}$ and $R^{2b}$ are both independently selected from the group consisting of hydrogen and fluorine.

In another aspect [A3] the invention relates to a compound of formula (I), (I*), (Ib), (Ib*), (Ic), (Ic*), (Id), (Id*), (Ie) or (Ie*) or a salt thereof, wherein $R^{1a}$, $R^{1b}$, $R^{2a}$ and $R^{2b}$ are hydrogen.

In another aspect [B1] the invention relates to a compound of formula (I), (I*), (Ib), (Ib*), (Ic), (Ic*), (Id), (Id*), (Ie) or (Ie*) or a salt thereof, wherein Z is $-(CR^{6a}R^{6b})_n-$;

n is 0.

In another aspect [B2] the invention relates to a compound of formula (I), (I*), (Ib), (Ib*), (Ic), (Ic*), (Id), (Id*), (Ie) or (Ie*) or a salt thereof, wherein Z is $-(CR^{6a}R^{6b})_n-$;

n is 1;

$R^{6a}$ and $R^{6b}$ are both independently selected from the group consisting of hydrogen, $C_{1-4}$alkyl, $C_{1-4}$haloalkyl, $C_{1-4}$alkoxy, $C_{1-4}$haloalkoxy, halogen, $-NH_2$, $-NH(C_{1-4}alkyl)$, $-N(C_{1-4}alkyl)_2$, $C_{3-5}$cycloalkyl and 3-5 membered heterocyclyl.

In another aspect [B3] the invention relates to a compound of formula (I), (I*), (Ib), (Ib*), (Ic), (Ic*), (Id), (Id*), (Ie) or (Ie*) or a salt thereof, wherein Z is $-CH_2-$.

In another aspect [B4] the invention relates to a compound of formula (I), (I*), (Ib), (Ib*), (Ic), (Ic*), (Id), (Id*), (Ie) or (Ie*) or a salt thereof, wherein Z is $-(CR^{6a}R^{6b})_n-$;

n is 2;

each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, $-NH_2$, $-NH(C_{1-4}alkyl)$, $-N(C_{1-4}alkyl)_2$, $C_{3-5}$cycloalkyl and 3-5 membered heterocyclyl.

In another aspect [B5] the invention relates to a compound of formula (I), (I*), (Ib), (Ib*), (Ic), (Ic*), (Id), (Id*), (Ie) or (Ie*) or a salt thereof, wherein Z is $-CH_2-CH_2-$.

In another aspect [C1] the invention relates to a compound of formula (I), (I*), (Ib), (Ib*), (Ic), (Ic*), (Id), (Id*), (Ie) or (Ie*) or a salt thereof, wherein $R^3$ is selected from the group consisting of hydrogen, $C_{1-4}$alkyl, $C_{1-4}$haloalkyl, $C_{1-4}$alkoxy, $C_{1-4}$haloalkoxy, cyano-$C_{1-4}$alkyl, halogen, $-OH$, $-NH_2$, $-NH(C_{1-4}alkyl)$, $-N(C_{1-4}alkyl)_2$ and $-CN$.

In another aspect [C2] the invention relates to a compound of formula (I), (I*), (Ib), (Ib*), (Ic), (Ic*), (Id), (Id*), (Ie) or (Ie*) or a salt thereof, wherein $R^3$ is selected from the group consisting of hydrogen, methyl, ethyl, $-CF_3$, $-CHF_2$, methoxy, trifluormethoxy, cyanomethyl, $-OH$ and $-CN$.

In another aspect [C3] the invention relates to a compound of formula (I), (I*), (Ib), (Ib*), (Ic), (Ic*), (Id), (Id*), (Ie) or (Ie*) or a salt thereof, wherein $R^3$ is hydrogen.

In another aspect [C4] the invention relates to a compound of formula (I), (I*), (Ib), (Ib*), (Ic), (Ic*), (Id), (Id*), (Ie) or (Ie*) or a salt thereof, wherein $R^3$ is $C_{1-4}$alkyl.

In another aspect [C5] the invention relates to a compound of formula (I), (I*), (Ib), (Ib*), (Ic), (Ic*), (Id), (Id*), (Ie) or (Ie*) or a salt thereof, wherein $R^3$ is methyl.

In another aspect [D1] the invention relates to a compound of formula (I) or (I*) or a salt thereof, wherein ring A is selected from the group consisting of

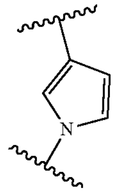, 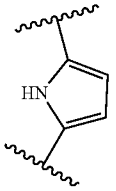, 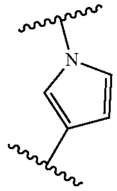,

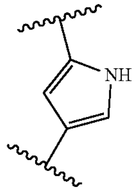, 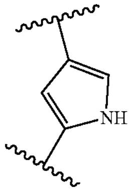, 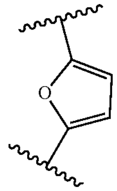,

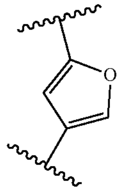, 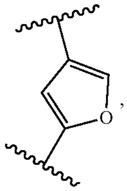, 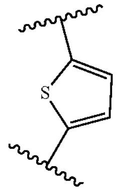,

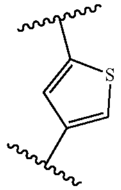, 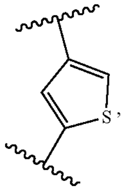, 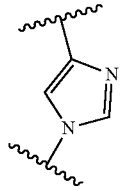,

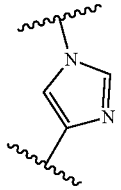, 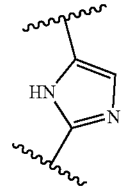, 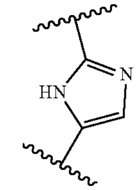,

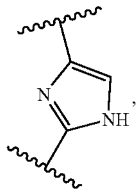, 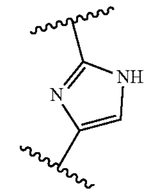, 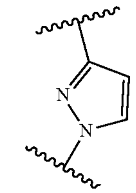,

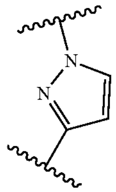, 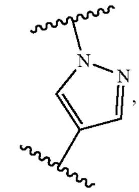, 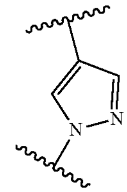,

-continued

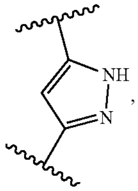,
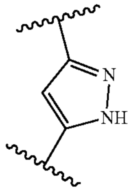,
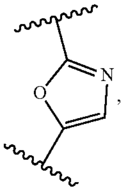,

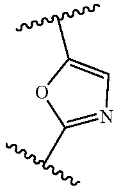,
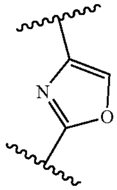,
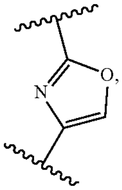

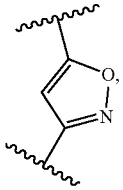
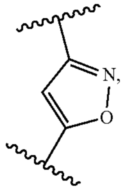
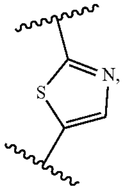

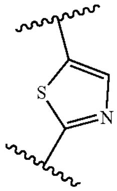,
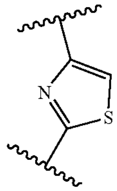,
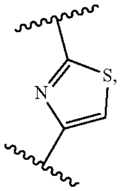

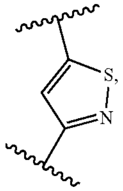
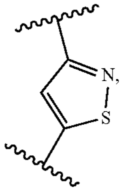
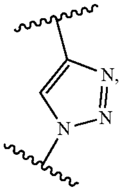

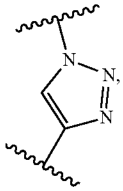
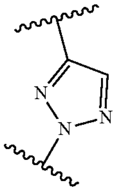,
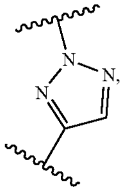

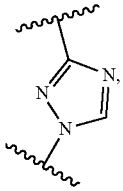
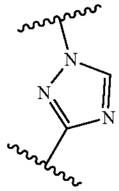,
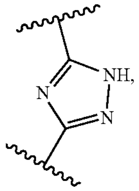

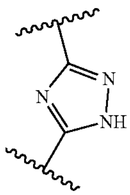
and
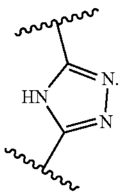

In another aspect [D2] the invention relates to a compound of formula (I) or (I*) or a salt thereof, wherein ring A is selected from the group consisting of

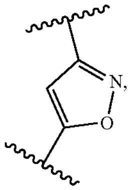
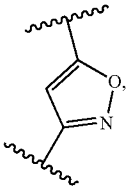
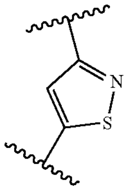
and
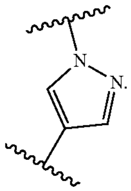

In another aspect [D3] the invention relates to a compound of formula (I) or (I*) or a salt thereof, wherein ring A is

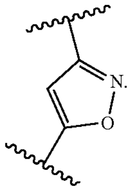 [SMILES: *c1cc(*)on1]

In another aspect [D4] the invention relates to a compound of formula (I) or (I*) or a salt thereof, wherein ring A is

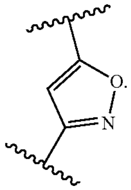 [SMILES: *c1cc(*)on1]

In another aspect [D5] the invention relates to a compound of formula (I) or (I*) or a salt thereof, wherein ring A is

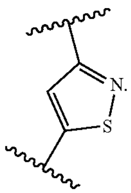 [SMILES: *c1cc(*)sn1]

In another aspect [D6] the invention relates to a compound of formula (I) or (I*) or a salt thereof, wherein ring A is

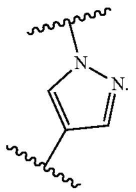 [SMILES: *c1cnn(*)c1]

In another aspect [E1] the invention relates to a compound of formula (I), (I*), (Ib), (Ib*), (Ic), (Ic*), (Id), (Id*), (Ie) or (Ie*) or a salt thereof, wherein p is 0.

In another aspect [E2] the invention relates to a compound of formula (I), (I*), (Ib), (Ib*), (Ic), (Ic*), (Id), (Id*), (Ie) or (Ie*) or a salt thereof, wherein $R^4$ is selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

p is 1.

In another aspect [E3] the invention relates to a compound of formula (I), (I*), (Ie) or (Ie*) or a salt thereof, wherein each $R^4$ is independently selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

p is 2.

In another aspect [E4] the invention relates to a compound of formula (I) or (I*) or a salt thereof, wherein each $R^4$ is independently selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

p is 3.

In another aspect [F1] the invention relates to a compound of formula (I), (I*), (Ib), (Ib*), (Ic), (Ic*), (Id), (Id*), (Ie) or (Ie*) or a salt thereof, wherein U is carbon substituted with $R^A$ (=C($R^A$)—);

V is carbon substituted with $R^B$ (=C($R^B$)—);

W is nitrogen (=N—);

$R^A$ and $R^B$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

In another aspect [F2] the invention relates to a compound of formula (I), (I*), (Ib), (Ib*), (Ic), (Ic*), (Id), (Id*), (Ie) or (Ie*) or a salt thereof, wherein U is =CH—;

V is =CH—;

W is nitrogen (=N—).

In another aspect [F3] the invention relates to a compound of formula (I), (I*), (Ib), (Ib*), (Ic), (Ic*), (Id), (Id*), (Ie) or (Ie*) or a salt thereof, wherein U is carbon substituted with $R^A$ (=C($R^A$)—);

V is carbon substituted with $R^B$ (=C($R^B$)—);

W is carbon substituted with $R^C$(=C($R^C$)—);

$R^A$, $R^B$ and $R^C$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

In another aspect [F4] the invention relates to a compound of formula (I), (I*), (Ib), (Ib*), (Ic), (Ic*), (Id), (Id*), (Ie) or (Ie*) or a salt thereof, wherein U is =CH—;

V is =CH—;

W is =CH—.

In another aspect [F5] the invention relates to a compound of formula (I), (I*), (Ib), (Ib*), (Ic), (Ic*), (Id), (Id*), (Ie) or (Ie*) or a salt thereof, wherein U is nitrogen (=N—);

V is carbon substituted with $R^B$ (=C($R^B$)—);

W is nitrogen (=N—);

$R^B$ is selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

In another aspect [F6] the invention relates to a compound of formula (I), (I*), (Ib), (Ib*), (Ic), (Ic*), (Id), (Id*), (Ie) or (Ie*) or a salt thereof, wherein U is nitrogen (=N—);

V is =CH—;

W is nitrogen (=N—).

In another aspect [F7] the invention relates to a compound of formula (I), (I*), (Ib), (Ib*), (Ic), (Ic*), (Id), (Id*), (Ie) or (Ie*) or a salt thereof, wherein U is carbon substituted with $R^A$ (=C($R^A$)—);

V is nitrogen (=N—);

W is nitrogen (=N—);

$R^A$ is selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

In another aspect [F8] the invention relates to a compound of formula (I), (I*), (Ib), (Ib*), (Ic), (Ic*), (Id), (Id*), (Ie) or (Ie*) or a salt thereof, wherein U is carbon substituted with $R^A$ (=C($R^A$)—);

V is nitrogen (=N—);

W is nitrogen (=N—);

$R^A$ is selected from the group consisting of hydrogen and halogen.

In another aspect [F9] the invention relates to a compound of formula (I), (I*), (Ib), (Ib*), (Ic), (Ic*), (Id), (Id*), (Ie) or (Ie*) or a salt thereof, wherein U is nitrogen (=N—);

V is nitrogen (=N—);

W is nitrogen (=N—).

In another aspect [G1] the invention relates to a compound of formula (I), (I*), (Ib), (Ib*), (Ic), (Ic*), (Id), (Id*), (Ie) or (Ie*) or a salt thereof, wherein $R^5$ is selected from the group consisting of $R^{a1}$ and $R^{b1}$;

$R^{a1}$ is selected from the group consisting of $C_{1-6}$alkyl, $C_{1-6}$haloalkyl, $C_{2-6}$alkynyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkynyl, $C_{3-10}$cycloalkyl, 3-11 membered heterocyclyl, $C_{6-10}$aryl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —CN, —C(=O)$R^{c1}$, —C(=O)O$R^{c1}$, —C(=O)$NR^{c1}R^{c1}$, —S(=O)$_2R^{c1}$, —S(=O)$_2NR^{c1}R^{c1}$, —NHC(=O)$R^{c1}$, —N($C_{1-4}$alkyl)C(=O)$R^{c1}$ and the bivalent substituent =O;

each $R^{c1}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$NR^{e1}R^{e1}$, halogen, —CN, —C(=O)$R^{e1}$, —C(=O)$NR^{e1}R^{e1}$ and the bivalent substituent =O;

each $R^{e1}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl optionally substituted with one or more, identical or different $C_{1-4}$alkyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —NH($C_{1-4}$alkyl), —N($C_{1-4}$alkyl)$_2$ and the bivalent substituent =O.

In another aspect [G2] the invention relates to a compound of formula (I), (I*), (Ib), (Ib*), (Ic), (Ic*), (Id), (Id*), (Ie) or (Ie*) or a salt thereof, wherein $R^5$ is $R^{a1}$;

$R^{a1}$ is selected from the group consisting of 3-11 membered heterocyclyl and 5-10 membered heteroaryl, wherein the 3-11 membered heterocyclyl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —C(=O)O$R^{c1}$ and the bivalent substituent =O;

each $R^{c1}$ is independently selected from the group consisting of hydrogen, $C_{1-6}$alkyl, $C_{1-6}$haloalkyl, $C_{3-10}$cycloalkyl and 3-11 membered heterocyclyl, wherein the $C_{1-6}$alkyl, $C_{1-6}$haloalkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of —$OR^{e1}$, —$NR^{e1}R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

In another aspect [G3] the invention relates to a compound of formula (I), (I*), (Ib), (Ib*), (Ic), (Ic*), (Id), (Id*), (Ie) or (Ie*) or a salt thereof, wherein $R^5$ is $R^{a1}$ selected from the group consisting of

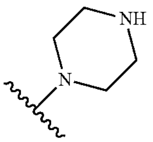 ,
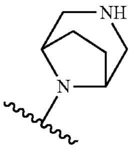 ,
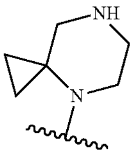 ,
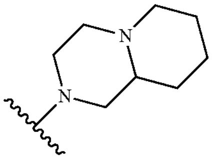 ,
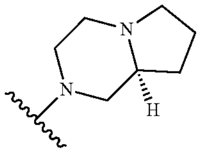 ,
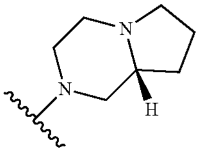 ,
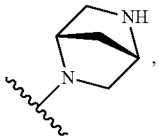 ,
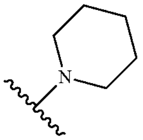 ,
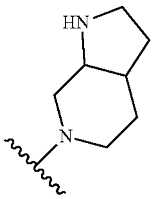 ,
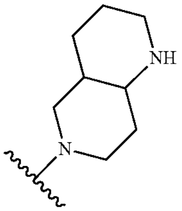 ,
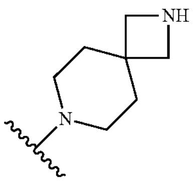 , -continued

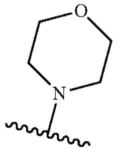,
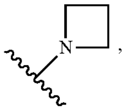,
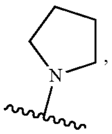,

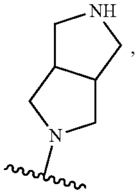,
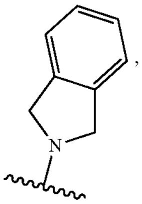,

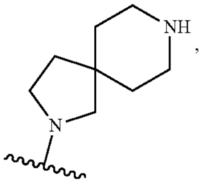,
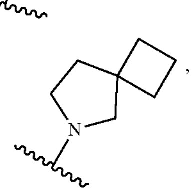,

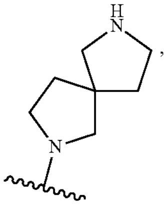,
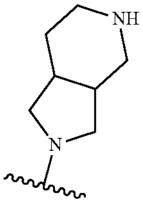,

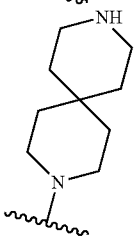,
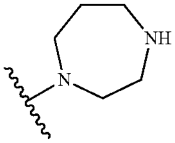

and

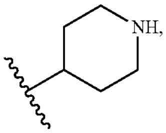

wherein each $R^{a1}$ is optionally substituted with one or more, identical or different $R^{b1}$ and/or $R^{c1}$;

each $R^{b1}$ is independently selected from the group consisting of $—OR^{c1}$, $—NR^{c1}R^{c1}$, halogen, $—C(=O)OR^{c1}$ and the bivalent substituent $=O$;

each $R^{c1}$ is independently selected from the group consisting of hydrogen, $C_{1-6}$alkyl, $C_{1-6}$haloalkyl, $C_{3-10}$cycloalkyl and 3-11 membered heterocyclyl, wherein the $C_{1-6}$alkyl, $C_{1-6}$haloalkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of $—OR^{e1}$, $—NR^{e1}R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

In another aspect [G4] the invention relates to a compound of formula (I), (I*), (Ib), (Ib*), (Ic), (Ic*), (Id), (Id*), (Ie) or (Ie*) or a salt thereof, wherein $R^5$ is $R^{a1}$ selected from the group consisting of

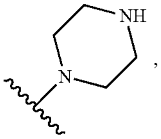,
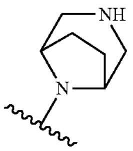,
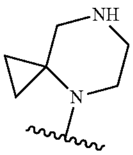,

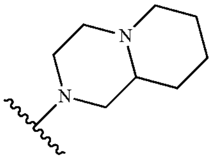,
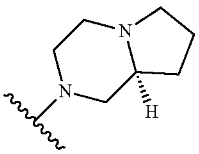,

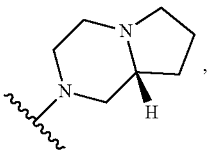,
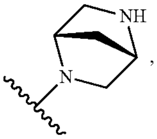,

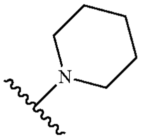,
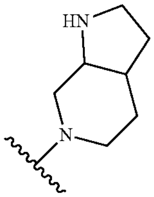,

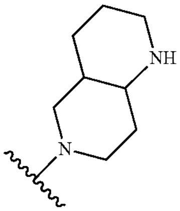,
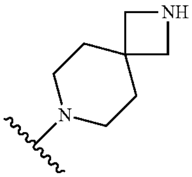,

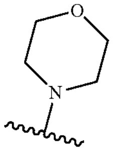,
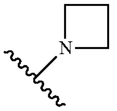,
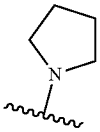,

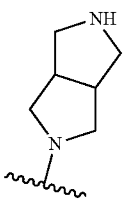,
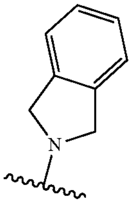,

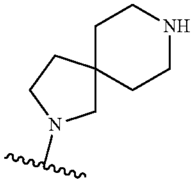,
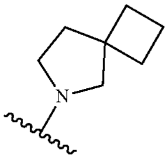,

-continued

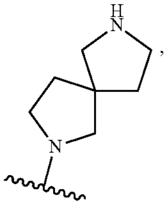,
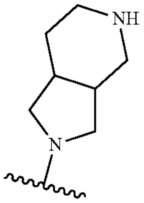,
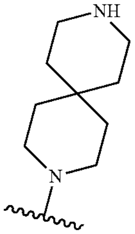,
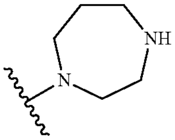
and
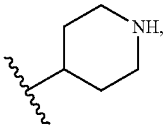

wherein each $R^{a1}$ is optionally substituted with one or more, identical or different of $C_{1-6}$alkyl optionally substituted with one or more, identical or different substituent(s) selected from the group consisting of $C_{3-6}$cycloalkyl, hydroxy, —$NH_2$, —$NH(C_{1-4}alkyl)$, —$N(C_{1-4}alkyl)_2$, $C_{1-4}$alkoxy and 3-7 membered heterocyclyl optionally substituted with $C_{1-4}$alkyl;

$C_{3-6}$cycloalkyl optionally substituted with one or more, identical or different halogen;

3-11 membered heterocyclyl optionally substituted with one or more, identical or different substituent(s) selected from the group consisting of $C_{1-4}$alkyl, $C_{3-6}$cycloalkyl and halogen; and a substituent selected from the group consisting of halogen, —C(═O)—$OC_{1-6}$alkyl, $C_{1-6}$haloalkyl, —OH, —$NH_2$, —$NH(C_{1-4}alkyl)$, —$N(C_{1-4}alkyl)_2$ and the bivalent substituent ═O.

In another aspect [G5] the invention relates to a compound of formula (I), (I*), (Ib), (Ib*), (Ic), (Ic*), (Id), (Id*), (Ie) or (Ie*) or a salt thereof, wherein $R^5$ is selected from the group consisting of

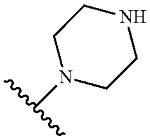,
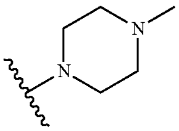,
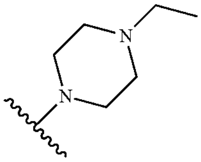,
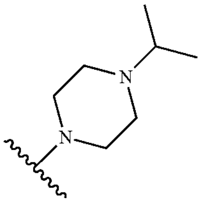,

-continued

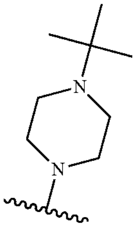,
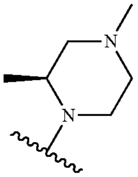,
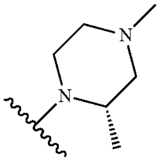,
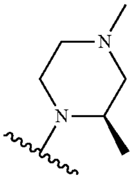,
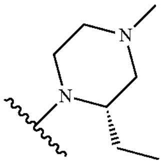,
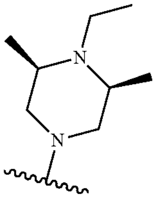,
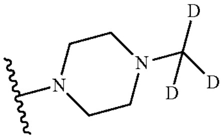,
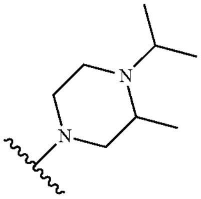,
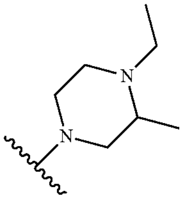,
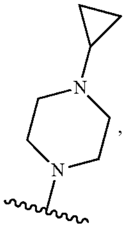,
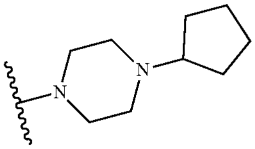,
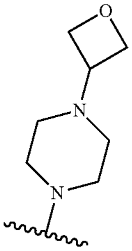,
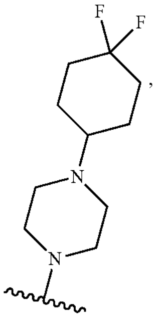,
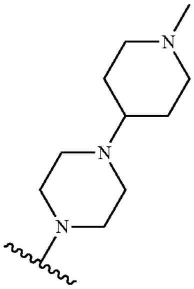, -continued
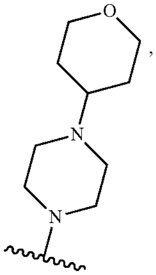,
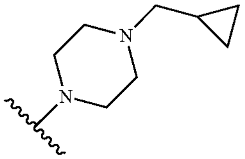,
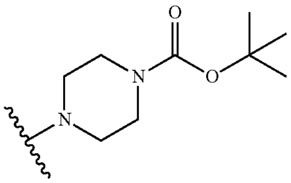,
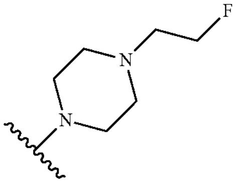,
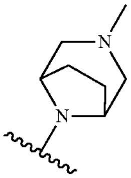,
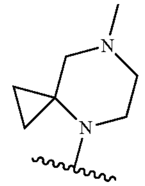,
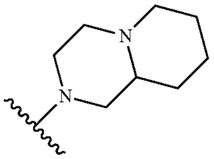,
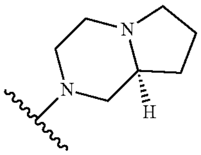,
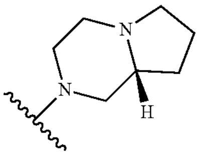,
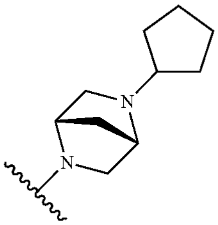,
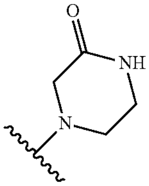,
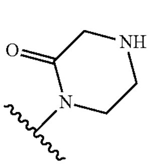,
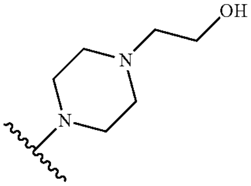,
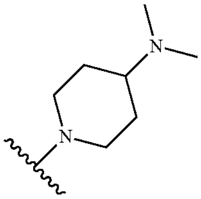,
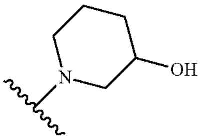,
-continued
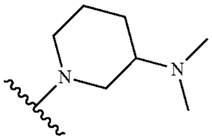,
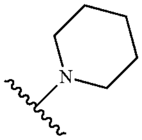,
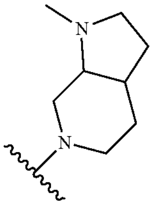,
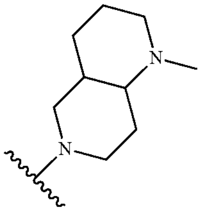,
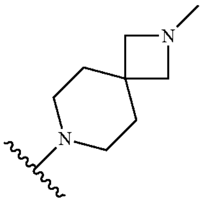,
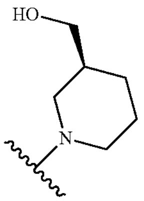,
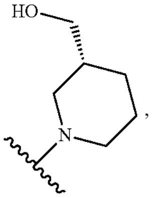,
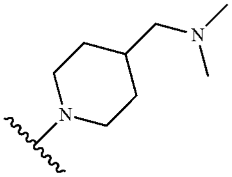,
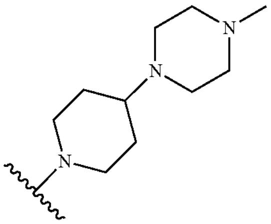,
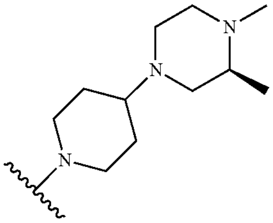,
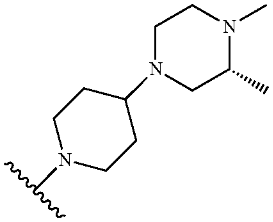,
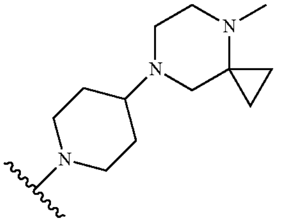, -continued
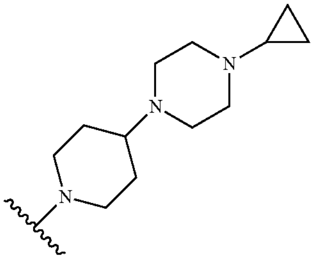 ,
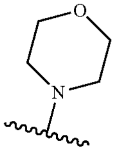 , 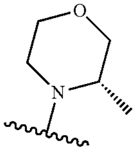 ,
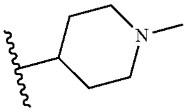 , 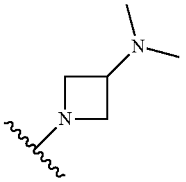 ,
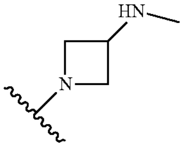 , 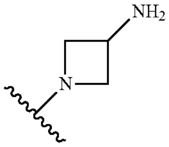 ,
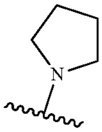 , 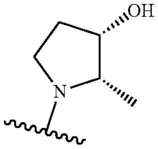 ,
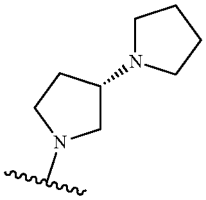 , 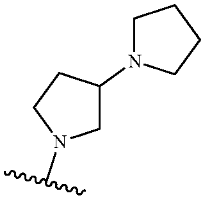 ,
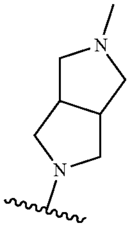 , 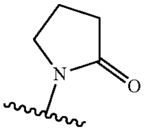 ,
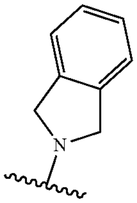 , 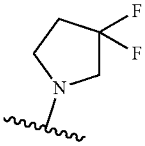 ,
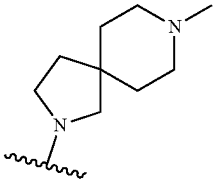 , 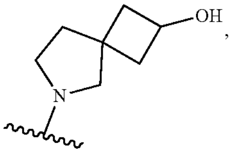 ,
-continued
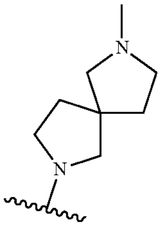 , 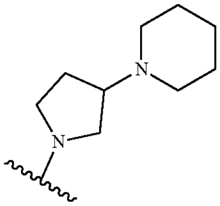 ,
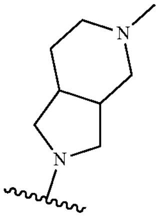 , 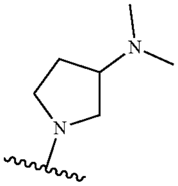 ,
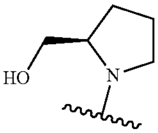 , 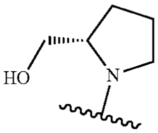 ,
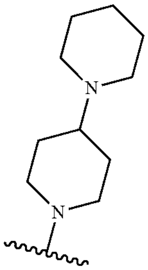 , 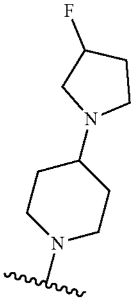 ,
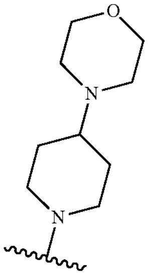 , 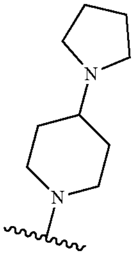 ,
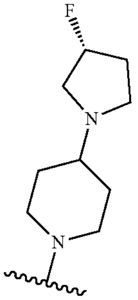 , 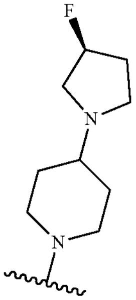 ,
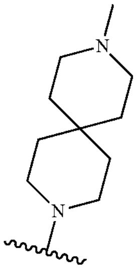 , 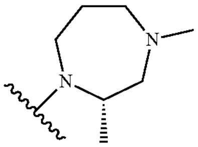 , -continued

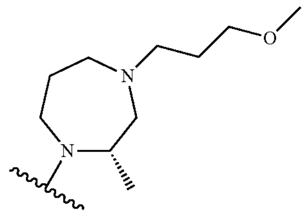,

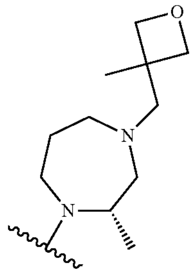,

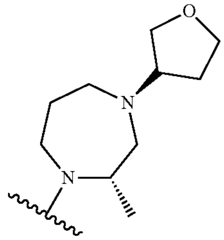,

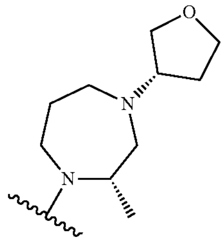, and

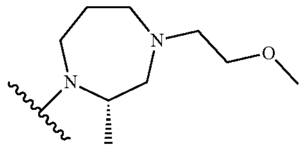.

In another aspect [G6] the invention relates to a compound of formula (I), (I*), (Ib), (Ib*), (Ic), (Ic*), (Id), (Id*), (Ie) or (Ie*) or a salt thereof, wherein $R^5$ is $R^{b1}$;

$R^{b1}$ is independently selected from the group consisting of —$OR^{c1}$ and —$NR^{c1}R^{c1}$;

each $R^{c1}$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$NR^{e1}R^{e1}$, halogen, —C(═O)$R^{e1}$ and —C(═O)$NR^{e1}R^{e1}$;

each $R^{e1}$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, 3-11 membered heterocyclyl optionally substituted with one or more, identical or different $C_{1-4}$alkyl, $C_{1-6}$alkoxy, halogen and the bivalent substituent ═O.

In another aspect [G7] the invention relates to a compound of formula (I), (I*), (Ib), (Ib*), (Ic), (Ic*), (Id), (Id*), (Ie) or (Ie*) or a salt thereof, wherein $R^5$ is $R^{b1}$;

$R^{b1}$ is —$OR^{c1}$;

each $R^{c1}$ is independently selected from the group consisting of $C_{1-6}$alkyl, $C_{3-10}$cycloalkyl, and 3-11 membered heterocyclyl, wherein the $C_{1-6}$alkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of —$NR^{e1}R^{e1}$ and halogen;

each $R^{e1}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

In another aspect [G8] the invention relates to a compound of formula (I), (I*), (Ib), (Ib*), (Ic), (Ic*), (Id), (Id*), (Ie) or (Ie*) or a salt thereof, wherein $R^5$ is selected from the group consisting of

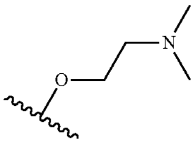,

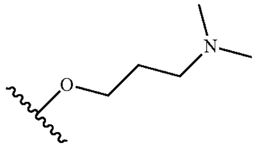,

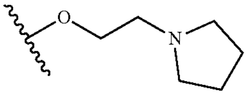,

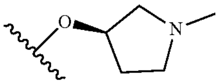,

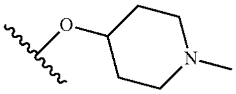,

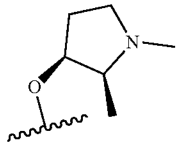,

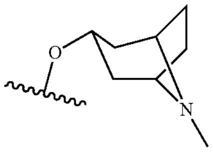,

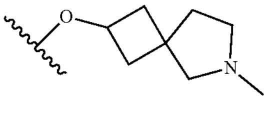,

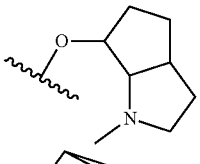,

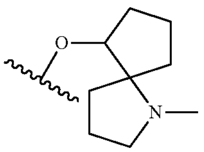,

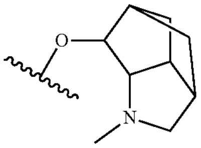,

-continued

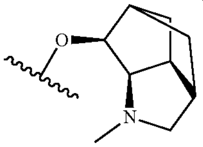,

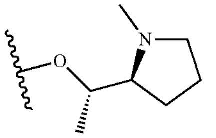,

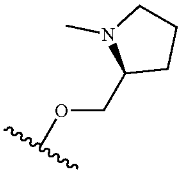,

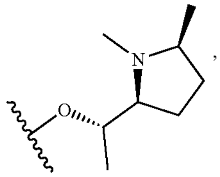,

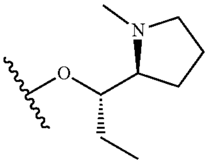,

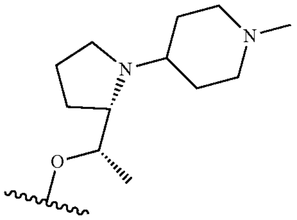,

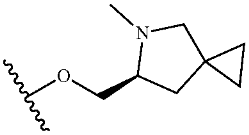,

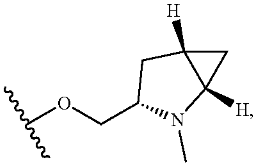,

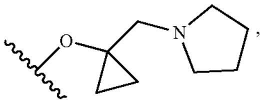,

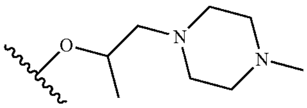

and

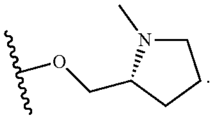.

In another aspect [H1] the invention relates to a compound of formula (I), (I*), (Ib), (Ib*), (Ic), (Ic*), (Id), (Id*), (Ie) or (Ie*) or a salt thereof, wherein L is $-L^1-L^2-L^3-$, wherein $L^1$ is linked to E;

$L^1$ is selected from the group consisting of a bond, $C_{1-6}$alkylen and 4-12 membered heterocyclylene;

$L^2$ is selected from the group consisting of $C_{1-6}$alkylen, phenylene and 4-12 membered heterocyclylene;

$L^3$ is selected from the group consisting of a bond, —NH—, —N($C_{1-4}$alkyl)- and —O—;

wherein each $C_{1-6}$alkylen, phenylene and 4-12 membered heterocyclylene in $L^1$ and $L^2$ is optionally and independently substituted with one or more, identical or different substituent(s) selected from the group consisting of $C_{2-6}$alkinyl, $C_{1-6}$haloalkyl, $C_{3-7}$cycloalkyl, phenyl, 5-6 membered heteroaryl, halogen, —OH, —CN, $C_{1-6}$alkoxy, —$NH_2$, —NH($C_{1-4}$alkyl), —N($C_{1-4}$alkyl)$_2$, —C(=O)OH, —C(=O)—O$C_{1-6}$alkyl, —C(=O)$NH_2$, —C(=O)NH($C_{1-4}$alkyl), —C(=O)N($C_{1-4}$alkyl)$_2$, the bivalent substituent =O and $C_{1-6}$alkyl optionally substituted with one or more, identical or different substituent(s) selected from the group consisting of halogen, —OH, —CN, —$NH_2$, $C_{1-4}$alkoxy, —NH($C_{1-4}$alkyl), —N($C_{1-4}$alkyl)$_2$, —C(=O)OH, —C(=O)—O$C_{1-6}$alkyl, —C(=O)$NH_2$, —C(=O)NH($C_{1-4}$alkyl) and —C(=O)N($C_{1-4}$alkyl)$_2$.

In another aspect [H2] the invention relates to a compound of formula (I), (I*), (Ib), (Ib*), (Ic), (Ic*), (Id), (Id*), (Ie) or (Ie*) or a salt thereof, wherein L is $-L^1-L^2-L^3-$, wherein $L^1$ is linked to E;

$L^1$ is selected from the group consisting of a bond, $C_{1-6}$alkylen and 4-12 membered heterocyclylene;

$L^2$ is selected from the group consisting of $C_{1-6}$alkylen, phenylene and 4-12 membered heterocyclylene;

$L^3$ is selected from the group consisting of a bond, —NH—, —N($C_{1-4}$alkyl)- and —O—;

wherein each $C_{1-6}$alkylen, phenylene and 4-12 membered heterocyclylene in $L^1$ and $L^2$ is optionally and independently substituted with one or more, identical or different $C_{1-6}$alkyl.

In another aspect [H3] the invention relates to a compound of formula (I), (I*), (Ib), (Ib*), (Ic), (Ic*), (Id), (Id*), (Ie) or (Ie*) or a salt thereof, wherein L is selected from the group consisting of

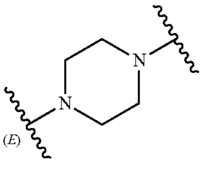,

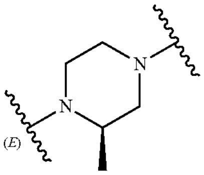,

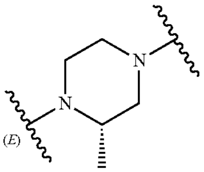,

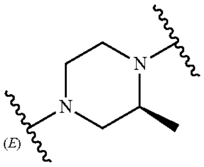,

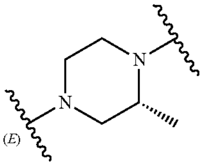,

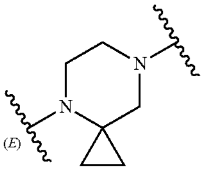,

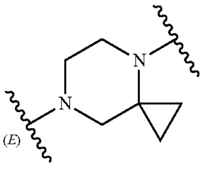,

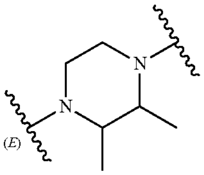,

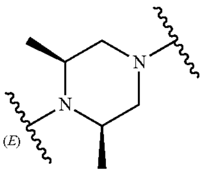,

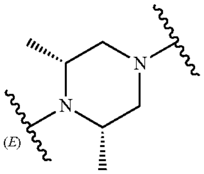,

-continued
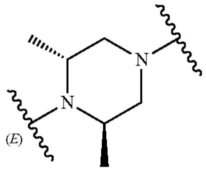,
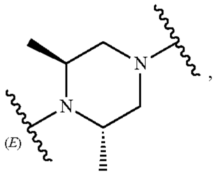,
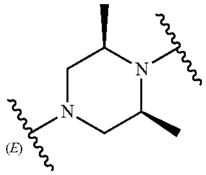,
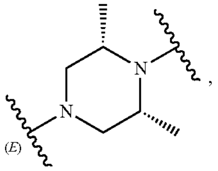,
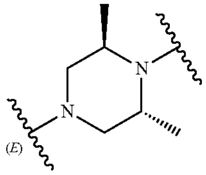,
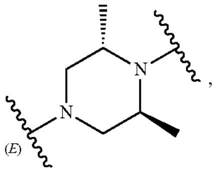,
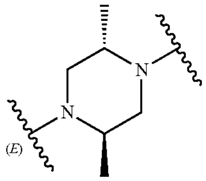,
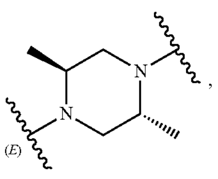,
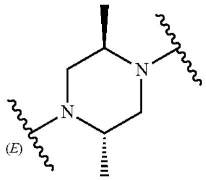,
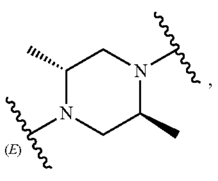,
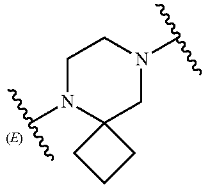,
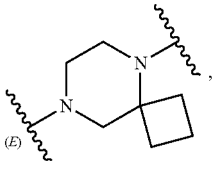,
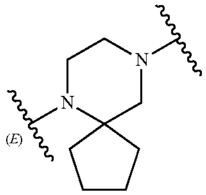,
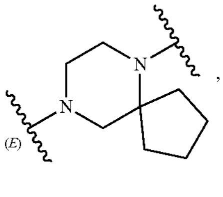,
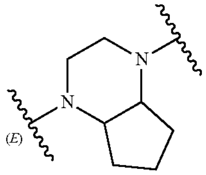,
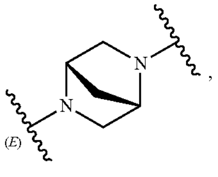,
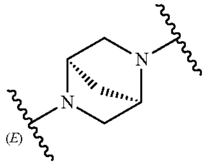,
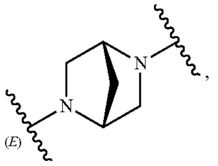,
-continued
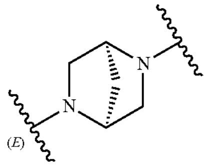,
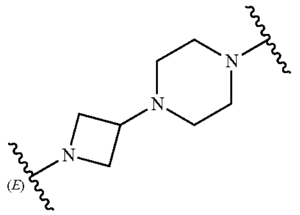,
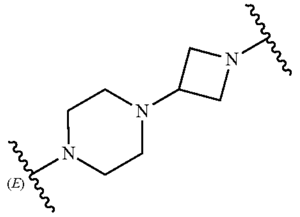,
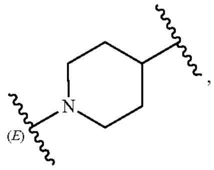,
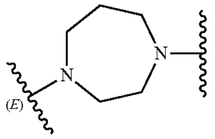,
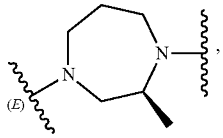,
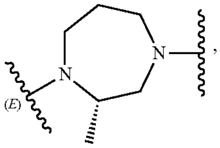,
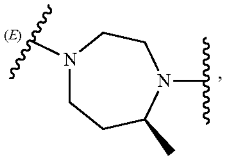,
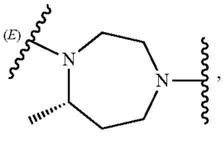,
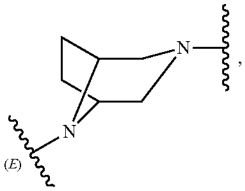,
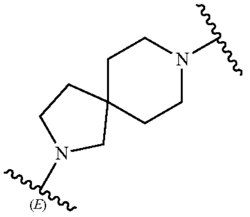,
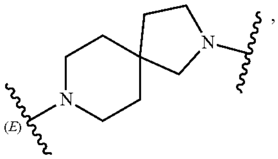,
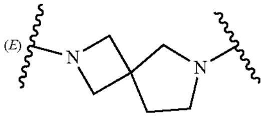,
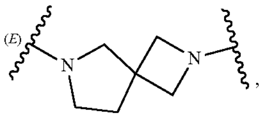, -continued

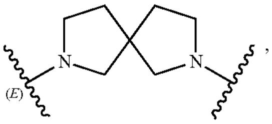,

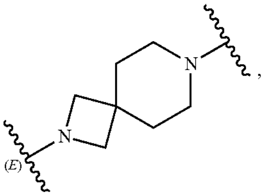,

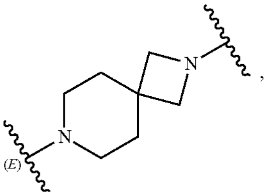,

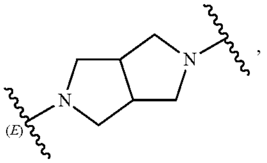, 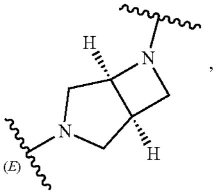,

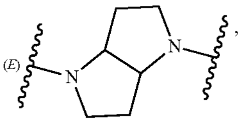, 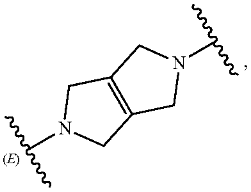,

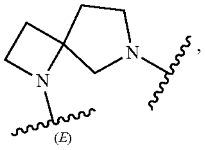, 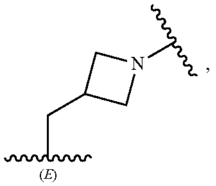,

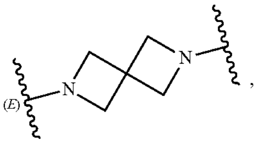,

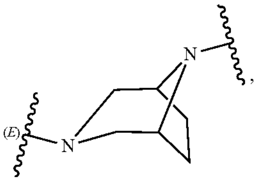, 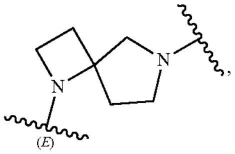,

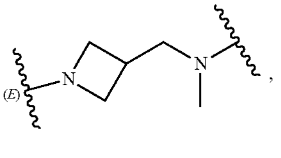, 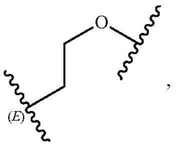,

-continued

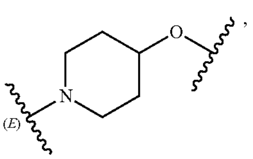, 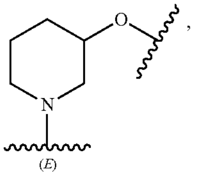,

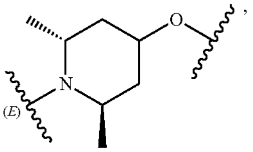, 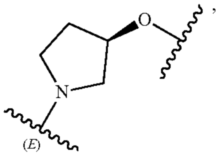,

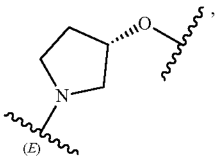, 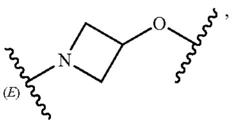,

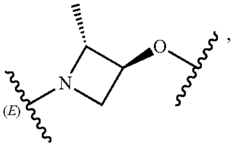,

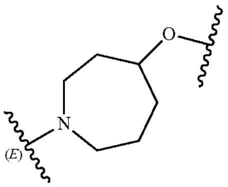 and 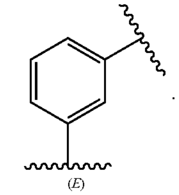.

In another aspect the invention relates to a compound of formula (I), (I*), (Ib), (Ib*), (Ic), (Ic*), (Id), (Id*), (Ie) or (Ie*) or a salt thereof, wherein E is (i)

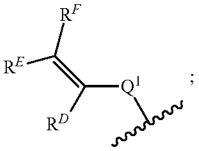;

$Q^1$ is selected from the group consisting of —$CH_2$—, —C(═O)—, —C(═O)N($R^{G1}$)—, —C(═O)O—, —S(═O)$_2$—, —S(═O)$_2$N($R^{G1}$)— and —C(═N$R^{H1}$)—;

each $R^{G1}$ is independently selected from the group consisting of hydrogen, $C_{1-6}$alkyl, $C_{1-6}$haloalkyl and hydroxy-$C_{1-6}$alkyl;

each $R^{H1}$ is independently selected from the group consisting of hydrogen, —OH, $C_{1-6}$alkoxy, —CN and $C_{1-6}$alkyl;

$R^D$ is selected from the group consisting of hydrogen, $C_{3-7}$cycloalkyl, phenyl, halogen, —CN, $C_{1-6}$alkoxy, —C(═O)O—$C_{1-6}$alkyl and $C_{1-6}$alkyl optionally substituted with one or more, identical or different substituent(s) selected from the group consisting of phenyl, 3-11 membered heterocyclyl, $C_{1-6}$alkoxy, halogen, —OH, —N($C_{1-6}$alkyl)$_2$, —C(═O)OH, —C(═O)O—$C_{1-6}$alkyl, —C(═O)NH ($C_{1-6}$alkyl), —NHC(═O)—$C_{1-6}$alkyl, —OC(═O)—$C_{1-6}$alkyl and phenyl-$C_{1-6}$alkoxy;

$R^E$ and $R^F$ is each independently selected from the group consisting of $R^{a2}$ and $R^{b2}$;

$R^{a2}$ is selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{b2}$ and/or $R^{c2}$;

each $R^{b2}$ is independently selected from the group consisting of —$OR^{c2}$, —$NR^{c2}R^{c2}$ halogen, —CN, —C(═O)$OR^{c2}$, —C(═O)$NR^{c2}R^{c2}$, —NHC(═O)$R^{c2}$, —N($C_{1-4}$alkyl)C(═O)$R^{c2}$, —NHC(═O)$OR^{c2}$ and —N($C_{1-4}$alkyl)C(═O)$OR^{c2}$;

each $R^{c2}$ is independently selected from the group consisting of hydrogen, $C_{1-6}$alkyl, $C_{1-6}$haloalkyl, 3-11 membered heterocyclyl, $C_{6-10}$aryl and 5-10 membered heteroaryl, wherein the $C_{1-6}$alkyl, $C_{1-6}$haloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$alkoxy, halogen, —OH, —C(═O)OH, —C(═O)O—$C_{1-6}$alkyl, —C(═O)$C_{1-6}$alkyl, —C(═O)$NH_2$, —C(═O)NH($C_{1-6}$alkyl), —C(═O)N($C_{1-6}$alkyl)$_2$, and the bivalent substituent ═O.

In another aspect the invention relates to a compound of formula (I), (I*), (Ib), (Ib*), (Ic), (Ic*), (Id), (Id*), (Ie) or (Ie*) or a salt thereof, wherein E is (i)

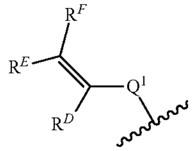

;

$Q^1$ is selected from the group consisting of —$CH_2$—, —C(═O)—, —C(═O)NH— and

—C(═O)N($C_{1-4}$alkyl)-;

$R^D$ is selected from the group consisting of hydrogen, halogen and $C_{1-6}$alkyl;

$R^E$ and $R^F$ is each independently selected from the group consisting of $R^{a2}$ and $R^{b2}$;

$R^{a2}$ is selected from the group consisting of hydrogen and $C_{1-6}$alkyl, wherein the $C_{1-6}$alkyl, is optionally substituted with one or more, identical or different $R^{b2}$ and/or $R^{c2}$;

each $R^{b2}$ is independently selected from the group consisting of —$OR^{c2}$ and —C(═O)$NR^{c2}R^{c2}$;

each $R^{c2}$ is independently selected from the group consisting of $C_{1-6}$alkyl and 3-11 membered heterocyclyl.

In another aspect the invention relates to a compound of formula (I), (I*), (Ib), (Ib*), (Ic), (Ic*), (Id), (Id*), (Ie) or (Ie*) or a salt thereof, wherein E is selected from the group consisting of

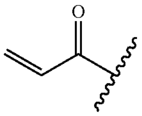, 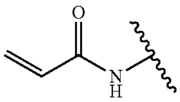,

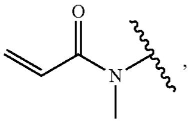, 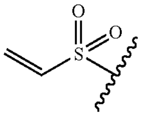,

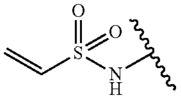, 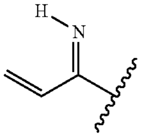, 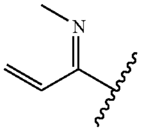,

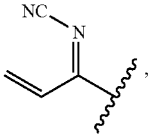, 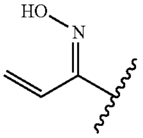, 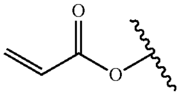,

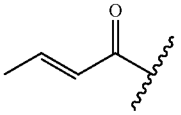, 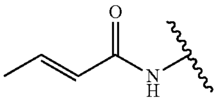,

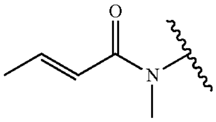, 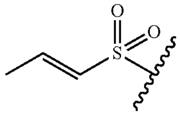,

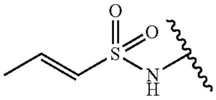, 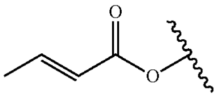,

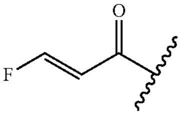, 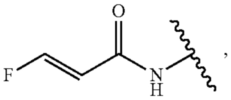,

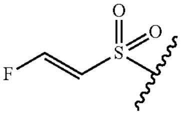, 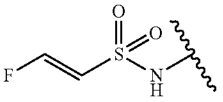,

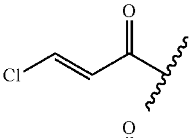, 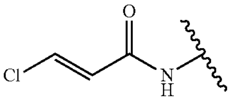,

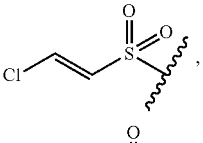, 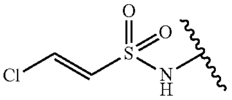,

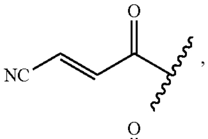, 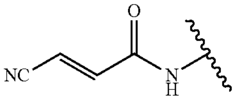,

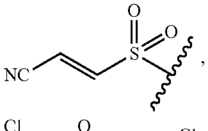, 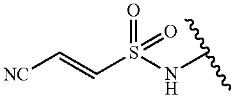,

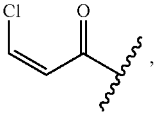, 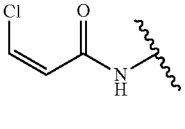,

-continued
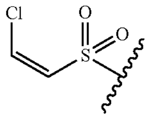,
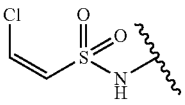,
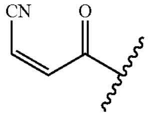,
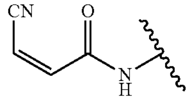,
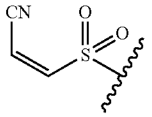,
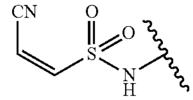,
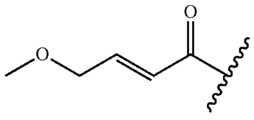,
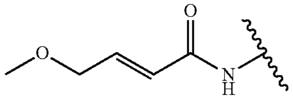,
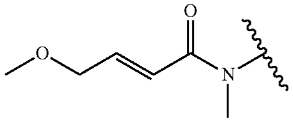,
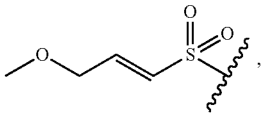,
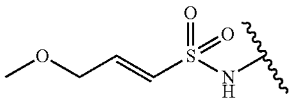,
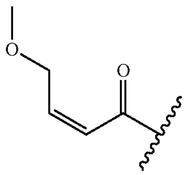,
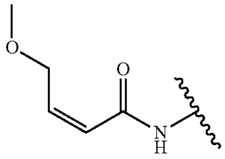,
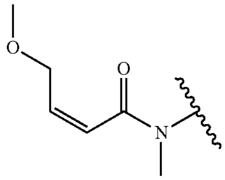,
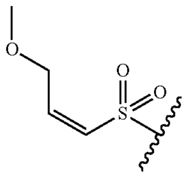,
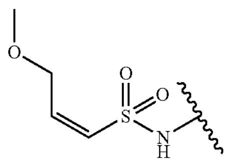,
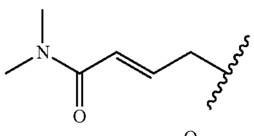,
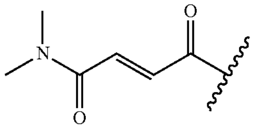,
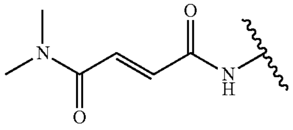,
-continued
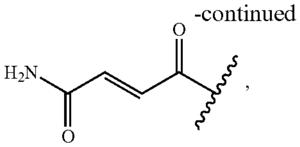,
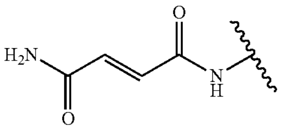,
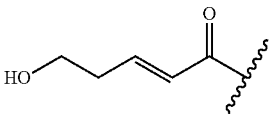,
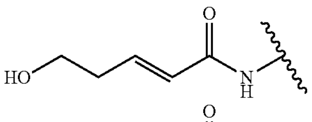,
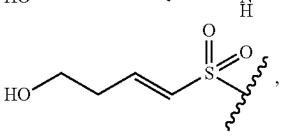,
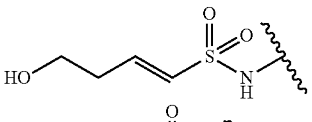,
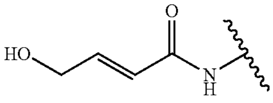,
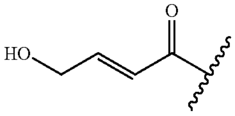,
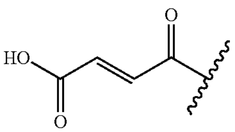,
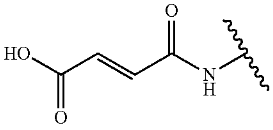,
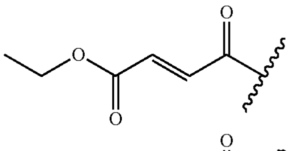,
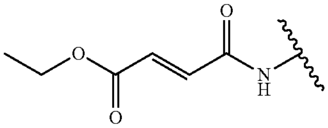,
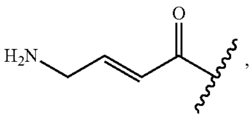,
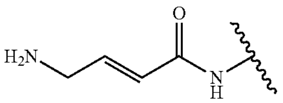,
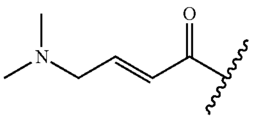,
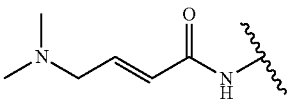, -continued
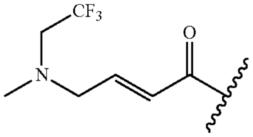,
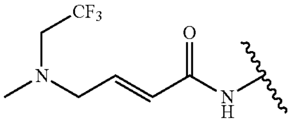,
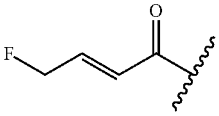, 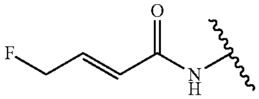,
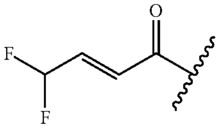, 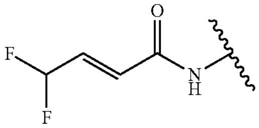,
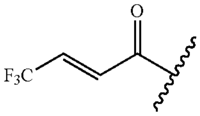, 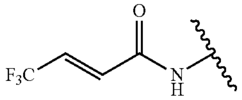,
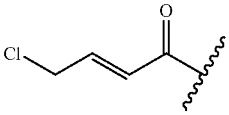, 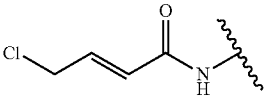,
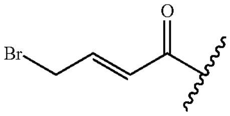,
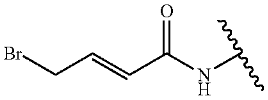,
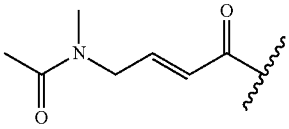,
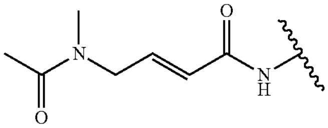,
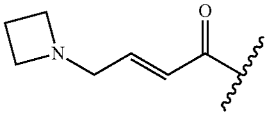,
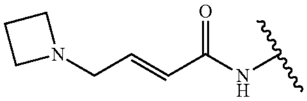,
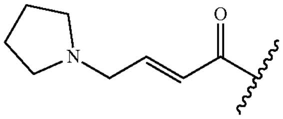,
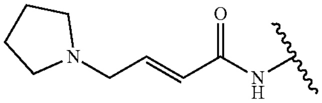,
-continued
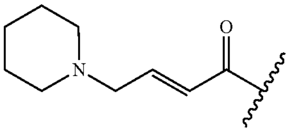,
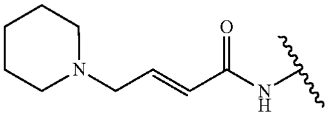,
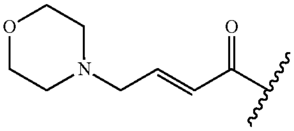,
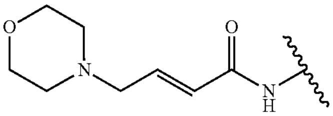,
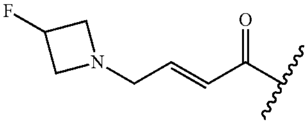,
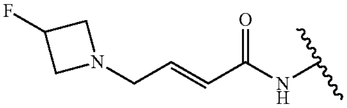,
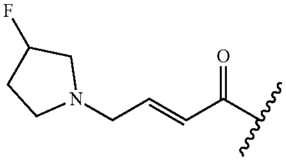,
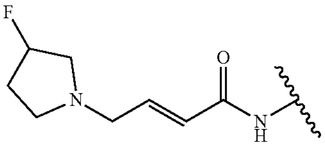,
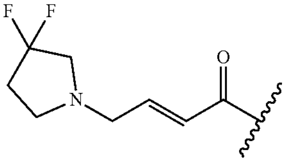,
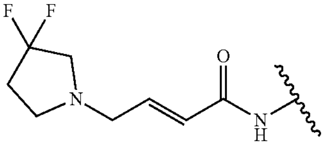,
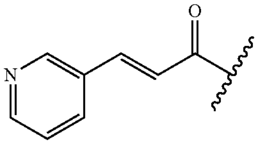,
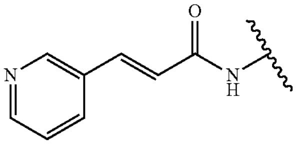, -continued
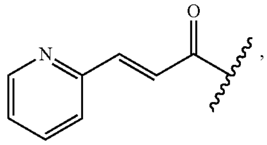,
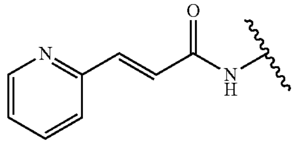,
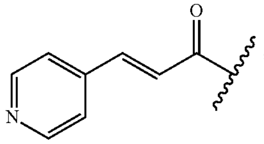,
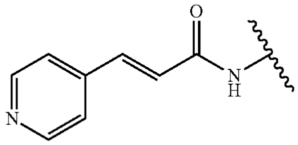,
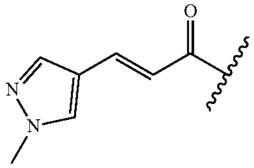,
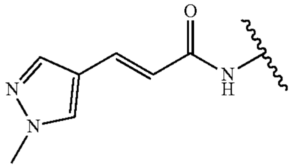,
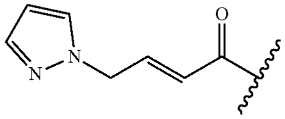,
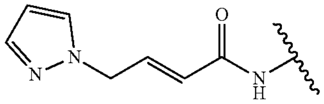,
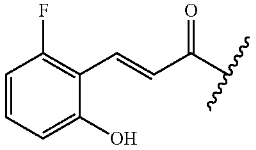,
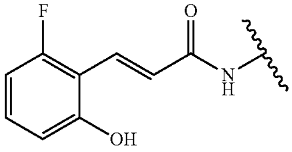, 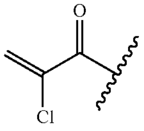,
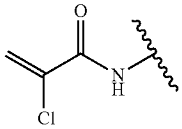, 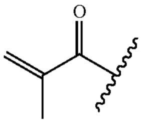,
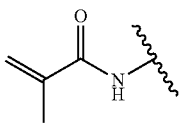, 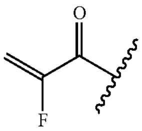,
-continued
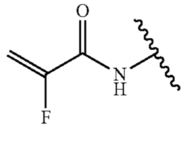, 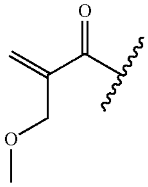,
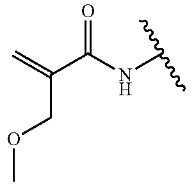, 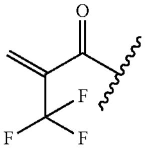,
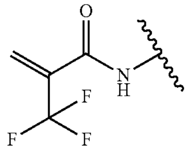, 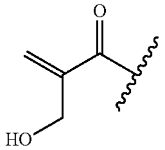,
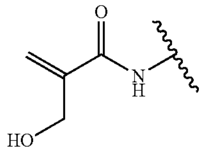, 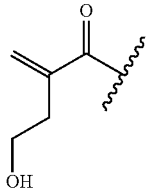,
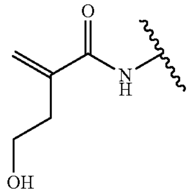, 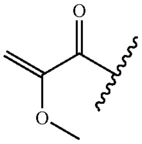,
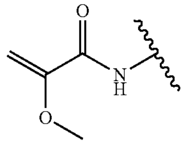, 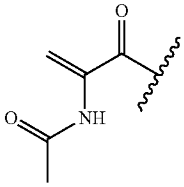,
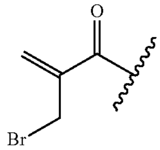, 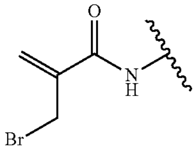,
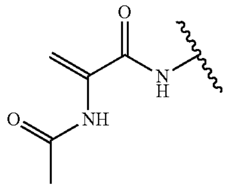, 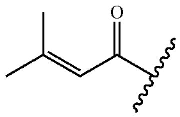,
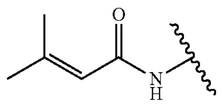, 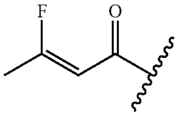,
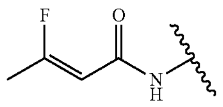, 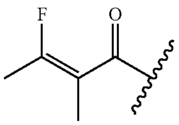, -continued
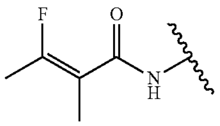,
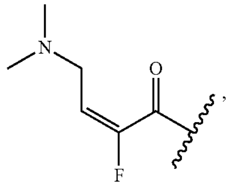,
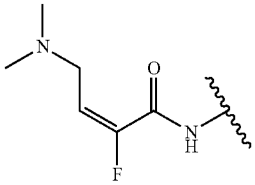,
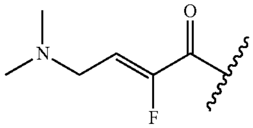,
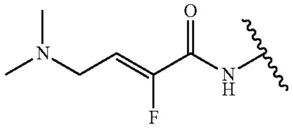,
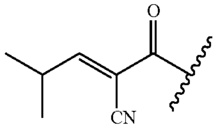,
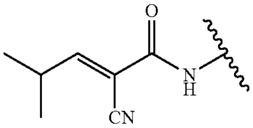,
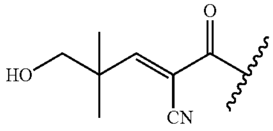,
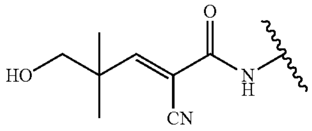,
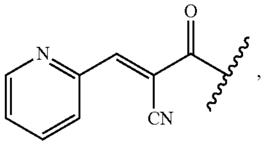,
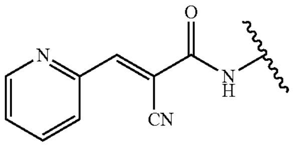,
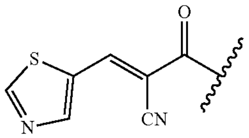,
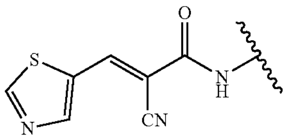,
-continued
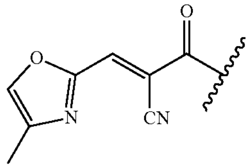,
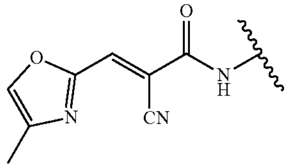,
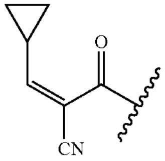,
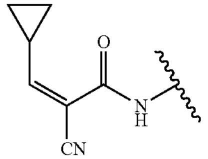,
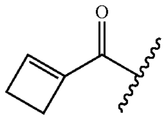,
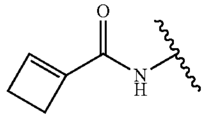,
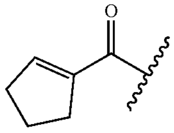,
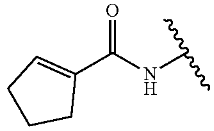,
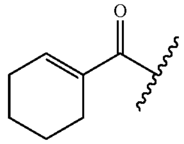,
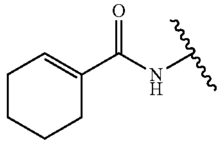,
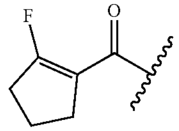,
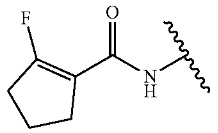,
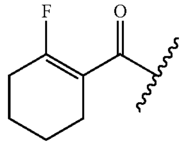,
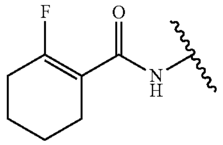,
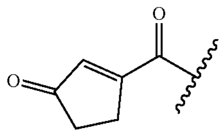,
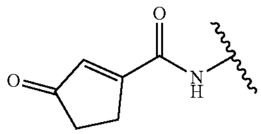,
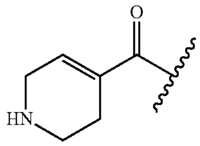 and
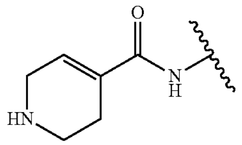.
In another aspect the invention relates to a compound of formula (I), (I*), (Ib), (Ib*), (Ic), (Ic*), (Id), (Id*), (Ie) or (Ie*) or a salt thereof, wherein E is selected from the group consisting of

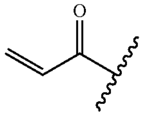, 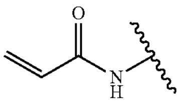, 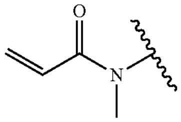, 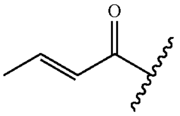, 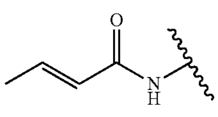, 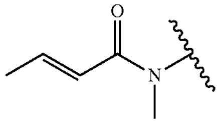, 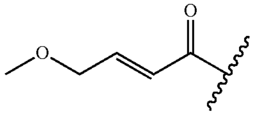, 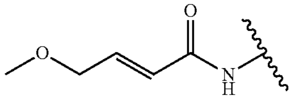, 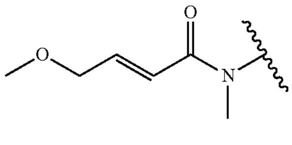, 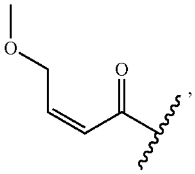, 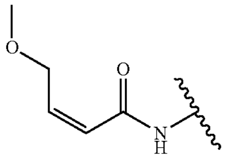, 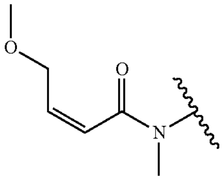, 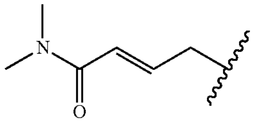, 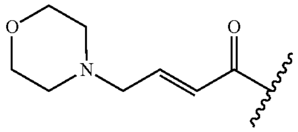, 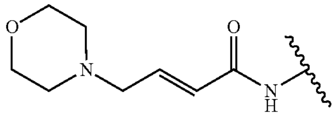, 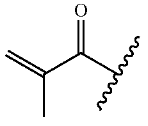, 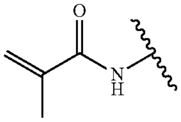, 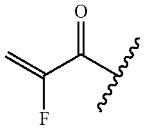, and 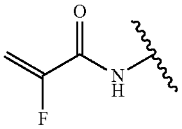.

In another aspect the invention relates to a compound of formula (I), (I*), (Ib), (Ib*), (Ic), (Ic*), (Id), (Id*), (Ie) or (Ie*) or a salt thereof, wherein E is

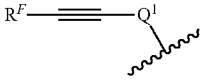

(i)

$Q^1$ is selected from the group consisting of —$CH_2$—, —C(═O)—, —C(═O)N($R^{G1}$)—, —C(═O)O—, —S(═O)$_2$—, —S(═O)$_2$N($R^{G1}$)— and —C(═NR$^{H1}$)—;

each $R^{G1}$ is independently selected from the group consisting of hydrogen, $C_{1-6}$alkyl, $C_{1-6}$haloalkyl and hydroxy-$C_{1-6}$alkyl;

each $R^{H1}$ is independently selected from the group consisting of hydrogen, —OH, $C_{1-6}$alkoxy, —CN and $C_{1-6}$alkyl; 10

$R^F$ is selected from the group consisting of hydrogen and $C_{1-6}$alkyl optionally substituted with a substituent selected from the group consisting of —OH, $C_{1-6}$alkoxy, —$NH_2$, —NH($C_{1-4}$alkyl) and —N($C_{1-4}$alkyl)$_2$.

In another aspect the invention relates to a compound of formula (I), (I*), (Ib), (Ib*), (Ic), (Ic*), (Id), (Id*), (Ie) or (Ie*) or a salt thereof, wherein E is

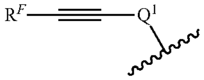

(i)

$Q^1$ is selected from the group consisting of —C(═O)—, —C(═O)N($R^{G1}$)—, —S(═O)$_2$— and —S(═O)$_2$N($R^{G1}$);

each $R^{G1}$ is independently selected from the group consisting of hydrogen and $C_{1-6}$alkyl;

$R^F$ is selected from the group consisting of hydrogen and $C_{1-6}$alkyl optionally substituted with a substituent selected from the group consisting of —OH, $C_{1-6}$alkoxy, —$NH_2$, —NH($C_{1-4}$alkyl) and —N($C_{1-4}$alkyl)$_2$.

In another aspect the invention relates to a compound of formula (I), (I*), (Ib), (Ib*), (Ic), (Ic*), (Id), (Id*), (Ie) or (Ie*) or a salt thereof, wherein E is selected from the group consisting of

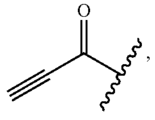, 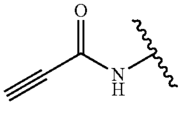, 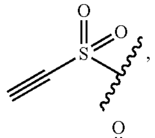, 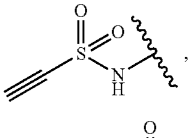, 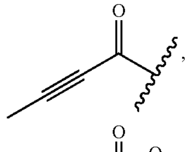, 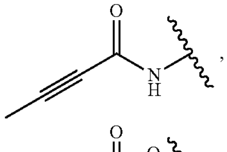, 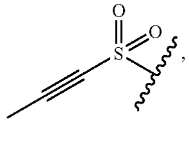, 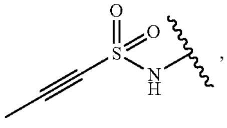, -continued

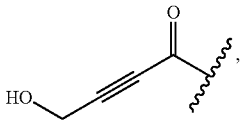, and

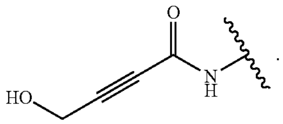.

In another aspect the invention relates to a compound of formula (I), (I*), (Ib), (Ib*), (Ic), (Ic*), (Id), (Id*), (Ie) or (Ie*) or a salt thereof, wherein E is selected from the group consisting of

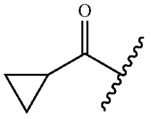, 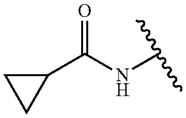,

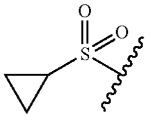, 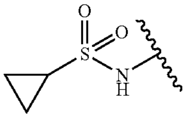,

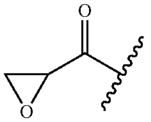, 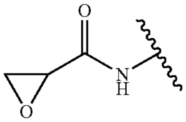,

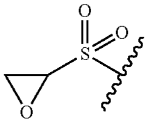, 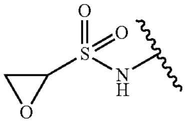,

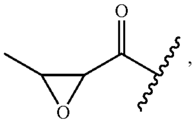, 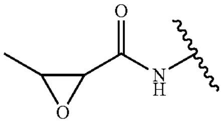,

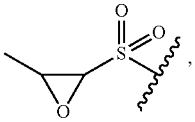, 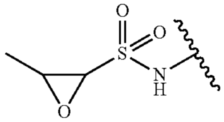,

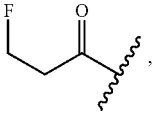, 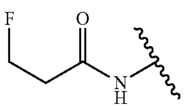,

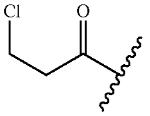, 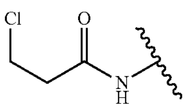,

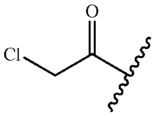, 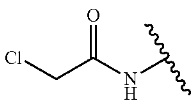,

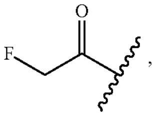, 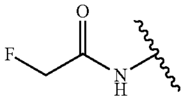,

-continued

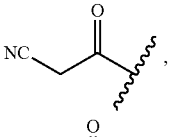, 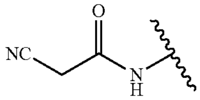,

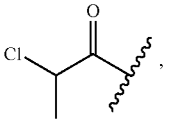, 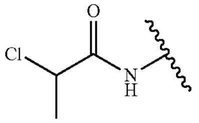 and

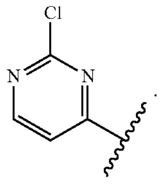 [SMILES: *c1ccnc(Cl)n1].

All above-mentioned structural aspects [A1] to [A3], to [B5], [C1] to [C5], [D1] to [D6], [E1] to [E4], [F1] to [F9], [G1] to [G8], [H1] to [H3] and to are preferred embodiments of the corresponding structural aspects [A0], [B0], [C0], [D0], [E0], [F0], [G0], [H0], and [I0], respectively. The structural aspects [A0] to [A3], [B0] to [B5], [C0] to [C5], [D0] to [D6], [E0] to [E4], [F0] to [F9], [G0] to [G8], [H0] to [H3] and to relating to different molecular parts of the compounds of formula (I), (I*), (Ib), (Ib*), (Ic), (Ic*), (Id), (Id*), (Ie) and (Ie*) according to the invention may be combined with one another as desired in combinations [A][B][C][D][E][F][G][H][I] (for compounds of formula (I) and (I*)) and combinations [A][B][C][E][F][G][H][I] (for compounds of formula (Ib), (Ib*), (Ic), (Ic*), (Id), (Id*), (Ie) and (Ie*)) to obtain preferred compounds (I), (I*), (Ib), (Ib*), (Ic), (Ic*), (Id), (Id*), (Ie) and (Ie*). Each such combination [A][B][C][D][E][F][G][H][I] represents and defines individual embodiments or generic subsets of compounds (I) and (I*) according to the invention. Each such combination [A][B][C][E][F][G][H][I] represents and defines individual embodiments or generic subsets of compounds (Ib), (Ib*), (Ic), (Ic*), (Id), (Id*), (Ie) and (Ie*) according to the invention.

Preferred embodiments of the invention of formula (Ib) are example compounds Ib-1 to Ib-16 and any subset thereof.

Preferred embodiments of the invention of formula (Ic) are example compounds Ic-1 to Ic-9 and any subset thereof.

Preferred embodiments of the invention of formula (Id) are example compounds Id-1 to Id-9 and any subset thereof.

Preferred embodiment of the invention of formula (Ie) is example compound Ie-1.

The present invention further relates to hydrates, solvates, polymorphs, metabolites, derivatives, stereoisomers and prodrugs of a compound of formula (I), (I*), (Ib), (Ib*), (Ic), (Ic*), (Id), (Id*), (Ie) and (Ie*) (including all its embodiments).

The present invention further relates to a hydrate of a compound of formula (I), (I*), (Ib), (Ib*), (Ic), (Ic*), (Id), (Id*), (Ie) and (Ie*) (including all its embodiments).

The present invention further relates to a solvate of a compound of formula (I), (I*), (Ib), (Ib*), (Ic), (Ic*), (Id), (Id*), (Ie) and (Ie*) (including all its embodiments).

Compounds of formula (I), (I*), (Ib), (Ib*), (Ic), (Ic*), (Id), (Id*), (Ie) and (Ie*) (including all its embodiments) which e.g. bear ester groups are potential prodrugs the ester being cleaved under physiological conditions and are also part of the invention.

The present invention further relates to a pharmaceutically acceptable salt of a compound of formula (I), (I*), (Ib), (Ib*), (Ic), (Ic*), (Id), (Id*), (Ie) and (Ie*) (including all its embodiments).

The present invention further relates to a pharmaceutically acceptable salt of a compound of formula (I), (I*), (Ib), (Ib*), (Ic), (Ic*), (Id), (Id*), (Ie) and (Ie*) (including all its embodiments) with anorganic or organic acids or bases.

Intermediates

In an eleventh aspect, the present invention relates to a compound of formula (II) or a salt thereof (II)

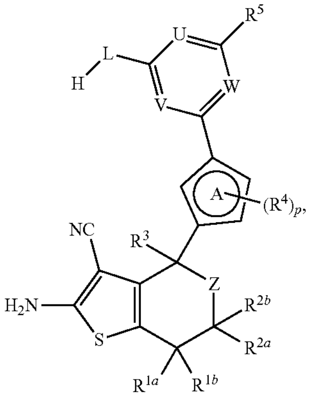

wherein $R^{1a}$, $R^{1b}$, $R^{2a}$, $R^{2b}$, Z, $R^3$, ring A, $R^4$, p, U, V, W, $R^5$ and L are defined as in formula (I) in the first aspect.

Compounds of formula (II) are intermediates in the synthesis of compounds of formula (I) (the hydrogen in residue H-L- is replaced/substituted by group E in the last synthetic step).

In a twelfth aspect, the present invention relates to a compound of formula (II*) or a salt thereof (II*)

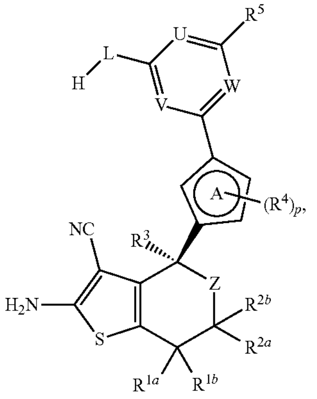

wherein $R^{1a}$, $R^{1b}$, $R^{2a}$, $R^{2b}$, Z, $R^3$, ring A, $R^4$, p, U, V, W, $R^5$ and L are defined as in formula (I) in the first aspect.

In a thirteenth aspect, the present invention relates to a compound of formula (C-4) or a salt thereof (C-4)

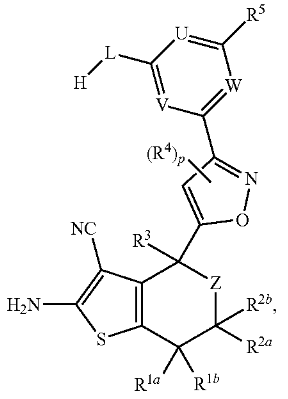

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a fourteenth aspect, the present invention relates to a compound of formula (C-4*) or a salt thereof (C-4*)

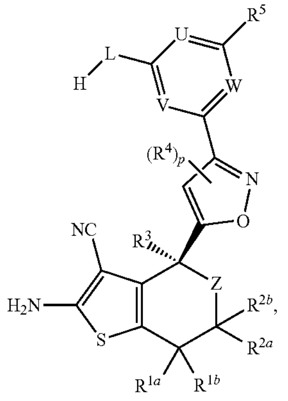

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a fifteenth aspect, the present invention relates to a compound of formula (C-5) or a salt thereof (C-5)

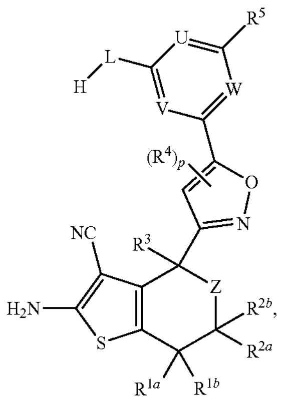

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a sixteenth aspect, the present invention relates to a compound of formula (C-5*) or a salt thereof (C-5*)

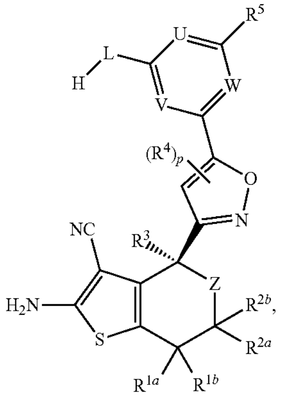

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a seventeenth aspect, the present invention relates to a compound of formula (C-7) or a salt thereof (C-7)

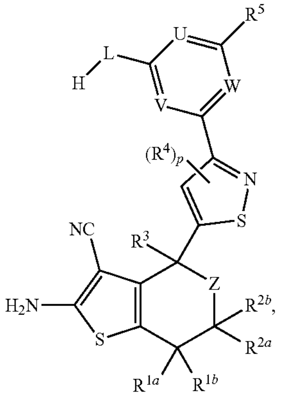

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In an eighteenth aspect, the present invention relates to a compound of formula (C-7*) or a salt thereof (C-7*)

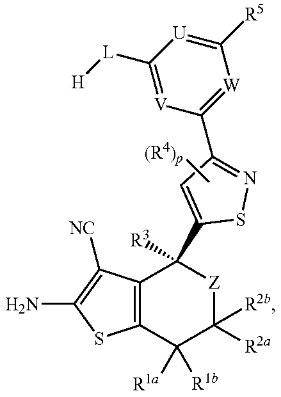

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a nineteenth aspect, the present invention relates to a compound of formula (D-7) or a salt thereof (D-7)

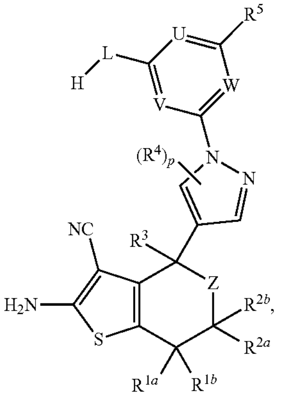

wherein $R^{1a}$, $R^{1b}$, $R^{2a}$, $R^{2b}$, Z, $R^3$, $R^4$, p, U, V, W, $R^5$ and L are defined as in formula (I) in the first aspect.

In a twentieth aspect, the present invention relates to a compound of formula (D-7*) or a salt thereof (D-7*)

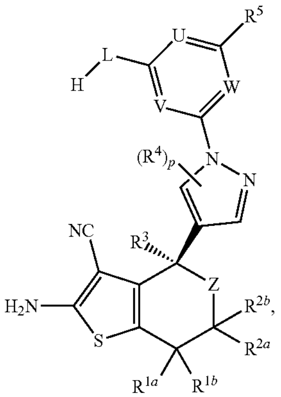

wherein $R^{1a}$, $R^{1b}$, $R^{2a}$, $R^{2b}$, Z, $R^3$, $R^4$, p, U, V, W, $R^5$ and L are defined as in formula (I) in the first aspect.

It is to be understood that compounds (II*), (C-4), (C-4*), (C-5), (C-5*), (C-7), (C-7*), (D-7) and (D-7*) each are a subset of compounds (II) and that whenever it is referred to compounds (II) this is meant to also refer to and include compounds (II*), (C-4), (C-4*), (C-5), (C-5*), (C-7), (C-7*), (D-7) and (D-7*) unless stated otherwise.

It is to be understood that compounds (C-4*), (C-5*), (C-7*) and (D-7*) each are a subset of the respective compounds (C-4), (C-5), (C-7) and (D-7), and that whenever it is referred to compounds (C-4), (C-5), (C-7) and/or (D-7) this is meant to also refer to and include compounds (C-4*), (C-5*), (C-7*) and/or (D-7*) unless stated otherwise.

All above-mentioned structural aspects [A1] to [A3], [B1] to [B5], [C1] to [C5], [D1] to [D6], [E1] to [E4], [F1] to [F9], [G1] to [G8] and [H1] to [H3] disclosed as preferred embodiments of the corresponding structural aspects [A0], [B0], [C0], [D0], [E0], [F0], [G0] and [H0] of compounds of formula (I), (I*), (Ib), (Ib*), (Ic), (Ic*), (Id), (Id*), (Ie) and (Ie*) are also the preferred embodiments of the corresponding structural aspects [A0], [B0], [C0], [D0], [E0], [F0], [G0] and [H0] of compounds of formula (II), (II*), (C-4), (C-4*), (C-5), (C-5*), (C-7), (C-7*), (D-7) and (D-7*).

Thus, these structural aspects [A0] to [A3], [B0] to [B5], [C0] to [C5], [D0] to [D6], [E0] to [E4], [F0] to [F9], [G0] to [G8] and [H0] to [H3] relating to different molecular parts of the compounds of formula (II), (II*), (C-4), (C-4*), (C-5), (C-5*), (C-7), (C-7*), (D-7) and (D-7*) may be combined with one another as desired in combinations [A][B][C][D][E][F][G][H] (for compounds of formula (II) and (II*)) and combinations [A][B][C][E][F][G][H] (for compounds of formula (C-4), (C-4*), (C-5), (C-5*), (C-7), (C-7*), (D-7) and (D-7*)) to obtain preferred compounds of formula (II), (II*), (C-4), (C-4*), (C-5), (C-5*), (C-7), (C-7*), (D-7) and (D-7*). Each such combination [A][B][C][D][E][F][G][H] represents and defines individual embodiments or generic subsets of compounds of formula (II) and (II*). Each such combination [A][B][C][E][F][G][H] represents and defines individual embodiments or generic subsets of compounds of formula (C-4), (C-4*), (C-5), (C-5*), (C-7), (C-7*), (D-7) and (D-7*).

Pharmaceutical Compositions

Suitable pharmaceutical compositions for administering the compounds of formula (I), (I*), (Ib), (Ib*), (Ic), (Ic*), (Id), (Id*), (Ie) or (Ie*) according to the invention will be apparent to those with ordinary skill in the art and include for example tablets, pills, capsules, suppositories, lozenges, troches, solutions-particularly solutions for injection (s.c., i.v., i.m.) and infusion (injectables)—elixirs, syrups, sachets, emulsions, inhalatives or dispersible powders. The content of the compounds (I), (I*), (Ib), (Ib*), (Ic), (Ic*), (Id), (Id*), (Ie) or (Ie*) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the compounds (I), (I*), (Ib), (Ib*), (Ic), (Ic*), (Id), (Id*), (Ie) or (Ie*) with known pharmaceutically acceptable excipients, for example inert diluents, carriers, disintegrants, adjuvants, surfactants, binders and/or lubricants. The tablets may also comprise several layers.

Coated tablets may be prepared accordingly by coating cores produced analogously to the tablets with excipients normally used for tablet coatings, for example collidine or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing one or more compounds (I), (I*), (Ib), (Ib*), (Ic), (Ic*), (Id), (Id*), (Ie) or (Ie*) or combinations with one or more other pharmaceutically active substance(s) may additionally contain excipients like a sweetener such as saccharine, cyclamate, glycerol or sugar and a flavour enhancer, e.g. a flavouring such as vanillin or orange extract. They may also contain excipients like suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of excipients like isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more compounds (I), (I*), (Ib), (Ib*), (Ic), (Ic*), (Id), (Id*), (Ie) or (Ie*) or combinations with one or more other pharmaceutically active substance(s) may for example be prepared by mixing the compounds/active substance(s) with inert excipients such as lactose or sorbitol and packing them into gelatine capsules.

Suitable suppositories may be made for example by mixing with excipients provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The pharmaceutical compositions are administered by the usual methods, preferably by oral or transdermal route, most preferably by oral route. For oral administration the tablets may of course contain, apart from the above-mentioned excipients, additional excipients such as sodium citrate, calcium carbonate and dicalcium phosphate together with various excipients such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid excipients may be used.

The dosage range of the compounds of formula (I), (I*), (Ib), (Ib*), (Ic), (Ic*), (Id), (Id*), (Ie) or (Ie*) applicable per day is usually from 1 mg to 2000 mg, preferably from 250 to 1250 mg.

However, it may sometimes be necessary to depart from the amounts specified, depending on the body weight, age, the route of administration, severity of the disease, the individual response to the drug, the nature of its formulation and the time or interval over which the drug is administered (continuous or intermittent treatment with one or multiple doses per day). Thus, in some cases it may be sufficient to use less than the minimum dose given above, whereas in other cases the upper limit may have to be exceeded. When administering large amounts it may be advisable to divide them up into a number of smaller doses spread over the day.

Thus, in a further aspect the invention relates to a pharmaceutical composition comprising at least one (preferably one) compound of formula (I), (I*), (Ib), (Ib*), (Ic), (Ic*), (Id), (Id*), (Ie) or (Ie*)—or a pharmaceutically acceptable salt thereof—and one or more pharmaceutically acceptable excipient(s).

The compounds of formula (I), (I*), (Ib), (Ib*), (Ic), (Ic*), (Id), (Id*), (Ie) or (Ie*)—or the pharmaceutically acceptable salts thereof—and the pharmaceutical compositions comprising such compound and salts may also be co-administered with other pharmacologically active substances, e.g. with other anti-neoplastic compounds (e.g. chemotherapy), i.e. used in combination (see combination treatment further below).

The elements of such combinations may be administered (whether dependently or independently) by methods customary to the skilled person and as they are used in monotherapy, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable excipients appropriate for each route of administration.

The combinations may be administered at therapeutically effective single or divided daily doses. The active components of the combinations may be administered in such doses which are therapeutically effective in monotherapy, or in such doses which are lower than the doses used in monotherapy, but when combined result in a desired (joint) therapeutically effective amount.

However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmacological or therapeutic effect.

Thus, in a further aspect the invention also relates to a pharmaceutical composition comprising a compound of formula (I), (I*), (Ib), (Ib*), (Ic), (Ic*), (Id), (Id*), (Ie) or (Ie*)—or a pharmaceutically acceptable salt thereof—and one or more (preferably one or two, most preferably one) other pharmacologically active substance(s).

In a further aspect the invention also relates to a pharmaceutical preparation comprising a compound of formula (I), (I*), (Ib), (Ib*), (Ic), (Ic*), (Id), (Id*), (Ie) or (Ie*)—or a pharmaceutically acceptable salt thereof—and one or more (preferably one or two, most preferably one) other pharmacologically active substance(s).

Pharmaceutical compositions to be co-administered or used in combination can also be provided in the form of a kit.

Thus, in a further aspect the invention also relates to a kit comprising

- a first pharmaceutical composition or dosage form comprising a compound of formula (I), (I*), (Ib), (Ib*), (Ic), (Ic*), (Id), (Id*), (Ie) or (Ie*) and, optionally, one or more pharmaceutically acceptable excipient(s), and
- a second pharmaceutical composition or dosage form comprising another pharmacologically active substance and, optionally, one or more pharmaceutically acceptable excipient(s).

In one aspect such kit comprises a third pharmaceutical composition or dosage form comprising still another pharmacologically active substance and, optionally, one or more pharmaceutically acceptable excipient(s).

Medical Uses—Methods of Treatment

Indications—Patient Populations

The present invention is mainly directed to RAS G12C inhibitors, in particular compounds of formula (I), (I*), (Ib), (Ib*), (Ic), (Ic*), (Id), (Id*), (Ie) and (Ie*) (including all its embodiments), which are potentially useful in the treatment and/or prevention of diseases and/or conditions mediated by RAS G12C mutations, e.g. and preferably KRAS G12C, NRAS G12C and HRAS G12C.

Thus, in a further aspect the invention relates to a compound of formula (I), (I*), (Ib), (Ib*), (Ic), (Ic*), (Id), (Id*), (Ie) or (Ie*)—or a pharmaceutically acceptable salt thereof—for use as a medicament.

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in a method of treatment of the human or animal body.

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in the treatment and/or prevention of a disease and/or condition mediated by RAS G12C mutations.

In a further aspect the invention relates to the use of a compound of formula (I), (I*), (Ib), (Ib*), (Ic), (Ic*), (Id), (Id*), (Ie) or (Ie*)—or a pharmaceutically acceptable salt thereof—in the manufacture of a medicament for the treatment and/or prevention of a disease and/or condition mediated by RAS G12C mutations.

In a further aspect the invention relates to a method for the treatment and/or prevention of a disease and/or condition mediated by RAS G12C mutations comprising administering a therapeutically effective amount of a compound of formula (I), (I*), (Ib), (Ib*), (Ic), (Ic*), (Id), (Id*), (Ie) or (Ie*)—or a pharmaceutically acceptable salt thereof—to a human being.

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in the treatment and/or prevention of cancer.

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in a method of treatment and/or prevention of cancer in the human or animal body.

In a further aspect the invention relates to the use of a compound of formula (I), (I*), (Ib), (Ib*), (Ic), (Ic*), (Id), (Id*), (Ie) or (Ie*)—or a pharmaceutically acceptable salt thereof—in the manufacture of a medicament for the treatment and/or prevention of cancer.

In a further aspect the invention relates to a method for the treatment and/or prevention of cancer comprising administering a therapeutically effective amount of a compound of formula (I), (I*), (Ib), (Ib*), (Ic), (Ic*), (Id), (Id*), (Ie) or (Ie*)—or a pharmaceutically acceptable salt thereof—to a human being.

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in providing an inhibitory effect on G12C mutant RAS.

In a further aspect the invention relates to the use of a compound of formula (I), (I*), (Ib), (Ib*), (Ic), (Ic*), (Id), (Id*), (Ie) or (Ie*)—or a pharmaceutically acceptable salt thereof—in the manufacture of a medicament for use in providing an inhibitory effect on G12C mutant RAS.

In a further aspect the invention relates to a method for providing an inhibitory effect on G12C mutant RAS comprising administering a therapeutically effective amount of a compound of formula (I), (I*), (Ib), (Ib*), (Ic), (Ic*), (Id), (Id*), (Ie) or (Ie*)—or a pharmaceutically acceptable salt thereof—to a human being.

Another aspect is based on identifying a link between the G12C mutation status of a patient and potential susceptibility to treatment with a compound of formula (I), (I*), (Ib), (Ib*), (Ic), (Ic*), (Id), (Id*), (Ie) or (Ie*). A RAS G12C inhibitor, such as a compound of formula (I), (I*), (Ib), (Ib*), (Ic), (Ic*), (Id), (Id*), (Ie) or (Ie*), may then advantageously be used to treat patients with KRAS G12C, HRAS G12C or NRAS G12C mutations who may be resistant to other therapies. This therefore provides opportunities, methods and tools for selecting patients for treatment with a compound of formula (I), (I*), (Ib), (Ib*), (Ic), (Ic*), (Id), (Id*), (Ie) or (Ie*), particularly cancer patients. The selection is based on whether the tumor cells to be treated possess wild-type or G12C mutant KRAS, HRAS or NRAS gene. The G12C KRAS, HRAS or NRAS gene status could therefore be used as a biomarker to indicate that selecting treatment with a compound of formula (I), (I*), (Ib), (Ib*), (Ic), (Ic*), (Id), (Id*), (Ie) or (Ie*) may be advantageous.

According to one aspect, there is provided a method for selecting a patient for treatment with a compound of formula (I), (I*), (Ib), (Ib*), (Ic), (Ic*), (Id), (Id*), (Ie) or (Ie*), the method comprising providing a tumor cell-containing sample from a patient;

determining whether the RAS gene in the patient's tumor cell-containing sample encodes for wild-type (glycine at position 12) or mutant (cysteine at position 12) KRAS, HRAS or NRAS protein; and selecting a patient for treatment with a compound of formula (I), (I*), (Ib), (Ib*), (Ic), (Ic*), (Id), (Id*), (Ie) or (Ie*) based thereon.

The method may include or exclude the actual patient sample isolation step.

In one aspect, the patient is selected for treatment with a compound of formula (I), (I*), (Ib), (Ib*), (Ic), (Ic*), (Id), (Id*), (Ie) or (Ie*) if the tumor cell DNA has a G12C mutant KRAS gene.

In another aspect, the patient is selected for treatment with a compound of formula (I), (I*), (Ib), (Ib*), (Ic), (Ic*), (Id), (Id*), (Ie) or (Ie*) if the tumor cell DNA has a G12C mutant HRAS gene.

In another aspect, the patient is selected for treatment with a compound of formula (I), (I*), (Ib), (Ib*), (Ic), (Ic*), (Id), (Id*), (Ie) or (Ie*) if the tumor cell DNA has a G12C mutant NRAS gene.

According to another aspect, there is provided a compound of formula (I), (I*), (Ib), (Ib*), (Ic), (Ic*), (Id), (Id*), (Ie) or (Ie*)—or a pharmaceutically acceptable salt thereof—for use in treating a cancer with tumor cells harbouring a G12C mutant RAS gene.

According to another aspect, there is provided a compound of formula (I), (I*), (Ib), (Ib*), (Ic), (Ic*), (Id), (Id*), (Ie) or (Ie*)—or a pharmaceutically acceptable salt thereof—for use in treating a cancer with tumor cells harbouring a G12C mutant KRAS gene.

According to another aspect, there is provided a compound of formula (I), (I*), (Ib), (Ib*), (Ic), (Ic*), (Id), (Id*), (Ie) or (Ie*)—or a pharmaceutically acceptable salt thereof—for use in treating a cancer with tumor cells harbouring a G12C mutant HRAS gene.

According to another aspect, there is provided a compound of formula (I), (I*), (Ib), (Ib*), (Ic), (Ic*), (Id), (Id*), (Ie) or (Ie*)—or a pharmaceutically acceptable salt thereof—for use in treating a cancer with tumor cells harbouring a G12C mutant NRAS gene.

According to another aspect, there is provided a method of treating a cancer with tumor cells harbouring a G12C mutant RAS gene comprising administering an effective amount of a compound of formula (I), (I*), (Ib), (Ib*), (Ic), (Ic*), (Id), (Id*), (Ie) or (Ie*)—or a pharmaceutically acceptable salt thereof—to a human being.

According to another aspect, there is provided a method of treating a cancer with tumor cells harbouring a G12C mutant KRAS, HRAS or NRAS gene comprising administering an effective amount of a compound of formula (I), (I*), (Ib), (Ib*), (Ic), (Ic*), (Id), (Id*), (Ie) or (Ie*)—or a pharmaceutically acceptable salt thereof.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art. Methods for detecting a mutation in a KRAS, HRAS or NRAS nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR—SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g. exon 2 and/or exon 3) in the KRAS, HRAS or NRAS gene. This technique will identify all possible mutations in the region sequenced. Methods for detecting a mutation in a KRAS, HRAS or NRAS protein are known by those of skill in the art. These methods include, but are not limited to, detection of a KRAS, HRAS or NRAS mutant using a binding agent (e.g. an antibody) specific for the mutant protein, protein electrophoresis, Western blotting and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA. In some embodiments the sample is a liquid biopsy and the test is done on a sample of blood to look for cancer cells from a tumor that are circulating in the blood or for pieces of DNA from tumor cells that are in the blood.

The disease/condition/cancer/tumors/cancer cells to be treated/prevented with a compound of formula (I), (I*), (Ib), (Ib*), (Ic), (Ic*), (Id), (Id*), (Ie) or (Ie*)—or a pharmaceutically acceptable salt thereof—according to the methods and uses as herein (above and below) defined and disclosed is selected from the group consisting of pancreatic cancer, lung cancer, colorectal cancer, cholangiocarcinoma, appendiceal cancer, multiple myeloma, melanoma, uterine cancer, endometrial cancer, thyroid cancer, acute myeloid leukaemia, bladder cancer, urothelial cancer, gastric cancer, cervical cancer, head and neck squamous cell carcinoma, diffuse large B cell lymphoma, oesophageal cancer, chronic lymphocytic leukaemia, hepatocellular cancer, breast cancer, ovarian cancer, prostate cancer, glioblastoma, renal cancer and sarcomas.

In another aspect, the disease/condition/cancer/tumors/cancer cells to be treated/prevented with a compound of formula (I), (I*), (Ib), (Ib*), (Ic), (Ic*), (Id), (Id*), (Ie) or (Ie*)—or a pharmaceutically acceptable salt thereof—according to the methods and uses as herein (above and below) defined and disclosed is selected from the group consisting of pancreatic cancer, lung cancer (preferably non-small cell lung cancer (NSCLC)), cholangiocarcinoma and colorectal cancer.

Particularly preferred, the cancer to be treated/prevented with a compound of formula (I), (I*), (Ib), (Ib*), (Ic), (Ic*), (Id), (Id*), (Ie) or (Ie*)—or a pharmaceutically acceptable salt thereof—according to the methods and uses as herein (above and below) defined and disclosed is selected from the group consisting of:

- lung adenocarcinoma (preferably non-small cell lung cancer (NSCLC)) harboring a KRAS G12C mutation;
- colorectal adenocarcinoma harboring a KRAS G12C mutation;
- pancreatic adenocarcinoma (preferably pancreatic ductal adenocarcinoma (PDAC)) harboring a KRAS G12C mutation.

Additionally, the following cancers, tumors and other proliferative diseases may be treated with compounds of formula (I), (I*), (Ib), (Ib*), (Ic), (Ic*), (Id), (Id*), (Ie) or (Ie*)—or a pharmaceutically acceptable salt thereof—without being restricted thereto. Preferably, the methods of treatment, methods, uses, compounds for use and pharmaceutical compositions for use as disclosed herein (above and below) are applied in treatments of diseases/conditions/cancers/tumors which (i.e. the respective cells) harbour a RAS G12C mutation (preferably a KRAS G12C mutation) or have been identified to harbour a RAS G12C mutation (preferably a KRAS G12C mutation) as herein described and/or referred:

- cancers/tumors/carcinomas of the head and neck: e.g. tumors/carcinomas/cancers of the nasal cavity, paranasal sinuses, nasopharynx, oral cavity (including lip, gum, alveolar ridge, retromolar trigone, floor of mouth, tongue, hard palate, buccal mucosa), oropharynx (including base of tongue, tonsil, tonsillar pilar, soft palate, tonsillar fossa, pharyngeal wall), middle ear, larynx (including supraglottis, glottis, subglottis, vocal cords), hypopharynx, salivary glands (including minor salivary glands);
- cancers/tumors/carcinomas of the lung: e.g. non-small cell lung cancer (NSCLC) (squamous cell carcinoma, spindle cell carcinoma, adenocarcinoma, large cell carcinoma, clear cell carcinoma, bronchioalveolar), small cell lung cancer (SCLC) (oat cell cancer, intermediate cell cancer, combined oat cell cancer);
- neoplasms of the mediastinum: e.g. neurogenic tumors (including neurofibroma, neurilemoma, malignant schwannoma, neurosarcoma, ganglioneuroblastoma, ganglioneuroma, neuroblastoma, pheochromocytoma, paraganglioma), germ cell tumors (including seminoma, teratoma, non-seminoma), thymic tumors (including thymoma, thymolipoma, thymic carcinoma, thymic carcinoid), mesenchymal tumors (including fibroma, fibrosarcoma, lipoma, liposarcoma, myxoma, mesothelioma, leiomyoma, leiomyosarcoma, rhabdomyosarcoma, xanthogranuloma, mesenchymoma, hemangioma, hemangioendothelioma, hemangiopericytoma, lymphangioma, lymphangiopericytoma, lymphangiomyoma);
- cancers/tumors/carcinomas of the gastrointestinal (GI) tract: e.g. tumors/carcinomas/cancers of the esophagus, stomach (gastric cancer), pancreas, liver and biliary tree (including hepatocellular carcinoma (HCC), e.g. childhood HCC, fibrolamellar HCC, combined HCC, spindle cell HCC, clear cell HCC, giant cell HCC, carcinosarcoma HCC, sclerosing HCC; hepatoblastoma; cholangiocarcinoma; cholangiocellular carcinoma; hepatic cystadenocarcinoma; angiosarcoma, hemangioendothelioma, leiomyosarcoma, malignant schwannoma, fibrosarcoma, Klatskin tumor), gall bladder, extrahepatic bile ducts, small intestine (including duodenum, jejunum, ileum), large intestine (including cecum, colon, rectum, anus; colorectal cancer, gastrointestinal stroma tumor (GIST)), genitourinary system (including kidney, e.g. renal pelvis, renal cell carcinoma (RCC), nephroblastoma (Wilms' tumor), hypernephroma, Grawitz tumor; ureter; urinary bladder, e.g. urachal cancer, urothelial cancer; urethra, e.g. distal, bulbomembranous, prostatic; prostate (androgen dependent, androgen independent, castration resistant, hormone independent, hormone refractory), penis);
- cancers/tumors/carcinomas of the testis: e.g. seminomas, non-seminomas, gynecologic cancers/tumors/carcinomas: e.g. tumors/carcinomas/cancers of the ovary, fallopian tube, peritoneum, cervix, vulva, vagina, uterine body (including endometrium, fundus);
- cancers/tumors/carcinomas of the breast: e.g. mammary carcinoma (infiltrating ductal, colloid, lobular invasive, tubular, adenocystic, papillary, medullary, mucinous), hormone receptor positive breast cancer (estrogen receptor positive breast cancer, progesterone receptor positive breast cancer), Her2 positive breast cancer, triple negative breast cancer, Paget's disease of the breast;
- cancers/tumors/carcinomas of the endocrine system: e.g. tumors/carcinomas/cancers of the endocrine glands, thyroid gland (thyroid carcinomas/tumors; papillary, follicular, anaplastic, medullary), parathyroid gland (parathyroid carcinoma/tumor), adrenal cortex (adrenal cortical carcinoma/tumors), pituitary gland (including prolactinoma, craniopharyngioma), thymus, adrenal glands, pineal gland, carotid body, islet cell tumors, paraganglion, pancreatic endocrine tumors (PET; nonfunctional PET, PPoma, gastrinoma, insulinoma, VIPoma, glucagonoma, somatostatinoma, GRFoma, ACTHoma), carcinoid tumors;

sarcomas of the soft tissues: e.g. fibrosarcoma, fibrous histiocytoma, liposarcoma, leiomyosarcoma, rhabdomyosarcoma, angiosarcoma, lymphangiosarcoma, Kaposi's sarcoma, glomus tumor, hemangiopericytoma, synovial sarcoma, giant cell tumor of tendon sheath, solitary fibrous tumor of pleura and peritoneum, diffuse mesothelioma, malignant peripheral nerve sheath tumor (MPNST), granular cell tumor, clear cell sarcoma, melanocytic schwannoma, plexosarcoma, neuroblastoma, ganglioneuroblastoma, neuroepithelioma, extraskeletal Ewing's sarcoma, paraganglioma, extraskeletal chondrosarcoma, extraskeletal osteosarcoma, mesenchymoma, alveolar soft part sarcoma, epithelioid sarcoma, extrarenal rhabdoid tumor, desmoplastic small cell tumor;

sarcomas of the bone: e.g. myeloma, reticulum cell sarcoma, chondrosarcoma (including central, peripheral, clear cell, mesenchymal chondrosarcoma), osteosarcoma (including parosteal, periosteal, high-grade surface, small cell, radiation-induced osteosarcoma, Paget's sarcoma), Ewing's tumor, malignant giant cell tumor, adamantinoma, (fibrous) histiocytoma, fibrosarcoma, chordoma, small round cell sarcoma, hemangioendothelioma, hemangiopericytoma, osteochondroma, osteoid osteoma, osteoblastoma, eosinophilic granuloma, chondroblastoma;

mesothelioma: e.g. pleural mesothelioma, peritoneal mesothelioma;

cancers of the skin: e.g. basal cell carcinoma, squamous cell carcinoma, Merkel's cell carcinoma, melanoma (including cutaneous, superficial spreading, lentigo maligna, acral lentiginous, nodular, intraocular melanoma), actinic keratosis, eyelid cancer; neoplasms of the central nervous system and brain: e.g. astrocytoma (cerebral, cerebellar, diffuse, fibrillary, anaplastic, pilocytic, protoplasmic, gemistocytary), glioblastoma, gliomas, oligodendrogliomas, oligoastrocytomas, ependymomas, ependymoblastomas, choroid plexus tumors, medulloblastomas, meningiomas, schwannomas, hemangioblastomas, hemangiomas, hemangiopericytomas, neuromas, ganglioneuromas, neuroblastomas, retinoblastomas, neurinomas (e.g. acoustic), spinal axis tumors;

lymphomas and leukemias: e.g. B-cell non-Hodgkin lymphomas (NHL) (including small lymphocytic lymphoma (SLL), lymphoplasmacytoid lymphoma (LPL), mantle cell lymphoma (MCL), follicular lymphoma (FL), diffuse large cell lymphoma (DLCL), Burkitt's lymphoma (BL)), T-cell non-Hodgkin lymphomas (including anaplastic large cell lymphoma (ALCL), adult T-cell leukemia/lymphoma (ATLL), cutaneous T-cell lymphoma (CTCL), peripheral T-cell lymphoma (PTCL)), lymphoblastic T-cell lymphoma (T-LBL), adult T-cell lymphoma, lymphoblastic B-cell lymphoma (B-LBL), immunocytoma, chronic B-cell lymphocytic leukemia (B-CLL), chronic T-cell lymphocytic leukemia (T-CLL) B-cell small lymphocytic lymphoma (B-SLL), cutaneous T-cell lymphoma (CTLC), primary central nervous system lymphoma (PCNSL), immunoblastoma, Hodgkin's disease (HD) (including nodular lymphocyte predominance HD (NLPHD), nodular sclerosis HD (NSHD), mixed-cellularity HD (MCHD), lymphocyte-rich classic HD, lymphocyte-depleted HD (LDHD)), large granular lymphocyte leukemia (LGL), chronic myelogenous leukemia (CML), acute myelogenous/myeloid leukemia (AML), acute lymphatic/lymphoblastic leukemia (ALL), acute promyelocytic leukemia (APL), chronic lymphocytic/lymphatic leukemia (CLL), prolymphocytic leukemia (PLL), hairy cell leukemia, chronic myelogenous/myeloid leukemia (CML), myeloma, plasmacytoma, multiple myeloma (MM), plasmacytoma, myelodysplastic syndromes (MDS), chronic myelomonocytic leukemia (CMML);

cancers of unknown primary site (CUP);

All cancers/tumors/carcinomas mentioned above which are characterized by their specific location/origin in the body are meant to include both the primary tumors and the metastatic tumors derived therefrom.

All cancers/tumors/carcinomas mentioned above may be further differentiated by their histopathological classification:

Epithelial cancers, e.g. squamous cell carcinoma (SCC) (carcinoma in situ, superficially invasive, verrucous carcinoma, pseudosarcoma, anaplastic, transitional cell, lymphoepithelial), adenocarcinoma (AC) (well-differentiated, mucinous, papillary, pleomorphic giant cell, ductal, small cell, signet-ring cell, spindle cell, clear cell, oat cell, colloid, adenosquamous, mucoepidermoid, adenoid cystic), mucinous cystadenocarcinoma, acinar cell carcinoma, large cell carcinoma, small cell carcinoma, neuroendocrine tumors (small cell carcinoma, paraganglioma, carcinoid); oncocytic carcinoma;

Nonepithilial cancers, e.g. sarcomas (fibrosarcoma, chondrosarcoma, rhabdomyosarcoma, leiomyosarcoma, hemangiosarcoma, giant cell sarcoma, lymphosarcoma, fibrous histiocytoma, liposarcoma, angiosarcoma, lymphangiosarcoma, neurofibrosarcoma), lymphoma, melanoma, germ cell tumors, hematological neoplasms, mixed and undifferentiated carcinomas;

The compounds of the invention may be used in therapeutic regimens in the context of first line, second line, or any further line treatments.

The compounds of the invention may be used for the prevention, short-term or long-term treatment of the above-mentioned diseases/conditions/cancers/tumors, optionally also in combination with radiotherapy and/or surgery.

The methods of treatment, methods, uses and compounds for use as disclosed herein (above and below) can be performed with any compound of formula (I), (I*), (Ib), (Ib*), (Ic), (Ic*), (Id), (Id*), (Ie) or (Ie*)—or a pharmaceutically acceptable salt thereof—as disclosed or defined herein and with any pharmaceutical composition or kit comprising a compound of formula (I), (I*), (Ib), (Ib*), (Ic), (Ic*), (Id), (Id*), (Ie) or (Ie*)—or a pharmaceutically acceptable salt thereof (each including all individual embodiments or generic subsets of compounds (I), (I*), (Ib), (Ib*), (Ic), (Ic*), (Id), (Id*), (Ie) or (Ie*)).

Combination Treatment

The compounds of formula (I), (I*), (Ib), (Ib*), (Ic), (Ic*), (Id), (Id*), (Ie) or (Ie*)—or the pharmaceutically acceptable salts thereof—and the pharmaceutical compositions comprising such compound and salts may also be co-administered with other pharmacologically active substances, e.g. with other anti-neoplastic compounds (e.g. chemotherapy), or used in combination with other treatments, such as radiation or surgical intervention, either as an adjuvant prior to surgery or post-operatively. Preferably, the pharmacologically active substance(s) for co-administration is/are (an) anti-neoplastic compound(s).

Thus, in a further aspect the invention relates to a compound of formula (I), (I*), (Ib), (Ib*), (Ic), (Ic*), (Id), (Id*), (Ie) or (Ie*)—or a pharmaceutically acceptable salt thereof—for use as hereinbefore defined wherein said compound is administered before, after or together with one or more other pharmacologically active substance(s).

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use as hereinbefore defined, wherein said compound is administered in combination with one or more other pharmacologically active substance(s).

In a further aspect the invention relates to the use of a compound of formula (I), (I*), (Ib), (Ib*), (Ic), (Ic*), (Id), (Id*), (Ie) or (Ie*)—or a pharmaceutically acceptable salt thereof—as hereinbefore defined wherein said compound is to be administered before, after or together with one or more other pharmacologically active substance(s).

In a further aspect the invention relates to a method (e.g. a method for the treatment and/or prevention) as hereinbefore defined wherein the compound of formula (I), (I*), (Ib), (Ib*), (Ic), (Ic*), (Id), (Id*), (Ie) or (Ie*)—or a pharmaceutically acceptable salt thereof—is administered before, after or together with a therapeutically effective amount of one or more other pharmacologically active substance(s).

In a further aspect the invention relates to a method (e.g. a method for the treatment and/or prevention) as hereinbefore defined wherein the compound of formula (I), (I*), (Ib), (Ib*), (Ic), (Ic*), (Id), (Id*), (Ie) or (Ie*)—or a pharmaceutically acceptable salt thereof—is administered in combination with a therapeutically effective amount of one or more other pharmacologically active substance(s).

In a further aspect the invention relates to a method for the treatment and/or prevention of cancer comprising administering to a patient in need thereof a therapeutically effective amount of a compound of formula (I), (I*), (Ib), (Ib*), (Ic), (Ic*), (Id), (Id*), (Ie) or (Ie*)—or a pharmaceutically acceptable salt thereof—and a therapeutically effective amount of one or more other pharmacologically active substance(s), wherein the compound of formula (I), (I*), (Ib), (Ib*), (Ic), (Ic*), (Id), (Id*), (Ie) or (Ie*)—or a pharmaceutically acceptable salt thereof—is administered simultaneously, concurrently, sequentially, successively, alternately or separately with the one or more other pharmacologically active substance(s).

In a further aspect the invention relates to a method for the treatment and/or prevention of cancer comprising administering to a patient in need thereof a therapeutically effective amount of a RAS G12C inhibitor (preferably a KRAS G12C inhibitor)—or a pharmaceutically acceptable salt thereof—and a therapeutically effective amount of one or more other pharmacologically active substance(s), wherein the RAS G12C inhibitor (preferably a KRAS G12C inhibitor)—or a pharmaceutically acceptable salt thereof—is administered in combination with the one or more other pharmacologically active substance(s).

In a further aspect the invention relates to a compound of formula (I), (I*), (Ib), (Ib*), (Ic), (Ic*), (Id), (Id*), (Ie) or (Ie*)—or a pharmaceutically acceptable salt thereof—for use in the treatment and/or prevention of cancer, wherein the compound of formula (I), (I*), (Ib), (Ib*), (Ic), (Ic*), (Id), (Id*), (Ie) or (Ie*)—or a pharmaceutically acceptable salt thereof—is administered simultaneously, concurrently, sequentially, successively, alternately or separately with the one or more other pharmacologically active substance(s).

In a further aspect the invention relates to a RAS G12C inhibitor (preferably a KRAS G12C inhibitor)—or a pharmaceutically acceptable salt thereof—for use in the treatment and/or prevention of cancer, wherein the RAS G12C inhibitor (preferably a KRAS G12C inhibitor)—or a pharmaceutically acceptable salt thereof—is administered in combination with the one or more other pharmacologically active substance(s).

In a further aspect the invention relates to a kit comprising a first pharmaceutical composition or dosage form comprising a compound of formula (I), (I*), (Ib), (Ib*), (Ic), (Ic*), (Id), (Id*), (Ie) or (Ie*)—or a pharmaceutically acceptable salt thereof—and, optionally, one or more pharmaceutically acceptable excipient(s), and a second pharmaceutical composition or dosage form comprising another pharmacologically active substance, and, optionally, one or more pharmaceutically acceptable excipient(s), for use in the treatment and/or prevention of cancer, wherein the first pharmaceutical composition is to be administered simultaneously, concurrently, sequentially, successively, alternately or separately with the second and/or additional pharmaceutical composition or dosage form.

In one aspect such kit for said use comprises a third pharmaceutical composition or dosage form comprising a third pharmaceutical composition or dosage form comprising still another pharmacologically active substance, and, optionally, one or more pharmaceutically acceptable excipient(s)

In a further embodiment of the invention the components (i.e. the combination partners) of the combinations, kits, uses, methods and compounds for use according to the invention (including all embodiments) are administered simultaneously.

In a further embodiment of the invention the components (i.e. the combination partners) of the combinations, kits, uses, methods and compounds for use according to the invention (including all embodiments) are administered concurrently.

In a further embodiment of the invention the components (i.e. the combination partners) of the combinations, kits, uses, methods and compounds for use according to the invention (including all embodiments) are administered sequentially.

In a further embodiment of the invention the components (i.e. the combination partners) of the combinations, kits, uses, methods and compounds for use according to the invention (including all embodiments) are administered successively.

In a further embodiment of the invention the components (i.e. the combination partners) of the combinations, kits, uses, methods and compounds for use according to the invention (including all embodiments) are administered alternately.

In a further embodiment of the invention the components (i.e. the combination partners) of the combinations, kits, uses, methods and compounds for use according to the invention (including all embodiments) are administered separately.

The pharmacologically active substance(s) to be used together/in combination with the RAS G12C inhibitor (preferably a KRAS G12C inhibitor) and/or to be used together/in combination with the compound of formula (I), (I*), (Ib), (Ib*), (Ic), (Ic*), (Id), (Id*), (Ie) or (Ie*)—or a pharmaceutically acceptable salt thereof—(including all individual embodiments or generic subsets of compounds (I), (I*), (Ib), (Ib*), (Ic), (Ic*), (Id), (Id*), (Ie) or (Ie*)) or in the medical uses, uses, methods of treatment and/or prevention as herein (above and below) defined can be selected from any one or more of the following (preferably there is one or two additional pharmacologically active substance used in all these embodiments):

1. an inhibitor of EGFR and/or ErbB2 (HER2) and/or ErbB3 (HER3) and/or ErbB4 (HER4) or of any mutants thereof
   a. irreversible inhibitors: e.g. afatinib, dacomitinib, canertinib, neratinib, avitinib, poziotinib, AV 412, PF-6274484, HKI 357, olmutinib, osimertinib, almonertinib, nazartinib, lazertinib, pelitinib;
   b. reversible inhibitors: e.g. erlotinib, gefitinib, icotinib, sapitinib, lapatinib, varlitinib, vandetanib, TAK-285, AEE788, BMS599626/AC-480, GW 583340;
   c. anti-EGFR antibodies: e.g. necitumumab, panitumumab, cetuximab, amivantamab;
   d. anti-HER2 antibodies: e.g. pertuzumab, trastuzumab, trastuzumab emtansine;
   e. inhibitors of mutant EGFR;
   f. an inhibitor of HER2 with exon 20 mutations;
   g. preferred irreversible inhibitor is afatinib;
   h. preferred anti-EGFR antibody is cetuximab.
2. an inhibitor of MEK and/or of mutants thereof
   a. e.g. trametinib, cobimetinib, binimetinib, selumetinib, refametinib, BI 3011441;
   b. preferred are trametinib and BI 3011441;
   c. most preferred is BI 3011441;
   d. a MEK inhibitor as disclosed in WO 2013/136249;
   e. a MEK inhibitor as disclosed in WO 2013/136254
3. an inhibitor of SOS1 and/or of any mutants thereof (i.e. a compound that modulates/inhibits the GEF functionality of SOS1, e.g. by binding to SOS1 and preventing protein-protein interaction between SOS1 and a (mutant)Ras protein, e.g. KRAS)
   a. e.g. BAY-293, BI-3406, BI 1701963;
   b. preferred are BI-3406 and BI 1701963;
   c. most preferred is BI 1701963;
   d. a SOS1 inhibitor as disclosed in WO 2018/115380;
   e. a SOS1 inhibitor as disclosed in WO 2019/122129;
   f. a SOS1 inhibitor as disclosed in WO 2020/180768, WO 2020/180770, WO 2018/172250 and WO 2019/201848.
4. an oncolytic virus
5. a RAS vaccine
   a. e.g. TG02 (Targovax).
6. a cell cycle inhibitor
   a. e.g. inhibitors of CDK4/6 and/or of any mutants thereof
      i. e.g. palbociclib, ribociclib, abemaciclib, trilaciclib, PF-06873600;
      ii. preferred are palbociclib and abemaciclib;
      iii. most preferred is abemaciclib.
   b. e.g. vinca alkaloids
      i. e.g. vinorelbine.
   c. e.g. inhibitors of Aurora kinase and/or of any mutants thereof
      i. e.g. alisertib, barasertib.
7. an inhibitor of PTK2 (=FAK) and/or of any mutants thereof
   a. e.g. TAE226, BI 853520.
8. an inhibitor of SHP2 and/or of any mutants thereof
   a. e.g. SHP099, TNO155, RMC-4550, RMC-4630, IACS-13909.
9. an inhibitor of PI3 kinase (=PI3K) and/or of any mutants thereof
   a. e.g. inhibitors of PI3Kα and/or of any mutants therof
      i. e.g. alpelisib, serabelisib, GDC-0077, HH—CYH33, AMG 511, buparlisib, dactolisib, pictilisib, taselisib.
10. an inhibitor of FGFR1 and/or FGFR2 and/or FGFR3 and/or of any mutants thereof
    a. e.g. ponatinib, infigratinib, nintedanib.
11. an inhibitor of AXL and/or of any mutants thereof
12. a taxane
    a. e.g. paclitaxel, nab-paclitaxel, docetaxel;
    b. preferred is paclitaxel.
13. a platinum-containing compound
    a. e.g. cisplatin, carboplatin, oxaliplatin
    b. preferred is oxaliplatin.
14. an anti-metabolite
    a. e.g. 5-fluorouracil, capecitabine, floxuridine, cytarabine, gemcitabine, pemetrexed, combination of trifluridine and tipiracil (=TAS102);
    b. preferred is 5-fluorouracil.
15. an immunotherapeutic agent
    a. e.g. an immune checkpoint inhibitor
       i. e.g. an anti-CTLA4 mAb, anti-PD1 mAb, anti-PD-L1 mAb, anti-PD-L2 mAb, anti-LAG3 mAb, anti-TIM3 mAb;
       ii. preferred is an anti-PD1 mAb;
       iii. e.g. ipilimumab, nivolumab, pembrolizumab, tislelizumab atezolizumab, avelumab, durvalumab, pidilizumab, PDR-001 (=spartalizumab), AMG-404, ezabenlimab;
       iv. preferred are nivolumab, pembrolizumab, ezabenlimab and PDR-001 (=spartalizumab);
       v. most preferred is ezabenlimab, pembrolizumab and nivolumab.
16. a topoisomerase inhibitor
    a. e.g. irinotecan, liposomal irinotecan (nal-IRI), topotecan, etoposide;
    b. most preferred is irinotecan and liposomal irinotecan (nal-IRI).
17. an inhibitor of A-Raf and/or B-Raf and/or C-Raf and/or of any mutants thereof
    a. e.g. encorafenib, dabrafenib, vemurafenib, PLX-8394, RAF-709 (=example 131 in WO 2014/151616), LXH254, sorafenib, LY-3009120 (=example 1 in WO 2013/134243), lifirafenib, TAK-632, agerafenib, CCT196969, RO5126766, RAF265.
18. an inhibitor of mTOR
    a. e.g. rapamycin, temsirolimus, everolimus, ridaforolimus, zotarolimus, sapanisertib, Torin 1, dactolisib, GDC-0349, VS-5584, vistusertib, AZD8055.
19. an epigenetic regulator
    a. e.g. a BET inhibitor
       i. e.g. JQ-1, GSK 525762, OTX-015, CPI-0610, TEN-010, OTX-015, PLX51107, ABBV-075, ABBV-744, BMS986158, TGI-1601, CC-90010, AZD5153, I-BET151, BI 894999;
       ii. preferred is BI 894999.
20. an inhibitor of IGF1/2 and/or of IGF1-R and/or of any mutants thereof
    a. e.g. xentuzumab (antibody 60833 in WO 2010/066868), MEDI-573 (=dusigitumab), linsitinib.
21. an inhibitor of a Src family kinase and/or of any mutants thereof
    a. e.g. an inhibitor of a kinase of the SrcA subfamily and/or of any mutants thereof, i.e. an inhibitor of Src, Yes, Fyn, Fgr and/or of any mutants thereof;
    b. e.g. an inhibitor of a kinase of the SrcB subfamily and/or of any mutants thereof, i.e. an inhibitor of Lck, Hck, Blk, Lyn and/or of any mutants thereof;

c. e.g. an inhibitor of a kinase of the Frk subfamily and/or of any mutants thereof, i.e. an inhibitor of Frk and/or of any mutants thereof;

d. e.g. dasatinib, ponatinib, bosutinib, vandetanib, KX-01, saracatinib, KX2-391, SU 6656, WH-4-023.

22. an apoptose regulator a. e.g. an MDM2 inhibitor, e.g. an inhibitor of the interaction between p53 (preferably functional p53, most preferably wt p53) and MDM2 and/or of any mutants thereof;

i. e.g. HDM-201, NVP-CGM097, RG-7112, MK-8242, RG-7388, SAR405838, AMG-232, DS-3032, RG-7775, APG-115, BI 907828;

ii. preferred are HDM-201, RG-7388, AMG-232 and BI 907828;

iii. most preferred is BI 907828;

iv. an MDM2 inhibitor as disclosed in WO 2015/155332;

v. an MDM2 inhibitor as disclosed in WO 2016/001376;

vi. an MDM2 inhibitor as disclosed in WO 2016/026937;

vii. an MDM2 inhibitor as disclosed in WO 2017/060431;

b. e.g. a PARP inhibitor;

c. e.g. an MCL-1 inhibitor;

i. e.g. AZD-5991, AMG-176, AMG-397, S64315, S63845, A-1210477;

23. an inhibitor of c-MET and/or of any mutants thereof a. e.g. savolitinib, cabozantinib, foretinib;

b. MET antibodies, e.g. emibetuzumab, amivantamab;

24. an inhibitor of ERK and/or of any mutants thereof a. e.g. ulixertinib, LTT462;

25. an inhibitor of farnesyl transferase and/or of any mutants thereof a. e.g. tipifarnib;

In a further embodiment of the (combined) use and method (e.g. method for the treatment and/or prevention) as hereinbefore described one other pharmacologically active substance is to be administered before, after or together with the compound of formula (I), (I*), (Ib), (Ib*), (Ic), (Ic*), (Id), (Id*), (Ie) or (Ie*)—or a pharmaceutically acceptable salt thereof—wherein said one other pharmacologically active substance is a SOS1 inhibitor; or
BI 1701963; or
a MEK inhibitor; or
trametinib, or
BI 3011441; or
an anti-PD-1 antibody; or
ezabenlimab; or
cetuximab; or
afatinib; or
standard of care (SoC) in a given indication; or
a PI3 kinase inhibitor.

In a further embodiment of the (combined) use and method (e.g. method for the treatment and/or prevention) as hereinbefore described one other pharmacologically active substance is to be administered in combination with the compound of formula (I), (I*), (Ib), (Ib*), (Ic), (Ic*), (Id), (Id*), (Ie) or (Ie*)—or a pharmaceutically acceptable salt thereof—wherein said one other pharmacologically active substance is a SOS1 inhibitor; or
BI 1701963; or
a MEK inhibitor; or
trametinib; or
BI 3011441; or
an anti-PD-1 antibody; or
ezabenlimab; or
cetuximab; or
afatinib; or
standard of care (SoC) in a given indication; or
a PI3 kinase inhibitor.

In a further aspect of the (combined) use and method (e.g. method for the treatment and/or prevention) as hereinbefore described two other pharmacologically active substances are to be administered before, after or together with the compound of formula (I), (I*), (Ib), (Ib*), (Ic), (Ic*), (Id), (Id*), (Ie) or (Ie*)—or a pharmaceutically acceptable salt thereof—wherein said two other pharmacologically active substances are a MEK inhibitor (preferably BI 3011441) and a SOS1 inhibitor (preferably BI 1701963); or
trametinib and a SOS1 inhibitor (preferably BI 1701963); or
an anti-PD-1 antibody (preferably ezabenlimab) and an anti-LAG-3 antibody; or
an anti-PD-1 antibody (preferably ezabenlimab) and a SOS1 inhibitor (preferably BI 1701963); or
a MEK inhibitor (preferably BI 3011441) and an inhibitor selected from the group consisting of an EGFR inhibitor and/or ErbB2 (HER2) inhibitor and/or inhibitor of any mutants thereof; or
a SOS1 inhibitor (preferably BI 1701963) and an inhibitor selected from the group consisting of an EGFR inhibitor and/or ErbB2 (HER2) inhibitor and/or inhibitor of any mutants thereof; or
a MEK inhibitor (preferably BI 3011441) and afatinib; or
a MEK inhibitor (preferably BI 3011441) and cetuximab; or
trametinib and afatinib; or
trametinib and cetuximab; or
a SOS1 inhibitor (preferably BI 1701963) and afatinib; or
a SOS1 inhibitor (preferably BI 1701963) and cetuximab.

In a further aspect of the (combined) use and method (e.g. method for the treatment and/or prevention) as hereinbefore described two other pharmacologically active substances are to be administered in combination with the compound of formula (I), (I*), (Ib), (Ib*), (Ic), (Ic*), (Id), (Id*), (Ie) or (Ie*)—or a pharmaceutically acceptable salt thereof—wherein said two other pharmacologically active substances are a MEK inhibitor (preferably BI 3011441) and a SOS1 inhibitor (preferably BI 1701963); or
trametinib and a SOS1 inhibitor (preferably BI 1701963); or
an anti-PD-1 antibody (preferably ezabenlimab) and an anti-LAG-3 antibody; or
an anti-PD-1 antibody (preferably ezabenlimab) and a SOS1 inhibitor (preferably BI 1701963); or
a MEK inhibitor (preferably BI 3011441) and an inhibitor selected from the group consisting of an EGFR inhibitor and/or ErbB2 (HER2) inhibitor and/or inhibitor of any mutants thereof; or
a SOS1 inhibitor (preferably BI 1701963) and an inhibitor selected from the group consisting of an EGFR inhibitor and/or ErbB2 (HER2) inhibitor and/or inhibitor of any mutants thereof; or
a MEK inhibitor (preferably BI 3011441) and afatinib; or
a MEK inhibitor (preferably BI 3011441) and cetuximab; or
trametinib and afatinib; or
trametinib and cetuximab; or a SOS1 inhibitor (preferably BI 1701963) and afatinib; or a SOS1 inhibitor (preferably BI 1701963) and cetuximab.

Additional pharmacologically active substance(s) which can also be used together/in combination with the compound of formula (I), (I*), (Ib), (Ib*), (Ic), (Ic*), (Id), (Id*), (Ie) or (Ie*)—or a pharmaceutically acceptable salt thereof—(including all individual embodiments or generic subsets of compounds (I), (I*), (Ib), (Ib*), (Ic), (Ic*), (Id), (Id*), (Ie) or (Ie*)) or in the medical uses, uses, methods of treatment and/or prevention as herein (above and below) defined include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors and/or of their corresponding receptors (growth factors such as for example platelet derived growth factor (PDGF), fibroblast growth factor (FGF), vascular endothelial growth factor (VEGF), epidermal growth factor (EGF), insuline-like growth factors (IGF), human epidermal growth factor (HER, e.g. HER2, HER3, HER4) and hepatocyte growth factor (HGF) and/or their corresponding receptors), inhibitors are for example (anti-)growth factor antibodies, (anti-)growth factor receptor antibodies and tyrosine kinase inhibitors, such as for example cetuximab, gefitinib, afatinib, nintedanib, imatinib, lapatinib, bosutinib, bevacizumab and trastuzumab); antimetabolites (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); antitumor antibiotics (e.g. anthracyclins such as doxorubicin, doxil (pegylated liposomal doxorubicin hydrochloride, myocet (non-pegylated liposomal doxorubicin), daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); angiogenesis inhibitors (e.g. tasquinimod), tubuline inhibitors; DNA synthesis inhibitors, PARP inhibitors, topoisomerase inhibitors (e.g. epipodophyllotoxins such as for example etoposide and etopophos, teniposide, amsacrin, topotecan, irinotecan, mitoxantrone), serine/threonine kinase inhibitors (e.g. PDK 1 inhibitors, Raf inhibitors, A-Raf inhibitors, B-Raf inhibitors, C-Raf inhibitors, mTOR inhibitors, mTORC1/2 inhibitors, PI3K inhibitors, PI3Kα inhibitors, dual mTOR/PI3K inhibitors, STK 33 inhibitors, AKT inhibitors, PLK 1 inhibitors, inhibitors of CDKs, Aurora kinase inhibitors), tyrosine kinase inhibitors (e.g. PTK2/FAK inhibitors), protein protein interaction inhibitors (e.g. IAP inhibitors/SMAC mimetics, Mcl-1, MDM2/MDMX), MEK inhibitors, ERK inhibitors, FLT3 inhibitors, BRD4 inhibitors, IGF-1R inhibitors, TRAILR2 agonists, Bcl-XL inhibitors, Bcl-2 inhibitors (e.g. venetoclax), Bcl-2/Bcl-xL inhibitors, ErbB receptor inhibitors, BCR-ABL inhibitors, ABL inhibitors, Src inhibitors, rapamycin analogs (e.g. everolimus, temsirolimus, ridaforolimus, sirolimus), androgen synthesis inhibitors, androgen receptor inhibitors, DNMT inhibitors, HDAC inhibitors, ANG1/2 inhibitors, CYP17 inhibitors, radiopharmaceuticals, proteasome inhibitors (e.g. carfilzomib), immunotherapeutic agents such as immune checkpont inhibitors (e.g. CTLA4, PD1, PD-L1, PD-L2, LAG3, and TIM3 binding molecules/immunoglobulins, such as e.g. ipilimumab, nivolumab, pembrolizumab), ADCC (antibody-dependent cell-mediated cytotoxicity) enhancers (e.g. anti-CD33 antibodies, anti-CD37 antibodies, anti-CD20 antibodies), t-cell engagers (e.g. bi-specific T-cell engagers (BiTEs®) like e.g. CD3×BCMA, CD3×CD33, CD3×CD19), PSMA×CD3), tumor vaccines and various chemotherapeutic agents such as amifostin, anagrelid, clodronat, filgrastin, interferon, interferon alpha, leucovorin, procarbazine, levamisole, mesna, mitotane, pamidronate and porfimer.

It is to be understood that the combinations, compositions, kits, methods, uses or compounds for use according to this invention may envisage the simultaneous, concurrent, sequential, successive, alternate or separate administration of the active ingredients or components. It will be appreciated that the compound of formula (I), (I*), (Ib), (Ib*), (Ic), (Ic*), (Id), (Id*), (Ie) or (Ie*)—or a pharmaceutically acceptable salt thereof—and the one or more other pharmacologically active substance(s) can be administered formulated either dependently or independently, such as e.g. the compound of formula (I), (I*), (Ib), (Ib*), (Ic), (Ic*), (Id), (Id*), (Ie) or (Ie*)—or a pharmaceutically acceptable salt thereof—and the one or more other pharmacologically active substance(s) may be administered either as part of the same pharmaceutical composition/dosage form or, preferably, in separate pharmaceutical compositions/dosage forms.

In this context, "combination" or "combined" within the meaning of this invention includes, without being limited, a product that results from the mixing or combining of more than one active ingredient and includes both fixed and non-fixed (e.g. free) combinations (including kits) and uses, such as e.g. the simultaneous, concurrent, sequential, successive, alternate or separate use of the components or ingredients. The term "fixed combination" means that the active ingredients are administered to a patient simultaneously in the form of a single entity or dosage. The term "non-fixed combination" means that the active ingredients are administered to a patient as separate entities either simultaneously, concurrently or sequentially with no specific time limits, wherein such administration provides therapeutically effective levels of the compounds in the body of the patient.

The administration of the compound of formula (I), (I*), (Ib), (Ib*), (Ic), (Ic*), (Id), (Id*), (Ie) or (Ie*)—or a pharmaceutically acceptable salt thereof—and the one or more other pharmacologically active substance(s) may take place by co-administering the active components or ingredients, such as e.g. by administering them simultaneously or concurrently in one single or in two or more separate formulations or dosage forms. Alternatively, the administration of the compound of formula (I), (I*), (Ib), (Ib*), (Ic), (Ic*), (Id), (Id*), (Ie) or (Ie*)—or a pharmaceutically acceptable salt thereof—and the one or more other pharmacologically active substance(s) may take place by administering the active components or ingredients sequentially or in alternation, such as e.g. in two or more separate formulations or dosage forms.

For example, simultaneous administration includes administration at substantially the same time. This form of administration may also be referred to as "concomitant"

administration. Concurrent administration includes administering the active agents within the same general time period, for example on the same day(s) but not necessarily at the same time. Alternate administration includes administration of one agent during a time period, for example over the course of a few days or a week, followed by administration of the other agent(s) during a subsequent period of time, for example over the course of a few days or a week, and then repeating the pattern for one or more cycles. Sequential or successive administration includes administration of one agent during a first time period (for example over the course of a few days or a week) using one or more doses, followed by administration of the other agent(s) during a second and/or additional time period (for example over the course of a few days or a week) using one or more doses. An overlapping schedule may also be employed, which includes administration of the active agents on different days over the treatment period, not necessarily according to a regular sequence. Variations on these general guidelines may also be employed, e.g. according to the agents used and the condition of the subject.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to:

The use of the prefix $C_{x-y}$, wherein x and y each represent a positive integer ($x<y$), indicates that the chain or ring structure or combination of chain and ring structure as a whole, specified and mentioned in direct association, may consist of a maximum of y and a minimum of x carbon atoms.

The indication of the number of members in groups that contain one or more heteroatom(s) (e.g. heteroaryl, heteroarylalkyl, heterocyclyl, heterocycylalkyl) relates to the total number of atoms of all the ring members or the total of all the ring and carbon chain members.

The indication of the number of carbon atoms in groups that consist of a combination of carbon chain and carbon ring structure (e.g. cycloalkylalkyl, arylalkyl) relates to the total number of carbon atoms of all the carbon ring and carbon chain members. Obviously, a ring structure has at least three members.

In general, for groups comprising two or more subgroups (e.g. heteroarylalkyl, heterocycylalkyl, cycloalkylalkyl, arylalkyl) the last named subgroup is the radical attachment point, for example, the substituent aryl-$C_{1-6}$alkyl means an aryl group which is bound to a $C_{1-6}$alkyl group, the latter of which is bound to the core or to the group to which the substituent is attached.

In groups like HO, $H_2N$, (O)S, $(O)_2S$, NC (cyano), HOOC, $F_3C$ or the like, the skilled artisan can see the radical attachment point(s) to the molecule from the free valences of the group itself.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

The term "$C_{1-5}$alkyl" includes for example $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

Further examples of alkyl are methyl (Me; $—CH_3$), ethyl (Et; $—CH_2CH_3$), 1-propyl (n-propyl; n-Pr; $—CH_2CH_2CH_3$), 2-propyl (i-Pr; iso-propyl; $—CH(CH_3)_2$), 1-butyl (n-butyl; n-Bu; $—CH_2CH_2CH_2CH_3$), 2-methyl-1-propyl (iso-butyl; i-Bu; $—CH_2CH(CH_3)_2$), 2-butyl (sec-butyl; sec-Bu; $—CH(CH_3)CH_2CH_3$), 2-methyl-2-propyl (tert-butyl; t-Bu; $—C(CH_3)_3$), 1-pentyl (n-pentyl; $—CH_2CH_2CH_2CH_2CH_3$), 2-pentyl ($—CH(CH_3)CH_2CH_2CH_3$), 3-pentyl ($—CH(CH_2CH_3)_2$), 3-methyl-1-butyl (iso-pentyl; $—CH_2CH_2CH(CH_3)_2$), 2-methyl-2-butyl ($—C(CH_3)_2CH_2CH_3$), 3-methyl-2-butyl ($—CH(CH_3)CH(CH_3)_2$), 2,2-dimethyl-1-propyl (neo-pentyl; $—CH_2C(CH_3)_3$), 2-methyl-1-butyl ($—CH_2CH(CH_3)CH_2CH_3$), 1-hexyl (n-hexyl; $—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$), 2,3-dimethyl-1-butyl ($—CH_2CH(CH_3)CH(CH_3)CH_3$), 2,2-dimethyl-1-butyl ($—CH_2C(CH_3)_2CH_2CH_3$), 3,3-dimethyl-1-butyl ($—CH_2CH_2C(CH_3)_3$), 2-methyl-1-pentyl ($—CH_2CH(CH_3)CH_2CH_2CH_3$), 3-methyl-1-pentyl ($—CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkyloxy.

The term alkylene can also be derived from alkyl. Alkylene is bivalent, unlike alkyl, and requires two binding partners. Formally, the second valency is produced by removing a hydrogen atom in an alkyl. Corresponding groups are for example $—CH_3$ and $—CH_2—$, $—CH_2CH_3$ and $—CH_2CH_2—$ or $>CHCH_3$ etc.

The term "$C_{1-4}$alkylene" includes for example $—(CH_2)—$, $—(CH_2—CH_2)—$, $—(CH(CH_3))—$, $—(CH_2—CH_2—CH_2)—$, $—(C(CH_3)_2)—$, $—(CH(CH_2CH_3))—$, $—(CH(CH_3)—CH_2)—$, $—(CH_2—CH(CH_3))—$, $—(CH_2—CH_2—CH_2—CH_2)—$, $—(CH_2—CH_2—CH(CH_3))—$, $—(CH(CH_3)—CH_2—CH_2)—$, $—(CH_2—CH(CH_3)—CH_2)—$, $—(CH_2—C(CH_3)_2)—$, $—(C(CH_3)_2—CH_2)—$, $—(CH(CH_3)—CH(CH_3)—$, $—(CH_2—CH(CH_2CH_3))—$, $—(CH(CH_2CH_3)—CH_2)—$, $—(CH(CH_2CH_2CH_3))—$, $—(CH(CH(CH_3))_2)—$ and $—C(CH_3)(CH_2CH_3)—$.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, hexylene etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another (combined) group such as for example in HO—$C_{x-y}$alkyleneamino or $H_2N$—$C_{x-y}$alkyleneoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkylene, alkenylene consists of at least two carbon atoms, wherein at least two adjacent carbon atoms are joined together by a C—C double bond and a carbon atom can only be part of one C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another (combined) group as for example in HO—$C_{x-y}$alkenyleneamino or $H_2N$—$C_{x-y}$alkenyleneoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc. By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, hexynylene etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another (combined) group, as for example in HO—$C_{x-y}$alkynyleneamino or $H_2N$—$C_{x-y}$alkynyleneoxy.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are $—CF_3$, $—CHF_2$, $—CH_2F$, $—CF_2CF_3$, $—CHFCF_3$, $—CH_2CF_3$, $—CF_2CH_3$, $—CHFCH_3$, $—CF_2CF_2CF_3$, $—CF_2CH_2CH_3$, $—CF{=}CF_2$, $—CCl{=}CH_2$, $—CBr{=}CH_2$, $—C{\equiv}C—CF_3$, $—CHFCH_2CH_3$, $—CHFCH_2CF_3$ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners.

Formally, the second valency is formed by removing a hydrogen atom from a haloalkyl (haloalkenyl, haloalkynyl).

Corresponding groups are for example —$CH_2F$ and —CHF—, —$CHFCH_2F$ and —CHFCHF— or >$CFCH_2F$ etc.

The above definitions also apply if the corresponding halogen-containing groups are part of another (combined) group.

Halogen relates to fluorine, chlorine, bromine and/or iodine atoms.

Cycloalkyl is made up of the subgroups monocyclic cycloalkyl, bicyclic cycloalkyl and spiro-cycloalkyl. The ring systems are saturated and formed by linked carbon atoms. In bicyclic cycloalkyl two rings are joined together so that they have at least two carbon atoms in common. In spiro-cycloalkyl one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, spiro[3.3]heptyl etc.

The above definition for cycloalkyl also applies if cycloalkyl is part of another (combined) group as for example in $C_{x-y}$cycloalkylamino, $C_{x-y}$cycloalkyloxy or $C_{x-y}$cycloalkylalkyl.

If the free valency of a cycloalkyl is saturated, then an alicycle is obtained.

The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example:

cyclohexyl and

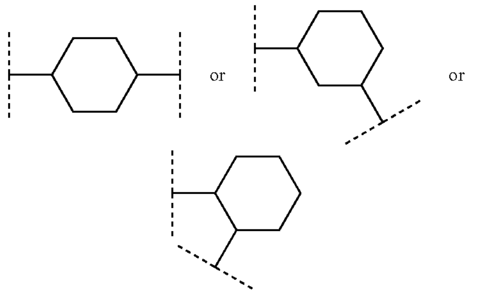

(cyclohexylene).

The above definition for cycloalkylene also applies if cycloalkylene is part of another (combined) group as for example in HO—$C_{x-y}$cycloalkyleneamino or $H_2N$—$C_{x-y}$cycloalkyleneoxy.

Cycloalkenyl is made up of the subgroups monocyclic cycloalkenyl, bicyclic cycloalkeny and spiro-cycloalkenyl. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained.

If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4,5]dec-2-enyl etc.

The above definition for cycloalkenyl also applies when cycloalkenyl is part of another (combined) group as for example in $C_{x-y}$cycloalkenylamino, $C_{x-y}$cycloalkenyloxy or $C_{x-y}$cycloalkenylalkyl.

If the free valency of a cycloalkenyl is saturated, then an unsaturated alicycle is obtained.

The term cycloalkenylene can thus be derived from the previously defined cycloalkenyl. Cycloalkenylene, unlike cycloalkenyl, is bivalent and requires two binding partners. Formally, the second valency is obtained by removing a hydrogen atom from a cycloalkenyl. Corresponding groups are for example:

cyclopentenyl and

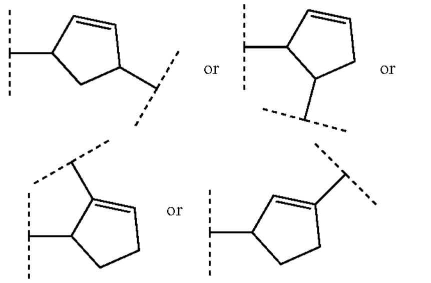

(cyclopentenylene) etc.

The above definition for cycloalkenylene also applies if cycloalkenylene is part of another (combined) group as for example in HO—$C_{x-y}$cycloalkenyleneamino or $H_2N$—$C_{x-y}$cycloalkenyleneoxy.

Aryl denotes mono-, bi- or tricyclic carbocycles with at least one aromatic carbocycle.

Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc. Most preferred is phenyl.

The above definition of aryl also applies if aryl is part of another (combined) group as for example in arylamino, aryloxy or arylalkyl.

If the free valency of an aryl is saturated, then an aromatic group is obtained.

The term arylene can also be derived from the previously defined aryl. Arylene, unlike aryl, is bivalent and requires two binding partners. Formally, the second valency is formed by removing a hydrogen atom from an aryl. Corresponding groups are for example:

phenyl and

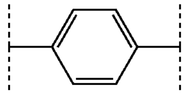

or

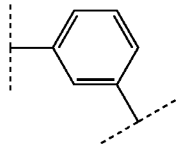

or

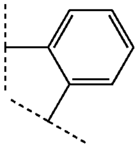

(o, m, p-phenylene), naphthyl and

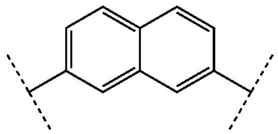

or

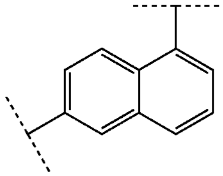

or

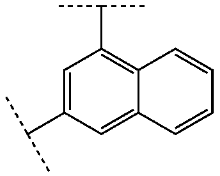

etc.

The above definition for arylene also applies if arylene is part of another (combined) group as for example in HO-aryleneamino or $H_2N$-aryleneoxy.

Heterocyclyl denotes ring systems, which are derived from the previously defined cycloalkyl, cycloalkenyl and aryl by replacing one or more of the groups —$CH_2$-independently of one another in the hydrocarbon rings by the groups —O—, —S—or —NH—or by replacing one or more of the groups =CH— by the group =N—, wherein a total of not more than five heteroatoms may be present, at least one carbon atom must be present between two oxygen atoms and between two sulphur atoms or between an oxygen and a sulphur atom and the ring as a whole must have chemical stability. Heteroatoms may optionally be present in all the possible oxidation stages (sulphur→sulphoxide —SO—, sulphone —$SO_2$—; nitrogen→N-oxide). In a heterocyclyl there is no heteroaromatic ring, i.e. no heteroatom is part of an aromatic system.

A direct result of the derivation from cycloalkyl, cycloalkenyl and aryl is that heterocyclyl is made up of the subgroups monocyclic heterocyclyl, bicyclic heterocyclyl, tricyclic heterocyclyl and spiro-heterocyclyl, which may be present in saturated or unsaturated form.

By unsaturated is meant that there is at least one double bond in the ring system in question, but no heteroaromatic system is formed. In bicyclic heterocyclyl two rings are linked together so that they have at least two (hetero) atoms in common. In spiro-heterocyclyl one carbon atom (spiroatom) belongs to two rings together.

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system. Substituents on heterocyclyl do not count for the number of members of a heterocyclyl.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, 1,3-dioxolanyl, tetrahydropyranyl, tetrahydrothiopyranyl, [1,4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, 8-aza-bicyclo[3.2.1]octyl, 8-aza-bicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]decyl, 1-oxa-3,8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro[5.5]undecyl, 2.8-diaza-spiro [4,5]decyl etc.

Further examples are the structures illustrated below, which may be attached via each hydrogen-carrying atom (exchanged for hydrogen):

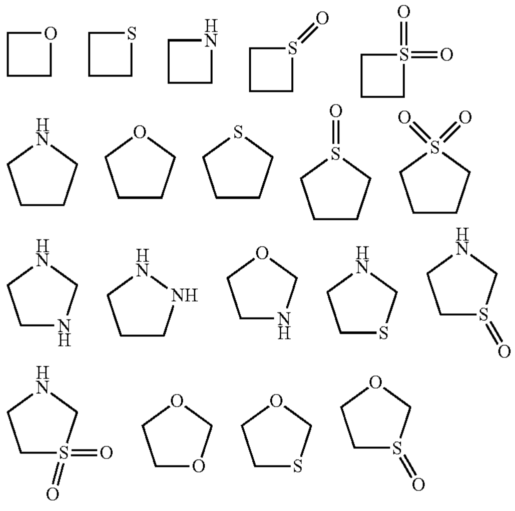

-continued
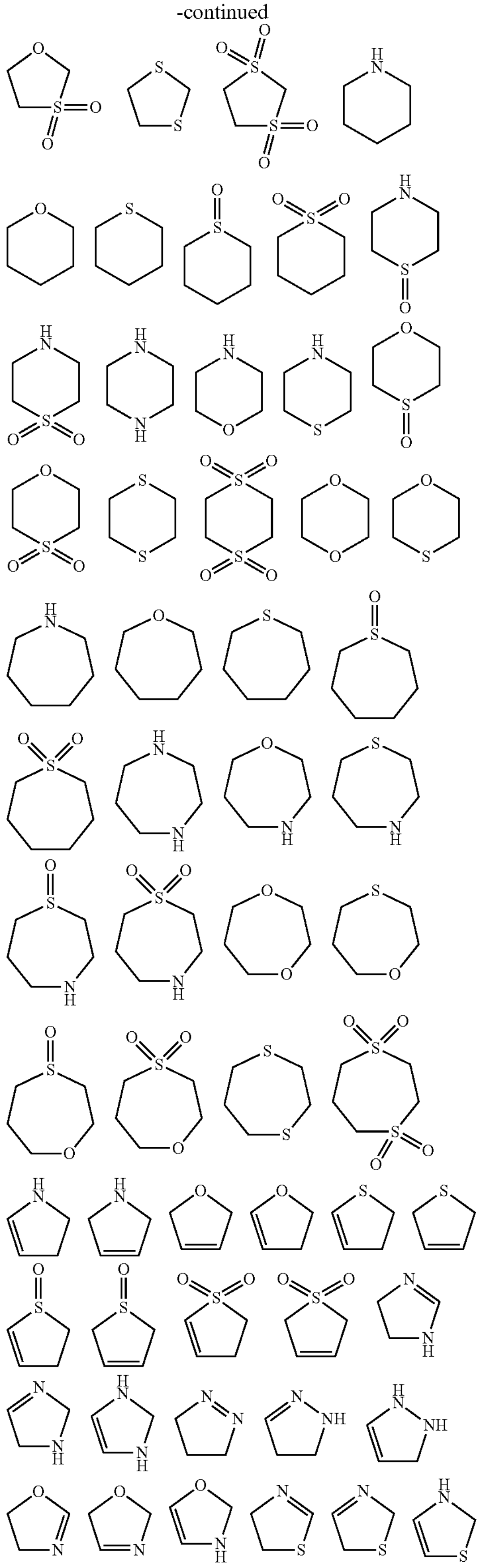
-continued
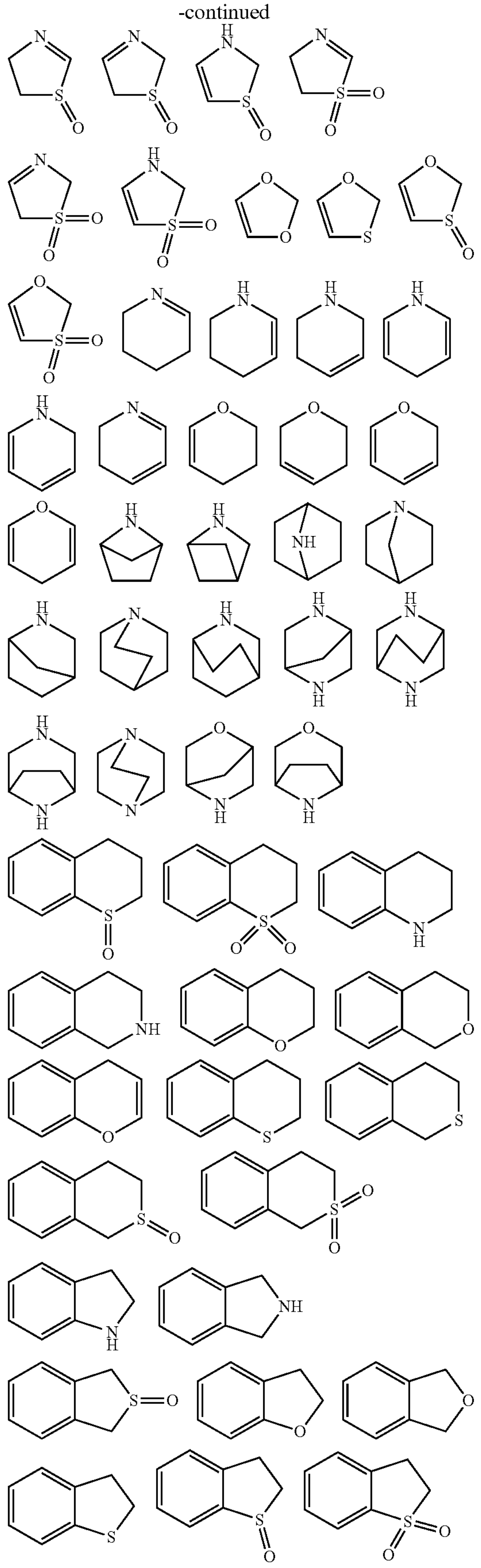

-continued

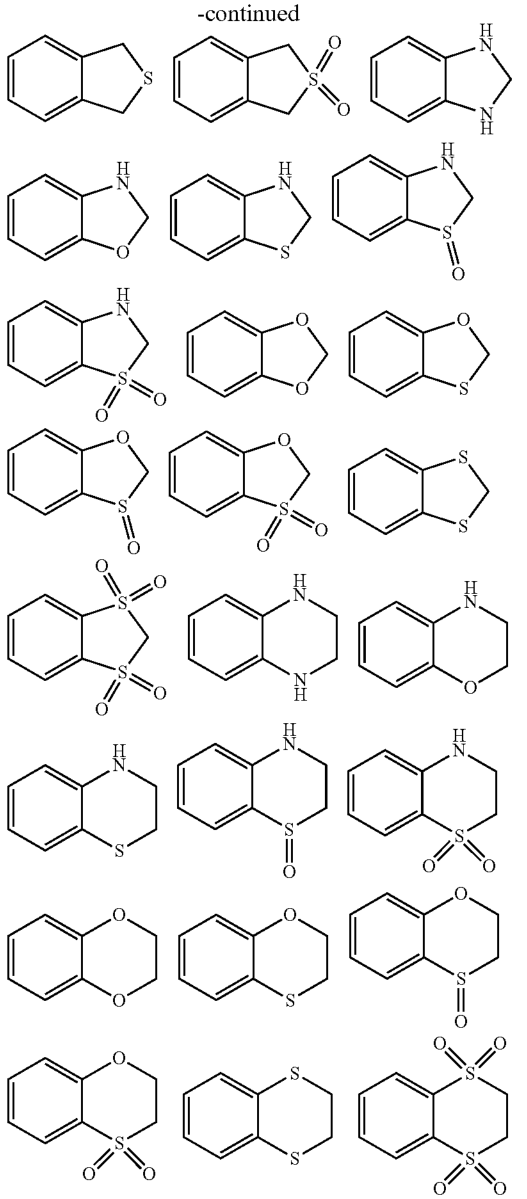

Preferred monocyclic heterocyclyl is 4 to 7 membered and has one or two heteroatoms independently selected from oxygen, nitrogen and sulfur.

Preferred monocyclic heterocyclyls are: piperazinyl, piperidinyl, morpholinyl, pyrrolidinyl, and azetidinyl.

Preferred bicyclic heterocyclyl is 6 to 10 membered and has one or two heteroatoms independently selected from oxygen, nitrogen and sulfur.

Preferred tricyclic heterocyclyl is 9 membered and has one or two heteroatoms independently selected from oxygen, nitrogen and sulfur.

Preferred spiro-heterocyclyl is 7 to 11 membered and has one or two heteroatoms independently selected from oxygen, nitrogen and sulfur.

The above definition of heterocyclyl also applies if heterocyclyl is part of another (combined) group as for example in heterocyclylamino, heterocyclyloxy or heterocyclylalkyl.

If the free valency of a heterocyclyl is saturated, then a heterocycle is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example:

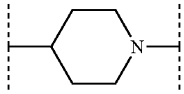

or

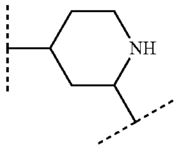

or

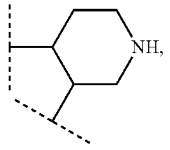

piperidinyl and
2,3-dihydro-1H-pyrrolyl and

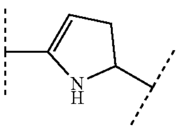

or

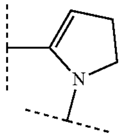

or

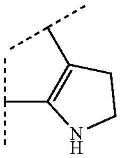

or

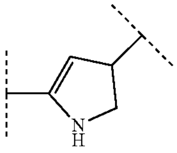

etc.

The above definition of heterocyclylene also applies if heterocyclylene is part of another (combined) group as for example in HO-heterocyclyleneamino or $H_2N$-heterocyclyleneoxy.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen. Substituents on heteroaryl do not count for the number of members of a heteroaryl.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, quinolinyl-N-oxide, indolyl-N-oxide, isoquinolyl-N-oxide, quinazolinyl-N-oxide, quinoxalinyl-N-oxide, phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

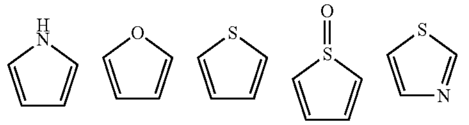
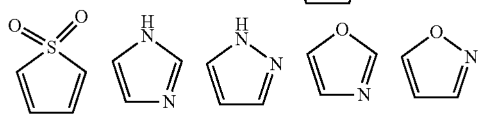
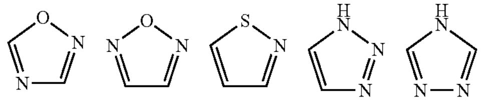
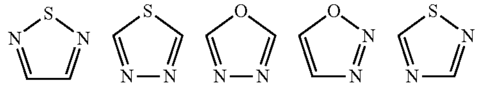
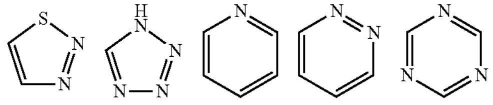
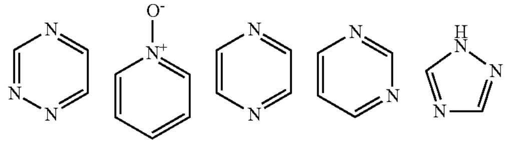
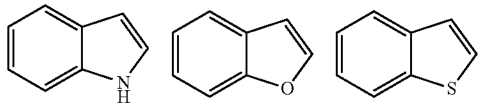
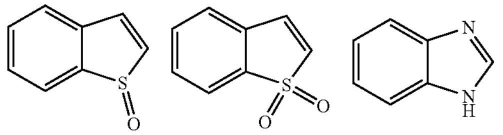
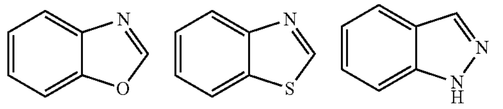
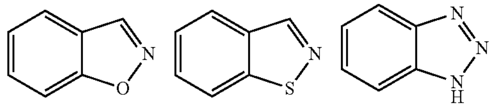
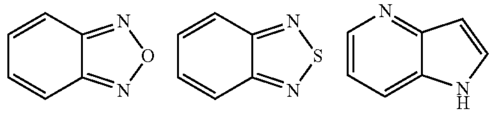
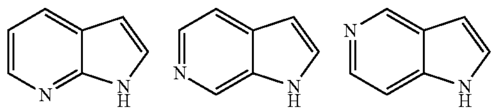

-continued

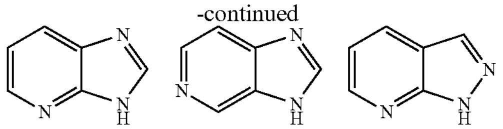
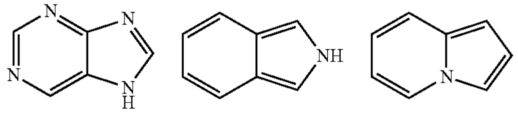
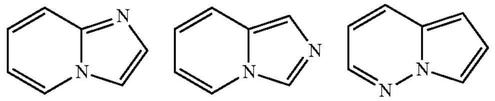
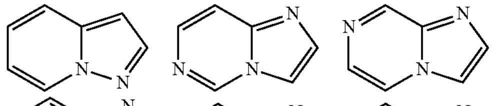
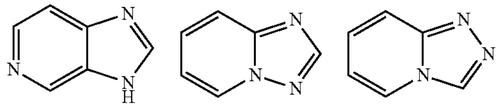
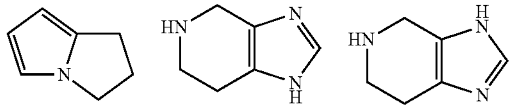
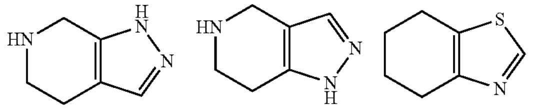

Preferably, heteroaryls are 5-6 membered monocyclic or 9-10 membered bicyclic, each with 1 to 4 heteroatoms independently selected from oxygen, nitrogen and sulfur.

The above definition of heteroaryl also applies if heteroaryl is part of another (combined) group as for example in heteroarylamino, heteroaryloxy or heteroarylalkyl.

If the free valency of a heteroaryl is saturated, a heteroaromatic group is obtained.

The term heteroarylene is also derived from the previously defined heteroaryl. Heteroarylene, unlike heteroaryl, is bivalent and requires two binding partners. Formally, the second valency is obtained by removing a hydrogen atom from a heteroaryl. Corresponding groups are for example:

pyrrolyl and

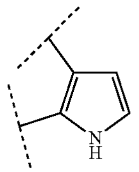 or 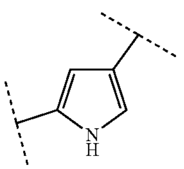 or

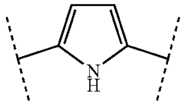 or 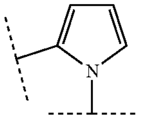

etc.

The above definition of heteroarylene also applies if heteroarylene is part of another (combined) group as for example in HO-heteroaryleneamino or $H_2N$-heteroaryleneoxy.

By substituted is meant that a hydrogen atom which is bound directly to the atom under consideration, is replaced by another atom or another group of atoms (substituent).

Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, $=N_2$ or the like, may only be substituents on carbon atoms, whereas the bivalent substituents =O and =NR may also be a substituent on sulphur. Generally, substitution may be carried out by a bivalent substituent only at ring systems and requires replacement of two geminal hydrogen atoms, i.e. hydrogen atoms that are bound to the same carbon atom that is saturated prior to the substitution. Substitution by a bivalent substituent is therefore only possible at the group-$CH_2$—or sulphur atoms (=O group or =NR group only, one or two =O groups possible or, e.g., one =O group and one =NR group, each group replacing a free electron pair) of a ring system.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates and hydrates of the free compound or solvates and hydrates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents.

Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases, or by resolution of a racemic mixture using an appropriate resolving agent, e.g. by means of diastereomeric salt formation of the racemic compound with optically active acids or bases, subsequent resolution of the salts and release of the desired compound from the salt, or by derivatization of the corresponding racemic compounds with optically active chiral auxiliary reagents, subsequent diastereomer separation and removal of the chiral auxiliary group, or by kinetic resolution of a racemate (e.g. by enzymatic resolution); by enantioselective crystallization from a conglomerate of enantiomorphous crystals under suitable conditions, or by (fractional) crystallization from a suitable solvent in the presence of an optically active chiral auxiliary.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts), also comprise a part of the invention.

In a representation such as for example

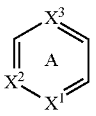 or 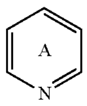 or 

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets where necessary for clarification purposes, as in the following representations:

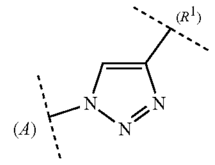

or ($R^2$)—C(=O)NH—or ($R^2$)—NHC(=O)—.

If such a clarification is missing then the bivalent group can bind in both directions, i.e., e.g., —C(═O)NH— also includes —NHC(═O)— (and vice versa).

Groups or substituents are frequently selected from among a number of alternative groups/substituents with a corresponding group designation (e.g. $R^a$, $R^b$ etc). If such a group is used repeatedly to define a compound according to the invention in different parts of the molecule, it is pointed out that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

Ras family proteins as used herein is meant to include KRAS (V-Ki-ras2 Kirsten rat sarcoma viral oncogene homolog), NRAS (neuroblastoma RAS viral oncogene homolog) and HRAS (Harvey murine sarcoma virus oncogene) and any mutants thereof.

A RAS G12C inhibitor as used herein refers to a compound, which binds to one or more of the G12C mutant RAS proteins KRAS G12C (=KRAS G12C inhibitor), NRAS G12C (=NRAS G12C inhibitor) and/or HRAS G12C (=HRAS G12C inhibitor), in particular to KRAS G12C, and is capable of negatively modulating or inhibiting all or a portion of the enzymatic activity of KRAS G12C and/or NRAS G12C and/or HRAS G12C, in particular of KRAS G12C. While not wishing to be bound by theory, it is believed that the compounds of the invention may selectively react with KRAS G12C and/or HRAS G12C and/or NRAS G12C proteins (preferably with KRAS G12C) by forming a covalent bond with the cysteine at the 12 position of KRAS G12C and/or HRAS G12C and/or NRAS G12C (preferably of KRAS G12C) resulting in the modulation/inhibition of the enzymatic activity of these mutant Ras proteins.

| List of abbreviations | |
|---|---|
| Ac | acetyl |
| ACN | acetonitrile |
| aq. | aquatic, aqueous |
| ATP | adenosine triphosphate |
| Bn | benzyl |
| Boc | tert-butyloxycarbonyl |
| Bu | butyl |
| c | concentration |
| Cbz | carboxybenzyl |
| CDI | 1,1'-carbonyldiimidazole |
| d | day(s) |
| TLC | thin layer chromatography |
| Davephos | 2-dimethylamino-2'-dicyclohexylaminophosphinobiphenyl |
| DBU | 1,8-Diazabicyclo(5.4.0)undec-7-ene |
| DCE | dichloro ethane |
| DCM | dichloro methane |
| DEA | diethyl amine |
| DIPEA | N-ethyl-N,N-diisopropylamine (Hünig's base) |
| DMA | dimethylacetamide |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| dppf | 1,1'-bis(diphenylphosphino)ferrocene |
| EDTA | ethylenediaminetetraacetic acid |
| EGTA | ethyleneglycoltetraacetic acid |
| eq. | equivalent(s) |
| ESI | electron spray ionization |
| Et | ethyl |

-continued

| List of abbreviations | |
|---|---|
| $Et_2O$ | diethyl ether |
| EtOAc | ethyl acetate |
| EtOH | ethanol |
| h | hour |
| HATU | O-(7-azabenzotriazol-1-yl)-N,N,N',N'-tetramethyl-uronium hexafluorophosphate |
| HPLC | high performance liquid chromatography |
| i | iso |
| conc. | concentrated |
| LC | liquid chromatography |
| LiHMDS | lithium bis(trimethylsilyl)amide |
| sln. | solution |
| Me | methyl |
| MeOH | methanol |
| min | minutes |
| MPLC | medium pressure liquid chromatography |
| MS | mass spectrometry |
| MTBE | methyl tert-butyl ether |
| NMM | N-methylmorpholine |
| NMP | N-methylpyrrolidone |
| NP | normal phase |
| n.a. | not available |
| PBS | phosphate-buffered saline |
| Ph | phenyl |
| Pr | propyl |
| PTSA | p-toluenesulfonic acid |
| Py | pyridine |
| rac | racemic |
| red. | reduction |
| Rf ($R_f$) | retention factor |
| RP | reversed phase |
| RRLC | Rapid resolution liquid chromatography |
| rt | ambient temperature |
| SFC | supercritical fluid chromatography |
| $S_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | triethyl amine |
| temp. | temperature |
| tert | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TRIS | tris(hydroxymethyl)-aminomethane |
| TsOH | p-toluenesulphonic acid |
| UPLC | ultra performance liquid chromatography |
| UV | ultraviolet |
| wt | weight |

Examples

Features and advantages of the present invention will become apparent from the following detailed examples which illustrate the principles of the invention by way of example without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

If a compound is to be represented both by a structural formula and by its nomenclature, in the event of a conflict the structural formula is decisive.

Microwave reactions are carried out in an initiator/reactor made by Biotage or in an Explorer made by CEM or in Synthos 3000 or Monowave 3000 made by Anton Paar in sealed containers (preferably 2, 5 or 20 mL), preferably with stirring.

Chromatography

The thin layer chromatography is carried out on ready-made silica gel 60 TLC plates on glass (with fluorescence indicator F-254) made by Merck.

The preparative high pressure chromatography (RP HPLC) of the example compounds according to the invention is carried out on Agilent or Gilson systems with columns made by Waters (names: SunFire™ Prep C18, OBD™ 10 μm, 50×150 mm or SunFire™ Prep C18 OBD™ 5 μm, 30×50 mm or XBridge™ Prep C18, OBD™ 10 μm, 50×150 mm or XBridge™ Prep C18, OBD™ 5 μm, 30×150 mm or XBridge™ Prep C18, OBD™ 5 μm, 30×50 mm) and YMC (names: Actus-Triart Prep C18, 5 μm, 30×50 mm).

Different gradients of $H_2O$/acetonitrile are used to elute the compounds, while for Agilent systems 5% acidic modifier (20 mL HCOOH to 1 L $H_2O$/acetonitrile (1/1)) is added to the water (acidic conditions). For Gilson systems the water is added 0.1% HCOOH.

For the chromatography under basic conditions for Agilent systems $H_2O$/acetonitrile gradients are used as well, while the water is made alkaline by addition of 5% basic modifier (50 g $NH_4HCO_3$+50 mL $NH_3$ (25% in $H_2O$) to 1 L with $H_2O$). For Gilson systems the water is made alkaline as follows: 5 mL $NH_4HCO^3$ solution (158 g in 1 L $H_2O$) and 2 mL $NH_3$ (28% in $H_2O$) are replenished to 1 L with $H_2O$.

The supercritical fluid chromatography (SFC) of the intermediates and example compounds according to the invention is carried out on a JASCO SFC-system with the following columns: Chiralcel OJ (250×20 mm, 5 μm), Chiralpak AD (250×20 mm, 5 μm), Chiralpak AS (250×20 mm, 5 μm), Chiralpak IC (250×20 mm, 5 μm), Chiralpak IA (250×20 mm, 5 μm), Chiralcel OJ (250×20 mm, 5 μm), Chiralcel OD (250×20 mm, 5 μm), Phenomenex Lux C2 (250×20 mm, 5 μm).

The analytical HPLC (reaction control) of intermediate and final compounds is carried out using columns made by Waters (names: XBridge™ C18, 2.5 μm, 2.1×20 mm or XBridge™ C18, 2.5 μm, 2.1×30 mm or Aquity UPLC BEH C18, 1.7 μm, 2.1×50 mm) and YMC (names: Triart C18, 3.0 μm, 2.0×30 mm) and Phenomenex (names: Luna C18, 5.0 μm, 2.0×30 mm). The analytical equipment is also equipped with a mass detector in each case.

HPLC-Mass Spectroscopy/UV-Spectrometry

The retention times/MS-$ESI^+$ for characterizing the example compounds according to the invention are produced using an HPLC-MS apparatus (high performance liquid chromatography with mass detector). Compounds that elute at the injection peak are given the retention time $t_{Ret.}$=0.00.

SFC-Method (Preparative)

Preparative SFC is performed in Waters Thar SFC 80 system

Column: Chiralpak AD-H (21×250 mm), 5 μm

Flow: 25 g/min

Mobile Phase: 75% $CO_{2+25}$% MeOH (0.5% isopropylamine)

ABPR: 120 bar

Temp: 35° C.

UV: 220 nm

Stack Time: 8 min

HPLC-Methods (Analytic)

Method A

Samples were analyzed on an Agilent 1200 series LC system coupled with an Agilent 6140 mass spectrometer. Purity was determined via UV detection with a bandwidth of 170 nm in the range from 230-400 nm. LC parameters were as follows:

| Method A | | |
|---|---|---|
| column | Waters Xbridge C18 column 3.5 μm particle size, 2.1 × 30 mm; | |
| flow | 1 mL/min; | |
| column temperature | 60° C.; | |
| injection | 5 μL injections; | |
| solvent | A: 20 mM $NH_4HCO_3/NH_3$ pH 9<br>B: MS grade acetonitrile; | |
| gradient | 0.0-1.5 min | 10%-95% B |
| | 1.5-2.0 min | 95% B |
| | 2.0-2.1 min | 95%-10% B |

| Method B | |
|---|---|
| HPLC | Agilent 1100/1200 Series |
| MS | Agilent LC/MSD SL |
| column | Waters X-Bridge BEH C18, 2.5 μm, 2.1 × 30 mm XP |
| solvent | A: 20 mM $NH_4HCO_3$/28 mM $NH_3$ in $H_2O$;<br>B: acetonitrile (HPLC grade) |
| detection | MS: positive and negative mode |
| mass range | 100-750 m/z |
| flow | 1.40 mL/min |
| column temperature | 45° C. |
| gradient: | 0.00-1.00 min: 15% B → 95% B<br>1.00-1.30 min: 95% B |

| Method C | |
|---|---|
| HPLC | Agilent 1100/1200 Series |
| MS | Agilent LC/MSD SL |
| column | Waters SunFire C18, 2.5 μm, 2.1 × 30 mm XP |
| solvent | A: 0.1% HCOOH in $H_2O$;<br>B: 0.1% HCOOH in acetonitrile (HPLC grade) |
| detection | MS: positive and negative mode |
| mass range | 150-750 m/z |
| flow | 1.40 mL/min |
| column temperature | 45° C. |
| gradient | 0.00-1.00 min: 15% B → 100% B<br>1.00-1.13 min: 100% B |

| Method D | | |
|---|---|---|
| HPLC | Agilent 1100/1200 system | |
| MS | 1200 Series LC/MSD (MM-ES + APCl +/− 3000 V, Quadrupol, G6130B) | |
| MSD signal settings | Scan pos 150-750 | |
| column | Waters, Part. No. 186003389, XBridge BEH C18, 2.5 μm, 2.1 × 30 mm) column | |
| eluent | A: 5 mM $NH_4HCO_3$/18 mM $NH_3$ (pH = 9.2)<br>B: acetonitrile (HPLC grade) | |
| detection signal | UV 254 nm, 230 nm, 214 nm (bandwidth 8, reference off) | |
| spectrum | range: 190-400 nm; slit: 4 nm | |
| peak width | >0.0031 min (0.063 s response time, 80 Hz) | |
| injection | 0.5 μL standard injection | |
| flow | 1.4 mL/min | |
| column temperature | 45° C. | |
| gradient | 0.0-1.0 min | 15% → 95% B |
| | 1.0-1.1 min | 95% B |
| | Stop time: 1.3 min | |

| Methode E | |
|---|---|
| HPLC | Agilent 1100/1200 system |
| MS | 1200 Series LC/MSD (API-ES +/− 3000/3500 V, Quadrupol, G6140A) |
| MSD signal settings | Scan pos 150-750 |
| column | YMC; Part. No. TA12S03-0302WT; Triart C18, 3 μm, 12 nm; 30 × 2.0 mm column |
| eluant | A: $H_2O$ + 0.11% formic acid<br>B: MeCN + 0.1% formic acid (HPLC grade) |
| detection signal | UV 254 nm, 230 nm, 214 nm (bandwidth 10, reference off) |
| spectrum | range: 190-400 nm; slit: 4 nm |
| peak width | >0.0031 min (0.063 s response time, 80 Hz) |
| injection | 0.5 μL standard injection |
| flow | 1.4 mL/min |
| column temperature | 45° C. |
| gradient | 0.0-1.0 min 15% → 95% B<br>1.0-1.1 min 95% B<br>Stop time: 1.23 min |

| Method F | |
|---|---|
| HPLC | Agilent 1100/1200 system |
| MS | 1200 Series LC/MSD (API-ES +/− 3000/3500 V, Quadrupol, G6140A) |
| MSD signal settings | Scan pos/neg 150-750 |
| column | YMC; Part. No. TA12S03-0302WT; Triart C18, 3 μm, 12 nm; 30 × 2.0 mm column |
| eluant | A: $H_2O$ + 0.11% formic acid<br>B: MeCN + 0.1% formic acid (HPLC grade) |
| detection signal | UV 254 nm, 230 nm, 214 nm (bandwidth 10, reference off) |
| spectrum | range: 190-400 nm; slit: 4 nm |
| peak width | >0.0031 min (0.063 s response time, 80 Hz) |
| injection | 0.5 μL standard injection |
| flow | 1.4 mL/min |
| column temperature | 45° C. |
| gradient | 0.0-1.0 min 15% → 95% B<br>1.0-1.1 min 95% B<br>Stop time: 1.23 min |

| Method G | |
|---|---|
| HPLC | Agilent 1100/1200 system |
| MS | 1200 Series LC/MSD (MM-ES + APCI +/− 3000 V, Quadrupol, G6130B) |
| MSD signal settings | Scan pos/neg 150-750 |
| column | Waters, Part.No. 186003389, XBridge BEH C18, 2.5 μm, 2.1 × 30 mm) column |
| eluant | A: 5 mM $NH_4HCO_3$/18 mM $NH_3$ (pH = 9.2)<br>B: acetonitrile (HPLC grade) |
| detection signal | UV 254 nm, 230 nm, 214 nm (bandwidth 8, reference off) |
| spectrum | range: 190-400 nm; slit: 4 nm |
| peak width | >0.0031 min (0.063 s response time, 80 Hz) |
| injection | 0.5 μL standard injection |
| flow | 1.4 mL/min |
| column temperature | 45° C. |
| gradient | 0.0-1.0 min 15% → 95% B<br>1.0-1.1 min 95% B<br>Stop time: 1.3 min |

The compounds according to the invention and intermediates are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or their synthesis is described in the prior art or they may be prepared analogously to known prior art compounds or methods described herein, i.e. it is within the skills of an organic chemist to synthesize these compounds. Substances described in the literature can be prepared according to the published methods of synthesis. If a chemical structure in the following is depicted without exact configuration of a stereo center, e.g. of an asymmetrically substituted carbon atom, then both configurations shall be deemed to be included and disclosed in such a representation. The representation of a stereo center in racemic form shall always deem to include and disclose both enantiomers (if no other defined stereo center exists) or all other potential diastereomers and enantiomers (if additional, defined or undefined, stereo centers exist).

General Reaction Schemes and Summary of the Syntheses Routes Towards Compounds (I) According to the Invention Scheme 1

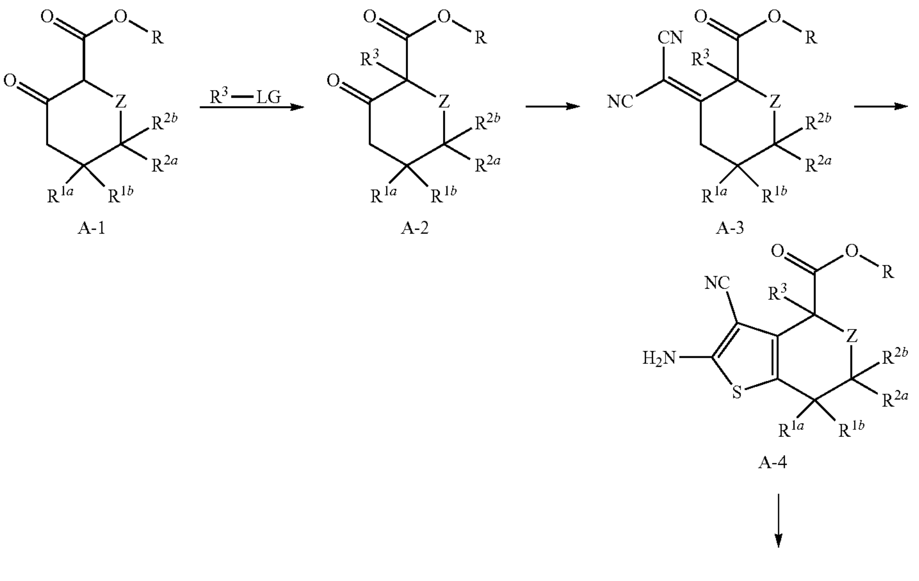

A-1 A-2 A-3 A-4

-continued

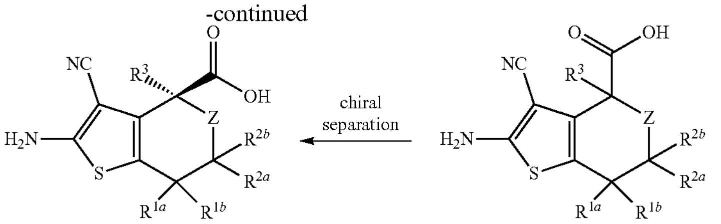

A-5 A-5

R = alkyl, Bn etc.
n = 0-2
LG = leaving group

Experimental Procedure for the Synthesis of A-2a

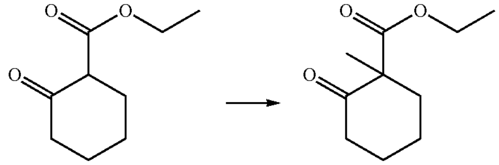

A-1a A-2a

To a suspension of sodium hydride, (60% in mineral oil, 25.85 g, 646.3 mmol, 1.1 eq.) in THF (2.0 L) is added A-1a (93.46 mL, 587.5 mmol, 1.0 eq.) dropwise at 0-10° C. The mixture is stirred at 10° C. for 30 min, then methyl iodide (55.11 mL, 881.3 mmol. 1.5 eq.) is added to the mixture dropwise at 10° C. The mixture is allowed to reach rt overnight. After complete conversion the reaction mixture is cooled to 0° C. and quenched with saturated aq. ammonium chloride solution. The product is extracted with EtOAc and the combined organic layers are washed with water and brine, dried over sodium sulfate and concentrated under reduced pressure to afford A-2a which is used for the next step without further purification.

The following intermediates A-2 (table 1) are available in an analogous manner using different cyclic β-keto esters A-1. The crude product A-2 is purified by chromatography if necessary.

TABLE 1

| # | structure | $t_{ret}$ [min] | $[M + H]^+$ | HPLC method |
|---|---|---|---|---|
| A-2a | 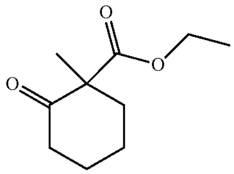 | 1.14 | 185 | A |
| A-2b | 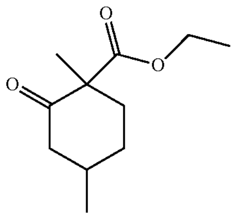 | 1.19 | 199 | A |

TABLE 1-continued

| # | structure | $t_{ret}$ [min] | $[M + H]^+$ | HPLC method |
|---|---|---|---|---|
| A-2c | 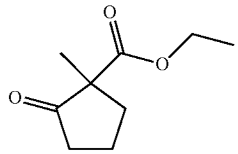 | 0.96 | 171 | A |

Experimental Procedure for the Synthesis of A-3a

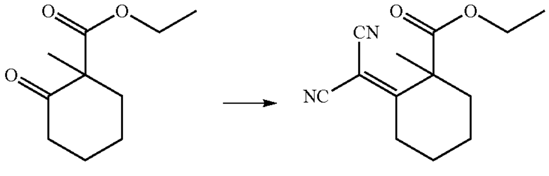

A-2a A-3a

To a solution of A-2a (108.00 g, 586.2 mmol) in toluene (1.03 L) is added malononitrile (58.04 g, 879.3 mmol, 1.5 eq.) followed by ammonium acetate (9.04 g, 117.2 mmol, 0.2 eq.) and acetic acid (13.41 mL, 234.5 mmol, 0.4 eq.) at rt. The mixture is stirred at 110° C. for 16 h. After complete conversion the mixture is diluted with EtOAc and washed with water and brine, dried over sodium sulfate and concentrated under reduced pressure to afford the crude product A-3a. This crude material is used for the next step without further purification (see also Naumann et al., Pharmazie 51 (1996), 4).

The following intermediates A-3 (table 2) are available in an analogous manner using different intermediates A-2. The crude product A-3 is purified by chromatography if necessary.

TABLE 2

| # | structure | $t_{ret}$ [min] | $[M + H]^+$ | HPLC method |
|---|---|---|---|---|
| A-3a | 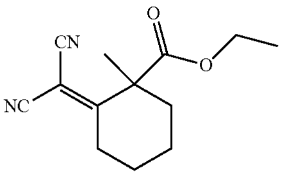 [SMILES: CCOC(=O)C1(C)CCCCC1=C(C#N)C#N] | n.a. | n.a. | — |

TABLE 2-continued

| # | structure | $t_{ret}$ [min] | $[M + H]^+$ | HPLC method |
|---|---|---|---|---|
| A-3b | 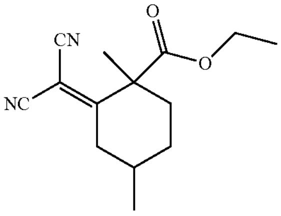 [SMILES: CCOC(=O)C1(C)CCC(C)CC1=C(C#N)C#N] | 1.34 | 245 | A |
| A-3c | 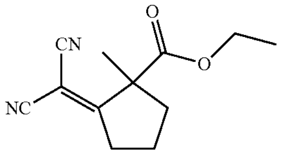 [SMILES: CCOC(=O)C1(C)CCCC1=C(C#N)C#N] | n.a. | n.a. | — |

Experimental Procedure for the Synthesis of A-4a

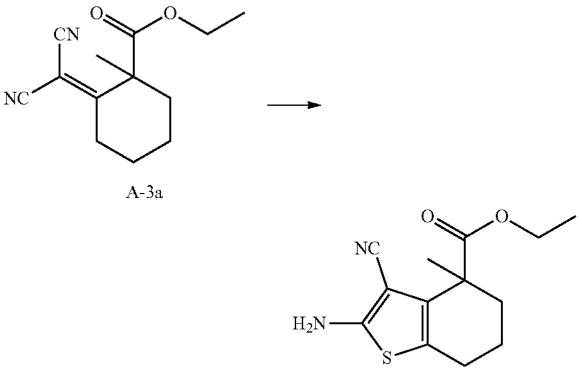

A-3a

A-4a

To a solution of A-3a (250.0 g, 1.1 mol) in DMF (3.0 L) is added sulphur (68.9 g, 2.2 mol, 2.0 eq.) and L-proline (24.8 g, 0.22 mol, 0.2 eq.) and the resulting mixture is stirred at 80° C. for 12 h. After complete conversion the mixture is partitioned between EtOAc and water and the organic layer is collected. The aqueous layer is further extracted with EtOAc and the combined organic layers are washed with water and brine, dried over sodium sulfate and concentrated under reduced pressure to afford the crude product. The crude product is purified through column chromatography yielding A-4a.

The following intermediates A-4 (table 3) are available in an analogous manner using different intermediates A-3. The crude product A-4 is purified by chromatography if necessary.

TABLE 3

| # | structure | $t_{ret}$ [min] | $[M + H]^+$ | HPLC method |
|---|---|---|---|---|
| A-4a | 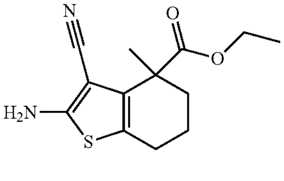 [SMILES: CCOC(=O)C1(C)CCCc2sc(N)c(C#N)c21] | 1.08 | 265 | A |

TABLE 3-continued

| # | structure | $t_{ret}$ [min] | $[M + H]^+$ | HPLC method |
|---|---|---|---|---|
| A-4b | 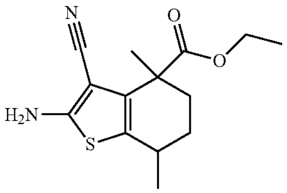 [SMILES: CCOC(=O)C1(C)CCC(C)c2sc(N)c(C#N)c21] | 1.25 | 279 | A |
| A-4c | 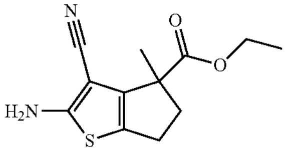 [SMILES: CCOC(=O)C1(C)CCc2sc(N)c(C#N)c21] | n.a. | n.a. | — |

Experimental Procedure for the Synthesis of A-4d

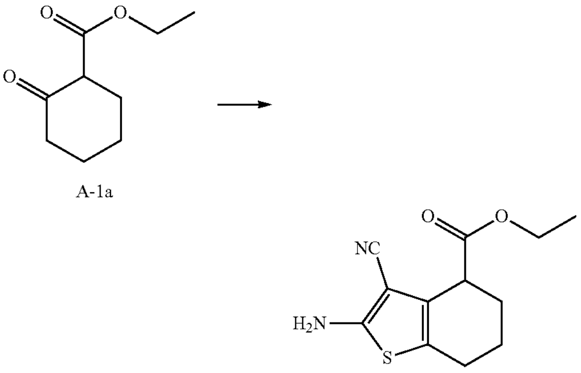

A-1a

A-4d

A stirred solution of A-1a (12.00 g, 70.5 mmol) in EtOH (60.0 mL) is treated with sulfur (2.26 g, 70.5 mmol, 1.00 eq.), morpholine (6.14 g, 70.5 mmol, 1.0 eq.) and malononitrile (4.66 g, 70.5 mmol, 1.0 eq.). Then the reaction mixture is stirred at 55° C. for 1 h. After complete conversion the reaction mixture is concentrated, diluted with water, extracted with EtOAc and the extracts are dried, filtered and concentrated under reduced pressure to get crude product. This crude material is purified by column chromatography (20-30% EtOH in hexane) to afford A-4d. (HPLC method A; $t_{ret}$=1.10 min; $[M+H]^+$=251).

Experimental Procedure for the Synthesis of A-5a

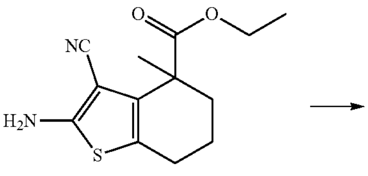

A-4a

-continued

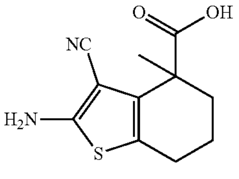

A-5a

A-4a (78.0 mg, 0.3 mmol, 1.0 eq.) is dissolved in EtOH (1.5 mL) and potassium hydroxide (4 M in water, 0.37 mL, 1.5 mmol, 5.0 eq.) is added. The mixture is stirred for 16 h at 78° C. After complete conversion, water and EtOAc is added to the mixture, the pH of the aqueous phase is set to pH 4 using $KHSO_4$ solution (10% in water), and the product is extracted using EtOAc. The combined organic layers are dried, filtered and concentrated. The crude product is purified via acidic reversed phase chromatography (gradient elution: 20% to 90% acetonitrile in water) yielding A-5a.

The following intermediates A-5 (table 4) are available in an analogous manner using different esters A-4. The crude product A-5 is purified by chromatography if necessary, enantiomers can be separated with preparative SFC chromatography as herein described, e.g. separation of A-5a into A-5b and its enantiomer.

TABLE 4

| # | structure | $t_{ret}$ [min] | $[M + H]^+$ | HPLC method |
|---|---|---|---|---|
| A-5a | 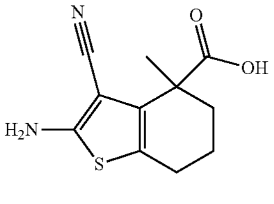 [SMILES: CC1(C(=O)O)CCCc2sc(N)c(C#N)c21] | 0.22 | 237 | A |
| A-5b | 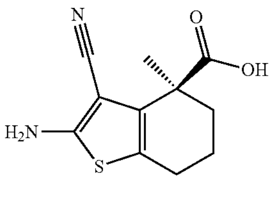 [SMILES: C[C@]1(C(=O)O)CCCc2sc(N)c(C#N)c21] | 0.25 | 237 | A |
| A-5c | 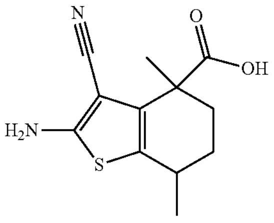 [SMILES: CC1CCC(C)(C(=O)O)c2c1sc(N)c2C#N] | 0.43 | 251 | A |

TABLE 4-continued

| # | structure | $t_{ret}$ [min] | $[M + H]^+$ | HPLC method |
|---|---|---|---|---|
| A-5d | 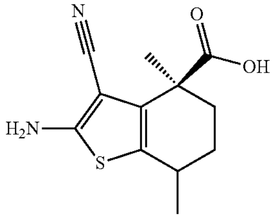 [SMILES: CC1CC[C@](C)(C(=O)O)c2c1sc(N)c2C#N] | n.a. | n.a. | — |
| A-5e | 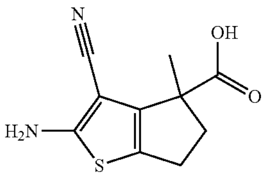 | 0.18 | 223 | A |
| A-5f | 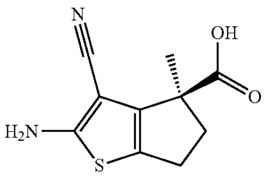 | n.a. | n.a. | — |
| A-5g | 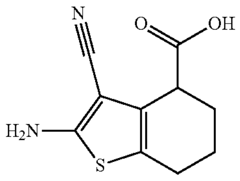 [SMILES: N#Cc1c(N)sc2c1C(C(=O)O)CCC2] | 0.09 | 223 | B |
| A-5h | 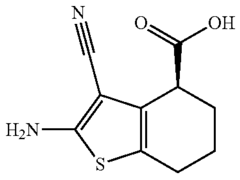 [SMILES: N#Cc1c(N)sc2c1[C@@H](C(=O)O)CCC2] | n.a. | n.a. | — |

Scheme 2a
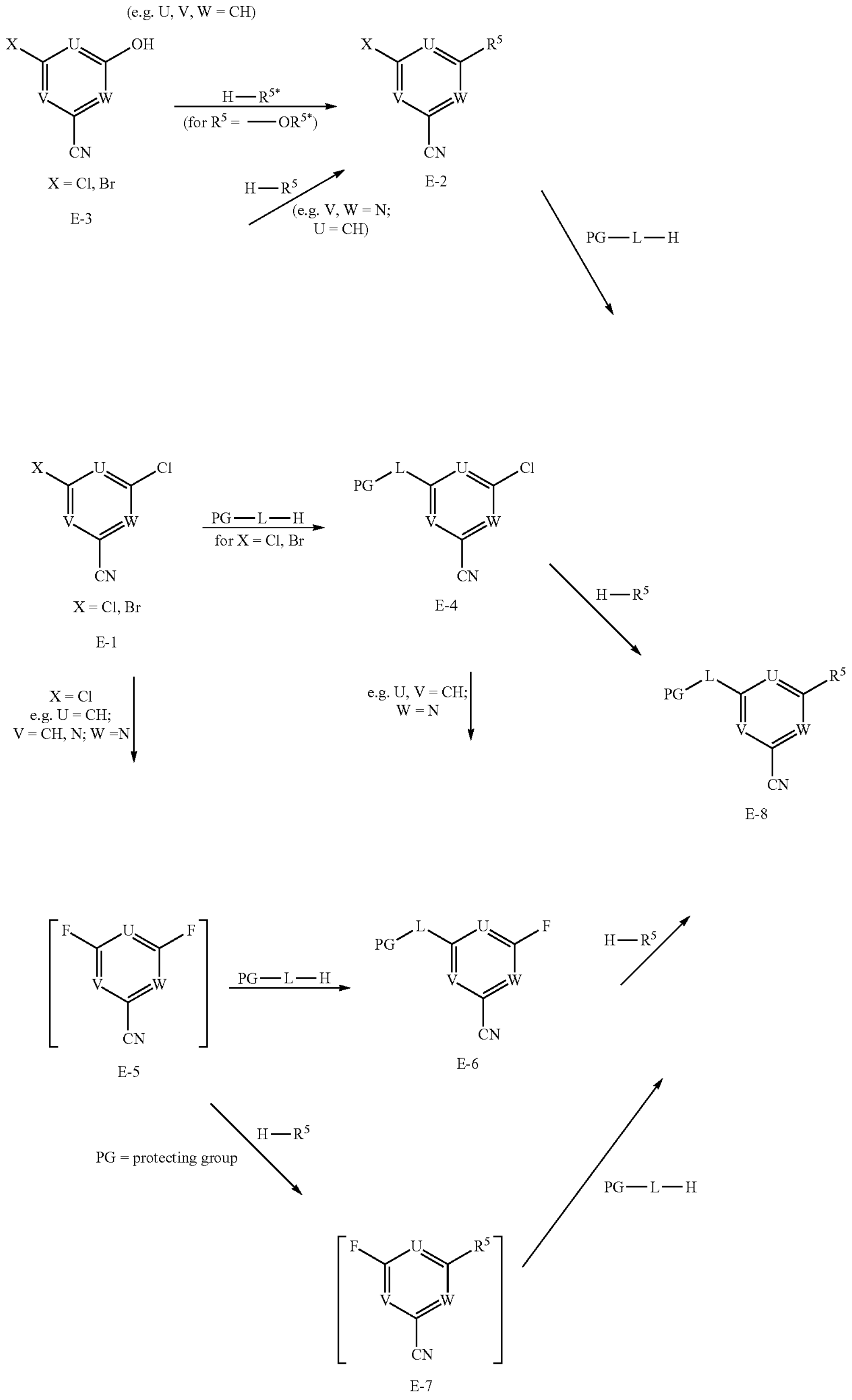

Scheme 2b

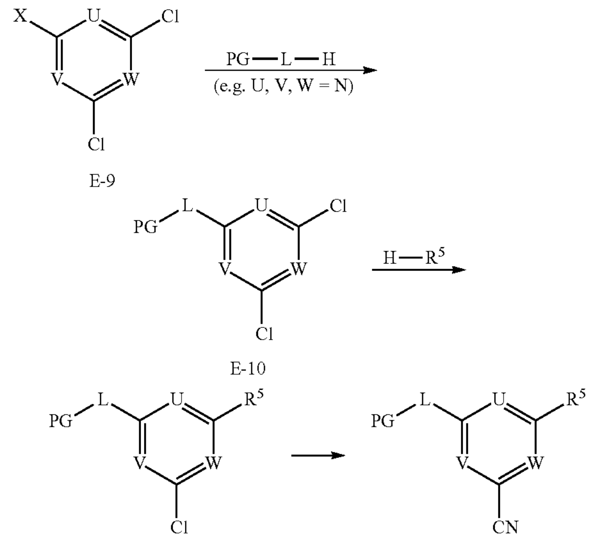

E-9
E-10
E-11
E-8

Experimental Procedure for the Synthesis of E-2a

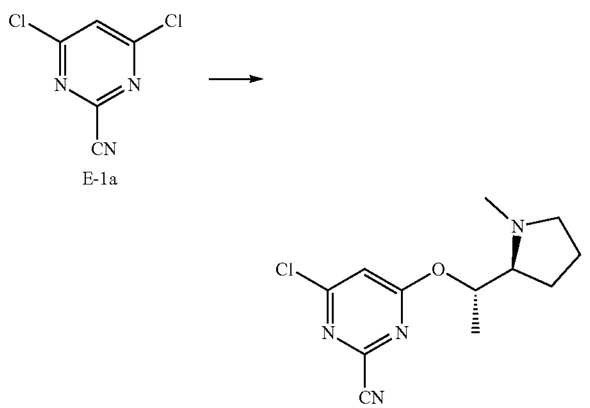

E-1a
E-2a

To a solution of(S)-1-((S)-1-methylpyrrolidin-2-yl)-ethan-1-ol (1.441 g, 11.15 mmol, 1.0 eq.) in DMSO is added DIPEA (2.882 g, 22.3 mmol, 2.0 eq.) and the mixture is cooled to 10° C. E-1a (2.0 g, 11.15 mmol, 97% purity, 1.0 eq.) is added and the mixture is stirred at 10° C. for 45 min. The mixture is filtered and the filtrate is purified via basic reversed phase chromatography (gradient elution: 30% to 98% acetonitrile in water) yielding E-2a. (HPLC method A; $t_{ret}$=1.36 min; $[M+H]^+$=267).

Additional intermediates E-2 are available in an analogous manner. The crude product E-2 can be purified by chromatography if necessary.

Experimental Procedure for the Synthesis of E-2b

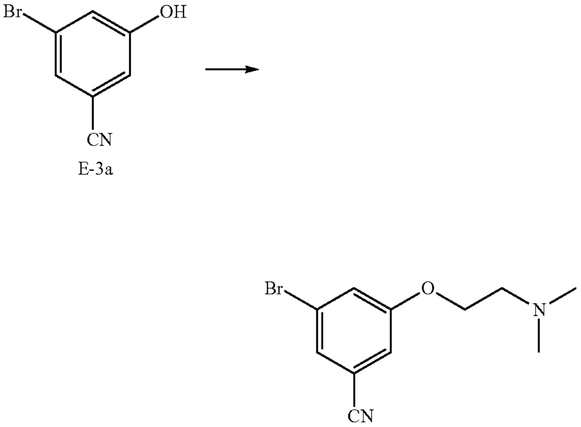

E-3a
E-2b

E-3a (3.50 g, 15.9 mmol) is dissolved in DMF (10 mL). 2-dimethylaminoethyl chloride HCl salt (6.87 g, 47.72 mmol) is added and the mixture stirred for 25 min at 150° C. The mixture is cooled to rt and filtered through a glass frit then washed with EtOAc. The solvent is removed by lyophilization. The residue is purified by normal phase chromatography (gradient elution: 0% to 20% MeOH in DCM) yielding E-2b.

The following intermediates E-2 (table 5) are available in an analogous manner. The crude product E-2 is purified by chromatography if necessary.

TABLE 5

| # | structure | $t_{ret}$ [min] | $[M+H]^+$ | HPLC method |
|---|---|---|---|---|
| E-2b | 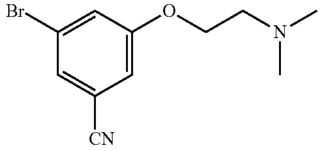 | 1.11 | 268 | A |
| E-2c | 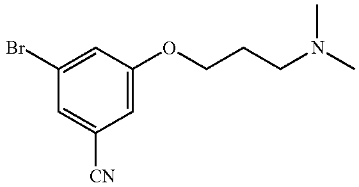 [SMILES: CN(C)CCCOc1cc(Br)cc(C#N)c1] | 1.21 | 283 | A |

TABLE 5-continued

| # | structure | $t_{ret}$ [min] | $[M + H]^+$ | HPLC method |
|---|---|---|---|---|
| E-2d | 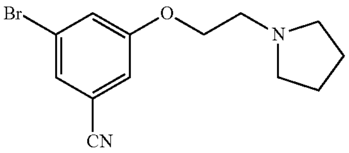 [SMILES: N#Cc1cc(Br)cc(OCCN2CCCC2)c1] | 1.22 | 295 | A |

Experimental Procedure for the Synthesis of E-4a (Method A)

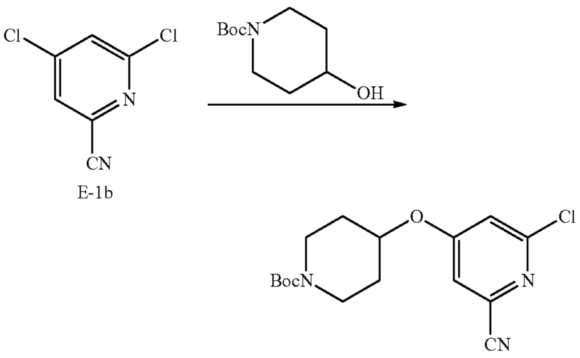

E-1b

E-4a

4-Hydroxypiperidine-1-carboxylic acid tert-butyl ester (2.76 g, 13.73 mmol) and cesium carbonate (2.76 g, 13.73 mmol) are dissolved in DMA (10 mL). E-1b (2.50 g, 13.73 mmol) is added and the mixture stirred at 90° C. for 1 h. The reaction mixture is extracted from water into EtOAc and the organic phase dried over magnesium sulfate. The solvent is removed in vacuo and the residue purified via basic reversed phase chromatography (gradient elution: 45% to 98% acetonitrile in water) yielding E-4a.

Experimental Procedure for the Synthesis of E-4b (Method B)

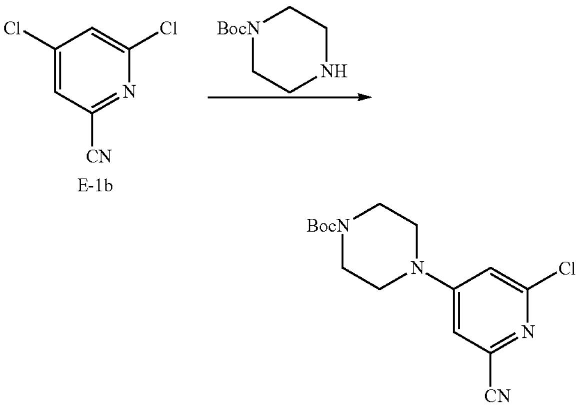

E-1b

E-4b

To a stirred solution of E-1b (5.00 g, 28.90 mmol) in DMSO (50.0 mL) is added piperazine-1-carboxylic acid tert-butyl ester (5.92 g, 31.79 mmol, 1.1 eq.). Then DIPEA (11.21 g, 86.71 mmol, 3.0 eq.) is added and the reaction mixture is stirred at 60° C. for 1 h. After complete conversion the mixture is dissolved in EtOAc and washed with water (3×). The organic phase is dried, filtered and concentrated under reduced pressure. The crude product is purified via column chromatography (EtOAc/hexane) yielding E-4b.

Experimental Procedure for the Synthesis of E-4c (Method C)

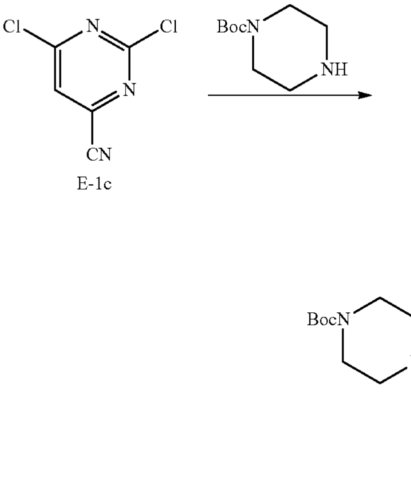

E-1c

E-4c

To a stirred solution of E-1c (10.20 g, 57.22 mmol) in DCM (60.0 mL) is added piperazine-1-carboxylic acid tert-butyl ester (11.22 g, 57.22 mmol, 1.0 eq.). Then DIPEA (20.71 g, 160.21 mmol, 2.8 eq.) is added and the reaction mixture is stirred at 60° C. for 1 h. After complete conversion the mixture is dissolved in EtOAc and washed with water (3×). The organic phase is dried, filtered and concentrated under reduced pressure. The crude product is purified via column chromatography (DCM/MeOH) yielding E-4c.

Experimental Procedure for the Synthesis of E-4d (Method D)

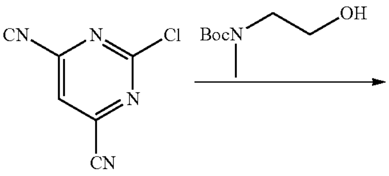

E-1c

-continued

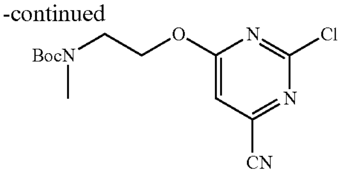

E-4d

To a stirred mixture of sodium hydride (22.8 mg, 0.95 mmol, 1.1 eq.) and THF (2 mL) under argon is added tert-butyl N-(2-hydroxyethyl)-N-methylcarbamate (171 mg, 0.95 mmol, 1.1 eq.) at rt and the mixture is stirred for 5 min. E-1c (150 mg, 0.86 mmol, 1.0 eq.) is added and the mixture is stirred for 1 h. The reaction is quenched by addition of a few drops of water and solvents are removed under vacuum. The crude product is dissolved in DCM and purified via column chromatography (DCM/MeOH) yielding E-4d.

Experimental Procedure for the Synthesis of E-4e (Method E)

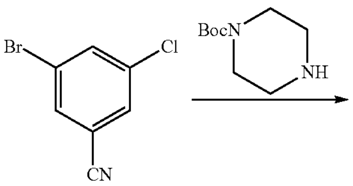

E-1d

-continued

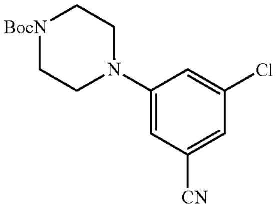

E-4e

E-1d (1.00 g, 6.62 mmol), piperazine-1-carboxylic acid tert-butyl ester (724.6 mg, 3.70 mmol, 0.8 eq.), sodium tert-butoxide (915.4 mg, 9.24 mmol, 2.0 eq.), 2-(di-tert-butylphosphino) biphenyl (275.7 mg, 0.92 mmol, 0.20 eq.), and tris(dibenzylideneacetone) dipalladium (0) (211.5 mg, 0.23 mmol, 0.05 eq.) are combined in dry dioxane (9.00 mL) and the mixture is stirred for 1 h at rt. After complete conversion the mixture is concentrated, diluted with water, the product is extracted with DCM and the combined organic layers are dried, filtered, and concentrated. The crude product is purified via basic reversed phase chromatography (gradient elution: 35% to 98% acetonitrile in water) yielding E-4e.

The following (additional) intermediates E-4 (table 6) are available in an analogous manner using different amines PG-L-H and intermediates E-1 according to methods A to E. The crude products E-4 can be purified by chromatography if necessary.

TABLE 6

| # | method | structure | $t_{ret}$ [min] | $[M + H]^+$ | HPLC method |
|---|---|---|---|---|---|
| E-4a | A | 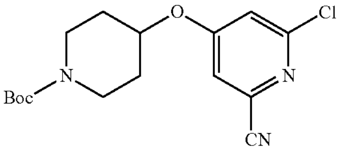 [SMILES: CC(C)(C)OC(=O)N1CCC(Oc2cc(Cl)nc(C#N)c2)CC1] | 1.43 | 338 | A |
| E-4b | B | 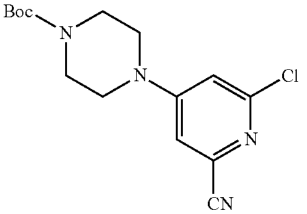 [SMILES: CC(C)(C)OC(=O)N1CCN(c2cc(Cl)nc(C#N)c2)CC1] | 0.73 | 323 | B |
| E-4c | C | 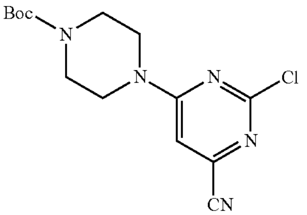 [SMILES: CC(C)(C)OC(=O)N1CCN(c2cc(C#N)nc(Cl)n2)CC1] | 0.72 | 324 | F |
| E-4d | D | 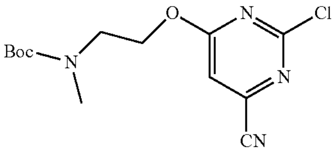 [SMILES: CN(CCOc1cc(C#N)nc(Cl)n1)C(=O)OC(C)(C)C] | 0.71 | 213 (M − Boc) | F |

TABLE 6-continued
| # | method | structure | $t_{ret}$ [min] | [M + H]$^+$ | HPLC method |
|---|---|---|---|---|---|
| E-4e | E | 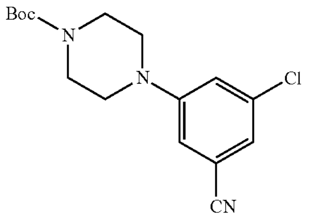 [SMILES: CC(C)(C)OC(=O)N1CCN(c2cc(Cl)cc(C#N)c2)CC1] | 0.83 | 266 | B |
| E-4f | A | 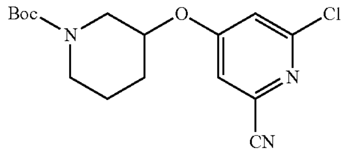 [SMILES: CC(C)(C)OC(=O)N1CCCC(Oc2cc(Cl)nc(C#N)c2)C1] | 1.44 | 338 | A |
| E-4g | B | 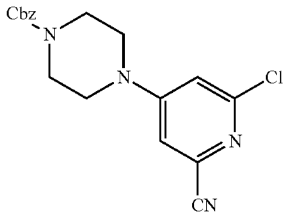 [SMILES: N#Cc1cc(N2CCN(C(=O)OCc3ccccc3)CC2)cc(Cl)n1] | 0.72 | 357 | B |
| E-4h | B | 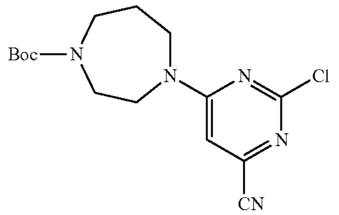 [SMILES: CC(C)(C)OC(=O)N1CCCN(c2cc(C#N)nc(Cl)n2)CC1] | 1.36 | 338 | A |
| E-4i | B | 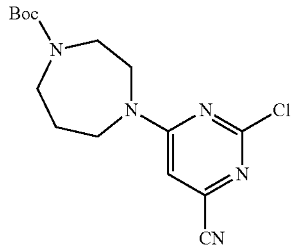 [SMILES: CC(C)(C)OC(=O)N1CCCN(c2cc(C#N)nc(Cl)n2)CC1] | 0.71 | 338 | F |
| E-4j | C | 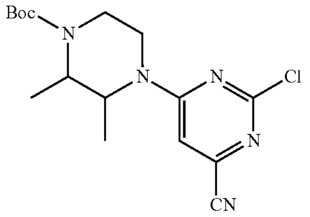 [SMILES: CC1C(C)N(c2cc(C#N)nc(Cl)n2)CCN1C(=O)OC(C)(C)C] | 1.57 | 352 | A |
| E-4k | C | 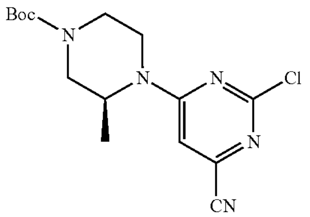 [SMILES: C[C@H]1CN(C(=O)OC(C)(C)C)CCN1c1cc(C#N)nc(Cl)n1] | 0.75 | 338 | G |

TABLE 6-continued
| # | method | structure | $t_{ret}$ [min] | $[M + H]^+$ | HPLC method |
|---|---|---|---|---|---|
| E-4l | C | 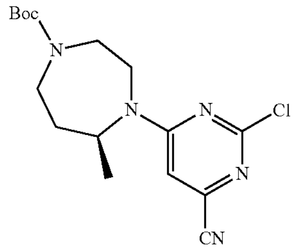 [SMILES: C[C@H]1CCN(C(=O)OC(C)(C)C)CCN1c1cc(C#N)nc(Cl)n1] | n.a. | n.a. | — |
| E-4m | C | 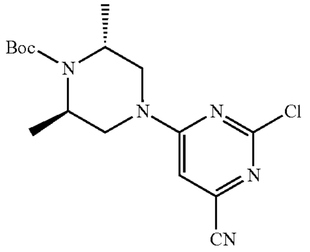 [SMILES: C[C@@H]1CN(c2cc(C#N)nc(Cl)n2)C[C@@H](C)N1C(=O)OC(C)(C)C] | 1.48 | 352 | A |
| E-4n | C | 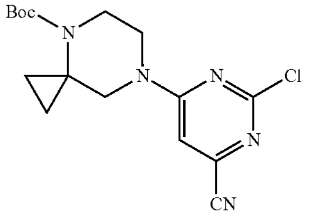 [SMILES: CC(C)(C)OC(=O)N1CCN(c2cc(C#N)nc(Cl)n2)CC12CC2] | 1.49 | 350 | A |
| E-4o | C | 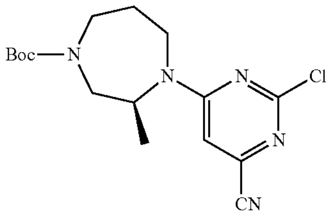 [SMILES: C[C@H]1CN(C(=O)OC(C)(C)C)CCCN1c1cc(C#N)nc(Cl)n1] | 1.41 | 352 | A |
| E-4p | C | 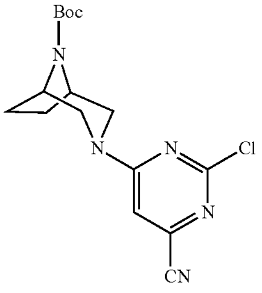 [SMILES: CC(C)(C)OC(=O)N1C2CCC1CN(c1cc(C#N)nc(Cl)n1)C2] | 1.44 | 350 | A |
| E-4q | C | 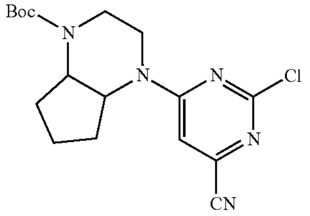 [SMILES: CC(C)(C)OC(=O)N1CCN(c2cc(C#N)nc(Cl)n2)C2CCCC21] | 0.79 | 364 | G |

TABLE 6-continued
| # | method | structure | $t_{ret}$ [min] | [M + H]$^+$ | HPLC method |
|---|---|---|---|---|---|
| E-4r | C | 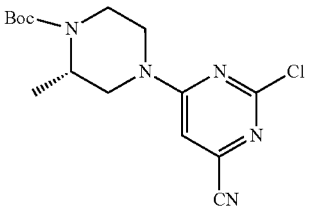 [SMILES: C[C@H]1CN(c2cc(C#N)nc(Cl)n2)CCN1C(=O)OC(C)(C)C] | 1.43 | 338 | A |
| E-4s | C | 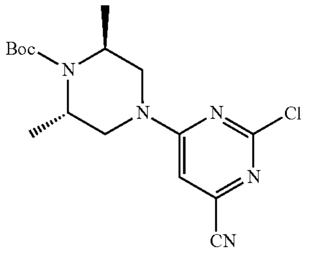 [SMILES: C[C@H]1CN(c2cc(C#N)nc(Cl)n2)C[C@H](C)N1C(=O)OC(C)(C)C] | 1.49 | 352 | A |
| E-4t | C | 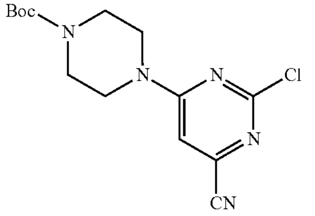 [SMILES: CC(C)(C)OC(=O)N1CCN(c2cc(C#N)nc(Cl)n2)CC1] | 0.72 | 324 | F |
| E-4u | B | 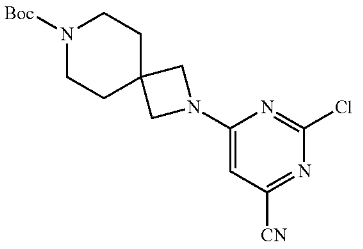 [SMILES: CC(C)(C)OC(=O)N1CCC2(CC1)CN(c1cc(C#N)nc(Cl)n1)C2] | 0.76 | 364 | B |
| E-4v | B | 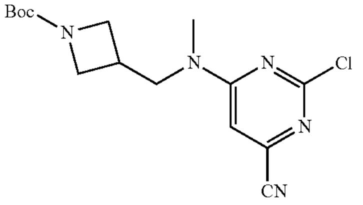 [SMILES: CN(CC1CN(C(=O)OC(C)(C)C)C1)c1cc(C#N)nc(Cl)n1] | 1.34 | 338 | A |
| E-4w | B | 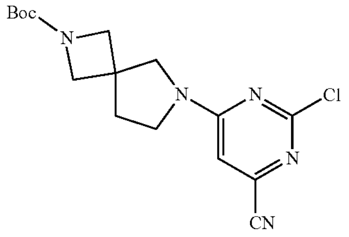 [SMILES: CC(C)(C)OC(=O)N1CC2(CCN(c3cc(C#N)nc(Cl)n3)C2)C1] | 1.42 | 350 | A |

TABLE 6-continued
| # | method | structure | $t_{ret}$ [min] | $[M + H]^+$ | HPLC method |
|---|---|---|---|---|---|
| E-4x | B | 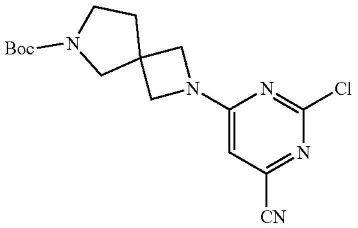 [SMILES: CC(C)(C)OC(=O)N1CCC2(C1)CN(c1cc(C#N)nc(Cl)n1)C2] | 1.40 | 350 | A |
| E-4y | B | 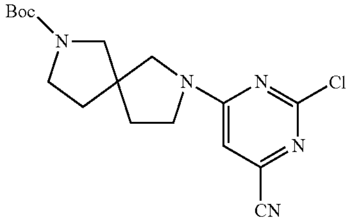 [SMILES: CC(C)(C)OC(=O)N1CCC2(CCN(c3cc(C#N)nc(Cl)n3)C2)C1] | 1.41 | 364 | A |
| E-4z | B | 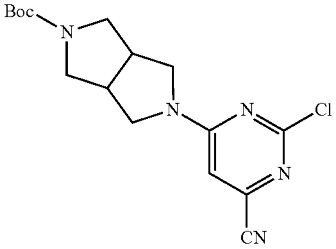 [SMILES: CC(C)(C)OC(=O)N1CC2CN(c3cc(C#N)nc(Cl)n3)CC2C1] | 0.70 | 350 | A |
| E-4aa | B | 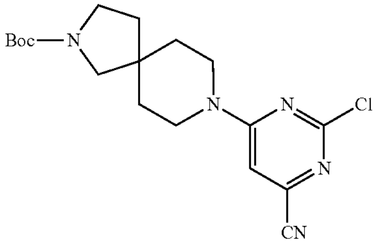 [SMILES: CC(C)(C)OC(=O)N1CCC2(CCN(c3cc(C#N)nc(Cl)n3)CC2)C1] | 1.47 | 376 | A |
| E-4ab | B | 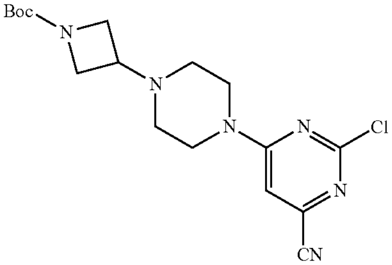 [SMILES: CC(C)(C)OC(=O)N1CC(N2CCN(c3cc(C#N)nc(Cl)n3)CC2)C1] | 1.34 | 377 (M − H) | A |
| E-4ac | B | 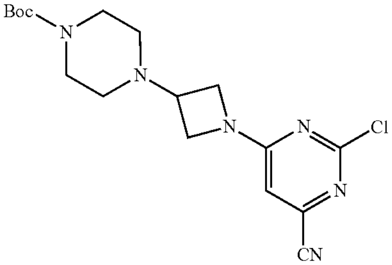 [SMILES: CC(C)(C)OC(=O)N1CCN(C2CN(c3cc(C#N)nc(Cl)n3)C2)CC1] | 1.31 | 377 (M − H) | A |

TABLE 6-continued
| # | method | structure | $t_{ret}$ [min] | $[M + H]^+$ | HPLC method |
|---|---|---|---|---|---|
| E-4ad | B | 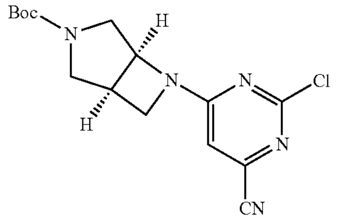 [SMILES: CC(C)(C)OC(=O)N1C[C@@H]2CN(c3cc(C#N)nc(Cl)n3)[C@@H]2C1] | 1.28 | 336 | A |
| E-4ae | B | 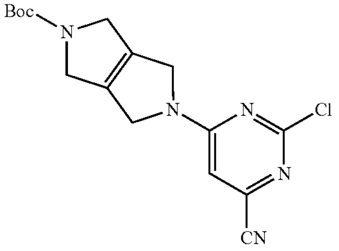 [SMILES: CC(C)(C)OC(=O)N1CC2=C(C1)CN(c1cc(C#N)nc(Cl)n1)C2] | 1.57 | 346 | A |
| E-4af | B | 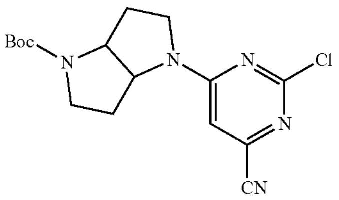 [SMILES: CC(C)(C)OC(=O)N1CCC2C1CCN2c1cc(C#N)nc(Cl)n1] | 1.42 | 350 | A |
| E-4ag | B | 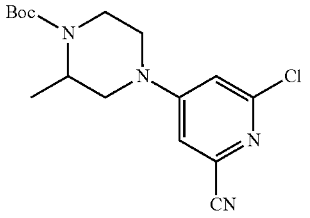 [SMILES: CC1CN(c2cc(Cl)nc(C#N)c2)CCN1C(=O)OC(C)(C)C] | 1.36 | 337 | A |
| E-4ah | B | 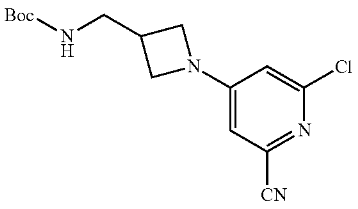 [SMILES: CC(C)(C)OC(=O)NCC1CN(c2cc(Cl)nc(C#N)c2)C1] | 1.19 | 323 | A |
| E-4ai | B | 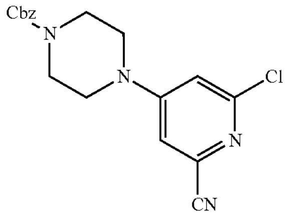 [SMILES: N#Cc1cc(N2CCN(C(=O)OCc3ccccc3)CC2)cc(Cl)n1] | 0.72 | 357 | B |
| E-4aj | A | 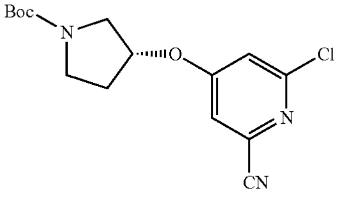 [SMILES: CC(C)(C)OC(=O)N1CC[C@@H](Oc2cc(Cl)nc(C#N)c2)C1] | 0.72 | 324 | F |

TABLE 6-continued
| # | method | structure | $t_{ret}$ [min] | [M + H]$^+$ | HPLC method |
|---|---|---|---|---|---|
| E-4ak | B | 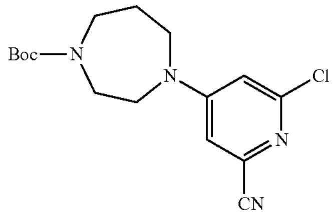 [SMILES: CC(C)(C)OC(=O)N1CCCN(c2cc(Cl)nc(C#N)c2)CC1] | 1.22 | 337 | A |
| E-4al | B | 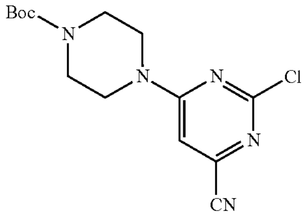 [SMILES: CC(C)(C)OC(=O)N1CCN(c2cc(C#N)nc(Cl)n2)CC1] | 0.72 | 324 | F |
| E-4am | B | 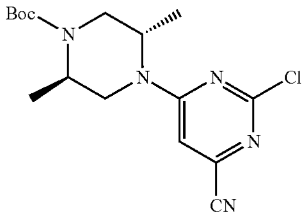 [SMILES: C[C@@H]1CN(c2cc(C#N)nc(Cl)n2)[C@@H](C)CN1C(=O)OC(C)(C)C] | 1.48 | 352 | A |
| E-4an | B | 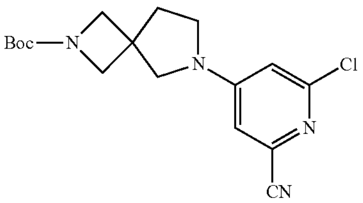 [SMILES: CC(C)(C)OC(=O)N1CC2(CCN(c3cc(Cl)nc(C#N)c3)C2)C1] | 1.29 | 349 | A |
| E-4ao | A | 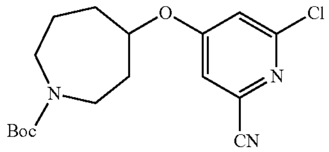 [SMILES: CC(C)(C)OC(=O)N1CCCC(Oc2cc(Cl)nc(C#N)c2)CC1] | 1.39 | 350 | A |
| E-4ap | A | 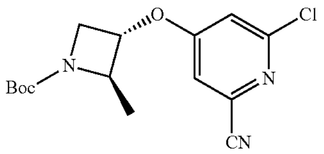 [SMILES: C[C@@H]1[C@@H](Oc2cc(Cl)nc(C#N)c2)CN1C(=O)OC(C)(C)C] | 0.77 | 324 | F |
Experimental Procedure for the Synthesis of E-6a
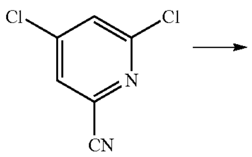
E-1b
-continued
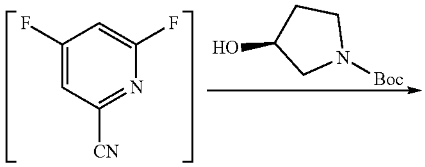
E-5a -continued

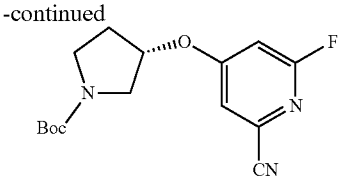

E-6a

E-1b (500 mg, 2.83 mmol, 1.0 eq.) and cesium fluoride (1.72 g, 11.33 mmol, 4.0 eq.) are dissolved in DMA (5 mL) and heated to 110° C. by microwave irradiation. The mixture is filtered and the solid is washed with a small amount of DMA to give a crude solution of E-5a in DMA.

To a solution of(S)-3-hydroxy-pyrrolidine-1-carboxylic acid tert-butyl ester (531 mg, 187.24 mmol, 1.0 eq.) in THF (5 mL) is added sodium hydride (158 mg, 3.97 mmol, 1.4 eq.) and the mixture is stirred for 30 min. This mixture is added slowly to the freshly prepared solution of E-5a (397 mg, 140.09 mmol, 1.0 eq.) in DMA and stirred for 5 min before water and EtOAc are added. The phases are separated and the aqueous phase is extracted twice with EtOAc (30 mL). The combined organic layer is dried with $MgSO_4$, filtered and the solvents are evaporated. The mixture is dissolved in acetonitrile and water and purified by acidic reversed phase chromatography to give the desired product E-6a.

The following intermediates E-6 (table 7) are available in an analogous manner. The crude product E-7 is purified by chromatography if necessary.

TABLE 7

| # | structure | $t_{ret}$ [min] | [M + H]+ | HPLC method |
|---|---|---|---|---|
| E-6a | 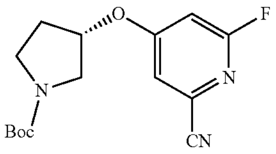 [SMILES: CC(C)(C)OC(=O)N1CC[C@H](Oc2cc(F)nc(C#N)c2)C1] | 1.32 | 308 | A |
| E-6b | 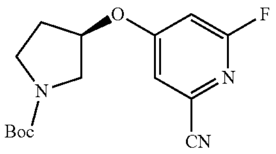 [SMILES: CC(C)(C)OC(=O)N1CC[C@@H](Oc2cc(F)nc(C#N)c2)C1] | 0.68 | 252 (M − tBu) | F |
| E-6c | 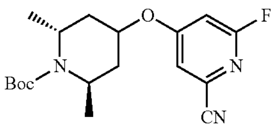 [SMILES: C[C@@H]1CC(Oc2cc(F)nc(C#N)c2)C[C@@H](C)N1C(=O)OC(C)(C)C] | 1.52 | 294 | A |

Experimental Procedure for the Synthesis of E-6d

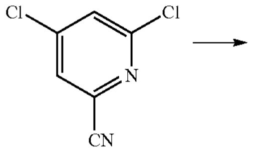

E-1b

-continued

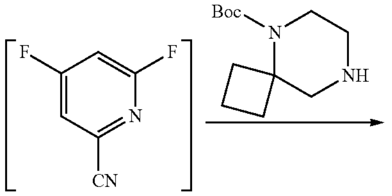

E-5a

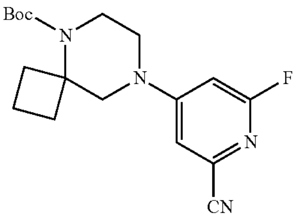 [SMILES: CC(C)(C)OC(=O)N1CCN(c2cc(F)nc(C#N)c2)CC12CCC2]

E-6d

E-1b (267 mg, 1.54 mmol, 1.0 eq.) and cesium fluoride (937 mg, 6.17 mmol, 4.0 eq.) are dissolved in DMA (3 mL) and heated to 110° C. by microwave irradiation. The mixture is filtered and the solid is washed with a small amount of DMA to give a crude solution of E-5a in DMA. Tert-butyl 5,8-diazaspiro[3.5]nonane-4-carboxylate (349 mg, 1.54 mmol, 1.0 eq.) and DIPEA (0.667 mL, 3.86 mmol, 2.5 eq.) are added to the mixture which is stirred at 60° C. for 30 min. The mixture is filtered and the filtrate purified by basic reversed phase chromatography to give the desired product E-6d.

The following intermediates E-6 (table 8) are available in an analogous manner. The crude product E-6 is purified by chromatography if necessary.

TABLE 8

| # | structure | $t_{ret}$ [min] | [M + H]+ | HPLC method |
|---|---|---|---|---|
| E-6d | 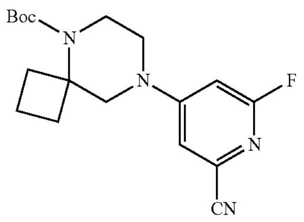 | 0.77 | 347 | G |
| E-6e | 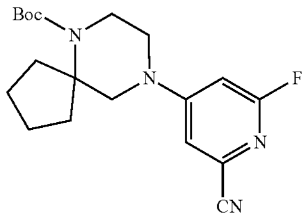 [SMILES: CC(C)(C)OC(=O)N1CCN(c2cc(F)nc(C#N)c2)CC12CCCC2] | 0.80 | 361 | G |

Experimental Procedure for the Synthesis of E-6f

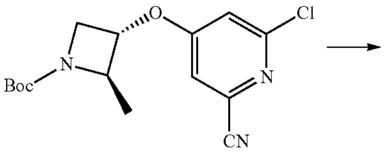

E-4ap

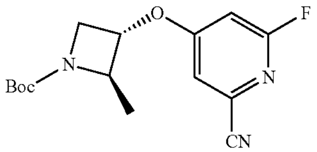

E-6f

Intermediate E-4ap (60 mg, 0.19 mmol, 1.0 eq.) and cesium fluoride (56 mg, 0.37 mmol, 2.0 eq.) are dissolved in DMSO (2 mL) and stirred at 80° C. over night and cooled to rt. Additional cesium fluoride (56 mg, 0.37 mmol, 2.0 eq.) is added and the mixture is stirred at 110° C. to complete the reaction. Water and acetonitrile are added and the mixture is purified by acidic reversed phase chromatography to give the desired product E-6f.

The following intermediates E-6 (table 9) are available in an analogous manner from other intermediates E-4. The crude product E-6 is purified by chromatography if necessary.

TABLE 9

| # | structure | $t_{ret}$ [min] | $[M + H]^+$ | HPLC method |
|---|---|---|---|---|
| E-6f | 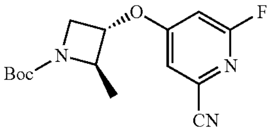 [SMILES: C[C@@H]1[C@@H](Oc2cc(F)nc(C#N)c2)CN1C(=O)OC(C)(C)C] | 0.73 | 308 | F |
| E-6g | 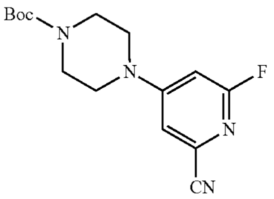 [SMILES: CC(C)(C)OC(=O)N1CCN(c2cc(F)nc(C#N)c2)CC1] | 1.26 | 307 | A |

Synthesis of Various Building Blocks H-$R^5$

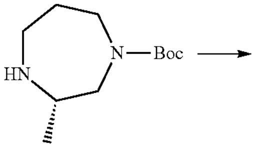

G-1a

-continued

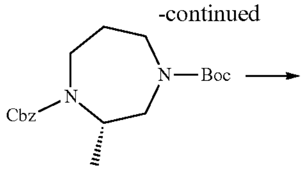

G-2a

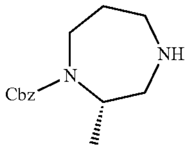

G-3a

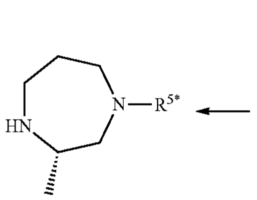

G-5
(= building block
H—$R^5$)

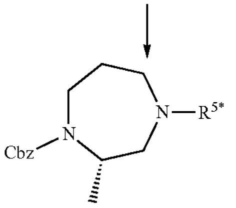

G-4

Experimental Procedure for the Synthesis of G-2a

G-1a (500 mg, 2.33 mmol) is dissolved in dry THF (5.00 mL) together with triethylamine (485 μL, 3.5 mmol, 1.5 eq.) and the mixture is cooled to 0° C. Benzyl chlorformate (519 μL, 3.5 mmol, 1.5 eq.) is added portionwise and the mixture is stirred for 2 h and allowed to reach rt over night. After complete conversion water is added to the mixture and the product is extracted with DCM and the combined extracts are dried, filtered and concentrated. The crude product is used for the next step without further purification. (HPLC method B, $t_{ret}$=0.766 min, $[M+H]^+$=249/293).

Experimental Procedure for the Synthesis of G-3a

G-2a (813 mg, 2.33 mmol) is dissolved in DCM (25.00 mL) and treated with HCl (4 M in dioxane, 11.67 mL, 46.66 mmol, 20.0 eq.). The mixture is stirred for 2 h at rt. After complete conversion the mixture is concentrated and the product is isolated via basic reversed phase chromatography (gradient elution: 10% to 70% acetonitrile in water). (HPLC method B, $t_{ret}$=0.478 min, $[M+H]^+$=249).

Experimental Procedure for the Synthesis of G-4a (Method F)

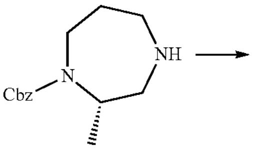

G-3a

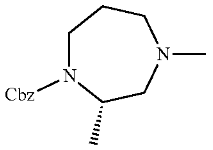

G-4a

G-3a (4.0 g, 16.12 mmol) is dissolved in dry DCM (50.00 mL) and treated with formaldehyde (37% in water, 1.21 mL, 16.12 mmol, 1.00 eq.) and acetic acid (92 μL, 1.61 mmol, 0.10 eq.). The mixture is stirred for 15 min and then sodium triacetoxyborohydride (6.335 g, 29.00 mmol, 1.80 eq.) is added and the mixture is stirred for 1 h at rt. After complete conversion water is added to the mixture and the product is extracted with DCM and the combined extracts are dried, filtered and concentrated. The crude product is purified via normal phase chromatography (DCM/MeOH).

Experimental Procedure for the Synthesis of G-4b (Method G)

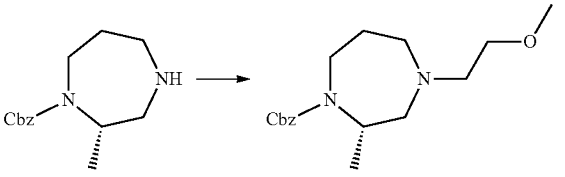

G-3a G-4b

To a stirred solution of G-3a (250.0 mg, 1.00 mmol) in dry DMF (5.00 mL), $K_2CO_3$ (0.303 g, 2.51 mmol, 2.50 eq.) is added followed by 1-bromo-2-methoxy-ethane (0.122 g, 1.00 mmol, 1.00 eq.). The reaction mixture is stirred at 80° C. for 16 h. After complete conversion water is added to the mixture and the product is extracted with EtOAc and the combined extracts are dried, filtered, and concentrated. The crude product is purified via normal phase chromatography (DCM/MeOH).

The following (additional) intermediates G-4 (table 10) are available in an analogous manner using G-3a and different aldehydes or ketones as alkylating agents according to methods F or G. The crude products G-4 can be purified by chromatography if necessary.

TABLE 10

| # | structure | method | $t_{ret}$ [min] | $[M+H]^+$ | HPLC method |
|---|---|---|---|---|---|
| G-4a | 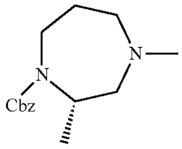 [SMILES: C[C@H]1CN(C)CCCN1C(=O)OCc1ccccc1] | A | 0.557 | 263 | B |
| G-4b | 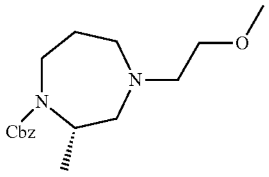 [SMILES: COCCN1CCCN(C(=O)OCc2ccccc2)[C@@H](C)C1] | B | n.a. | n.a. | — |
| G-4c | 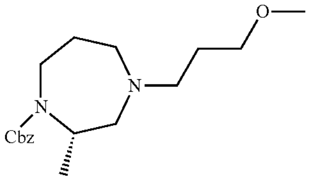 [SMILES: COCCCN1CCCN(C(=O)OCc2ccccc2)[C@@H](C)C1] | B | n.a. | n.a. | — |
| G-4d | 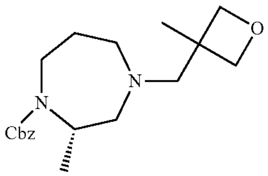 [SMILES: C[C@H]1CN(CC2(C)COC2)CCCN1C(=O)OCc1ccccc1] | A | 1.34 | 333 | A |
| G-4e | 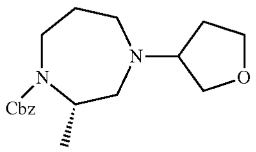 [SMILES: C[C@H]1CN(C2CCOC2)CCCN1C(=O)OCc1ccccc1] | A | 1.20 | 319 | A |

Experimental Procedure for the Synthesis of G-5a

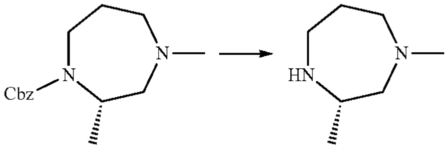

G-4a G-5a

G-5a (3.00 g, 11.44 mmol) is dissolved in MeOH (20.0 mL) and palladium (10% on carbon, 360 mg) is added. The mixture is stirred in a hydrogenation reactor under 5 bar of hydrogen pressure for 16 h at rt. After complete conversion the catalyst is filtered off and the residue is concentrated. The crude product is used for the following step without purification.

The following intermediates G-5 (A building bocks H—$R^5$; table 11) are available in an analogous manner using differently substituted analogues G-4.

TABLE 11

| # | structure | $t_{ret}$ [min] | [M + H]+ | HPLC method |
|---|---|---|---|---|
| G-5a | 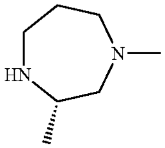 | broad | 129 | A |
| G-5b | 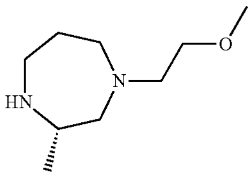 | n.a. | n.a. | — |
| G-5c | 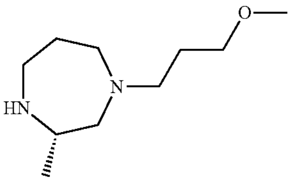 | n.a. | n.a. | — |
| G-5d | 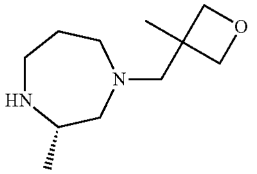 | 0.43 | 199 | A |
| G-5e | 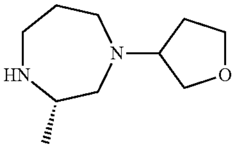 | 0.35 | 185 | A |

Experimental Procedure for the Synthesis of G-7a

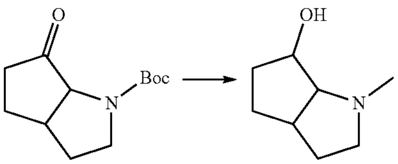

G-6a G-7a

G-6a (590.0 mg, 2.49 mmol) is dissolved in dry THF (1.50 mL) and the mixture is cooled to 0° C. $LiAlH_4$ (2 M in THF, 6.22 mL, 12.44 mmol, 5.00 eq.) is added dropwise and the mixture is stirred in a closed vessel for 1.5 h at 70° C. After complete conversion the mixture is diluted with THF (15 mL), potassium sodium tartrate tetrahydrate is slowly added and the mixture is stirred for 1.5 h at rt. The mixture is filtered, the filtrate is concentrated and the crude product is used for the following step without purification.

The following intermediates G-7 (≙ building bocks H—$R^5$; table 12) are available in an analogous manner starting from the corresponding N-Boc-amino ketones G-6.

TABLE 12

| # | structure | $t_{ret}$ [min] | [M + H]+ | HPLC method |
|---|---|---|---|---|
| G-7a | 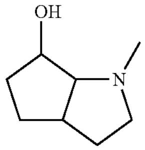 | 0.28 | 142 | A |
| G-7b | 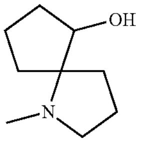 | 0.30 | 156 | A |
| G-7c | 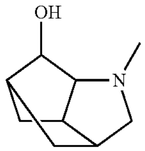 | 0.30 | 154 | A |

Experimental Procedure for the Synthesis of E-10a

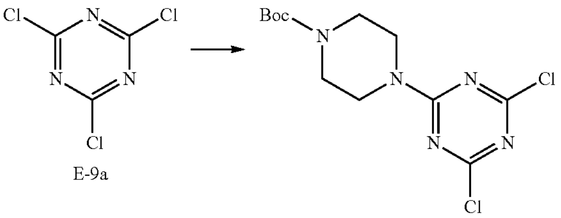

E-9a E-10a

To E-9a (500 mg, 2.71 mmol, 1.0 eq.) in acetone (11 mL) at 0° C. is added a solution of piperazine-1-carboxylic acid tert-butyl ester (505 mg, 2.71 mmol; 1.0 eq.) in acetone (6 mL). An aqueous solution of sodium bicarbonate (225.00 mg, 2.12 mmol; 0.78 eq.) in water (5 mL) is added and the reaction is stirred at 0° C. for 3 h. The reaction mixture is filtered and the solid washed with water and dried to afford the desired compound E-10a (HPLC method A, $t_{ret}$=1.47 min, $[M+H]^+$=334).

Experimental Procedure for the Synthesis of E-11a

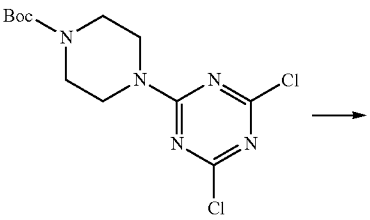

E-10a

-continued

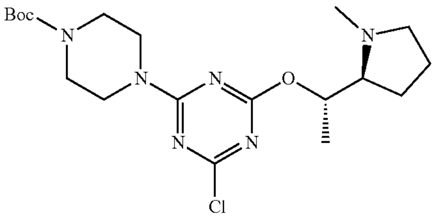

E-11a

E-10a (1.04 g, 3.11 mmol, 1.0 eq.), (S)-1-((S)-1-methylpyrrolidin-2-yl) ethan-1-ol (561.41 mg, 4.05 mmol, 1.3 eq.) and DIPEA (808.47 mg, 6.22 mmol, 2.0 eq.) are dissolved in anhydrous THF (12 mL) and stirred at rt for 3 h, then at 40° C. for 1 h. The solvent is removed in vacuo and the residue is purified by normal phase chromatography (cyclohexane:EtOAc from 10:90→80:20) to afford E-11a (HPLC method A, $t_{ret}$=1.54 min, $[M+H]^+$=427).

Experimental Procedure for the Synthesis of E-8a

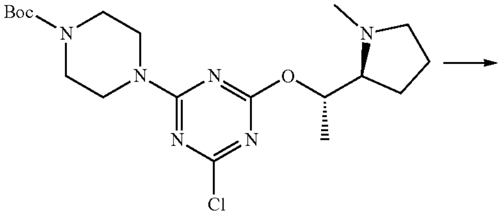

E-11a

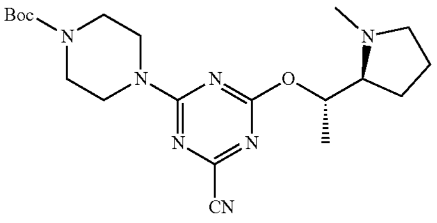

E-8a

E-11a (898 mg, 1.68 mmol, 1.0 eq.) and sodium cyanide (329.85 mg, 6.73 mmol, 4.0 eq.) are dissolved in DMSO (5 mL) and stirred at 60° C. for 3 h. The solvent is removed and the residue purified by reverse phase chromatography to afford the desired compound E-8a (HPLC method A, $t_{ret}$=1.53 min, $[M+H]^+$=418)

Experimental Procedure for the Synthesis of E-8b

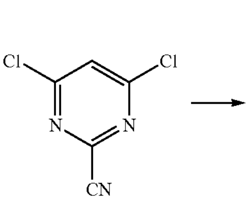

E-1a

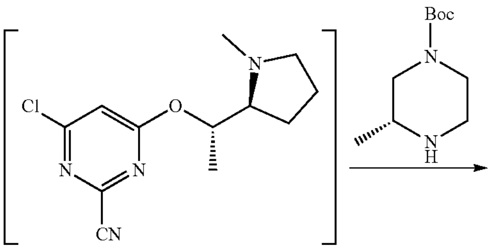

E-2a

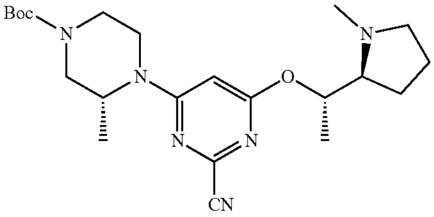

E-8b

To a solution of(S)-1-((S)-1-methylpyrrolidin-2-yl) ethan-1-ol (792 mg, 6.13 mmol, 1.1 eq.) and DIPEA (1.94 mL, 11.15 mmol, 2 eq.) in DMSO (3 mL) is slowly added a solution of E-1a (1000 mg, 97% purity, 5.58 mmol, 1.0 eq.) in DMSO (3 mL). The mixture is stirred at rt for 30 min. After full conversion of the starting materials is observed tert-butyl (R)-3-methylpiperazine-1-carboxylate (1.50 mg, 97% purity, 7.25 mmol, 1.3 eq.) and DIPEA (0.97 mL, 5.58 mmol, 1 eq.) are added to the mixture. The mixture is stirred at 60° C. for 60 min and DIPEA (0.97 mL, 5.58 mmol, 1 eq.) is added. The mixture is stirred at 70° C. for 50 min and at rt over night. After full conversion is observed the reaction is diluted with water and DCM and the phases are separated. The aqueous phase is extracted with DCM (3×) and the organic phases are combined. The solvent is removed under vacuum to give the crude product E-8a. The crude product is dissolved in acetonitrile and water, filtered and purified by basic reversed phase chromatography (gradient elution: 35% to 95% acetonitrile in water) to give the desired purified product E-8b.

The following intermediates E-8 (table 13) are available in an analogous manner without isolation of the corresponding intermediates E-2. The crude product E-8 is purified by chromatography if necessary.

TABLE 13

| # | structure | $t_{ret}$ [min] | [M + H]$^+$ | HPLC method |
| --- | --- | --- | --- | --- |
| E-8b | 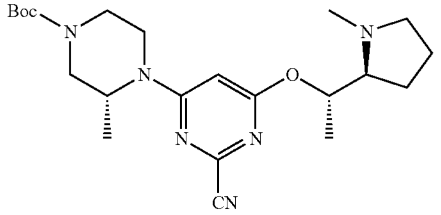 [SMILES: C[C@H](Oc1cc(N2CCN(C(=O)OC(C)(C)C)C[C@H]2C)nc(C#N)n1)[C@@H]1CCCN1C] | 1.62 | 431 | A |
| E-8c | 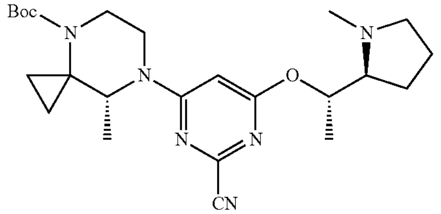 [SMILES: C[C@H](Oc1cc(N2CCN(C(=O)OC(C)(C)C)C3(CC3)[C@H]2C)nc(C#N)n1)[C@@H]1CCCN1C] | 1.67 | 443 | A |

Experimental Procedure for the Synthesis of E-8d

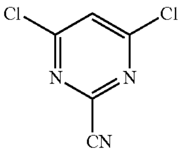

E-1a

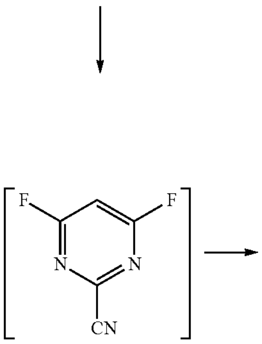

E-5b

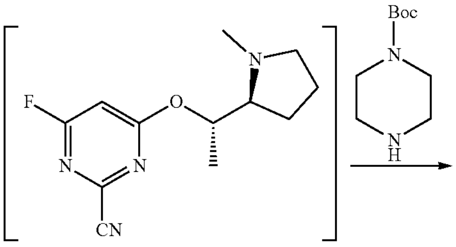

E-7a

-continued

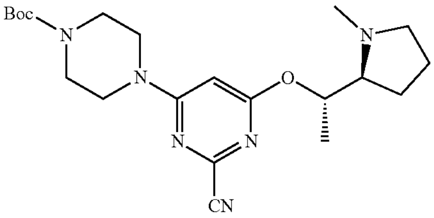

E-8d

To a solution of E-1a (600 mg, 3.21 mmol, 93% purity, 1.0 eq.) in anhydrous DMSO (6 mL) is added cesium fluoride (1.218 g, 8.02 mmol, 2.5 eq.) and the resulting mixture is stirred at rt for 1 h until full conversion of the staring material is observed. The resulting suspension is filtered and the filtered solid is washed with anhydrous DMSO (2 mL). The filtrate (8 mL) is added to(S)-1-((S)-1-methylpyrrolidin-2-yl) ethan-1-ol (453 mg, 3.51 mmol, 1.1 eq.) and DIPEA (1.085 mL, 6.38 mmol, 2 eq.) is added. The mixture is stirred at rt for 1 h. After full conversion of the starting materials is observed a solution of tert-butyl piperazine-1-carboxylate (674 mg, 3.51 mmol, 97% purity, 1.1. eq.) in anhydrous DMSO (3 mL) and DIPEA (1.085 mL, 6.38 mmol, 2 eq.) is added to the mixture. The mixture is stirred at rt for 30 min. After full conversion is observed the reaction is diluted with acetonitrile and water, filtered and purified by basic reversed phase chromatography (gradient elution: 30% to 98% acetonitrile in water) to give the desired product E-8d.

The following intermediates E-8 (table 14) are available in an analogous manner without isolation of the corresponding intermediates E-5 and E-7, respectively. The crude product E-8 is purified by chromatography if necessary.

TABLE 14

| # | structure | $t_{ret}$ [min] | $[M + H]^+$ | HPLC method |
|---|---|---|---|---|
| E-8d | 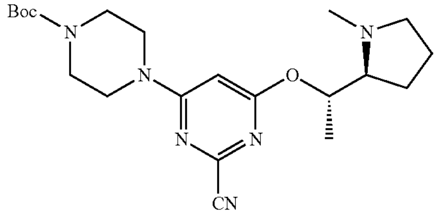 | 1.55 | 417 | A |
| E-8e | 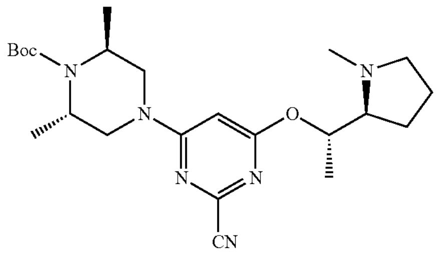 | 1.67 | 445 | A |
| E-8f | 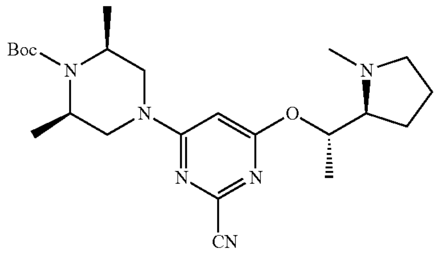 [SMILES: C[C@H](Oc1cc(N2C[C@@H](C)N(C(=O)OC(C)(C)C)[C@@H](C)C2)nc(C#N)n1)[C@@H]1CCCN1C] | 1.66 | 445 | A |

Experimental Procedure for the Synthesis of E-8g (Method A)

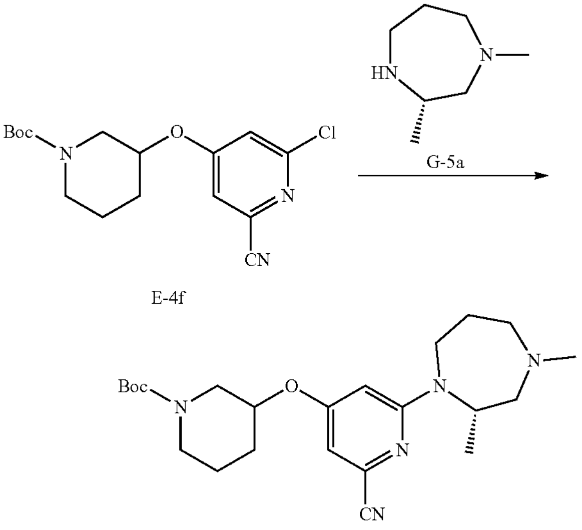

E-4f

E-8g

E-4f (50.0 mg, 0.148 mmol), G-5a (115 mg, 0.740 mmol, 5.0 eq.) and DIPEA (25.78 μL, 0.15 mmol, 1.0 eq.) are combined with dry NMP (10 μL) and the mixture is stirred in a closed vessel for 1 h at 120° C. The product is isolated via basic reversed phase chromatography (gradient elution: 40% to 98% acetonitrile in water) yielding E-8g.

Intermediates E-8 marked "A" (table 15) are available in an analogous manner. The crude product E-8 is purified by chromatography if necessary.

Experimental Procedure for the Synthesis of E-8h (Method B)

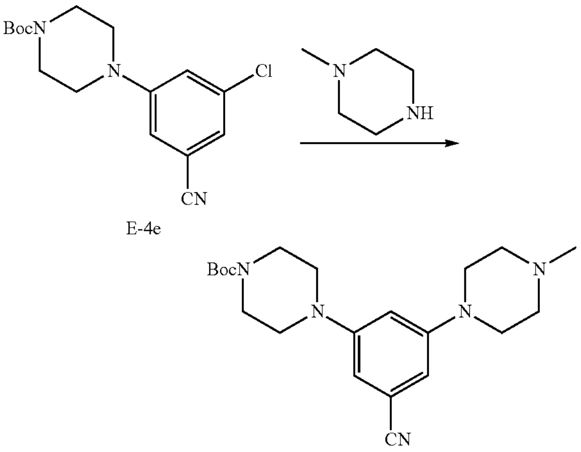

E-4e

E-8h

E-4e (400.0 mg, 1.24 mmol), N-methylpiperazine (352.1 mg, 3.48 mmol, 2.8 eq.), sodium tert-butoxide (246.3 mg, 2.49 mmol, 2.0 eq.), 2-(di-tert-butylphosphino) biphenyl (74.18 mg, 0.25 mmol, 0.20 eq.), and tris(dibenzylideneacetone) dipalladium (0) (56.9 mg, 0.062 mmol, 0.05 eq.) are combined in dry dioxane (2.50 mL) and the mixture is stirred for 1 h at 110° C. After complete conversion the mixture is concentrated, diluted with water, the product is extracted with DCM and the combined organic layers are dried, filtered, and concentrated.

The crude product is purified via basic reversed phase chromatography (gradient elution: 35% to 98% acetonitrile in water) yielding E-8h.

The intermediates E-8 marked "B" (table 15) are available in an analogous manner. The crude product E-8 is purified by chromatography if necessary.

Experimental Procedure for the Synthesis of E-8i (Method C)

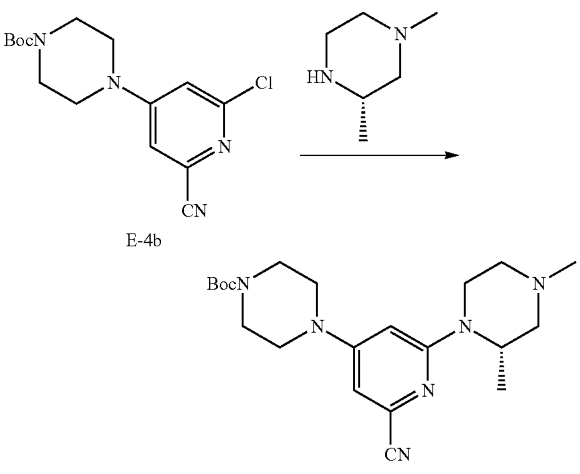

E-4b

E-8i

E-4b (1.00 g, 3.10 mmol), (S)-1,3-dimethylpiperazine (0.99 g, 8.67 mmol, 2.80 eq.), tris(dibenzylideneacetone) dipalladium (0) (141.85 mg, 0.154 mmol, 0.05 eq.), xantphos (184.80 mg, 0.31 mmol, 0.10 eq.), cesium carbonate (2.019 g, 6.196 mmol, 2.00 eq.) and dry dioxane (8.00 mL) are combined and stirred in a closed vessel under argon atmosphere for 16 h at 110° C. After complete conversion brine is added to the mixture and the product is extracted with DCM. The combined organic phases are dried, filtered and concentrated under reduced pressure. The crude product is purified via basic reversed phase chromatography (gradient elution: 30% to 98% acetonitrile in water) yielding E-8i.

The intermediates E-8 marked "C" (table 15) are available in an analogous manner. The crude product E-8 is purified by chromatography if necessary.

Experimental Procedure for the Synthesis of E-8j (Method D)

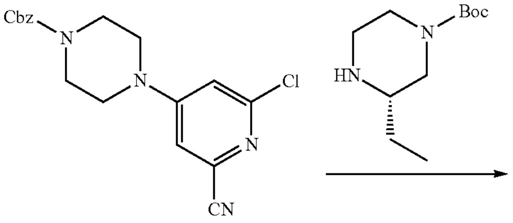

E-4g

-continued

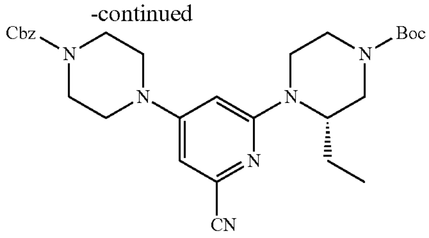

E-8j

E-4g (3.035 g, 8.51 mmol), tert-butyl(S)-3-ethylpiperazine-1-carboxylate (3.645 g, 17.01 mmol, 2.00 eq.), tris (dibenzylideneacetone) dipalladium (0) (778.82 mg, 0.850 mmol, 0.10 eq.), 1,3-bis(2,6-di-i-propylphenyl) imidazolium chloride (723.0 mg, 1.701 mmol, 0.20 eq.), cesium carbonate (8.313 g, 25.514 mmol, 3.00 eq.) and dry dioxane (32.00 mL) are combined and stirred in a closed vessel under argon atmosphere for 16 h at 110° C. After complete conversion brine is added to the mixture and the product is extracted with DCM. The combined organic phases are dried, filtered and concentrated under reduced pressure. The crude product is purified via basic reversed phase chromatography (gradient elution: 30% to 98% acetonitrile in water) yielding E-8j.

Intermediates E-8 marked "D" (table 15) are available in an analogous manner. The crude product E-8 is purified by chromatography if necessary.

Experimental Procedure for the Synthesis of E-8k (Method E)

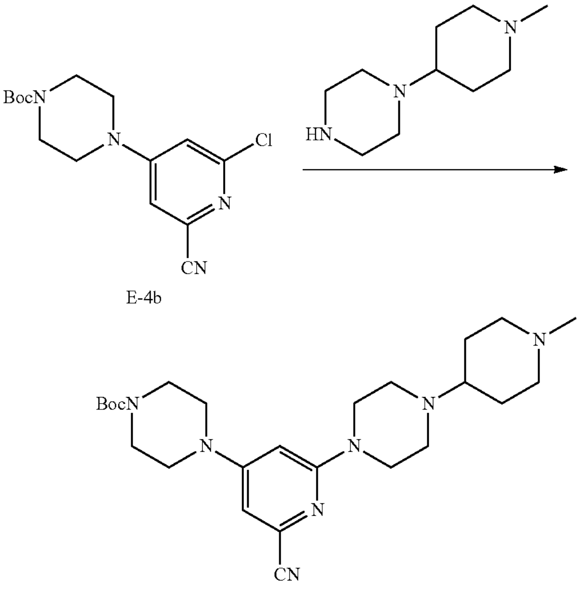

E-4b

E-8k

E-4b (400 mg, 1.239 mmol), 1-(1-methylpiperidin-4-yl) piperazine (273.0 mg, 1.49 mmol, 1.20 eq.), RuPhos Pd G3 (106.0 mg, 0.120 mmol, 0.10 eq.), potassium phosphate tribasic (553.0 mg, 2.605 mmol, 2.10 eq.) and dry dioxane (3.10 mL) are combined and stirred in a closed vessel under argon atmosphere for 2 h at 85° C. After complete conversion the mixture is diluted with DCM and filtered. The crude mixture is purified via normal phase chromatography ($DCM/MeOH/NH_3$) yielding E-8k.

Intermediates E-8 marked "E" (table 15) are available in an analogous manner. The crude product E-8 is purified by chromatography if necessary.

Experimental procedure for the synthesis of E-81 (Method F)

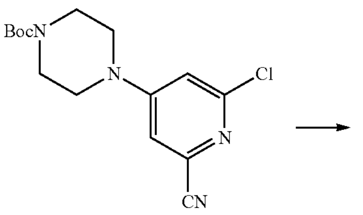

E-4b

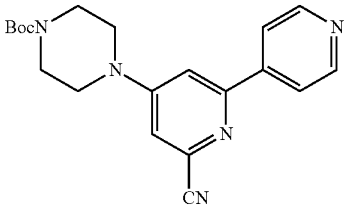

E-81

E-4b (100 mg, 0.31 mmol), pyridine-4-boronic acid (45.70 mg, 0.37 mmol, 1.20 eq.), RuPhos Pd G3 (27.3 mg, 0.031 mmol, 0.10 eq.), potassium phosphate tribasic (138.1 mg, 0.65 mmol, 2.10 eq.) and dry dioxane (0.9 mL) are combined and stirred in a closed vessel under argon atmosphere for 1 h at 80° C. After complete conversion the mixture is concentrated. The crude product is purified via basic reversed phase chromatography yielding E-81.

Intermediates E-8 marked "F" (table 15) are available in an analogous manner. The crude product E-8 is purified by chromatography if necessary.

Experimental Procedure for the Synthesis of E-8m (Method G)

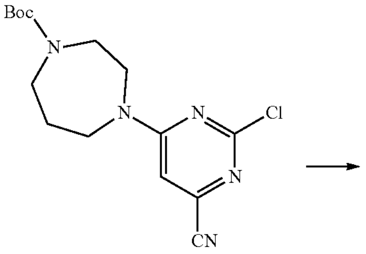

E-4i

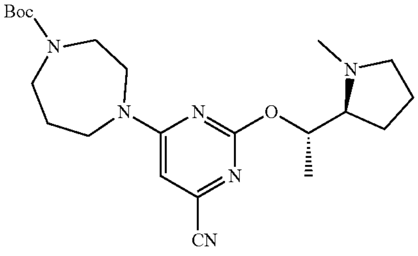

E-8m

To a mixture of DIPEA (736.3 μL, 4.23 mmol, 3 eq.) and E-4i (560 mg, 1.41 mmol, 85% purity, 1 eq.) in DMSO (1 mL) is added(S)-1-((S)-1-methylpyrrolidin-2-yl) ethan-1-ol (922 mg, 5.64 mmol, 79% purity, 4.0 eq.) and the mixture is stirred at 100° C. for 16 h. The mixture is cooled to rt, diluted with acetonitrile and water, filtered and purified by acidic reversed phase chromatography (gradient elution: 10% to 98% acetonitrile in water) to give the desired product E-8m.

Intermediates E-8 marked "G" (table 15) are available in an analogous manner. The crude product E-8 is purified by chromatography if necessary.

Experimental Procedure for the Synthesis of E-8n (Method H)

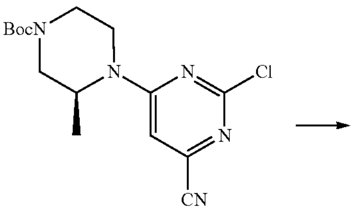

E-4k

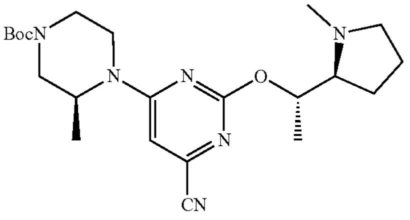

E-8n

A mixture of E-4k (1.50 g, 4.44 mmol, 1.0 eq.) and(S)-1-((S)-1-methylpyrrolidin-2-yl) ethan-1-ol (688 mg, 5.33 mmol, 1.2 eq.) in THF (45 mL) is cooled to 0° C. Sodium tert-butoxide (854 mg, 8.88 mmol, 2.0 eq.) is added at 0° C. to the mixture. The mixture is slowly warmed to rt and stirred for 2 h at rt. The reaction is quenched by the addition of cold water and EtOAc. The phases are separated and the aqueous layer is extracted with EtOAc. The combined organic layers are washed with brine solution and concentrated under vacuum. The crude product is purified by normal phase chromatography (2% MeOH in DCM) to give the desired product E-8n.

Intermediates E-8 marked "H" (table 15) are available in an analogous manner. The crude product E-8 is purified by chromatography if necessary.

Experimental Procedure for the Synthesis of E-80 (Method I)

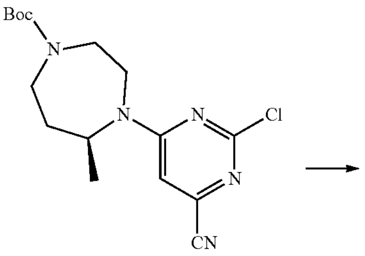

E-4l

-continued

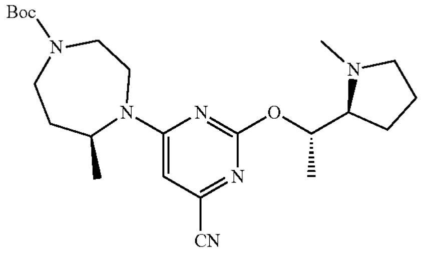

E-8o

A solution of(S)-1-((S)-1-methylpyrrolidin-2-yl) ethan-1-ol (312 mg, 2.42 mmol, 1.7 eq.) in THF (3 mL) is cooled to 0° C. and sodium hydride (74 mg, 1.85 mmol, 1.3 eq.) is added portion wise over 10 min. To the mixture is slowly added a solution of E-41 (500 mg, 1.42 mmol, 1.0 eq.) in THF (5 mL) and the mixture is stirred for 18 h. The reaction is quenched by the addition of saturated aqueous ammonium chloride solution. The mixture is extracted with a mixture of DCM and MeOH (9:1). The phases are separated and the organic layer is concentrated under vacuum. The crude product is purified by normal phase chromatography (2% MeOH in DCM) to give the desired product E-80.

The intermediates E-8 marked "I" (table 15) are available in an analogous manner. The crude product E-8 is purified by chromatography if necessary.

Experimental Procedure for the Synthesis of E-8p (Method J)

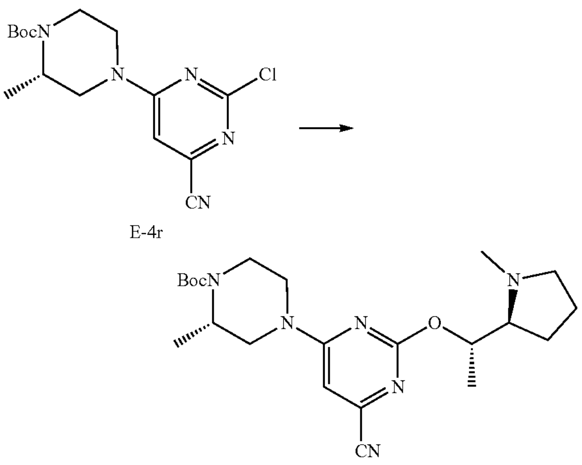

E-4r

E-8p

To a mixture of E-4r (200 mg, 0.59 mmol, 1.0 eq.) and(S)-1-((S)-1-methylpyrrolidin-2-yl) ethan-1-ol (91.8 mg, 0.71 mmol, 1.2 eq.) in acetonitrile (1.5 mL) is added trimethylamine (149.8 mg, 1.48 mmol, 2.5 eq.). The mixture is stirred at 40° C. for 2 h. The mixture is stirred at 80° C. for 16 h. The solvent is removed under reduced pressure and the crude product is purified by normal phase chromatography (gradient elution: 0% to 90% MeOH in DCM+ammonia) to give the desired product E-8p.

Intermediates E-8 marked "J" (table 15) are available in an analogous manner. The crude product E-8 is purified by chromatography if necessary.

TABLE 15

| # | method | structure | $t_{ret}$ [min] | [M + H]$^+$ | HPLC method |
|---|---|---|---|---|---|
| E-8g | A | 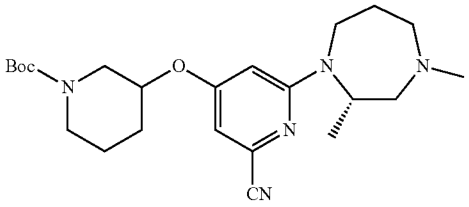 [SMILES: C[C@H]1CN(C)CCCN1c1cc(OC2CCCN(C(=O)OC(C)(C)C)C2)cc(C#N)n1] | 1.49 | 430 | A |
| E-8h | B | 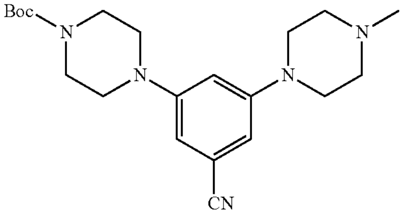 | 0.71 | 386 | B |
| E-8i | C | 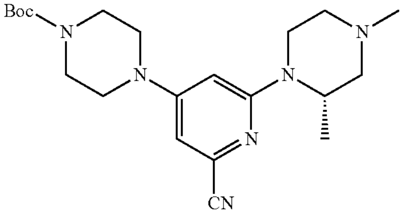 [SMILES: C[C@H]1CN(C)CCN1c1cc(N2CCN(C(=O)OC(C)(C)C)CC2)cc(C#N)n1] | 0.76 | 401 | B |

TABLE 15-continued
| # | method | structure | $t_{ret}$ [min] | $[M + H]^+$ | HPLC method |
|---|---|---|---|---|---|
| E-8j | D | 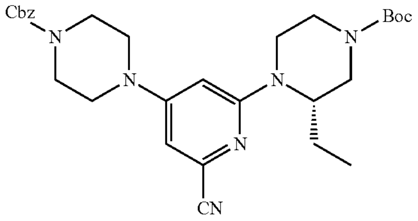 [SMILES: CC[C@H]1CN(C(=O)OC(C)(C)C)CCN1c1cc(N2CCN(C(=O)OCc3ccccc3)CC2)cc(C#N)n1] | 1.65 | 535 | A |
| E-8k | E | 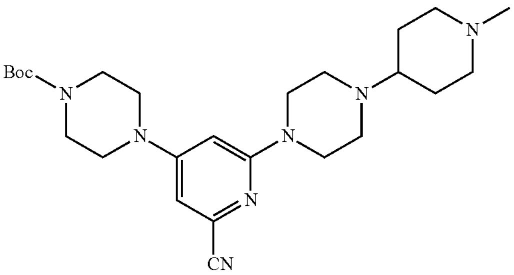 [SMILES: CN1CCC(N2CCN(c3cc(N4CCN(C(=O)OC(C)(C)C)CC4)cc(C#N)n3)CC2)CC1] | 0.68 | 470 | D |
| E-8l | F | 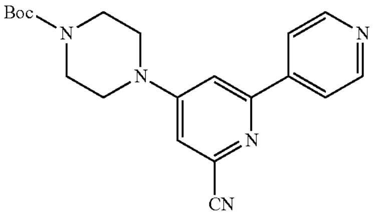 | 0.54 | 366 | F |
| E-8m | G | 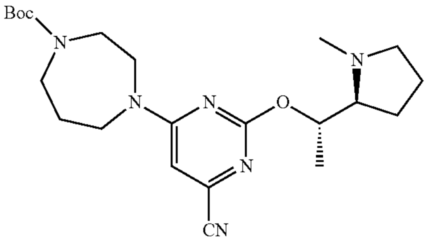 [SMILES: C[C@H](Oc1nc(C#N)cc(N2CCCN(C(=O)OC(C)(C)C)CC2)n1)[C@@H]1CCCN1C] | 0.43 | 431 | F |
| E-8n | H | 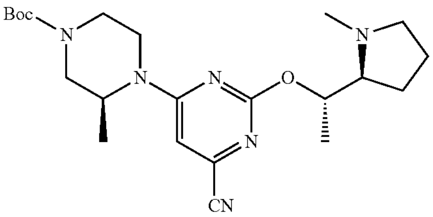 [SMILES: C[C@H](Oc1nc(C#N)cc(N2CCN(C(=O)OC(C)(C)C)C[C@@H]2C)n1)[C@@H]1CCCN1C] | n.a. | n.a. | — |
| E-8o | I | 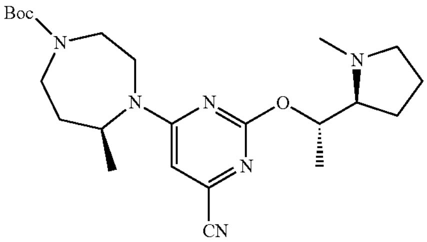 [SMILES: C[C@H](Oc1nc(C#N)cc(N2CCN(C(=O)OC(C)(C)C)CC[C@@H]2C)n1)[C@@H]1CCCN1C] | n.a. | n.a. | — |

TABLE 15-continued
| # | method | structure | $t_{ret}$ [min] | [M + H]+ | HPLC method |
|---|---|---|---|---|---|
| E-8p | J | 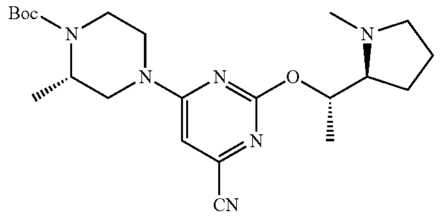 [SMILES: C[C@H](Oc1nc(C#N)cc(N2CCN(C(=O)OC(C)(C)C)[C@@H](C)C2)n1)[C@@H]1CCCN1C] | 0.46 | 431 | F |
| E-8q | C | 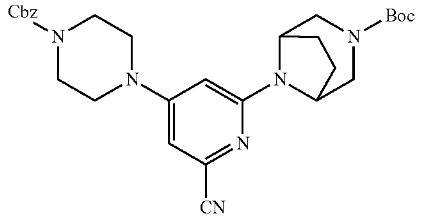 [SMILES: CC(C)(C)OC(=O)N1CC2CCC(C1)N2c1cc(N2CCN(C(=O)OCc3ccccc3)CC2)cc(C#N)n1] | 0.90 | 533 | B |
| E-8r | C | 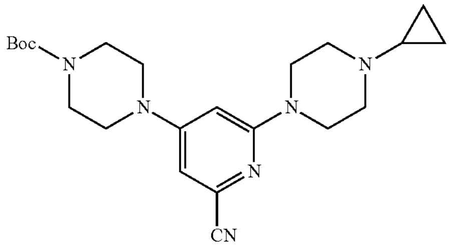 [SMILES: CC(C)(C)OC(=O)N1CCN(c2cc(C#N)nc(N3CCN(C4CC4)CC3)c2)CC1] | 0.82 | 413 | B |
| E-8s | C | 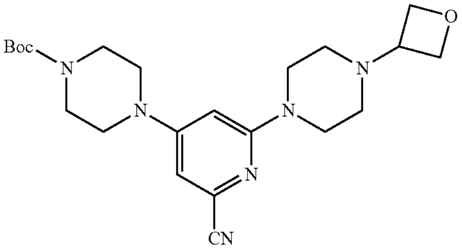 [SMILES: CC(C)(C)OC(=O)N1CCN(c2cc(C#N)nc(N3CCN(C4COC4)CC3)c2)CC1] | 0.66 | 429 | B |
| E-8t | D | 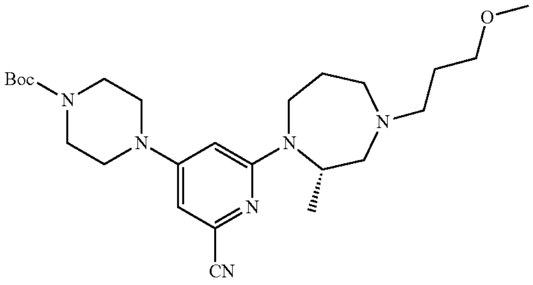 [SMILES: COCCCN1CCCN(c2cc(N3CCN(C(=O)OC(C)(C)C)CC3)cc(C#N)n2)[C@@H](C)C1] | 1.55 | 473 | A |
| E-8u | C | 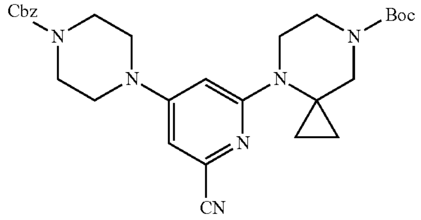 [SMILES: CC(C)(C)OC(=O)N1CCN(c2cc(N3CCN(C(=O)OCc4ccccc4)CC3)cc(C#N)n2)C2(CC2)C1] | 0.91 | 533 | B |

TABLE 15-continued
| # | method | structure | $t_{ret}$ [min] | $[M + H]^+$ | HPLC method |
|---|---|---|---|---|---|
| E-8v | B | 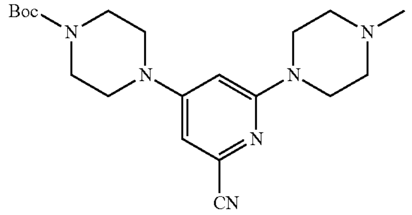 [SMILES: CN1CCN(c2cc(N3CCN(C(=O)OC(C)(C)C)CC3)cc(C#N)n2)CC1] | 1.23 | 387 | A |
| E-8w | E | 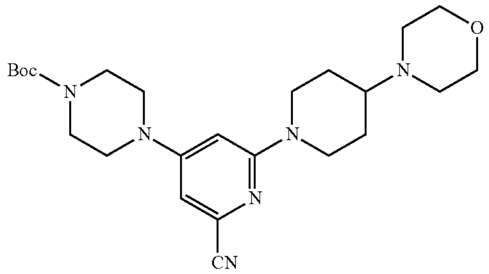 [SMILES: CC(C)(C)OC(=O)N1CCN(c2cc(C#N)nc(N3CCC(N4CCOCC4)CC3)c2)CC1] | 0.70 | 457 | D |
| E-8x | E | 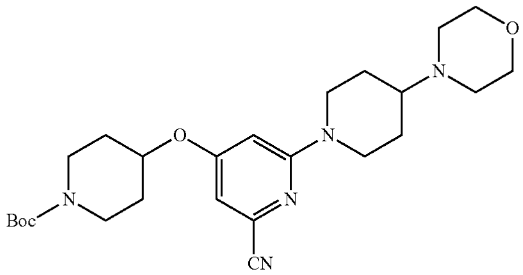 [SMILES: CC(C)(C)OC(=O)N1CCC(Oc2cc(C#N)nc(N3CCC(N4CCOCC4)CC3)c2)CC1] | 0.77 | 472 | D |
| E-8y | E | 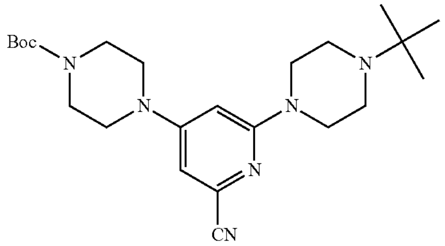 [SMILES: CC(C)(C)OC(=O)N1CCN(c2cc(C#N)nc(N3CCN(C(C)(C)C)CC3)c2)CC1] | 0.84 | 429 | D |
| E-8z | E | 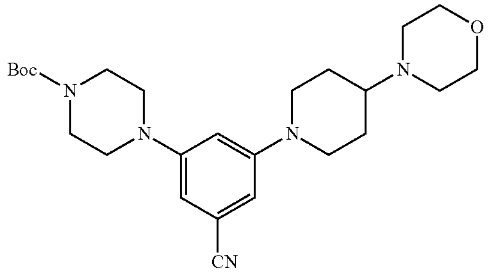 [SMILES: CC(C)(C)OC(=O)N1CCN(c2cc(C#N)cc(N3CCC(N4CCOCC4)CC3)c2)CC1] | 0.73 | 456 | D |
| E-8aa | E | 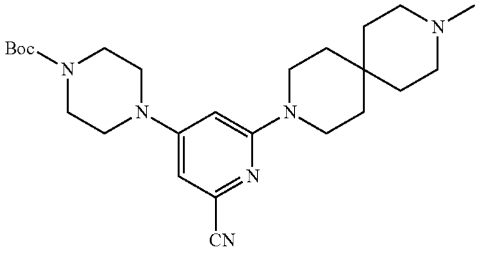 [SMILES: CN1CCC2(CC1)CCN(c1cc(N3CCN(C(=O)OC(C)(C)C)CC3)cc(C#N)n1)CC2] | 0.50 | 455 | F |

TABLE 15-continued
| # | method | structure | $t_{ret}$ [min] | $[M + H]^+$ | HPLC method |
| --- | --- | --- | --- | --- | --- |
| E-8ab | G | 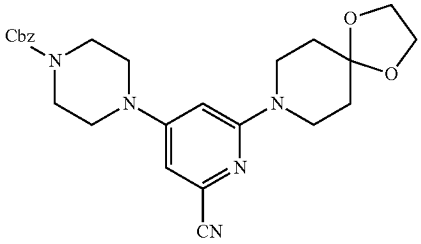 [SMILES: N#Cc1cc(N2CCN(C(=O)OCc3ccccc3)CC2)cc(N2CCC3(CC2)OCCO3)n1] | n.a. | n.a. | — |
| E-8ac | A | 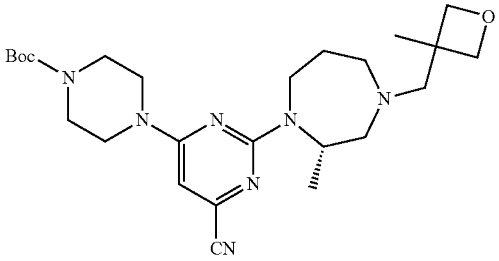 [SMILES: C[C@H]1CN(CC2(C)COC2)CCCN1c1nc(C#N)cc(N2CCN(C(=O)OC(C)(C)C)CC2)n1] | 1.64 | 486 | A |
| E-8ad | A | 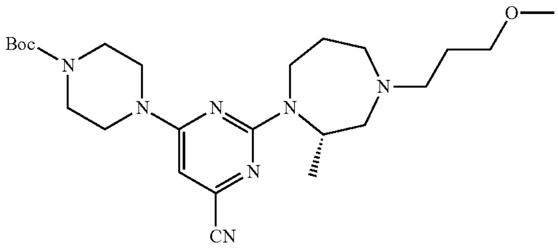 [SMILES: COCCCN1CCCN(c2nc(C#N)cc(N3CCN(C(=O)OC(C)(C)C)CC3)n2)[C@@H](C)C1] | 1.61 | 474 | A |
| E-8ae | A | 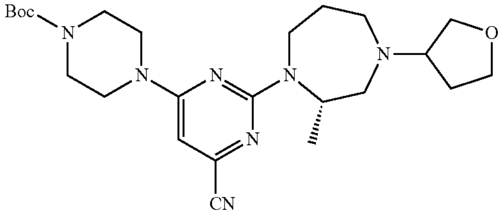 [SMILES: C[C@H]1CN(C2CCOC2)CCCN1c1nc(C#N)cc(N2CCN(C(=O)OC(C)(C)C)CC2)n1] | 0.83 | 472 | B |
| E-8af | A | 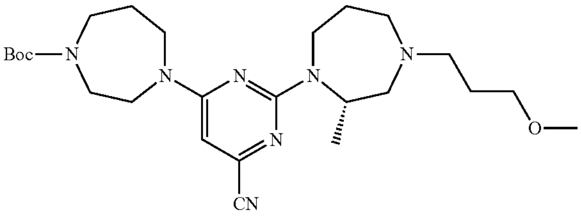 [SMILES: COCCCN1CCCN(c2nc(C#N)cc(N3CCCN(C(=O)OC(C)(C)C)CC3)n2)[C@@H](C)C1] | 1.58 | 488 | A |
| E-8ag | A | 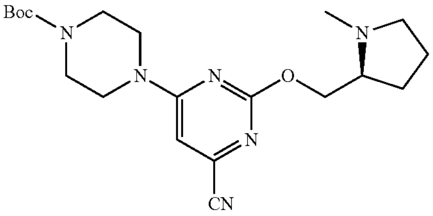 [SMILES: CN1CCC[C@H]1COc1nc(C#N)cc(N2CCN(C(=O)OC(C)(C)C)CC2)n1] | 1.36 | 403 | A |

TABLE 15-continued
| # | method | structure | $t_{ret}$ [min] | [M + H]+ | HPLC method |
| --- | --- | --- | --- | --- | --- |
| E-8ah | G | 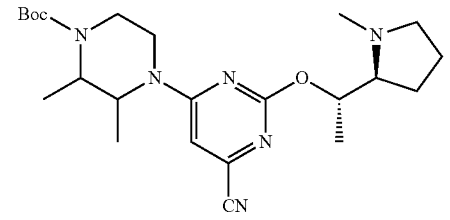 [SMILES: CC1C(C)N(c2cc(C#N)nc(O[C@@H](C)[C@@H]3CCCN3C)n2)CCN1C(=O)OC(C)(C)C] | 1.53 | 445 | A |
| E-8ai | G | 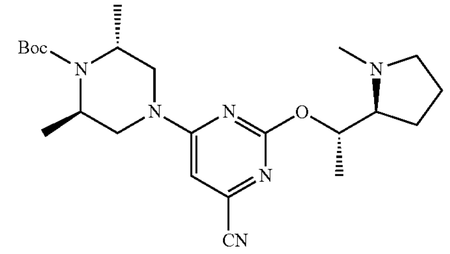 [SMILES: C[C@H](Oc1nc(C#N)cc(N2C[C@@H](C)N(C(=O)OC(C)(C)C)[C@H](C)C2)n1)[C@@H]1CCCN1C] | 1.53 | 445 | A |
| E-8aj | G | 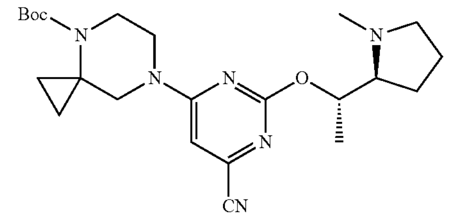 [SMILES: C[C@H](Oc1nc(C#N)cc(N2CCN(C(=O)OC(C)(C)C)C3(CC3)C2)n1)[C@@H]1CCCN1C] | 1.51 | 443 | A |
| E-8ak | I | 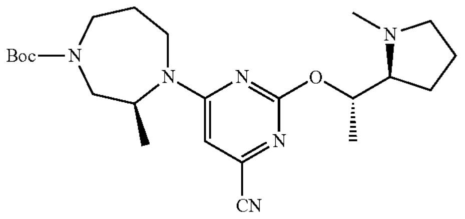 [SMILES: C[C@H](Oc1nc(C#N)cc(N2CCCN(C(=O)OC(C)(C)C)C[C@@H]2C)n1)[C@@H]1CCCN1C] | n.a. | n.a. | — |
| E-8al | J | 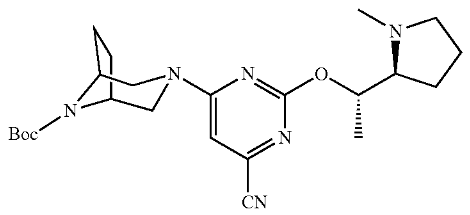 [SMILES: C[C@H](Oc1nc(C#N)cc(N2CC3CCC(C2)N3C(=O)OC(C)(C)C)n1)[C@@H]1CCCN1C] | 0.75 | 443 | G |
| E-8am | J | 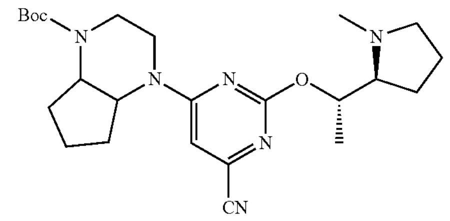 [SMILES: C[C@H](Oc1nc(C#N)cc(N2CCN(C(=O)OC(C)(C)C)C3CCCC32)n1)[C@@H]1CCCN1C] | 0.79 | 457 | G |

TABLE 15-continued
| # | method | structure | $t_{ret}$ [min] | $[M + H]^+$ | HPLC method |
|---|---|---|---|---|---|
| E-8an | J | 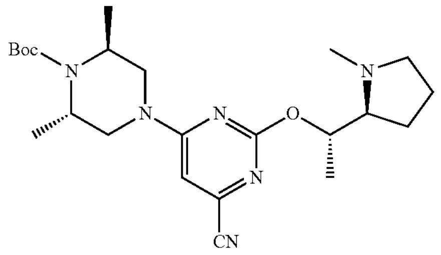 [SMILES: C[C@H](Oc1nc(C#N)cc(N2C[C@H](C)N(C(=O)OC(C)(C)C)[C@@H](C)C2)n1)[C@@H]1CCCN1C] | 0.50 | 455 | F |
| E-8ao | G | 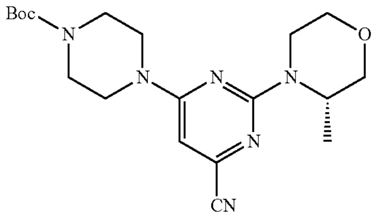 [SMILES: C[C@H]1COCCN1c1nc(C#N)cc(N2CCN(C(=O)OC(C)(C)C)CC2)n1] | n.a. | n.a. | — |
| E-8ap | G | 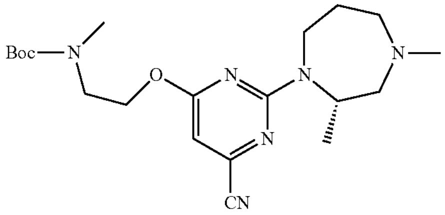 [SMILES: C[C@H]1CN(C)CCCN1c1nc(C#N)cc(OCCN(C)C(=O)OC(C)(C)C)n1] | 1.50 | 405 | A |
| E-8aq | G | 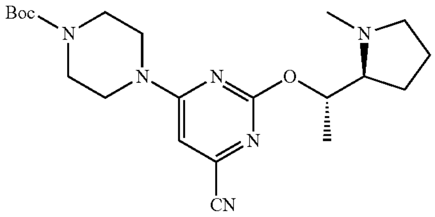 [SMILES: C[C@H](Oc1nc(C#N)cc(N2CCN(C(=O)OC(C)(C)C)CC2)n1)[C@@H]1CCCN1C] | 1.42 | 417 | A |
| E-8ar | B | 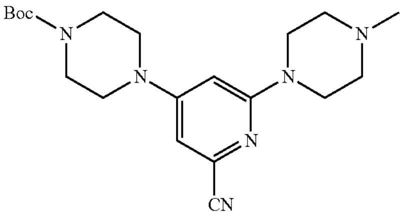 [SMILES: CN1CCN(c2cc(N3CCN(C(=O)OC(C)(C)C)CC3)cc(C#N)n2)CC1] | 0.70 | 387 | B |
| E-8as | A | 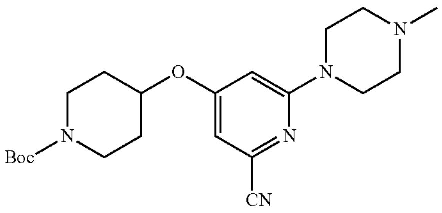 [SMILES: CN1CCN(c2cc(OC3CCN(C(=O)OC(C)(C)C)CC3)cc(C#N)n2)CC1] | 1.36 | 402 | A |
| E-8at | G | 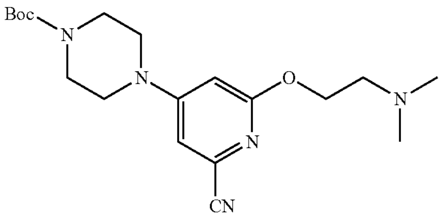 [SMILES: CN(C)CCOc1cc(N2CCN(C(=O)OC(C)(C)C)CC2)cc(C#N)n1] | 1.30 | 376 | A |

TABLE 15-continued
| # | method | structure | $t_{ret}$ [min] | $[M + H]^+$ | HPLC method |
|---|---|---|---|---|---|
| E-8au | A | 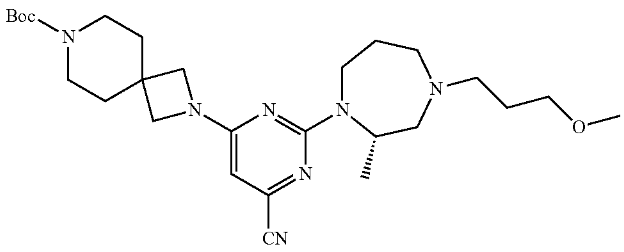 [SMILES: COCCCN1CCCN(c2nc(C#N)cc(N3CC4(CCN(C(=O)OC(C)(C)C)CC4)C3)n2)[C@@H](C)C1] | 0.94 | 514 | B |
| E-8av | A | 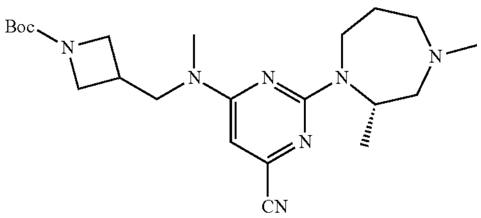 [SMILES: C[C@H]1CN(C)CCCN1c1nc(C#N)cc(N(C)CC2CN(C(=O)OC(C)(C)C)C2)n1] | 0.73 | 430 | B |
| E-8aw | A | 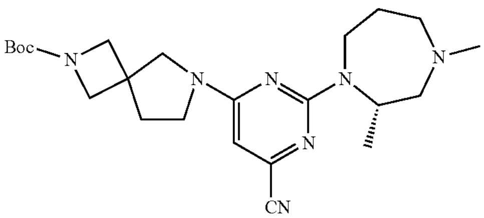 [SMILES: C[C@H]1CN(C)CCCN1c1nc(C#N)cc(N2CCC3(CN(C(=O)OC(C)(C)C)C3)C2)n1] | 0.77 | 442 | B |
| E-8ax | A | 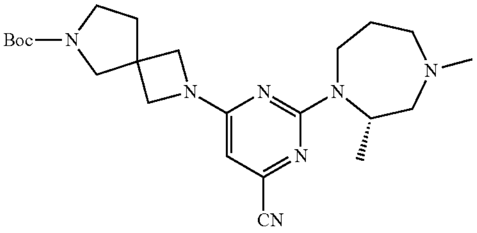 [SMILES: C[C@H]1CN(C)CCCN1c1nc(C#N)cc(N2CC3(CCN(C(=O)OC(C)(C)C)C3)C2)n1] | 0.78 | 442 | B |
| E-8ay | A | 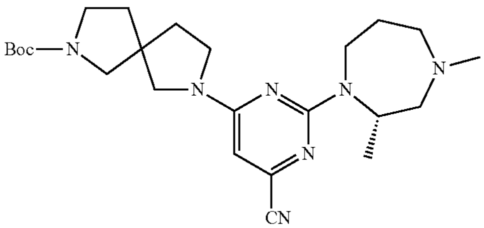 [SMILES: C[C@H]1CN(C)CCCN1c1nc(C#N)cc(N2CCC3(CCN(C(=O)OC(C)(C)C)C3)C2)n1] | 1.53 | 456 | A |
| E-8az | A | 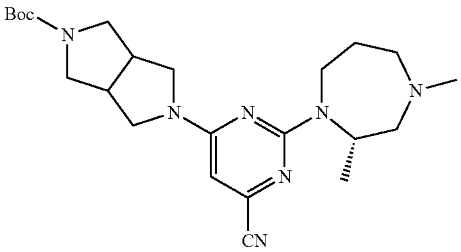 [SMILES: C[C@H]1CN(C)CCCN1c1nc(C#N)cc(N2CC3CN(C(=O)OC(C)(C)C)CC3C2)n1] | 1.48 | 442 | A |

TABLE 15-continued
| # | method | structure | $t_{ret}$ [min] | $[M + H]^+$ | HPLC method |
| --- | --- | --- | --- | --- | --- |
| E-8ba | A | 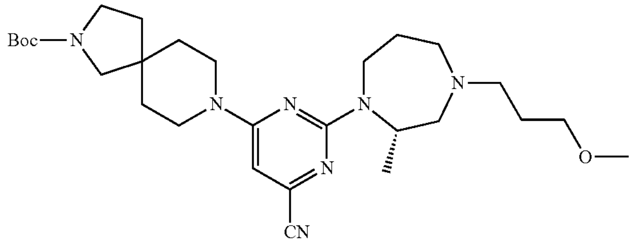 [SMILES: COCCCN1CCCN(c2nc(C#N)cc(N3CCC4(CCN(C(=O)OC(C)(C)C)C4)CC3)n2)[C@@H](C)C1] | 1.69 | 528 | A |
| E-8bb | A | 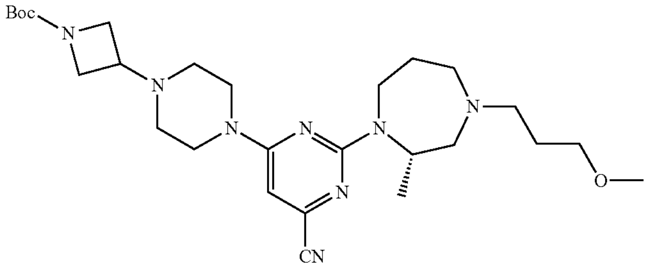 [SMILES: COCCCN1CCCN(c2nc(C#N)cc(N3CCN(C4CN(C(=O)OC(C)(C)C)C4)CC3)n2)[C@@H](C)C1] | 1.55 | 529 | A |
| E-8bc | A | 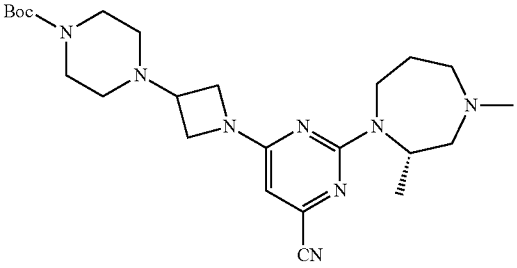 [SMILES: C[C@H]1CN(C)CCCN1c1nc(C#N)cc(N2CC(N3CCN(C(=O)OC(C)(C)C)CC3)C2)n1] | 1.52 | 471 | A |
| E-8bd | A | 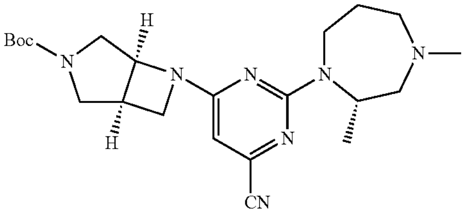 [SMILES: C[C@H]1CN(C)CCCN1c1nc(C#N)cc(N2C[C@H]3CN(C(=O)OC(C)(C)C)C[C@H]32)n1] | 1.40 | 428 | A |
| E-8be | A | 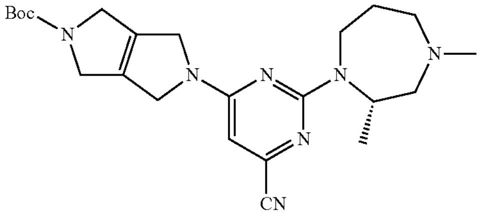 [SMILES: C[C@H]1CN(C)CCCN1c1nc(C#N)cc(N2CC3=C(CN(C(=O)OC(C)(C)C)C3)C2)n1] | 1.55 | 440 | A |
| E-8bf | A | 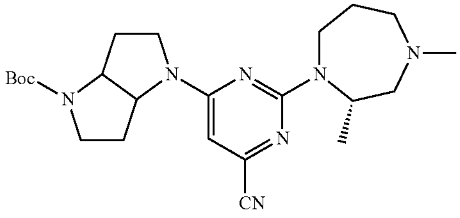 [SMILES: C[C@H]1CN(C)CCCN1c1nc(C#N)cc(N2CCC3C2CCN3C(=O)OC(C)(C)C)n1] | 1.51 | 442 | A |

TABLE 15-continued
| # | method | structure | $t_{ret}$ [min] | $[M + H]^+$ | HPLC method |
| --- | --- | --- | --- | --- | --- |
| E-8bg | A | 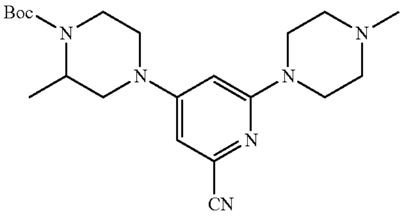 | 0.73 | 401 | B |
| E-8bh | A | 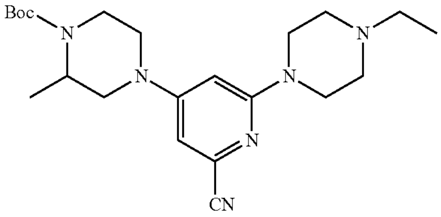 [SMILES: CCN1CCN(c2cc(N3CCN(C(=O)OC(C)(C)C)C(C)C3)cc(C#N)n2)CC1] | 0.80 | 415 | B |
| E-8bi | A | 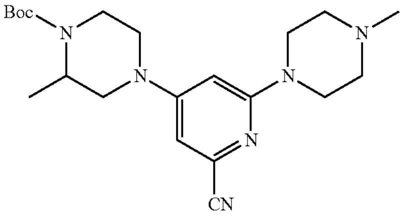 | 0.74 | 401 | B |
| E-8bj | A | 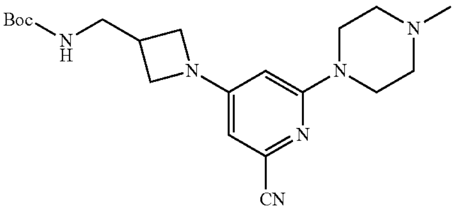 [SMILES: CN1CCN(c2cc(N3CC(CNC(=O)OC(C)(C)C)C3)cc(C#N)n2)CC1] | 0.65 | 387 | B |
| E-8bk | A | 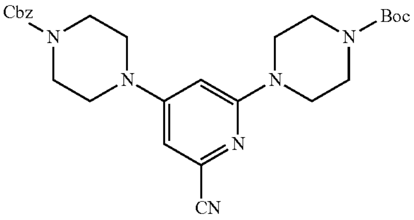 [SMILES: CC(C)(C)OC(=O)N1CCN(c2cc(N3CCN(C(=O)OCc4ccccc4)CC3)cc(C#N)n2)CC1] | n.a. | n.a. | — |
| E-8bl | A | 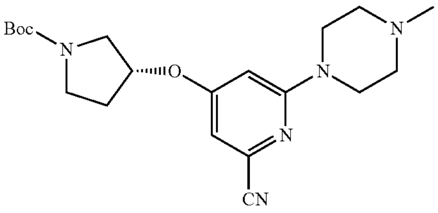 [SMILES: CN1CCN(c2cc(O[C@@H]3CCN(C(=O)OC(C)(C)C)C3)cc(C#N)n2)CC1] | n.a. | n.a. | — |
| E-8bm | C | 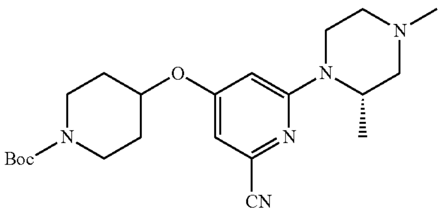 [SMILES: C[C@H]1CN(C)CCN1c1cc(OC2CCN(C(=O)OC(C)(C)C)CC2)cc(C#N)n1] | 1.41 | 416 | A |

TABLE 15-continued
| # | method | structure | $t_{ret}$ [min] | $[M + H]^+$ | HPLC method |
|---|---|---|---|---|---|
| E-8bn | I | 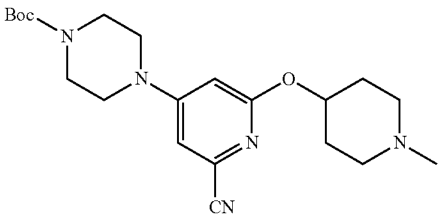 [SMILES: CN1CCC(Oc2cc(N3CCN(C(=O)OC(C)(C)C)CC3)cc(C#N)n2)CC1] | 0.73 | 402 | B |
| E-8bo | A | 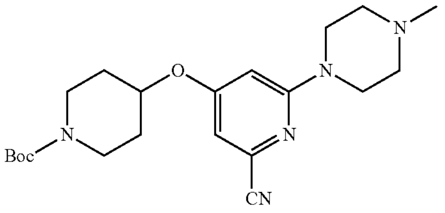 [SMILES: CN1CCN(c2cc(OC3CCN(C(=O)OC(C)(C)C)CC3)cc(C#N)n2)CC1] | 1.39 | 402 | A |
| E-8bp | G | 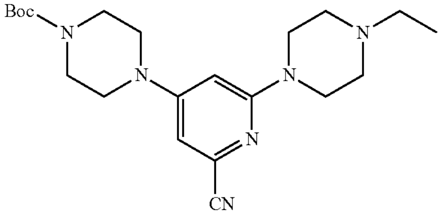 [SMILES: CCN1CCN(c2cc(N3CCN(C(=O)OC(C)(C)C)CC3)cc(C#N)n2)CC1] | 0.76 | 401 | B |
| E-8bq | G | 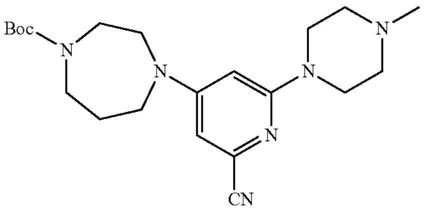 [SMILES: CN1CCN(c2cc(N3CCCN(C(=O)OC(C)(C)C)CC3)cc(C#N)n2)CC1] | 1.24 | 401 | A |
| E-8br | I | 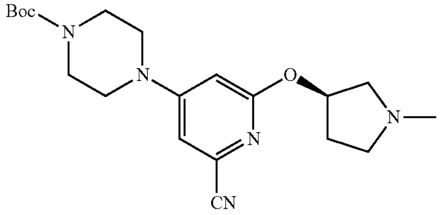 [SMILES: CN1CC[C@@H](Oc2cc(N3CCN(C(=O)OC(C)(C)C)CC3)cc(C#N)n2)C1] | 0.70 | 388 | B |
| E-8bs | G | 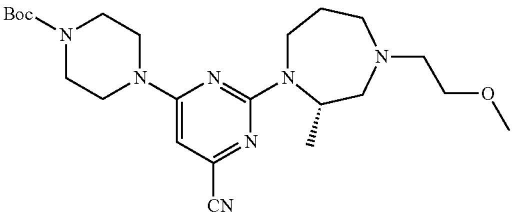 [SMILES: COCCN1CCCN(c2nc(C#N)cc(N3CCN(C(=O)OC(C)(C)C)CC3)n2)[C@@H](C)C1] | 1.57 | 460 | A |
| E-8bt | D | 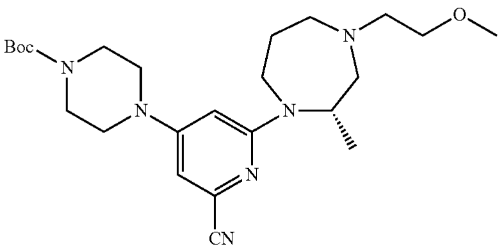 [SMILES: COCCN1CCCN(c2cc(N3CCN(C(=O)OC(C)(C)C)CC3)cc(C#N)n2)[C@@H](C)C1] | 1.51 | 459 | A |

TABLE 15-continued
| # | method | structure | $t_{ret}$ [min] | [M + H]$^+$ | HPLC method |
|---|---|---|---|---|---|
| E-8bu | G | 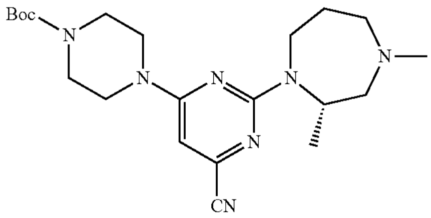 [SMILES: C[C@H]1CN(C)CCCN1c1nc(C#N)cc(N2CCN(C(=O)OC(C)(C)C)CC2)n1] | 1.56 | 416 | A |
| E-8bv | I | 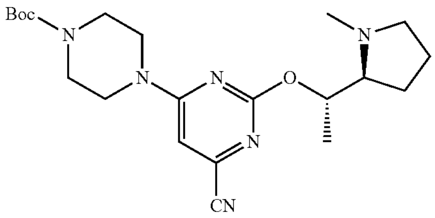 [SMILES: C[C@H](Oc1nc(C#N)cc(N2CCN(C(=O)OC(C)(C)C)CC2)n1)[C@@H]1CCCN1C] | 1.44 | 417 | A |
| E-8bw | J | 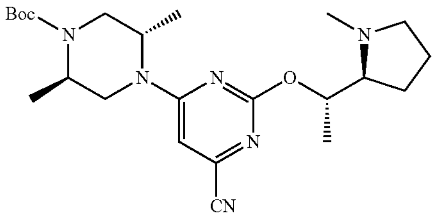 [SMILES: C[C@H](Oc1nc(C#N)cc(N2C[C@@H](C)N(C(=O)OC(C)(C)C)C[C@@H]2C)n1)[C@@H]1CCCN1C] | 1.54 | 445 | A |
| E-8bx | I | 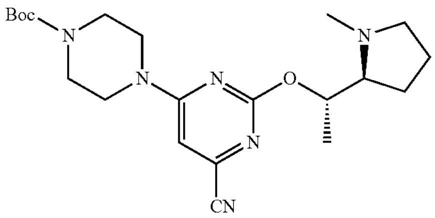 | 1.44 | 417 | A |
| E-8by | J | 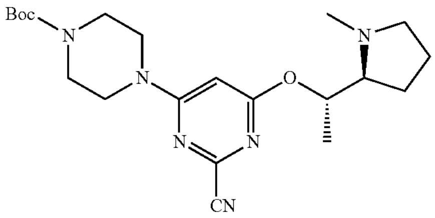 [SMILES: C[C@H](Oc1cc(N2CCN(C(=O)OC(C)(C)C)CC2)nc(C#N)n1)[C@@H]1CCCN1C] | 1.58 | 417 | A |
| E-8bz | G | 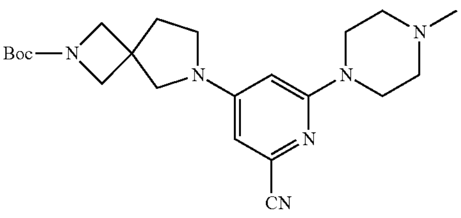 [SMILES: CN1CCN(c2cc(N3CCC4(CN(C(=O)OC(C)(C)C)C4)C3)cc(C#N)n2)CC1] | 1.32 | 413 | A |
| E-8ca | G | 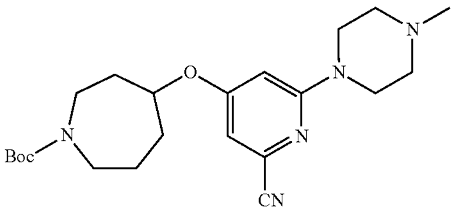 [SMILES: CN1CCN(c2cc(OC3CCCN(C(=O)OC(C)(C)C)CC3)cc(C#N)n2)CC1] | 1.36 | 416 | A |

Experimental Procedures for the Synthesis of Intermediates E-8cc

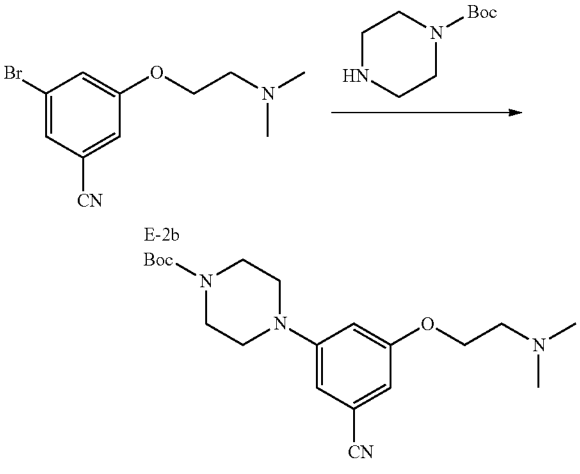

E-2b

E-8cc

E-2b (3.94 g, 20.93 mmol, 4.0 eq.), tert-butyl piperazine-1-carboxylate (1.76 g, 5.23 mmol, 1.0 eq.), sodium tert-butoxide (2.01 g, 20.93 mmol, 4.0 eq.), 2-(di-tert-butylphosphino)-biphenyl (624.45 mg, 0.21 mmol, 0.4 eq.), tris-(dibenzylideneacton)-dipalladium (479.05 mg, 0.052 mmol, 0.1 eq.) in dioxane (10 mL) are added to a sealed tube and shaken at 45° C. under nitrogen overnight. The reaction mixture is mixed with EtOAc and water and extracted into EtOAc. The organic phase is dried over magnesium sulfate and purified by normal phase chromatography on silica gel (DCM: MeOH from 100:0 to 80:20). 10 The following intermediates E-8 (table 16) are available in an analogous manner. The crude product E-8 is purified by chromatography if necessary.

TABLE 16

| # | structure | $t_{ret}$ [min] | $[M + H]^+$ | HPLC method |
|---|---|---|---|---|
| E-8cc | 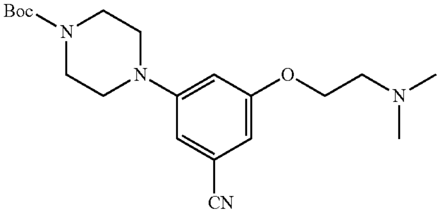 [SMILES: CN(C)CCOc1cc(C#N)cc(N2CCN(C(=O)OC(C)(C)C)CC2)c1] | 1.28 | 375 | A |
| E-8cd | 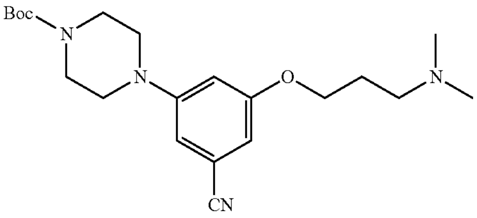 [SMILES: CN(C)CCCOc1cc(C#N)cc(N2CCN(C(=O)OC(C)(C)C)CC2)c1] | 1.35 | 389 | A |
| E-8ce | 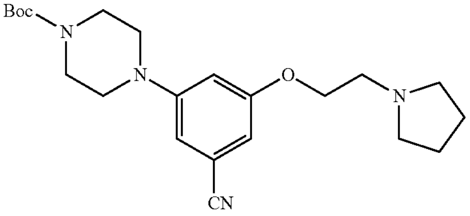 [SMILES: CC(C)(C)OC(=O)N1CCN(c2cc(C#N)cc(OCCN3CCCC3)c2)CC1] | 1.43 | 401 | A |

Experimental Procedure for the Synthesis of E-8cf (Method K)

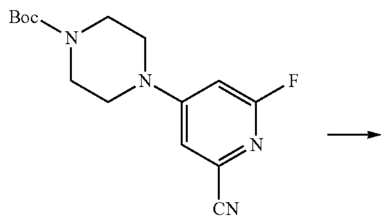

E-6g

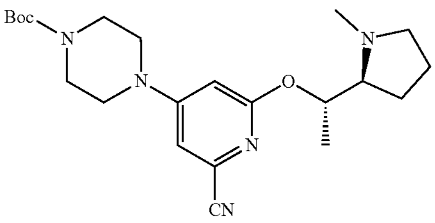

E-8cf

To a solution of(S)-1-((S)-1-methylpyrrolidin-2-yl) ethan-1-ol (1.335 g, 8.16 mmol, 2.5 eq.) in DMF (50 mL) is added sodium hydride (60% dispersion in mineral oil, 652.8 mg, 16.32 mmol, 5.0 eq.) at rt. The mixture is stirred for 10 min at rt and E-6g (1.00 g, 3.26 mmol, 1.0 eq.) is added. The mixture is stirred for 3 h at rt. The reaction is quenched by the addition of water and EtOAc. The phases are separated and the aqueous phase is extracted with EtOAc. The organic layers are combined, dried, filtered, and the solvent is removed under vacuum. The crude product is purified by basic reversed phase chromatography to give E-8cf.

Intermediates E-8 marked "K" (table 17) are available in an analogous manner. The crude product E-8 is purified by chromatography if necessary.

Experimental Procedure for the Synthesis of E-8cg (Method L)

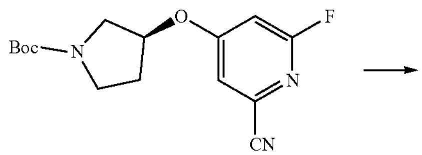

E-6b

-continued

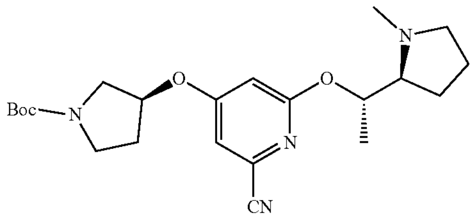

E-8cg

To a solution of(S)-1-((S)-1-methylpyrrolidin-2-yl) ethan-1-ol (52.6 mg, 0.41 mmol, 5.0 eq.) in THF (2 mL) is added potassium tert-butoxide (45.6 mg, 0.41 mmol, 5.0 eq.) at rt. The mixture is stirred for 30 min at rt and E-6b (25.0 mg, 0.081 mmol, 1.0 eq.) is added. The mixture is stirred for 15 min at rt. The reaction is quenched by the addition of water and EtOAc. The phases are separated and the aqueous phase is extracted with EtOAc. The organic layers are combined and the solvent is removed under vacuum. The crude product is purified by acidic reversed phase chromatography to give E-8cg.

Intermediates E-8 marked "L" (table 17) are available in an analogous manner. The crude product E-8 is purified by chromatography if necessary.

Experimental Procedure for the Synthesis of E-8ch (Method M)

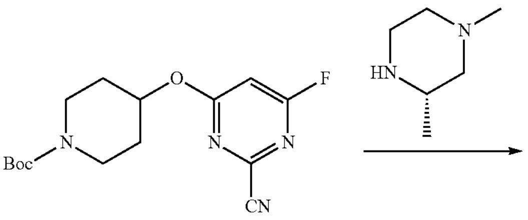

E-6h

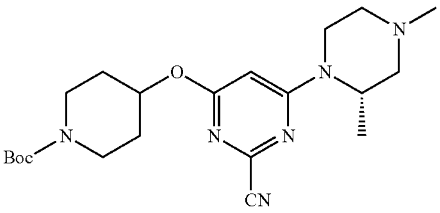

E-8ch

E-6h (100.0 mg, 0.31 mmol, 1.0 eq.) and(S)-1,3-dimethylpiperazine (42.5 mg, 0.37 mmol, 1.2 eq.) are dissolved in DMSO (1 mL) at rt and DIPEA (115.0 μL, 0.62 mmol, 2.0 eq.) is added and the mixture is stirred for 1 h. The mixture is diluted with acetonitrile and water and purified by acidic reversed phase chromatography to give E-8ch.

Intermediates E-8 marked "M" (table 17) are available in an analogous manner. The crude product E-8 is purified by chromatography if necessary.
TABLE 17
| # | method | structure | $t_{ret}$ [min] | $[M+H]^+$ | HPLC method |
|---|---|---|---|---|---|
| E-8cf | K | 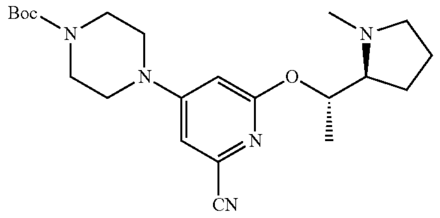 [SMILES: C[C@H](Oc1cc(N2CCN(C(=O)OC(C)(C)C)CC2)cc(C#N)n1)[C@@H]1CCCN1C] | 0.80 | 416 | B |
| E-8cg | L | 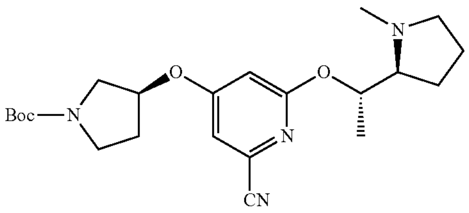 [SMILES: C[C@H](Oc1cc(O[C@H]2CCN(C(=O)OC(C)(C)C)C2)cc(C#N)n1)[C@@H]1CCCN1C] | 1.52 | 417 | A |
| E-8ch | M | 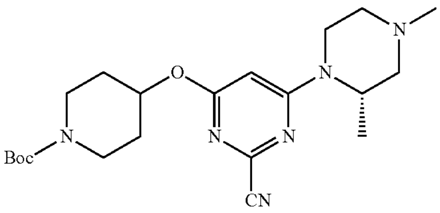 [SMILES: C[C@H]1CN(C)CCN1c1cc(OC2CCN(C(=O)OC(C)(C)C)CC2)nc(C#N)n1] | 1.55 | 417 | A |
| E-8ci | L | 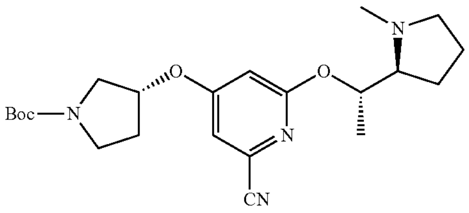 [SMILES: C[C@H](Oc1cc(O[C@@H]2CCN(C(=O)OC(C)(C)C)C2)cc(C#N)n1)[C@@H]1CCCN1C] | 1.53 | 417 | A |
| E-8cj | L | 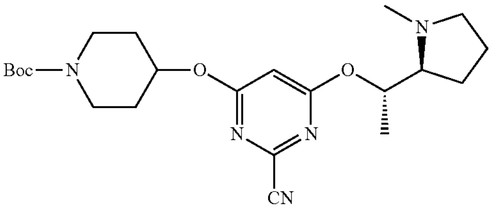 [SMILES: C[C@H](Oc1cc(OC2CCN(C(=O)OC(C)(C)C)CC2)nc(C#N)n1)[C@@H]1CCCN1C] | 1.66 | 432 | A |
| E-8ck | L | 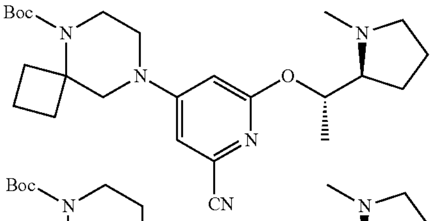 | 0.92 | 456 | G |
| E-8cl | L | 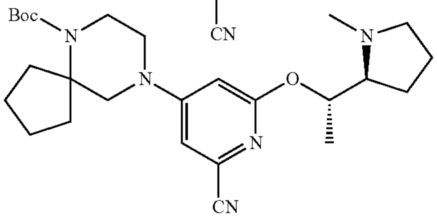 | 0.95 | 470 | G |

TABLE 17-continued

| # | method | structure | $t_{ret}$ [min] | [M + H]$^+$ | HPLC method |
|---|---|---|---|---|---|
| E-8cm | L | 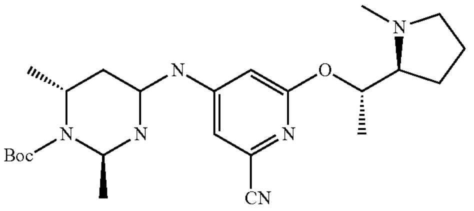 [SMILES: C[C@H](Oc1cc(NC2C[C@@H](C)N(C(=O)OC(C)(C)C)[C@H](C)N2)cc(C#N)n1)[C@@H]1CCCN1C] | 0.59 | 459 | F |

Experimental Procedure for the Synthesis of E-8cn

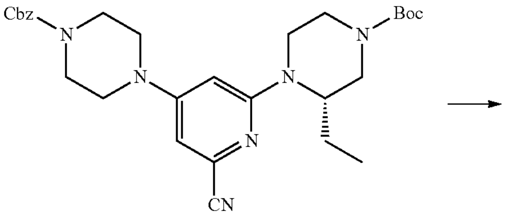

E-8j

-continued

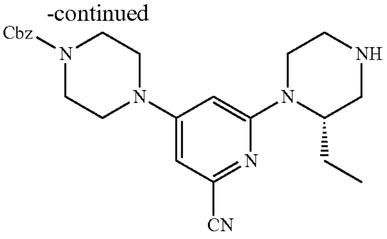

E-8cn

E-8j (2.404 g, 4.50 mmol) in DCM (41 mL) is treated with HCl (4 M in dioxane, 8.33 mL, 33.31 mmol, 7.4 eq.) and the mixture is stirred for 5 h at rt. After complete conversion, the mixture is concentrated and the crude product is purified via basic reversed phase chromatography (gradient elution: 25% to 100% acetonitrile in water) yielding E-8cn.

The following intermediates E-8 (table 18) are available in an analogous manner. The crude product E-8 is purified by chromatography if necessary.

TABLE 18

| # | structure | $t_{ret}$ [min] | [M + H]$^+$ | HPLC method |
|---|---|---|---|---|
| E-8cn | 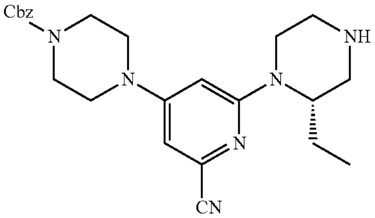 [SMILES: CC[C@H]1CNCCN1c1cc(N2CCN(C(=O)OCc3ccccc3)CC2)cc(C#N)n1] | 1.35 | 435 | A |
| E-8co | 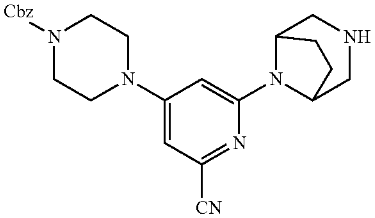 [SMILES: N#Cc1cc(N2CCN(C(=O)OCc3ccccc3)CC2)cc(N2C3CCC2CNC3)n1] | 0.66 | 433 | B |
| E-8cp | 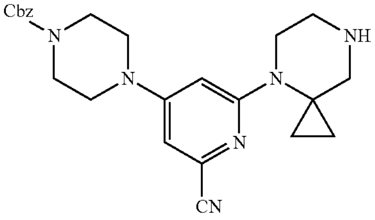 [SMILES: N#Cc1cc(N2CCN(C(=O)OCc3ccccc3)CC2)cc(N2CCNCC23CC3)n1] | 0.65 | 433 | B |

Experimental Procedure for the Synthesis of E-8cq

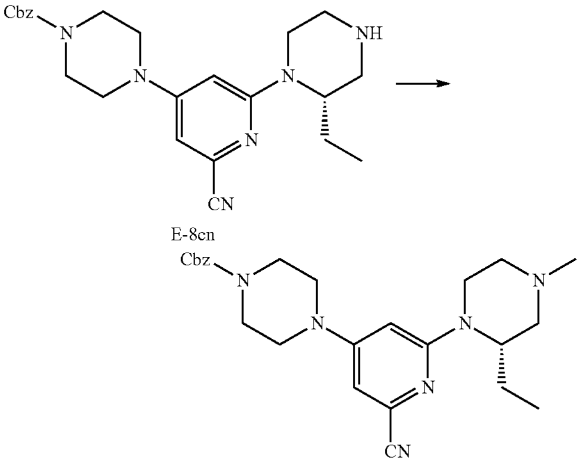

E-8cn

E-8cq

E-8cn (231 mg, 0.532 mmol) in DCM (10.72 mL) is treated with formaldehyde (37% in water, 79.89 μL, 1.06 mmol, 2.0 eq.), acetic acid (304.0 μL, 5.32 mmol, 10.0 eq.), and a small amount of molecular sieves and the mixture is stirred for 15 min. Sodium triacetoxyborohydride (232.3 mg, 1.06 mmol, 2.0 eq.) is added and the mixture ist stirred for 2 h at rt. After complete conversion the mixture is diluted with brine and the product is extracted with DCM. The combined organic extracts are dried, filtered and concentrated and the crude product is purified via basic reversed phase chromatography (gradient elution: 35% to 98% acetonitrile in water) yielding E-8cq.

The following intermediates E-8 (table 19) are available in an analogous manner. The crude product E-8 is purified by chromatography if necessary.

TABLE 19

| # | structure | $t_{ret}$ [min] | [M + H]$^+$ | HPLC method |
|---|---|---|---|---|
| E-8cq | 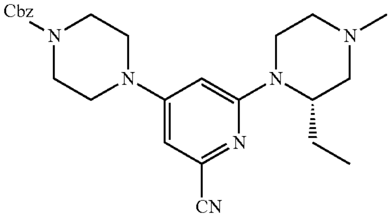 [SMILES: CC[C@H]1CN(C)CCN1c1cc(N2CCN(C(=O)OCc3ccccc3)CC2)cc(C#N)n1] | 1.47 | 449 | A |
| E-8cr | 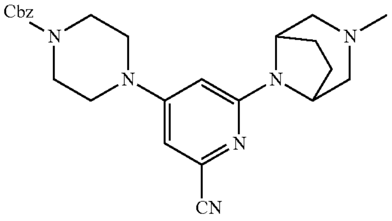 [SMILES: CN1CC2CCC(C1)N2c1cc(N2CCN(C(=O)OCc3ccccc3)CC2)cc(C#N)n1] | 1.43 | 447 | A |
| E-8cs | 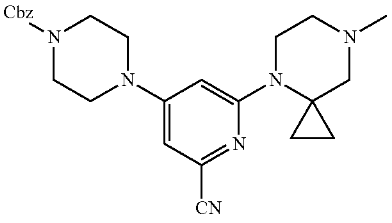 [SMILES: CN1CCN(c2cc(N3CCN(C(=O)OCc4ccccc4)CC3)cc(C#N)n2)C2(CC2)C1] | 1.34 | 447 | A |

Scheme 3

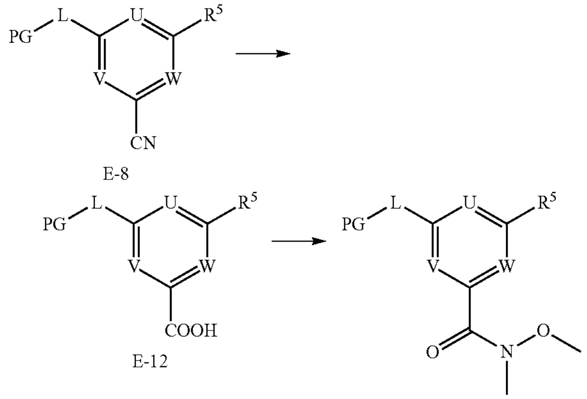

E-8

E-12

E-13

PG = protecting group

Experimental Procedure for the Synthesis of E-12a

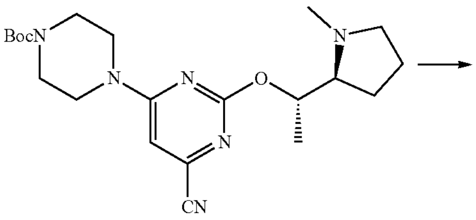

E-8aq

-continued

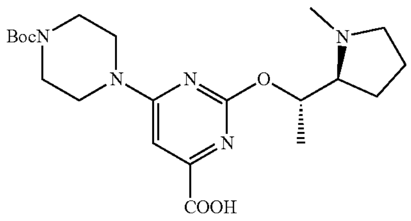

E-12a

To a solution of E-8aq (1.776 g, 4.26 mmol, 1 eq.) in MeOH (35 mL) is added a solution of sodium hydroxide in water (16 mL, 4 M, 63.96 mmol, 15.0 eq.) and the resulting mixture is stirred at 65° C. for 1.5 h. The reaction volume is reduced under reduced pressure to remove large parts of the MeOH and the remaining aqueous solution is carefully neutralized with an aqueous solution of HCl (8 M). The mixture is diluted with acetonitrile and purified by acidic reversed phase chromatography (gradient elution: 10% to 85% acetonitrile in water) to give the desired product E-12a.

The following intermediates E-12 (table 20) are available in an analogous manner starting from different intermediates E-8. The crude product E-8 is purified by chromatography if necessary.

TABLE 20

| # | structure | $t_{ret}$ [min] | $[M + H]^+$ | HPLC method |
|---|---|---|---|---|
| E-12a | 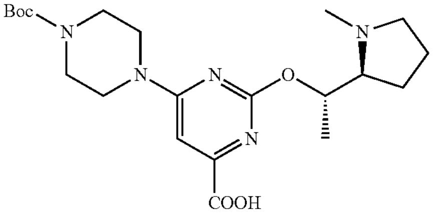 [SMILES: C[C@H](Oc1nc(C(=O)O)cc(N2CCN(C(=O)OC(C)(C)C)CC2)n1)[C@@H]1CCCN1C] | 0.92 | 436 | A |
| E-12b | 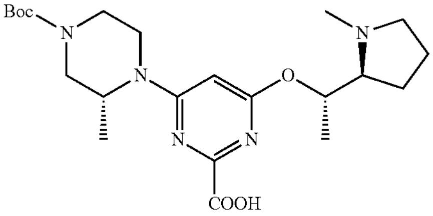 [SMILES: C[C@H](Oc1cc(N2CCN(C(=O)OC(C)(C)C)C[C@H]2C)nc(C(=O)O)n1)[C@@H]1CCCN1C] | 0.92 | 450 | A |

TABLE 20-continued
| # | structure | $t_{ret}$ [min] | $[M + H]^+$ | HPLC method |
|---|---|---|---|---|
| E-12c | 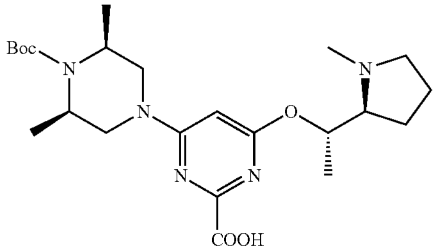 [SMILES: C[C@H](Oc1cc(N2C[C@@H](C)N(C(=O)OC(C)(C)C)[C@@H](C)C2)nc(C(=O)O)n1)[C@@H]1CCCN1C] | 1.02 | 464 | A |
| E-12d | 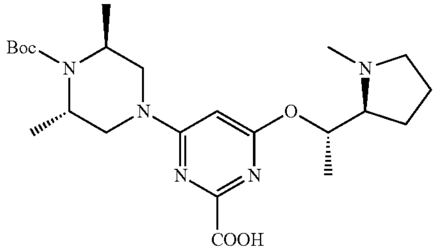 [SMILES: C[C@H](Oc1cc(N2C[C@H](C)N(C(=O)OC(C)(C)C)[C@@H](C)C2)nc(C(=O)O)n1)[C@@H]1CCCN1C] | 1.02 | 464 | A |
| E-12e | 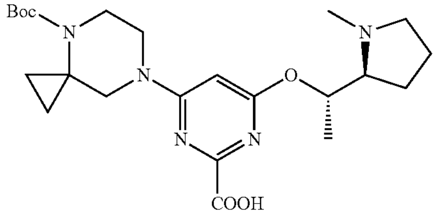 [SMILES: C[C@H](Oc1cc(N2CCN(C(=O)OC(C)(C)C)C3(CC3)C2)nc(C(=O)O)n1)[C@@H]1CCCN1C] | 1.02 | 462 | A |
| E-12f | 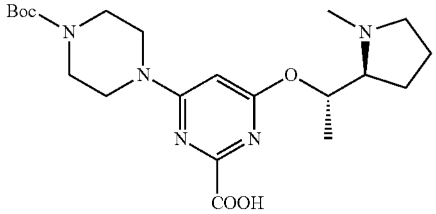 [SMILES: C[C@H](Oc1cc(N2CCN(C(=O)OC(C)(C)C)CC2)nc(C(=O)O)n1)[C@@H]1CCCN1C] | 0.94 | 436 | A |
| E-12g | 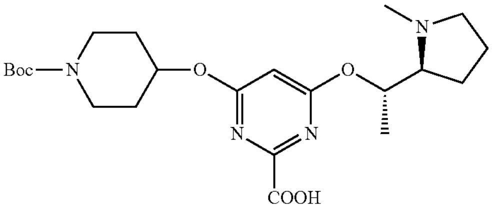 [SMILES: C[C@H](Oc1cc(OC2CCN(C(=O)OC(C)(C)C)CC2)nc(C(=O)O)n1)[C@@H]1CCCN1C] | 1.02 | 451 | A |
| E-12h | 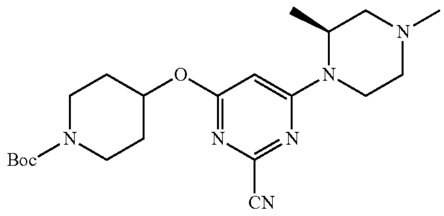 [SMILES: C[C@H]1CN(C)CCN1c1cc(OC2CCN(C(=O)OC(C)(C)C)CC2)nc(C#N)n1] | 0.94 | 436 | A |

Experimental Procedure for the Synthesis of E-13a

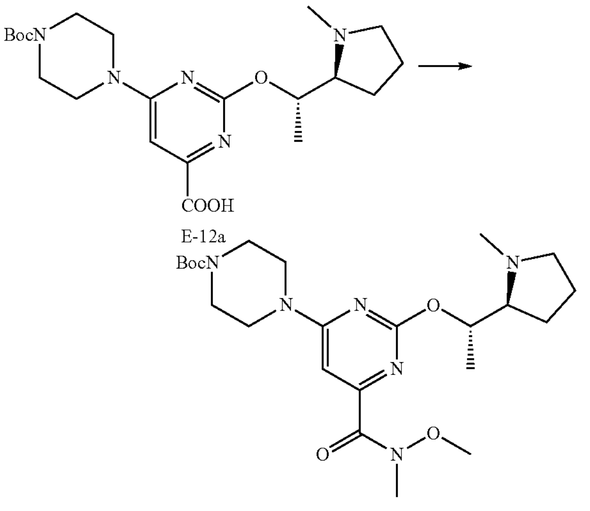

E-12a

E-13a

N,O-Dimethylhydroxylamine hydrochloride (725 mg, 7.43 mmol, 2.0 eq.) is suspended in THF (10 mL) and DIPEA (3.236 mL, 18.58 mmol, 5.0 eq.) is added and the mixture is stirred for 15 min at rt. A solution of intermediate E-12a (1.618 g, 3.72 mmol, 1.0 eq.) in THF (10 mL) and HATU (1.586 g, 4.09 mmol, 1.1 equiv.) are added to the mixture and the mixture is stirred for 45 min. Water is added to the mixture, it is diluted with acetonitrile and filtered. The filtrate is purified by basic reversed phase chromatography (gradient elution: 20% to 90% acetonitrile in water) to give the desired product E-13a.

The following intermediates E-13 (table 21) are available in an analogous manner starting from different intermediates E-12. The crude product E-13 is purified by chromatography if necessary.

TABLE 21

| # | structure | $t_{ret}$ [min] | $[M + H]^+$ | HPLC method |
|---|---|---|---|---|
| E-13a | 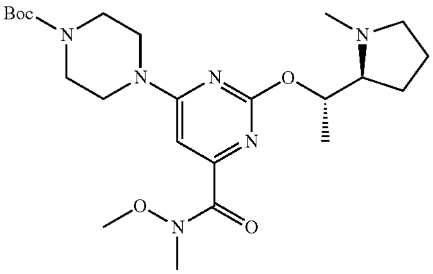 [SMILES: CON(C)C(=O)c1cc(N2CCN(C(=O)OC(C)(C)C)CC2)nc(O[C@@H](C)[C@@H]2CCCN2C)n1] | 1.28 | 479 | A |
| E-13b | 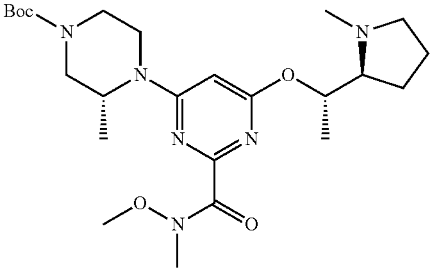 [SMILES: CON(C)C(=O)c1nc(O[C@@H](C)[C@@H]2CCCN2C)cc(N2CCN(C(=O)OC(C)(C)C)C[C@H]2C)n1] | 1.40 | 493 | A |
| E-13c | 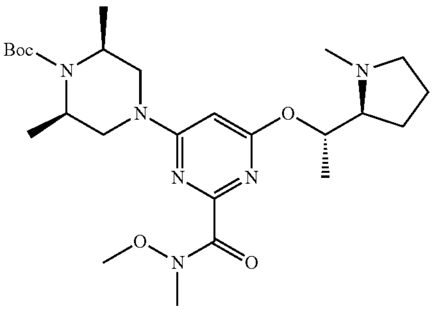 [SMILES: CON(C)C(=O)c1nc(O[C@@H](C)[C@@H]2CCCN2C)cc(N2C[C@@H](C)N(C(=O)OC(C)(C)C)[C@@H](C)C2)n1] | 1.45 | 507 | A |

TABLE 21-continued
| # | structure | $t_{ret}$ [min] | $[M + H]^+$ | HPLC method |
|---|---|---|---|---|
| E-13d | 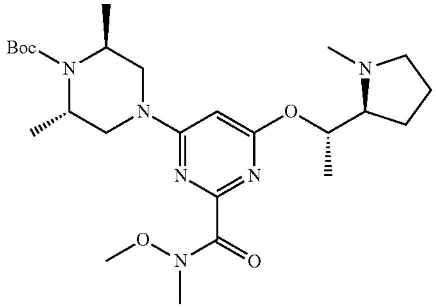 [SMILES: CON(C)C(=O)c1nc(O[C@@H](C)[C@@H]2CCCN2C)cc(N2C[C@H](C)N(C(=O)OC(C)(C)C)[C@@H](C)C2)n1] | 1.45 | 507 | A |
| E-13e | 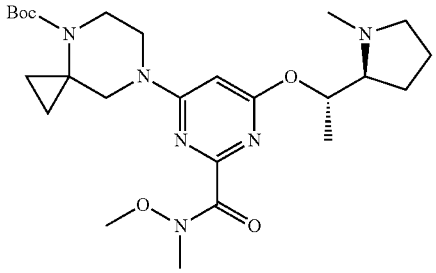 [SMILES: CON(C)C(=O)c1nc(O[C@@H](C)[C@@H]2CCCN2C)cc(N2CCN(C(=O)OC(C)(C)C)C3(CC3)C2)n1] | 1.46 | 505 | A |
| E-13f | 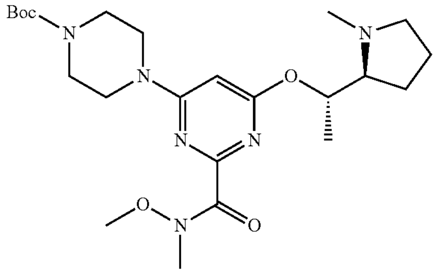 [SMILES: CON(C)C(=O)c1nc(O[C@@H](C)[C@@H]2CCCN2C)cc(N2CCN(C(=O)OC(C)(C)C)CC2)n1] | 1.36 | 479 | A |
| E-13g | 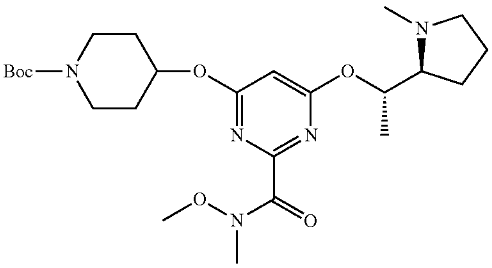 [SMILES: CON(C)C(=O)c1nc(OC2CCN(C(=O)OC(C)(C)C)CC2)cc(O[C@@H](C)[C@@H]2CCCN2C)n1] | 1.48 | 494 | A |
| E-13h | 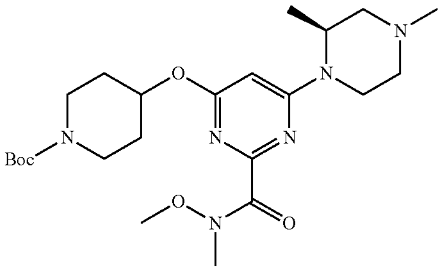 [SMILES: CON(C)C(=O)c1nc(OC2CCN(C(=O)OC(C)(C)C)CC2)cc(N2CCN(C)C[C@@H]2C)n1] | 1.35 | 479 | A |

Scheme 4

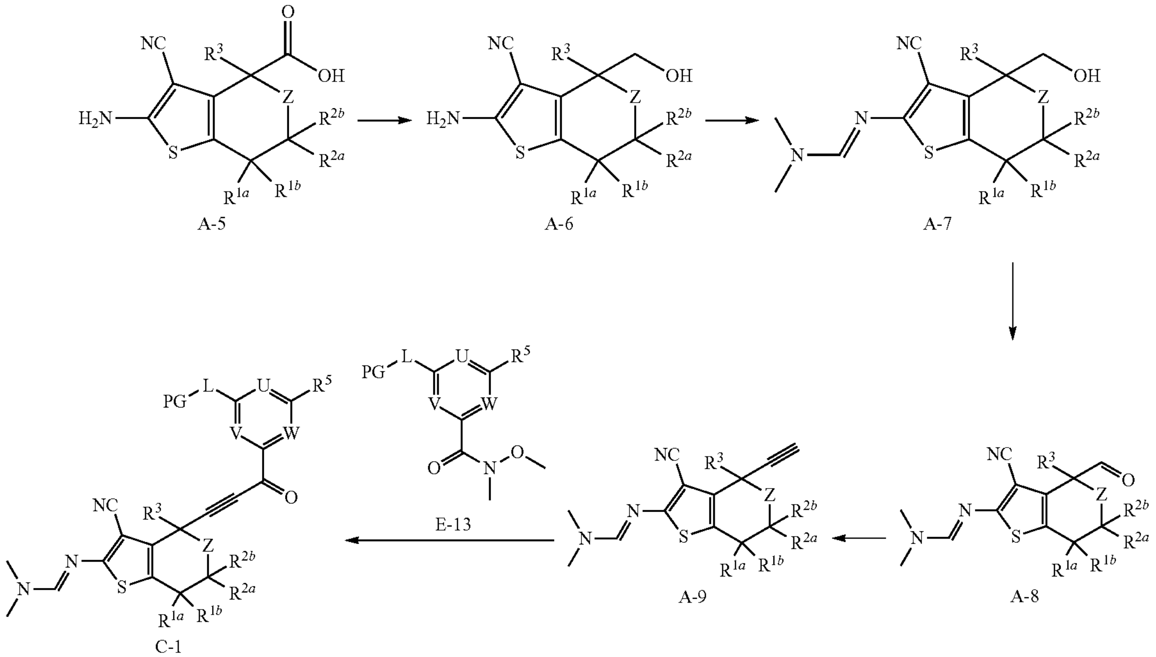

A-5 A-6 A-7 A-8 A-9 C-1

PG = protecting group

Experimental Procedure for the Synthesis of A-6a

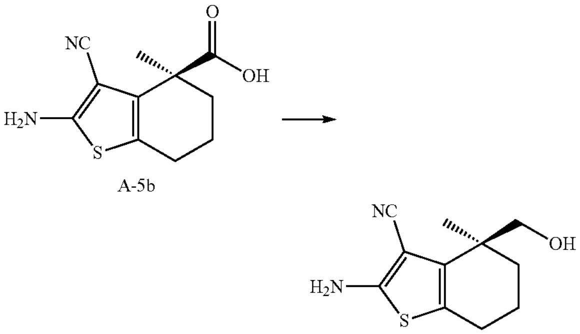
A-5b A-6a

To a solution A-5b (22.00 g, 93.11 mmol, 1.0 eq.) in THF (300 mL) is added CDI (17.12 g, 102.42 mmol, 1.1 eq.) and the mixture is stirred at 50° C. for 1 h. The mixture is cooled to rt and sodium borohydride (10.78 g, 279.32 mmol, 3.0 eq.) suspended in 5 mL water is slowly added to the reaction mixture (exothermic reaction). After the addition the mixture is stirred for 1 h and subsequently quenched by slow addition of water (250 mL). The THF is removed under vacuum and the resulting mixture is extracted with EtOAc (3×120 mL). The combined organic layer is washed with water (3×100 mL) and the organic layer is dried with $MgSO_4$. The solvents are removed under vacuum and the crude product is used for the next steps without further purification.

The following intermediates A-6 (table 22) are available in an analogous manner starting from different intermediates A-5. The crude product A-6 is purified by chromatography if necessary.

TABLE 22

| # | structure | $t_{ret}$ [min] | [M + H]+ | HPLC method |
|---|---|---|---|---|
| A-6a | 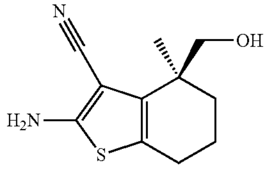 | 0.91 | 223 | A |
| A-6b | 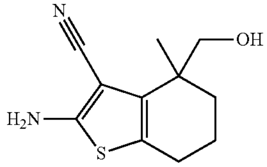 | 0.91 | 223 | A |

Experimental Procedure for the Synthesis of A-7a

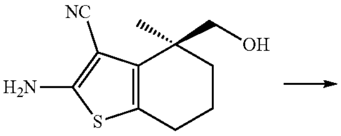
A-6a

-continued

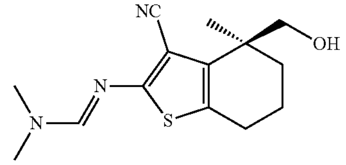

A-7a

A-6a (21.10 g, 75.93 mmol, 80% purity, 1.0 eq.) is mixed with N,N-dimethylformamide dimethyl acetal (57.6 g, 454.37 mmol, 94% purity, 6.0 eq.) and is irradiated in an ultrasound bath for 15 min until the mixture is a clear solution. Water (200 mL) is added and the reaction mixture is stirred for 30 min at rt until a precipitate forms. The precipitate is filtered and water (100 mL) is added. The mixture is irradiated in an ultrasound bath for 15 min and the precipitate is filtered. The precipitate is washed with iso-propanol (25 mL) and dried under vacuum at 45° C. over night to give A-7a which is used for the next steps without further purification.

The following intermediates A-7 (table 23) are available in an analogous manner starting from different intermediates A-6. The crude product A-7 is purified by chromatography if necessary.

TABLE 23

| # | structure | $t_{ret}$ [min] | $[M + H]^+$ | HPLC method |
|---|---|---|---|---|
| A-7a | 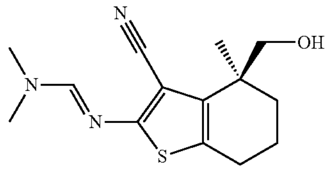 [SMILES: CN(C)/C=N/c1sc2c(c1C#N)[C@@](C)(CO)CCC2] | 1.11 | 278 | A |
| A-7b | 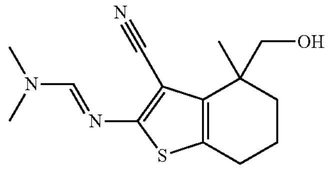 [SMILES: CN(C)/C=N/c1sc2c(c1C#N)C(C)(CO)CCC2] | 1.11 | 278 | A |

Experimental Procedure for the Synthesis of A-8a

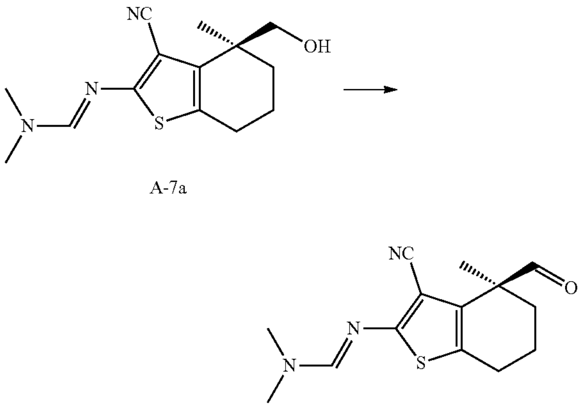

A-7a

A-8a

A solution of oxalyl chloride (12.2 mL, 144.20 mmol, 2.5 eq.) in DCM (120 mL) is cooled to −78° C. A solution of dry DMSO (18.44 mL, 259.57 mmol, 4.5 eq.) in DCM (60 mL) is added dropwise to the reaction mixture (exothermic reaction). The mixture is stirred for 30 min at −78° C. A-7a (16.00 g, 57.68 mmol, 1.0 eq.) is added slowly to the reaction mixture. The mixture is stirred for 30 min at −78° C. and trimethylamine (71.96 mL, 519.32 mmol, 9.0 eq.) is added dropwise. The reaction mixture is slowly warmed to rt and stirred for additional 2 h. Water and DCM is added to the mixture and the phases are separated. The aqueous layer is extracted two times with DCM and the combined organic layer is washed three times with water. The organic layer is dried with $MgSO_4$ and the solvents are removed under vacuum to give crude intermediate A-8a which is used without further purification in the next steps.

The following intermediates A-8 (table 24) are available in an analogous manner starting from different intermediates A-7. The crude product A-8 is purified by chromatography if necessary.

TABLE 24

| # | structure | $t_{ret}$ [min] | $[M + H]^+$ | HPLC method |
|---|---|---|---|---|
| A-8a | 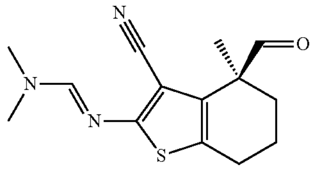 [SMILES: CN(C)/C=N/c1sc2c(c1C#N)[C@@](C)(C=O)CCC2] | 1.21 | 276 | A |
| A-8b | 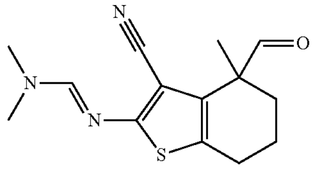 [SMILES: CN(C)/C=N/c1sc2c(c1C#N)C(C)(C=O)CCC2] | 1.21 | 276 | A |

Experimental Procedure for the Synthesis of A-9a

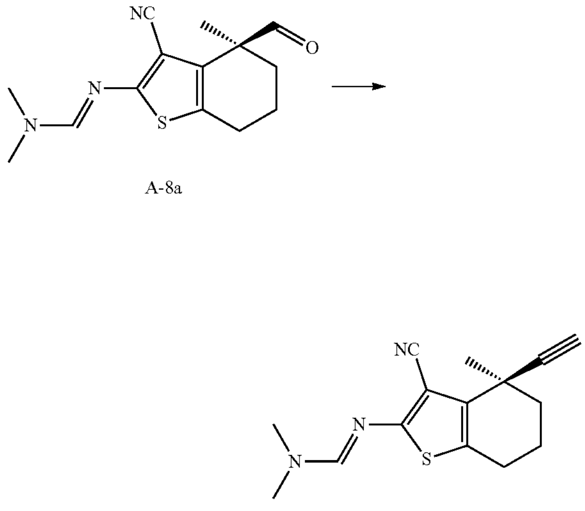

A-8a

A-9a

A mixture of A-8a (15.90 g, 57.75 mmol, 1.0 eq.), $Cs_2CO_3$ (22.58 g, 69.26 mmol, 1.2 eq.) and MeOH (120 mL) is cooled to 0° C. and a solution of Bestmann-Ohira reagent (dimethyl (1-diazo-2-oxopropyl)phosphonate; 12.20 g, 63.52 mmol, 1.1 eq.) in MeOH (5 mL) is added dropwise to the reaction mixture. After 3 h at 0° C. the reaction mixture is slowly warmed to rt. After full conversion, the MeOH is removed under vacuum and water (500 mL) and EtOAc (500 mL) are added to the mixture. The phases are separated and the aqueous layer is extracted two times with EtOAc. The combined organic layer is washed with water three times and dried over $MgSO_4$ and the solvents are removed under vacuum. The residue is mixed with diethyl ether and stirred for 30 min at rt. The mixture is cooled to 0° C. and stirred for additional 30 min before it is filtered and washed with small amounts of cold diethyl ether. The precipitate is dried under vacuum at 45° C. to give intermediate A-9a which is used for the next steps without further purification.

The following intermediates A-9 (table 25) are available in an analogous manner starting from different intermediates A-8. The crude product A-9 is purified by chromatography if necessary.

TABLE 25

| # | structure | $t_{ret}$ [min] | $[M + H]^+$ | HPLC method |
|---|---|---|---|---|
| A-9a | 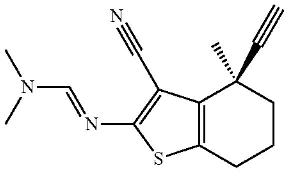 [SMILES: C#C[C@@]1(C)CCCc2sc(/N=C/N(C)C)c(C#N)c21] | 1.33 | 272 | A |
| A-9b | 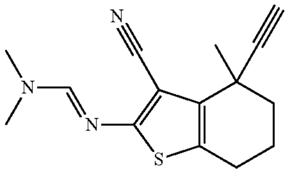 [SMILES: C#CC1(C)CCCc2sc(/N=C/N(C)C)c(C#N)c21] | 1.33 | 272 | A |

Experimental Procedure for the Synthesis of C-1a

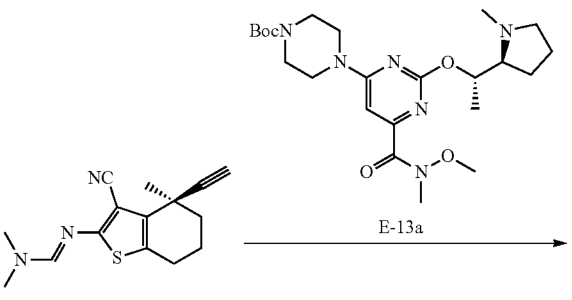

E-13a

A-9a

-continued

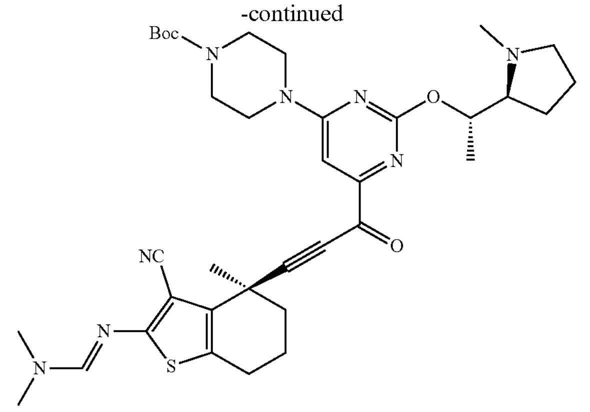

C-1a

To a solution of A-9a (132 mg, 0.47 mmo., 1.01 eq.) in THF (1 mL) at −78° C. is added LiHMDS (1.123 mL, 1.123 mmol, 2.4 eq., 1 M in THF) dropwise. A solution of E-13a (224 mg, 0.47 mmol, 1.00 eq.) in THF (2 mL) is added to the mixture at −78° C. and the mixture is stirred for 30 min at −78° C. The mixture is slowly warmed to rt and stirred for 5 min. Reaction control via HPLC-MS shows the formation of product and some remaining starting materials A-9a and E-13a. The mixture is cooled to −78° C. and additional LiHMDS (0.56 mmol, 0.56 mmol, 1.2 eq., 1 M in THF) is added dropwise to the mixture. The mixture is stirred at −78° C. for 25 min and slowly warmed to rt and stirred at this temperature for 10 min. After completion the reaction is quenched with water and diluted with EtOAc. The phases are separated and the aqueous layer is extracted three times with EtOAc. The combined organic layer is concentrated under reduced pressure. The residue is taken up in acetonitrile and water and purified by basic reversed phase chromatography (gradient elution: 35% to 98% acetonitrile in water) to give the desired product C-1a.

The following intermediates C-1 (table 26) are available in an analogous manner starting from different intermediates E-13 and A-9. The crude product C-1 is purified by chromatography if necessary.

TABLE 26

| # | structure | $t_{ret}$ [min] | [M + H]$^+$ | HPLC method |
|---|---|---|---|---|
| C-1a | 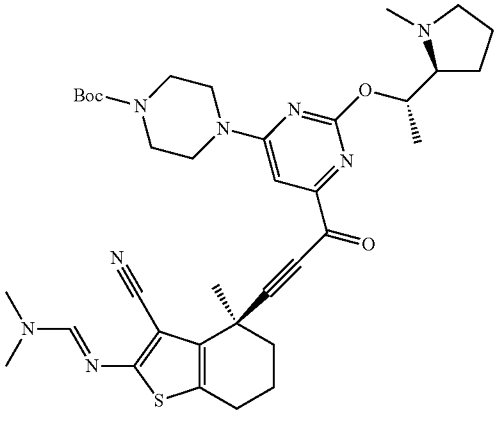 [SMILES: C[C@H](Oc1nc(C(=O)C#C[C@@]2(C)CCCc3sc(/N=C/N(C)C)c(C#N)c32)cc(N2CCN(C(=O)OC(C)(C)C)CC2)n1)[C@@H]1CCCN1C] | 1.72 | 689 | A |
| C-1b | 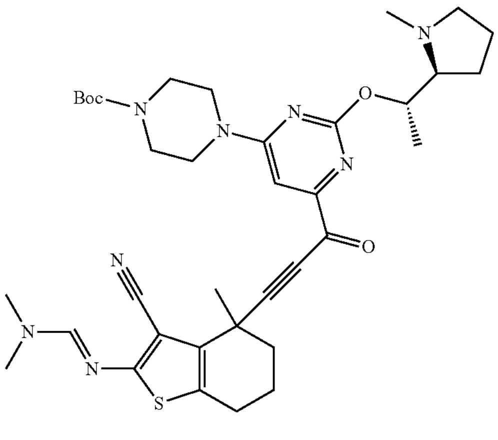 [SMILES: C[C@H](Oc1nc(C(=O)C#CC2(C)CCCc3sc(/N=C/N(C)C)c(C#N)c32)cc(N2CCN(C(=O)OC(C)(C)C)CC2)n1)[C@@H]1CCCN1C] | 1.76 | 689 | A |

TABLE 26-continued
| # | structure | $t_{ret}$ [min] | [M + H]$^+$ | HPLC method |
|---|---|---|---|---|
| C-1c | 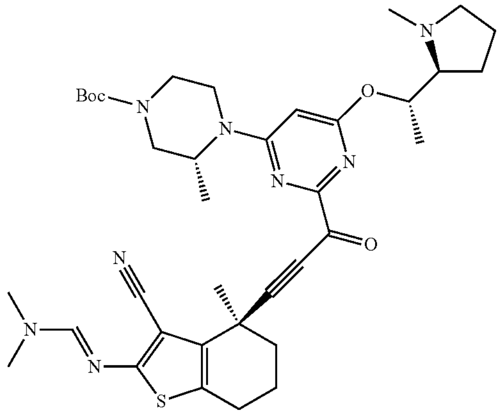 [SMILES: C[C@H](Oc1cc(N2CCN(C(=O)OC(C)(C)C)C[C@H]2C)nc(C(=O)C#C[C@@]2(C)CCCc3sc(/N=C/N(C)C)c(C#N)c32)n1)[C@@H]1CCCN1C] | 1.76 | 703 | A |
| C-1d | 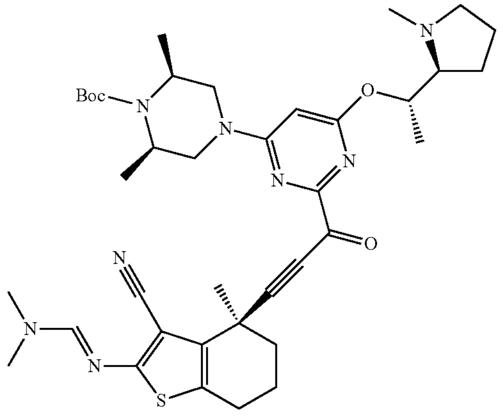 [SMILES: C[C@H](Oc1cc(N2C[C@@H](C)N(C(=O)OC(C)(C)C)[C@@H](C)C2)nc(C(=O)C#C[C@@]2(C)CCCc3sc(/N=C/N(C)C)c(C#N)c32)n1)[C@@H]1CCCN1C] | 1.79 | 717 | A |
| C-1e | 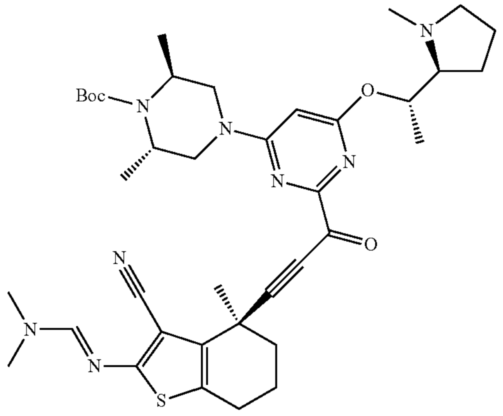 [SMILES: C[C@H](Oc1cc(N2C[C@H](C)N(C(=O)OC(C)(C)C)[C@@H](C)C2)nc(C(=O)C#C[C@@]2(C)CCCc3sc(/N=C/N(C)C)c(C#N)c32)n1)[C@@H]1CCCN1C] | 1.81 | 717 | A |

TABLE 26-continued
| # | structure | $t_{ret}$ [min] | $[M + H]^+$ | HPLC method |
|---|---|---|---|---|
| C-1f | 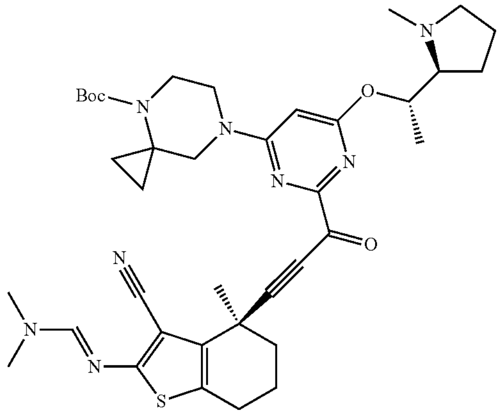 [SMILES: C[C@H](Oc1cc(N2CCN(C(=O)OC(C)(C)C)C3(CC3)C2)nc(C(=O)C#C[C@@]2(C)CCCc3sc(/N=C/N(C)C)c(C#N)c32)n1)[C@@H]1CCCN1C] | 1.78 | 715 | A |
| C-1g | 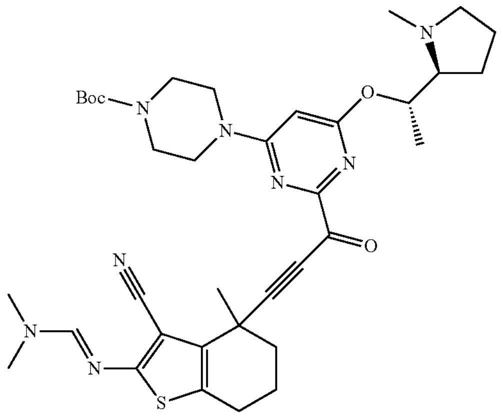 [SMILES: C[C@H](Oc1cc(N2CCN(C(=O)OC(C)(C)C)CC2)nc(C(=O)C#CC2(C)CCCc3sc(/N=C/N(C)C)c(C#N)c32)n1)[C@@H]1CCCN1C] | 1.80 | 689.00 | A |
| C-1h | 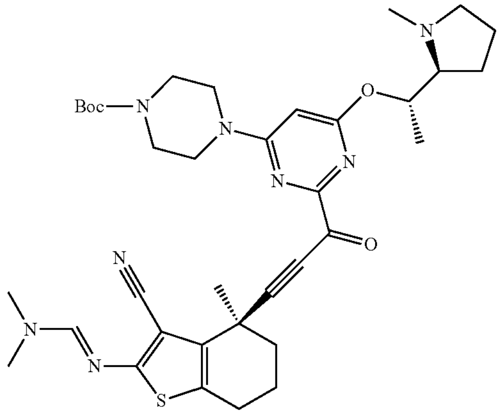 [SMILES: C[C@H](Oc1cc(N2CCN(C(=O)OC(C)(C)C)CC2)nc(C(=O)C#C[C@@]2(C)CCCc3sc(/N=C/N(C)C)c(C#N)c32)n1)[C@@H]1CCCN1C] | 1.70 | 689 | A |

TABLE 26-continued
| # | structure | $t_{ret}$ [min] | $[M + H]^+$ | HPLC method |
|---|---|---|---|---|
| C-1i | 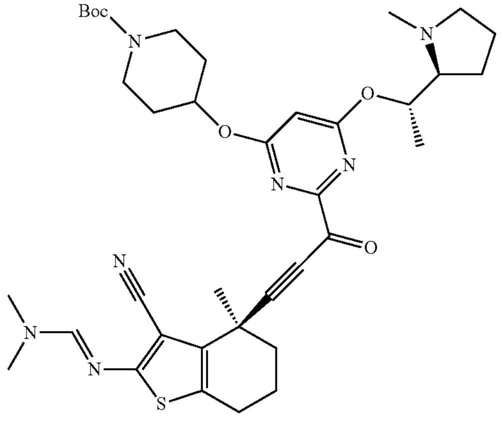 [SMILES: C[C@H](Oc1cc(OC2CCN(C(=O)OC(C)(C)C)CC2)nc(C(=O)C#C[C@@]2(C)CCCc3sc(/N=C/N(C)C)c(C#N)c32)n1)[C@@H]1CCCN1C] | 1.82 | 704 | A |
| C-1j | 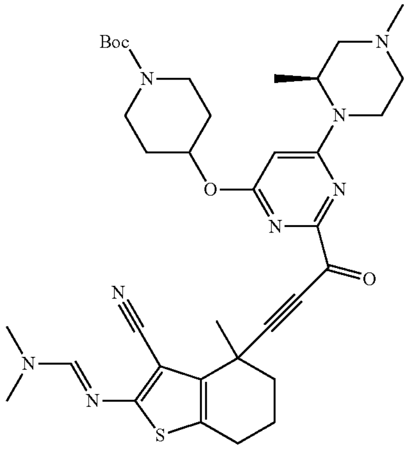 | 1.70 | 689 | A |
Alternative Synthesis of Building Block A-9
Scheme 5
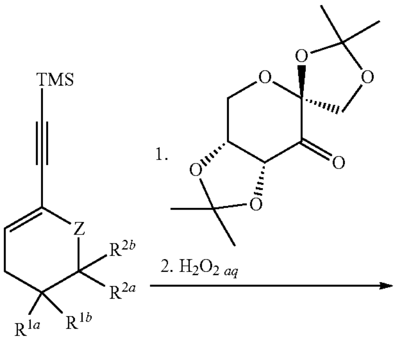
A-15
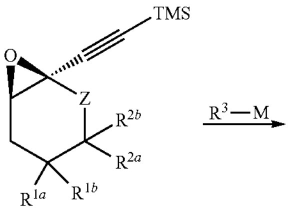
A-14
-continued
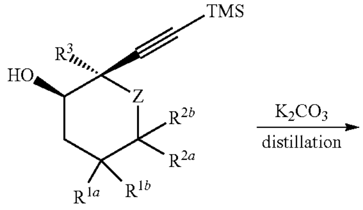
A-13
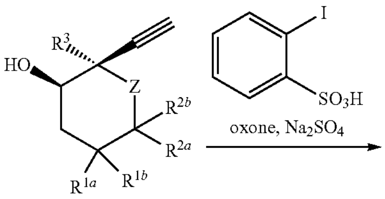
A-12
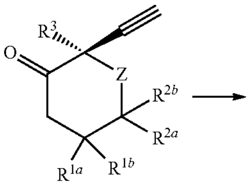
A-11

-continued

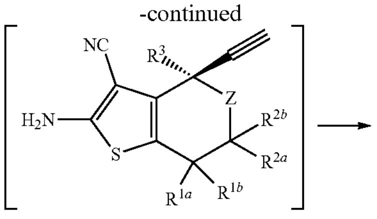

A-10

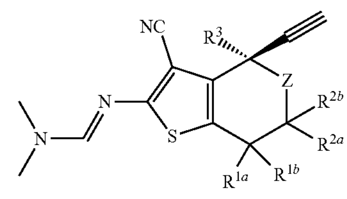

A-9

An alternative synthesis toward building block A-9 starts from TMS-protected alkyne A-15, which undergoes an asymmetric epoxidation using SHI catalyst (→A-14) followed by treatment with an organometallic nucleophile, e.g. a GRIGNARD reagent, to introduce residue $R^3$ (→A-13). TMS deprotection in the presence of a base, e.g. $K_2CO_3$, result in a hydroxy intermediate A-12 which subsequently undergoes an oxidation to afford cyclic ketone A-11. Bicyclic ring closure with malononitrile and sulfur finally yields aminocycanothiothene A-10. A-9 is then obtained after protection of the amino group as a formamidine.

Experimental Procedure for the Synthesis of A-14a

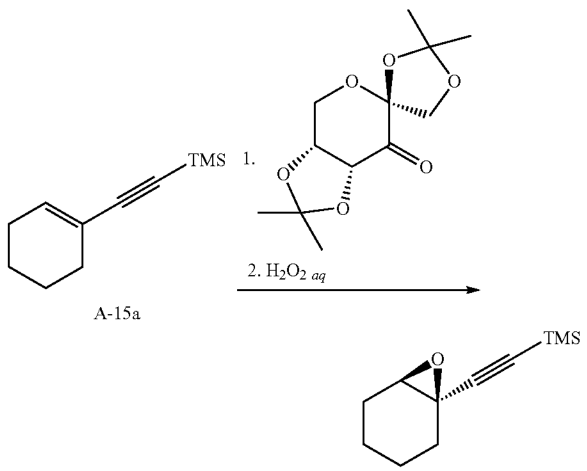

A-15a

A-14a

To a solution of A-15a (25.0 g, 140.18 mmol, 1.0 eq.) and Shi catalyst ((3a'R,4S,7a'R)-2,2,2',2'-tetramethyldihydrospiro[[1,3]dioxolane-4,6'-[1,3]dioxolo[4,5-c]pyran]-7'(4'H)-one; 7.24 g, 28.04 mmol, 0.2 eq.) in acetonitrile (175 mL) at 0° C. is added a solution of $K_2CO_3$ (48.37 g, 350.00 mmol, 2.5 eq.) and ETDA (ethylenediaminetetraacetic acid; 20.5 mg, 0.07 mmol, $4.99\times10^{-4}$ eq.) in water (175 mL). To the vigorously stirring reaction mixture is added $H_2O_2$ (56.1 mL, 560.71 mmol, 30%, 4.0 eq.) slowly over 0.5-1 h. Upon addition completion, reaction is stirred at 0° C. for 2.5 h. The reaction mixture is quenched with heptane (125 mL). The phases are separated, and aqueous layer is extracted with heptane (125 mL) three times. Combined organic layer is washed with sat. $Na_2SO_3$ aqueous solution (50 mL), dried over $Na_2SO_4$ and concentrated in vacuo to give the desired product A-14a. $^1$H-NMR ($CDCl_3$, 400 mHz): δ 3.34-3.32 (m, 1H), 2.10-2.09 (m, 1H), 2.03-2.00 (m, 1H), 1.91-1.87 (m, 2H), 1.41-1.37 (m, 2H), 1.32-1.22 (m, 2H), 0.16 (m, 9H).

Experimental Procedure for the Synthesis of A-13a

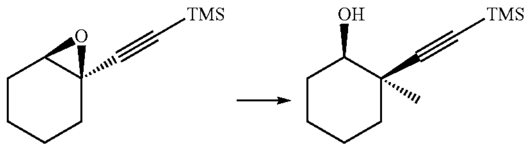

A-14a A-13a

To a dry flask under $N_2$ is added LiCl (0.5 M in THF; 12.35 mL, 61.75 mmol, 1.2 eq.). The solution is cooled to −5 to 0° C., and to this chilled solution is added $LaCl_3\cdot2LiCl$ (0.6 M in THF; 1.03 mL, 0.62 mmol, 0.012 eq.) and MeMgCl (3 M in THF; 20.58 mL, 61.75 mmol, 1.2 eq.) sequentially. The resulting mixture is stirred for 10-15 min, at which point A-14a (10.00 g, 51.45 mmol, 1.0 eq.) is added dropwise. The reaction mixture is warmed to rt. Upon reaction completion, reaction mixture is cooled to −5 to 0° C. and is quenched with sat. $NH_4Cl$ aqueous solution (40 mL). Gas evolution is observed, and cooling batch is removed. The phases are separated. Aqueous layer is extracted with MTBE (50 mL) three times. Combined organic layer is dried over $Na_2SO_4$ and then concentrated in vacuo. The crude product is purified by flash column chromatography (isocratic 10% MTBE in hexane) to give the desired product A-13a. $^1$H-NMR (DMSO-$d_6$, 400 mHz): δ 4.56 (d, J=5.0 Hz, 1H), 3.03-2.98 (m, 1H), 1.62-1.58 (m, 3H), 1.50-1.42 (m, 3H), 1.19-1.18 (m, 2H), 1.14 (s, 3H), 0.12 (t, J=3.5 Hz, 9H).

Experimental Procedure for the Synthesis of A-12a

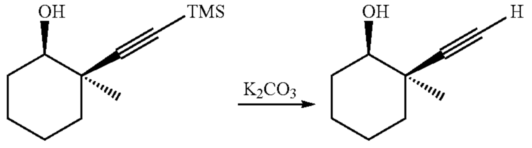

A-13a A-12a

To a solution of A-13a (6.76 g, 32.13 mmol, 1.0 eq.) in MeOH (87.5 mL) is added $K_2CO_3$ (6.21 g, 44.95 mmol, 1.4 eq.). The reaction mixture is stirred for 2 h at rt. Upon reaction completion, the reaction mixture is filtered. Filtered solids are washed with MeOH (20 mL). Filtrate is concentrated in vacuo and then subsequently diluted with MTBE (100 mL). Precipitation is observed and solids are filtered. Filtered solids are rinsed with MTBE (25 mL) twice. Collected filtrate is washed with 14 wt % $NH_4Cl$ aqueous solution. Aqueous layer is back extracted with MTBE (25 mL), then dried over $Na_2SO_4$ and concentrated in vacuo. The crude is purified by distillation (25-30 mbar, bath temperature 125-150° C., head temperature 85-87° C.) to give the desired product A-12a. $^1$H-NMR (DMSO-$d_6$, 400 mHz): δ 4.59 (d, J=5.0 Hz, 1H), 3.03-2.99 (m, 1H), 1.63-1.61 (m, 3H), 1.49-1.42 (m, 3H), 1.20-1.16 (m, 2H), 1.18 (s, 3H).

Experimental Procedure for the Synthesis of A-11a

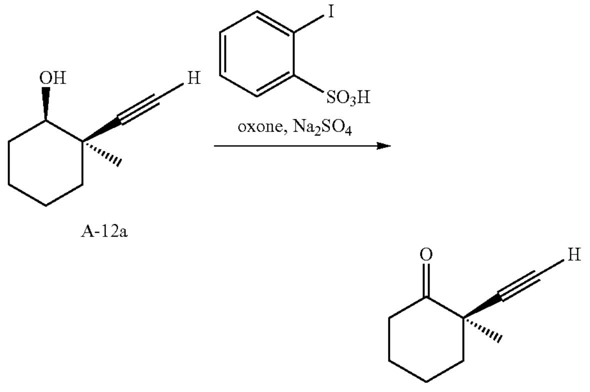

A-12a

A-11a

To a solution of $Na_2SO_4$ (20.0 g), 2-iodobenzenesulfonic acid (0.78 g, 2.75 mmol, 0.04 eq) and oxone (35.90 g, 116.7 mmol, 1.7 eq.) in acetonitrile (100 mL) is added A-12a (10.0 g, 68.67 mmol, 94% purity, 1 eq.). The reaction is stirred vigorously and is heated to 70-75° C. After 20-24 h, reaction is cooled to 20-25° C., at which point MTBE (100 mL) is added. The resulting slurry is filtered; solids are washed with MTBE (20 mL). Filtrate is concentrated at >35 torr. Crude is purified by fractional distillation (30-35 torr, 110-120° C.) to give the desired product A-11a. $^1$H-NMR ($CDCl_3$, 500 mHz): δ 3.02-2.95 (td, J=13.6, 6.0 Hz, 1H), 2.36 (s, 1H), 2.34-2.31 (d, J=13.2 Hz, 1H), 2.16-2.08 (m, 3H), 1.76-1.74 (m, 1H), 1.69-1.63 (m, 1H), 1.61-1.54 (m, 2H), 1.33 (s, 3H).

Experimental Procedure for the Synthesis of A-10b

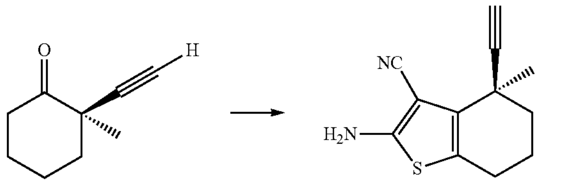

A-11a

A-10b

To a solution of A-11a (9.72 g, 71.37 mmol, 1.00 eq.), sulfur (2.42 g, 74.94 mmol, 1.05 eq.) and $NH_4OAc$ (5.5 g, 71.37 mmol, 1.00 eq.) in EtOH (9.7 mL) at 50° C. is added a solution of malononitrile (5.02 g, 74.94 mmol, 1.50 eq.) in EtOH (38.9 mL) slowly. After 2 h, conversion to A-10b is complete, reaction mixture is carried onto the next step without isolation.

Experimental Procedure for the Synthesis of A-9a

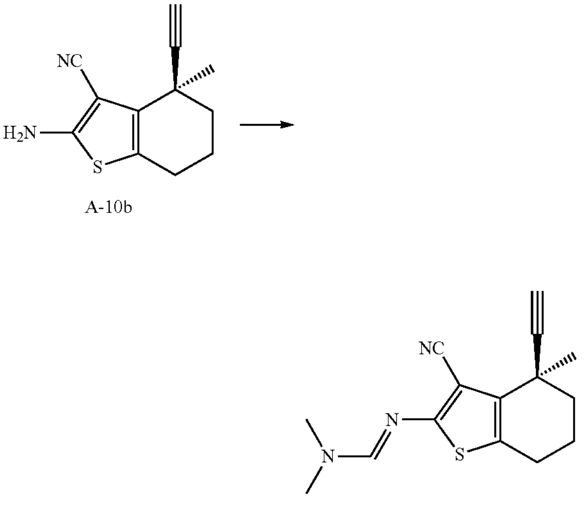

A-10b

A-9a

To the reaction mixture containing A-10b in EtOH at 50° C. is added DMF-DMA (47.41 mL, 357 mmol, 5.0 eq.). The reaction is stirred for an additional 5-6 h, at which point the reaction is quenched with $H_2O$ (97.2 mL) and is allowed to stir at room cooled to rt overnight. Crude is filtered and filtered wet solids are taken up in EtOH (48.6 mL). The resulting slurry is stirred at 70° C. for 3 h and then at rt overnight. Solids are filtered and washed with heptane (29.2 mL). Solids are recrystallized from EtOH (29.2 mL); the resulting slurry is stirred at 70° C. for 3 h and then at rt for 10-12 h. Solids are filtered, washed with heptane (29.2 mL), and further dried under vacuum at 60° C. to give A-9a.

Scheme 6

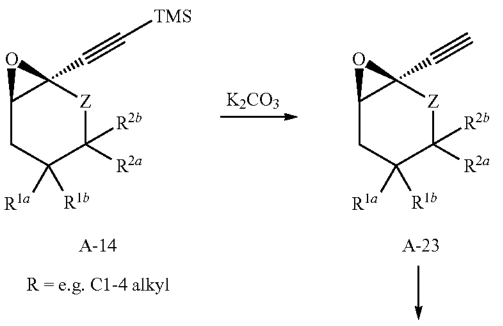

A-14

A-23

R = e.g. C1-4 alkyl

-continued

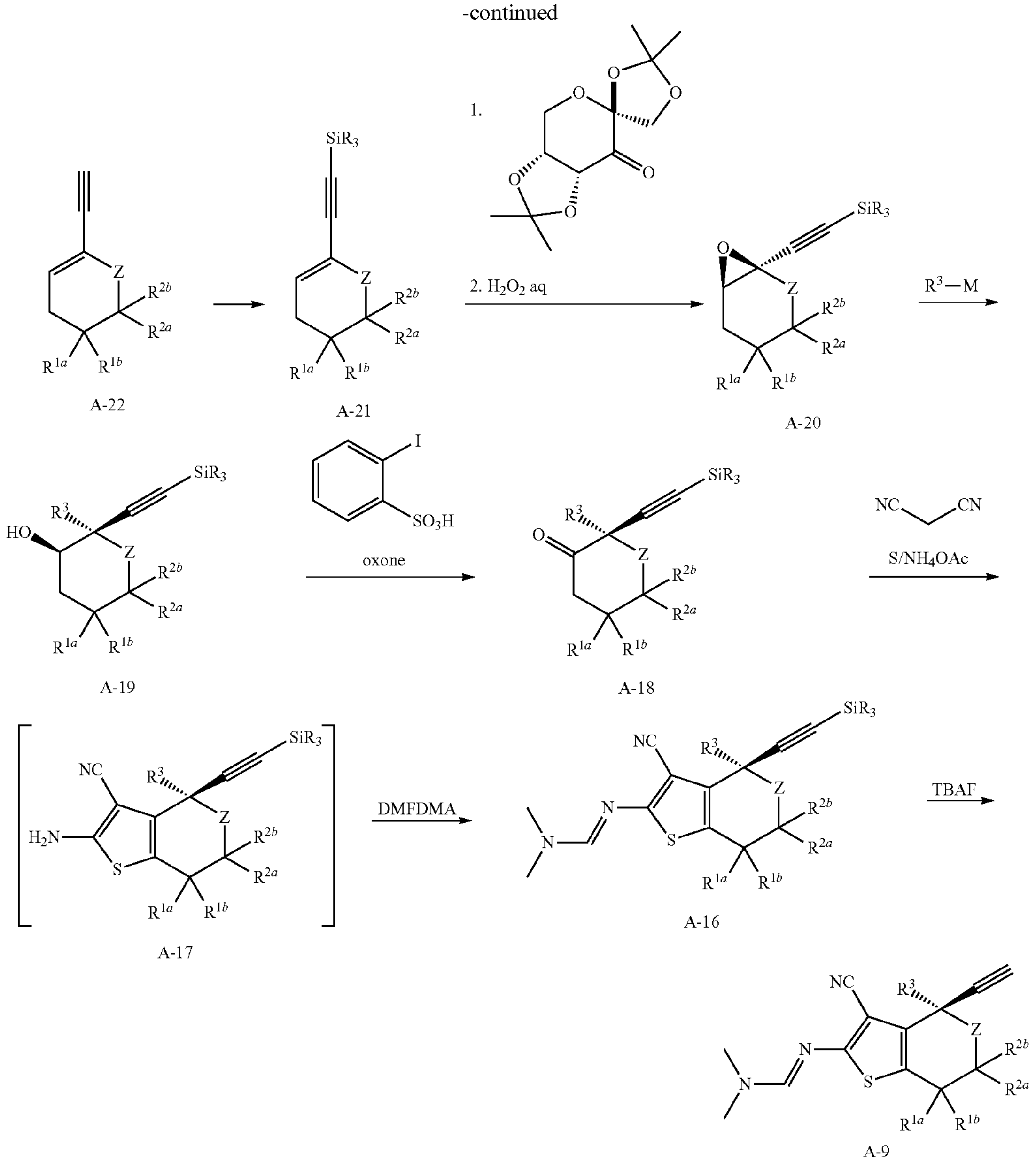

A-22, A-21, A-20, A-19, A-18, A-17, A-16, A-9

Experimental Procedure for the Synthesis of A-23a

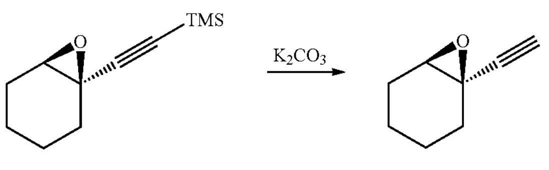

A-14a A-23a

To a solution of A-14a (10.0 g, 40.2 mmol, 78.1% purity, 1.00 eq.) in MeOH (100 mL) is added $K_2CO_3$ (0.056 g, 0.41 mmol, 0.01 eq.). The reaction mixture is stirred at rt for 3-5 h. Upon reaction completion, heptane (50 mL) and $H_2O$ (20 mL) are added to the stirring reaction mixture. The phases are separated, and aqueous layer is extracted with heptane (25 mL). The combined organic layer containing A-23a is carried onto the next step without solvent concentration to avoid product loss due to product volatility.

Experimental Procedure for the Synthesis of A-20a

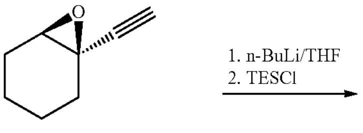

A-23a

-continued

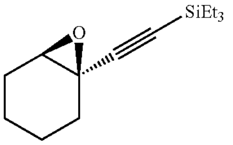

A-20a

To a solution of A-23a (15 g, 8.72 mmol, 7.1% purity, 1.00 eq.) in heptane from the previous operation is added THF (15 mL). The solution mixture is cooled to −25° C., at which point n-BuLi (2.5 M in hexane, 6.97 mL, 17.44 mmol, 2.00 eq.) is added via additional funnel. After stirring for 10-15 min, TESCl (1.83 mL, 10.90 mmol, 1.25 eq.) is added slowly. After an additional 30 min, A-23a is consumed and reaction mixture is warmed to −5° C., at which point it is quenched with 20 wt % $NH_4Cl$ aqueous solution (14 mL). The solution mixture is further warmed to rt. Phases are separated. Organic layer is washed with 18 wt % $NH_4Cl$ aqueous solution (7 mL) and then concentrated in vacuo to give A-20a. $^1H$-NMR ($CDCl_3$, 500 mHz): δ 3.30 (s, 1H), 2.25-2.15 (m, 1H), 2.10-2.00 (m, 1H), 1.95-1.85 (m, 1H), 1.45-1.20 (m, 3H), 0.96 (t, J=7.88 Hz, 9H), 0.57 (q, J=7.88 Hz, 6H).

The corresponding intermediate A-20b (tert-butyldimethylsilyl protecting group (TBS) instead of triethylsilyl protecting group (TES)) can be obtained in an analoguous manner using TBSCl:

A-20b

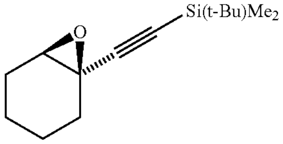

Experimental procedure for the synthesis of A-21a

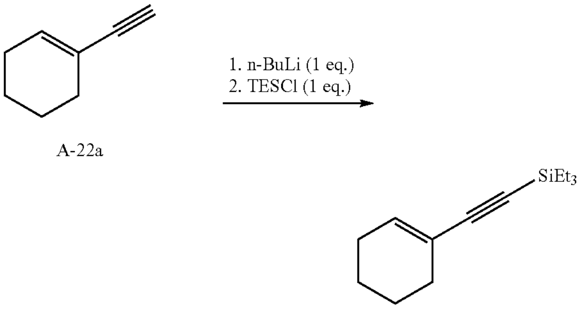

A-22a

A-21a

To a solution of A-22a (25 g, 233.83 mmol, 1.00 eq.) in THF (250 mL) at −25° C. is added n-BuLi (2.5 M in hexane, 95.0 mL, 237.50 mmol, 1.02 eq.) via additional funnel over 30-40 min. After stirring for 10-15 min, TESCl (40.65 mL, 241.43 mmol, 1.03 eq.) is added slowly. After an additional 30 min, reaction mixture is warmed to −5° C., at which point it is quenched with 20 wt % $NH_4Cl$ aqueous solution (200 mL). The solution mixture is further warmed to rt. Phases are separated. Organic layer is concentrated in vacuo to give A-21a. $^1H$-NMR ($CDCl_3$, 500 mHz): δ 6.25-6.20 (m, 1H), 2.20-2.05 (m, 4H), 1.70-1.50 (m, 4H), 0.95 (t, J=7.84 Hz, 9H), 0.60 (q, J=7.84 Hz, 9H).

The corresponding intermediate A-21b (tert-butyldimethylsilyl protecting group (TBS) instead of triethylsilyl protecting group (TES)) can be obtained in an analoguous manner using TBSCl:

A-21b

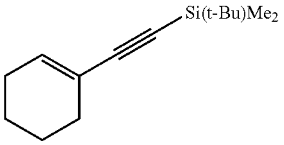

Experimental Procedure for the Synthesis of A-20a

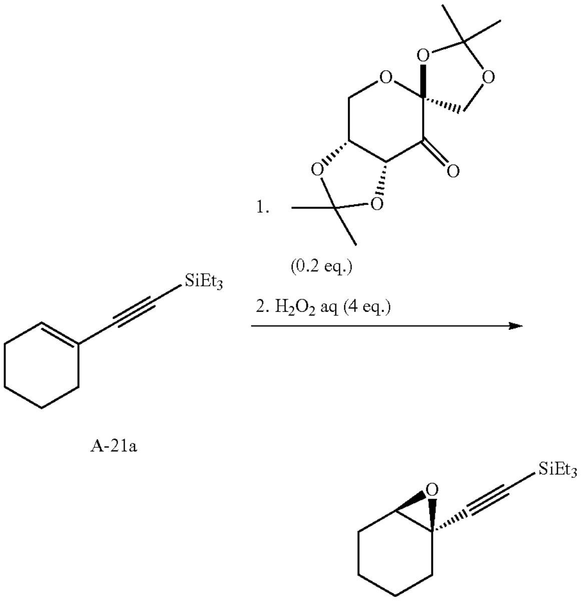

A-21a

A-20a

To a solution of A-21a (20.0 g, 82.03 mmol, 90.4% purity, 1.0 eq.) and SHI catalyst ((3a'R,4S,7a'R)-2,2,2',2'-tetramethyldihydrospiro[[1,3]dioxolane-4,6'-[1,3]dioxolo[4,5-c] pyran]-7'(4'H)-one; 4.39 g, 16.43 mmol, 0.2 eq.) in acetonitrile (160 mL) at 0° C. is added a solution of $K_2CO_3$ (28.3 g, 205.06 mmol, 2.5 eq) and ETDA (ethylenediaminetetraacetic acid; 11.98 mg, 0.04 mmol, 4.99×$10^{-4}$ eq.) in water (102.5 mL). To the vigorously stirring reaction mixture is added $H_2O_2$ (33.5 mL, 328.09 mmol, 30%, 4.0 eq.) slowly over 1.5-2 h. Upon addition completion, reaction is stirred at 0° C. for 14-16 h. The reaction mixture is quenched with heptane (100 mL). The phases are separated, and aqueous layer is extracted with heptane (100 mL) three times. Combined organic layer is washed with sat. $Na_2SO_3$ aqueous solution (40 mL), dried over $Na_2SO_4$ and concentrated in vacuo to give the desired product A-20a.

The corresponding intermediate A-20b (tert-butyldimethylsilyl protecting group (TBS) instead of triethylsilyl protecting group (TES)) can be obtained in an analoguous manner from A-21b:

A-20b

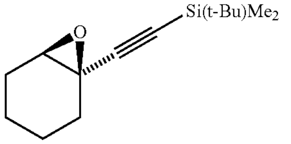

Experimental Procedure for the Synthesis of A-19a

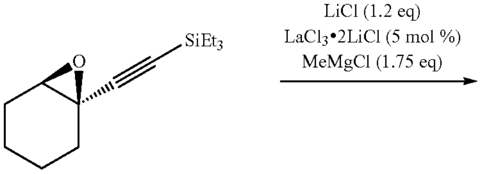

A-20a

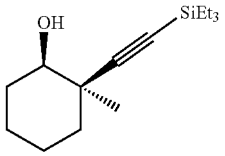

A-19a

To a dry flask under $N_2$ is added A-20a (10.00 g, 34.43 mmol, 81.4% purity, 1.0 eq.), LiCl (0.5 M in THF; 82.6 mL, 61.75 mmol, 1.2 eq.) and $LaCl_3$·2LiCl (0.6 M in THF; 1.72 mmol, 2.9 mL, 0.05 eq.). The solution is cooled to −5 to 0° C. and MeMgCl (3 M in THF; 20.0 mL, 60.25 mmol, 1.75 eq.) is added over 20-30 min. The resulting mixture is stirred for at 0° C. for 30 min, and then at rt for 14-16 h. Upon reaction completion, MTBE (105 mL) is added and reaction mixture is cooled to −5 to 0° C. The reaction is quenched with 1N HCl (69.0 mL, 69.0 mmol, 2 eq.) dropwise. After stirring for an additional 15-20 min, the phases are separated. Aqueous layer is extracted with MTBE (52.5 mL). Combined organic layer is dried over $Na_2SO_4$ and then concentrated in vacuo to give the desired product A-19a. $^1$H-NMR ($CDCl_3$, 500 mHz): δ 3.20-3.10 (m, 1H), 1.90-1.80 (m, 2H), 1.75-1.65 (m, 1H), 1.60-1.55 (m, 5H), 1.35 (s, 3H), 1.30-1.10 (m, 2H), 0.97 (t, J=7.85 Hz, 9H), 0.60 (q, J=7.85 Hz, 6H).

The corresponding intermediate A-19b (tert-butyldimethylsilyl protecting group (TBS) instead of triethylsilyl protecting group (TES)) can be obtained in an analoguous manner from A-20b:

A-19b

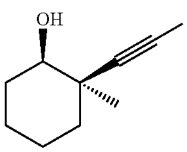

Experimental Procedure for the Synthesis of A-18a

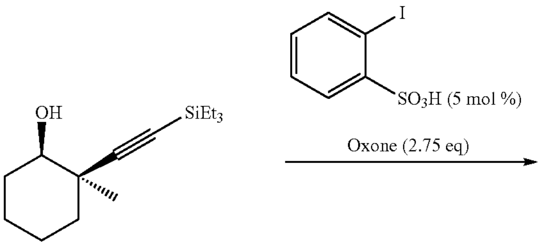

A-19a

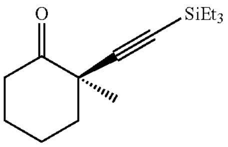

A-18a

To a vigorously stirred solution of oxone (23.72 g, 77.16 mmol, 2.75 eq.), 2-iodobenzenesulfonic acid (407 mg, 1.40 mmol, 0.05 eq.) and A-19a (10.7 g, 28.06 mmol, 66.2% purity, 1.0 eq.) in acetonitrile (71 mL) at rt is added $H_2O$ (0.51 mL, 28.06 mmol, 1 eq.). The resulting reaction mixture is heated at 70-75° C. for 16-18 h. After reaction completion, reaction mixture is cooled to 20-25° C. and is diluted with MTBE (71 mL). The resulting slurry is stirred for 10-15 min and then filtered via vacuum filtration. Filtered solids are washed with MTBE (71 mL). Filtrate is concentrated at 40° C. under vacuum to give A-18a. $^1$H-NMR ($CDCl_3$, 500 mHz): δ 3.10-2.95 (m, 1H), 2.35-2.25 (m, 1H), 2.20-2.00 (m, 3H), 1.75-1.65 (m, 1H), 1.60-1.50 (m, 3H), 1.30 (s, 3H), 0.95 (t, J=7.85 Hz, 9H), 0.57 (q, J=7.85 Hz, 6H).

The corresponding intermediate A-18b (tert-butyldimethylsilyl protecting group (TBS) instead of triethylsilyl protecting group (TES)) can be obtained in an analoguous manner from A-19b:

A-18b

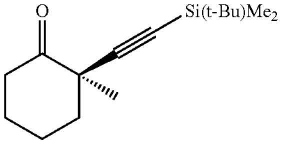

Experimental Procedure for the Synthesis of A-17a

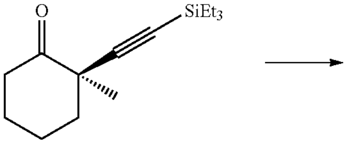

A-18a

-continued

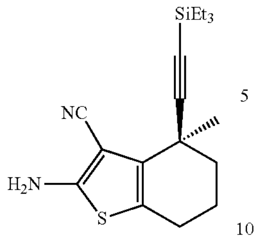

A-17a

To a solution of A-18a (10.0 g, 28.23 mmol, 70.7% purity 1.0 eq.), sulfur (1.36 g, 42.34 mmol, 1.5 eq.) and $NH_4OAc$ (3.26 g, 42.34 mmol, 1.5 eq.) in EtOH (50 mL) at 50-55° C. is added a solution of malononitrile (2.85 g, 42.34 mmol, 1.5 eq.) in EtOH (21 mL) slowly. After 14-18 h, conversion to A-17a is complete, reaction mixture is carried onto the next step without isolation.

The corresponding intermediate A-17b (tert-butyldimethylsilyl protecting group (TBS) instead of triethylsilyl protecting group (TES)) can be obtained in an analoguous manner from A-18b:

A-17b

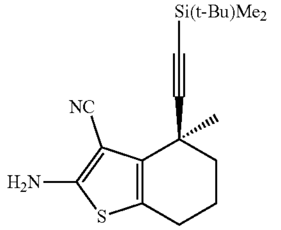

Experimental Procedure for the Synthesis of A-16a

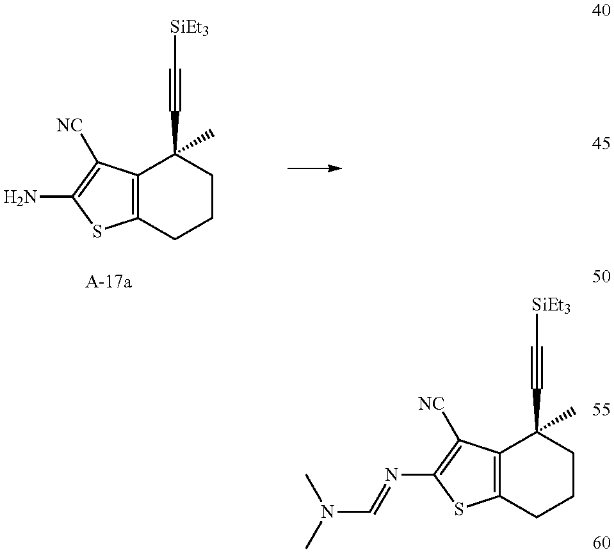

A-17a

A-16a

To the reaction mixture containing A-17a in EtOH at 50-55° C. is added DMF-DMA (19.9 mL, 141.14 mmol, 5.0 eq.). The reaction is stirred for an additional 5-6 h, at which point the reaction is cooled to about 40° C. and is added $H_2O$ (71 mL) dropwise over 1 h. The resulting slurry is further cooled to 15-20° C. over 1 h. After stirring for an additional 30 min, solids are filtered and washed with cold EtOH/$H_2O$ (1:1 v/v, 100 mL). Solids are further dried under vacuum at 40-45° C. overnight to give A-16a. $^1$H-NMR ($CDCl_3$, 500 mHz): δ 7.65 (s, 1H), 3.09 (s, 3H), 3.06 (s, 3H), 2.65-2.50 (m, 2H), 2.10-2.03 (m, 1H), 1.97-1.90 (m, 1H), 1.85-1.70 (m, 2H), 1.65 (s, 3H), 1.00 (t, J=7.90 Hz, 9H), 0.58 (q, J=7.90 Hz, 6H).

The corresponding intermediate A-16b (tert-butyldimethylsilyl protecting group (TBS) instead of triethylsilyl protecting group (TES)) can be obtained in an analoguous manner from A-17b:

A-16b

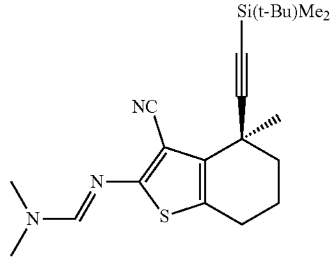

Experimental Procedure for the Synthesis of A-9a

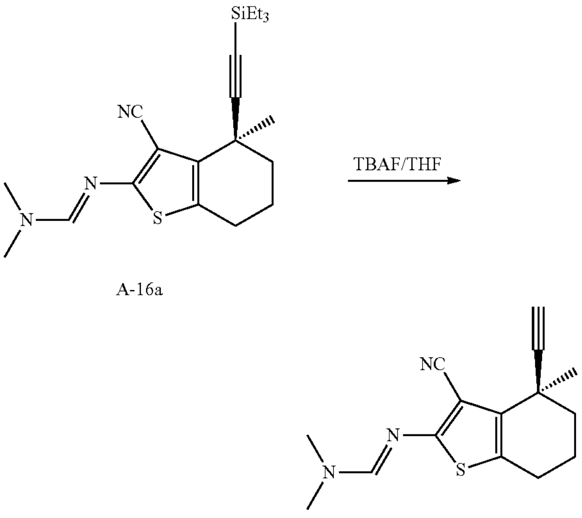

A-16a

A-9a

A solution of A-16a (8.0 g, 16.53 mmol, 79.7% purity, 1.0 eq.) in THF (32 mL) is cooled to 0-5° C. To the stirring mixture is added TBAF (1.0 M in THF; 19.85 mL, 19.85 mmol, 1.2 eq.) slowly. The reaction mixture is stirred for an additional 30 min, at which point MTBE (52 mL) is added, followed by addition of $H_2O$. The resulting mixture is warmed to rt and stirred for an additional 10 min. Solids are filtered by vacuum filtration as $1^{st}$ crop. Phases of filtrates are separated. Organic layer is concentrated at 40° C. under vacuum. Oil residue is dissolved in isopropanol (20 mL). To the stirring solution is added heptane (20 mL) dropwise to afford a slurry. After stirring for an additional 1-2 h, solids are filtered by vacuum filtration as $2^{nd}$ crop. Both $1^{st}$ and $2^{nd}$ crops of product are combined and washed with isopropanol/heptane (1:1 v/v, 40 mL), followed by a wash with heptane (40 mL). Solids are further dried at 40-45° C. under vacuum to give A-9a.

A-9a can also be obtained from A-16b in an analoguous manner.
Scheme 7
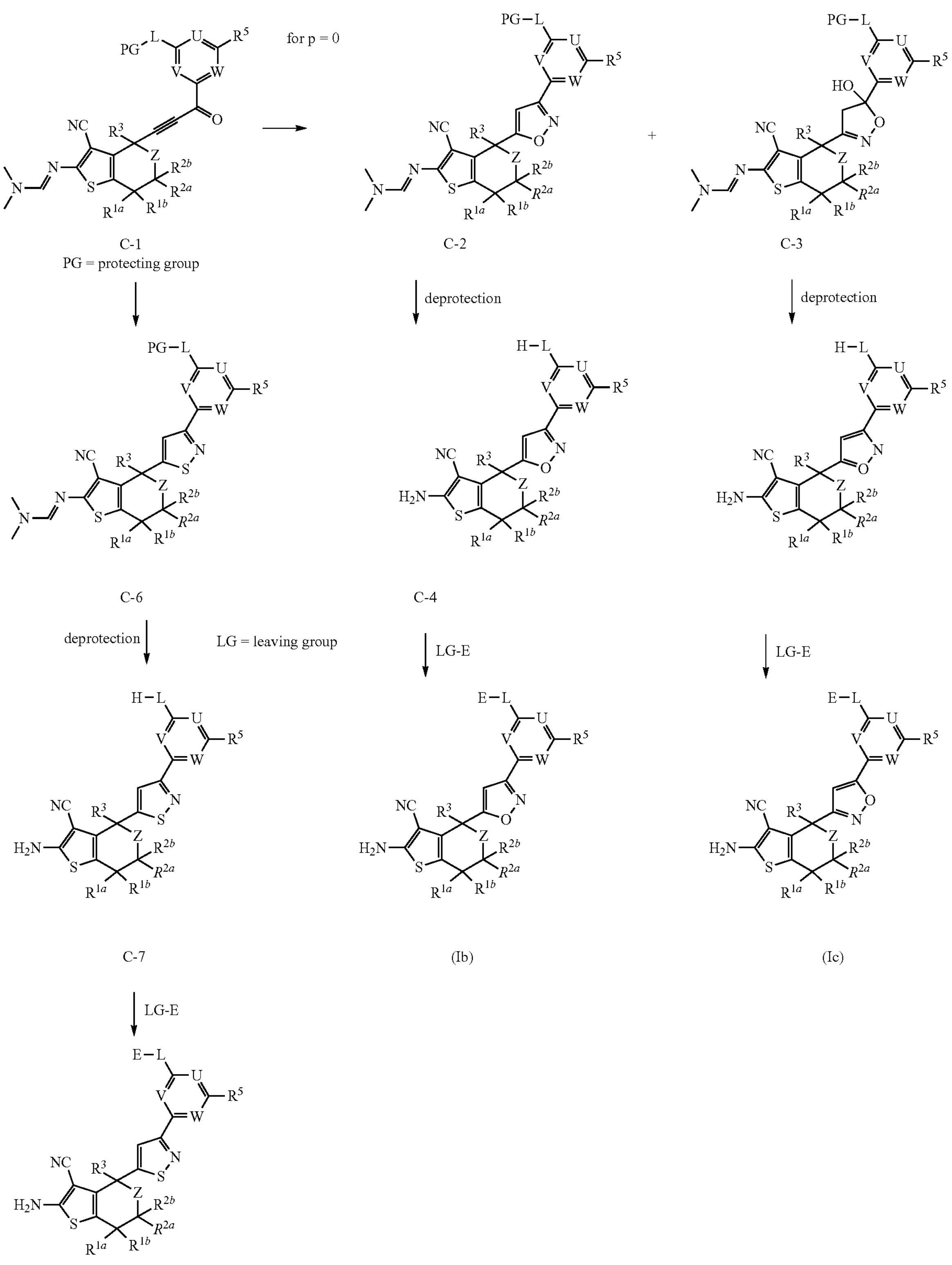
C-1, C-2, C-3, C-6, C-4, C-7, (Ib), (Ic), (Id)

Experimental Procedure for the Synthesis of C-2a and C-3a

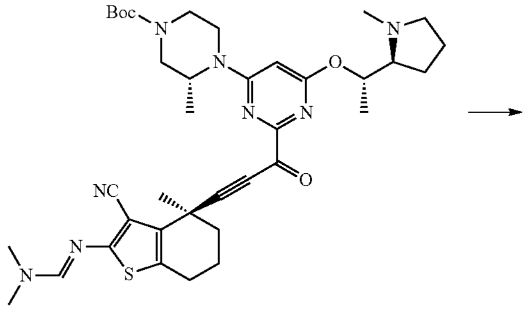

C-1c

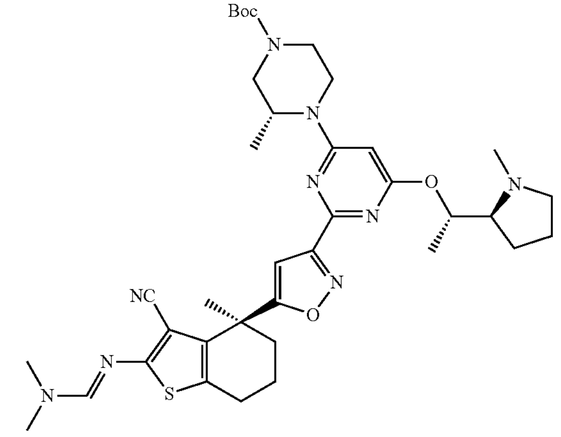

C-2a

+

-continued

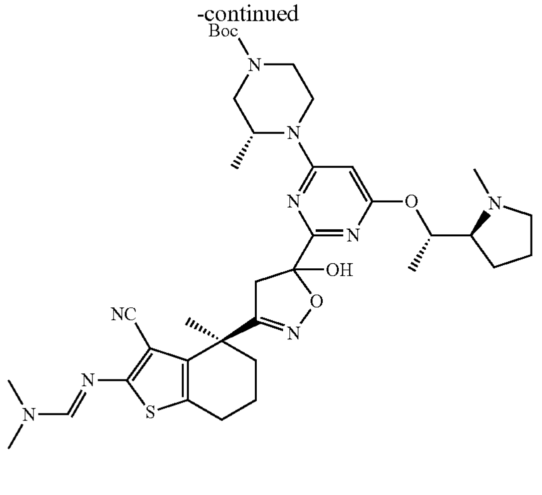

C-3a

To a solution of C-1c (450 mg, 0.64 mmol, 1.0 eq.) in MeOH (6 mL) is added hydroxylamine hydrochloride (133.6 mg, 1.92 mmol, 3.0 eq.) and the reaction mixture is stirred for 1 h at rt. Additional hydroxylamine hydrochloride (44.5 mg, 0.64 mmol, 1.0 eq.) is added and the reaction mixture is stirred for 1 h at rt. After completion of the reaction the mixture is diluted with acetonitrile and water, filtered and purified by basic reversed phase chromatography (gradient elution: 35% to 98% acetonitrile in water) to give the desired intermediates C-2a (second eluting, major product) and C-3a (first eluting, minor product).

The following intermediates C-2 and C-3 (table 27) are available in an analogous manner starting from different intermediates C-1. The crude products C-2 and C-3 are purified by chromatography if necessary.

TABLE 27

| # | structure | $t_{ret}$ [min] | $[M + H]^+$ | HPLC method |
|---|---|---|---|---|
| C-2a | 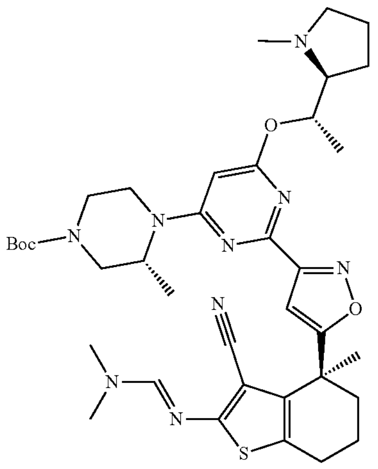 [SMILES: C[C@H](Oc1cc(N2CCN(C(=O)OC(C)(C)C)C[C@H]2C)nc(-c2cc([C@@]3(C)CCCc4sc(/N=C/N(C)C)c(C#N)c43)on2)n1)[C@@H]1CCCN1C] | 1.76 | 718 | A |

TABLE 27-continued
| # | structure | $t_{ret}$ [min] | [M + H]+ | HPLC method |
|---|---|---|---|---|
| C-3a | 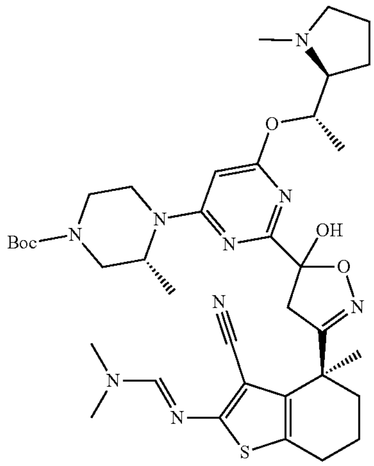 [SMILES: C[C@H](Oc1cc(N2CCN(C(=O)OC(C)(C)C)C[C@H]2C)nc(C2(O)CC([C@@]3(C)CCCc4sc(/N=C/N(C)C)c(C#N)c43)=NO2)n1)[C@@H]1CCCN1C] | 1.67 | 736 | A |
| C-2b | 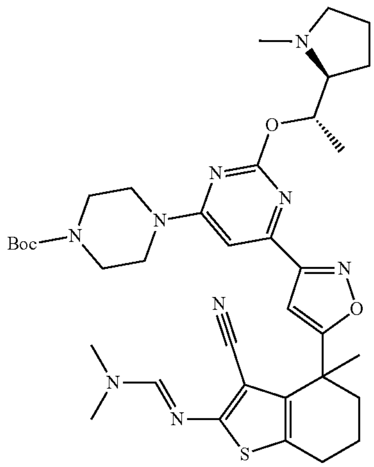 [SMILES: C[C@H](Oc1nc(-c2cc(C3(C)CCCc4sc(/N=C/N(C)C)c(C#N)c43)on2)cc(N2CCN(C(=O)OC(C)(C)C)CC2)n1)[C@@H]1CCCN1C] | 0.929 | 704 | G |
| C-2c | 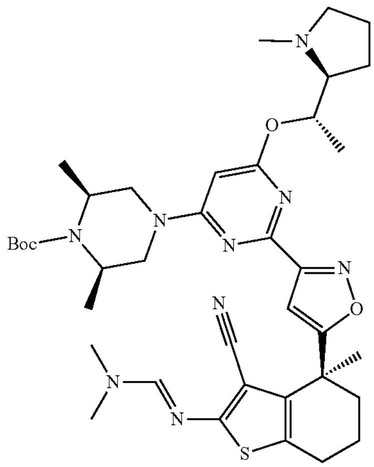 | 1.83 | 732 | A |

TABLE 27-continued
| # | structure | $t_{ret}$ [min] | $[M + H]^+$ | HPLC method |
|---|---|---|---|---|
| C-3c | 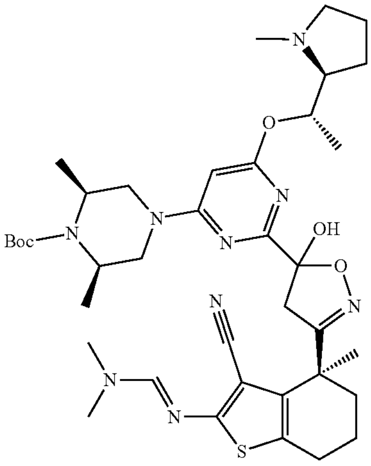 [SMILES: C[C@H](Oc1cc(N2C[C@@H](C)N(C(=O)OC(C)(C)C)[C@@H](C)C2)nc(C2(O)CC([C@@]3(C)CCCc4sc(/N=C/N(C)C)c(C#N)c43)=NO2)n1)[C@@H]1CCCN1C] | 1.74 | 750.00 | A |
| C-2d | 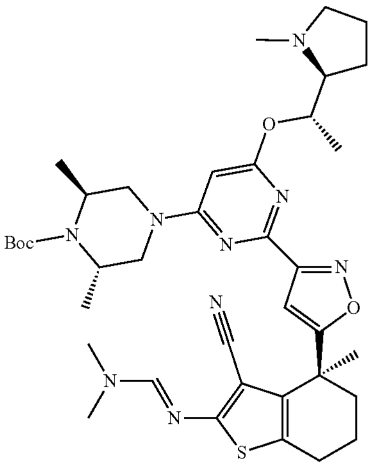 | 1.83 | 732 | A |
| C-3d | 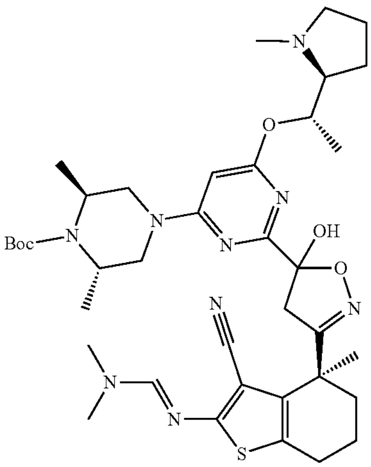 [SMILES: C[C@H](Oc1cc(N2C[C@H](C)N(C(=O)OC(C)(C)C)[C@@H](C)C2)nc(C2(O)CC([C@@]3(C)CCCc4sc(/N=C/N(C)C)c(C#N)c43)=NO2)n1)[C@@H]1CCCN1C] | 1.73 | 750.00 | A |

TABLE 27-continued
| # | structure | $t_{ret}$ [min] | $[M + H]^+$ | HPLC method |
|---|---|---|---|---|
| C-2e | 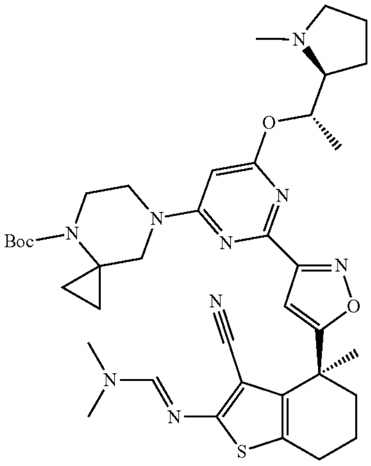 [SMILES: C[C@H](Oc1cc(N2CCN(C(=O)OC(C)(C)C)C3(CC3)C2)nc(-c2cc([C@@]3(C)CCCc4sc(/N=C/N(C)C)c(C#N)c43)on2)n1)[C@@H]1CCCN1C] | 1.80 | 730 | A |
| C-3e | 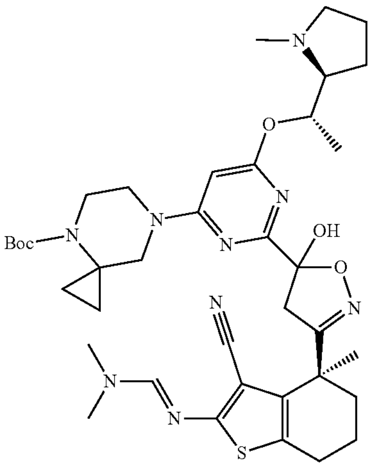 [SMILES: C[C@H](Oc1cc(N2CCN(C(=O)OC(C)(C)C)C3(CC3)C2)nc(C2(O)CC([C@@]3(C)CCCc4sc(/N=C/N(C)C)c(C#N)c43)=NO2)n1)[C@@H]1CCCN1C] | 1.71 | 748.00 | A |
| C-2f | 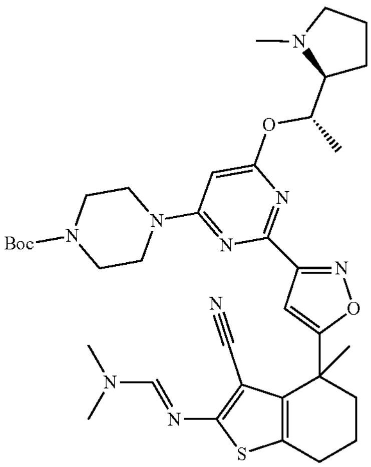 [SMILES: C[C@H](Oc1cc(N2CCN(C(=O)OC(C)(C)C)CC2)nc(-c2cc(C3(C)CCCc4sc(/N=C/N(C)C)c(C#N)c43)on2)n1)[C@@H]1CCCN1C] | 1.86 | 704.00 | A |

TABLE 27-continued
| # | structure | $t_{ret}$ [min] | [M + H]$^+$ | HPLC method |
|---|---|---|---|---|
| C-3f | 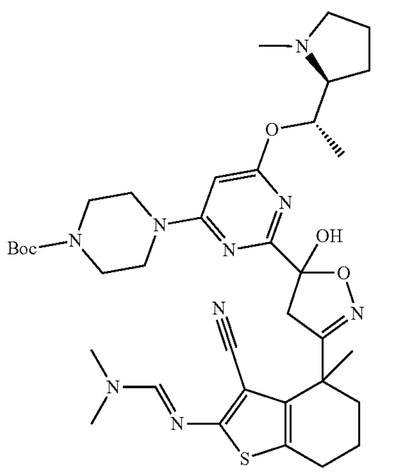 [SMILES: C[C@H](Oc1cc(N2CCN(C(=O)OC(C)(C)C)CC2)nc(C2(O)CC(C3(C)CCCc4sc(/N=C/N(C)C)c(C#N)c43)=NO2)n1)[C@@H]1CCCN1C] | 1.73 | 722.00 | A |
| C-2g | 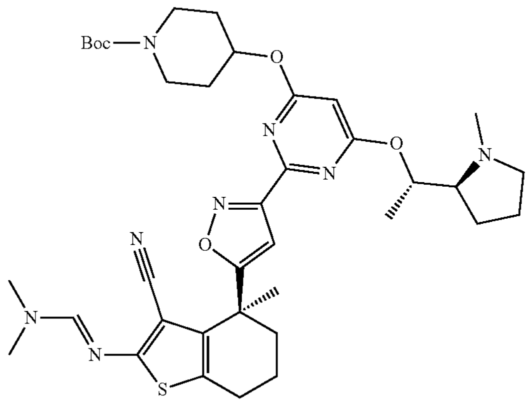 [SMILES: C[C@H](Oc1cc(OC2CCN(C(=O)OC(C)(C)C)CC2)nc(-c2cc([C@@]3(C)CCCc4sc(/N=C/N(C)C)c(C#N)c43)on2)n1)[C@@H]1CCCN1C] | 1.84 | 719.00 | A |
| C-3g | 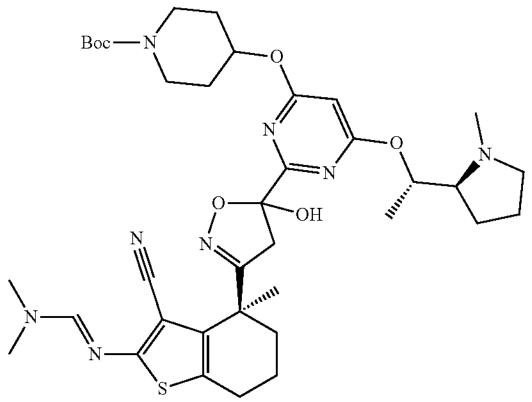 [SMILES: C[C@H](Oc1cc(OC2CCN(C(=O)OC(C)(C)C)CC2)nc(C2(O)CC([C@@]3(C)CCCc4sc(/N=C/N(C)C)c(C#N)c43)=NO2)n1)[C@@H]1CCCN1C] | 1.74 | 737.00 | A |

TABLE 27-continued
| # | structure | $t_{ret}$ [min] | $[M + H]^+$ | HPLC method |
|---|---|---|---|---|
| C-2h | 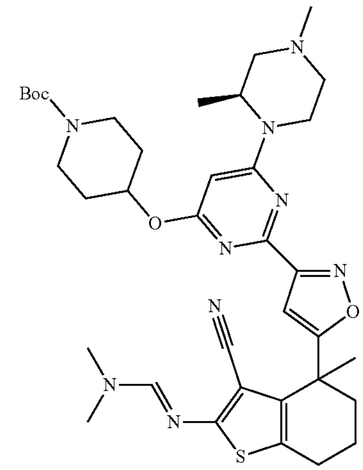 [SMILES: C[C@H]1CN(C)CCN1c1cc(OC2CCN(C(=O)OC(C)(C)C)CC2)nc(-c2cc(C3(C)CCCc4sc(/N=C/N(C)C)c(C#N)c43)on2)n1] | 1.72 | 704.00 | A |
| C-3h | 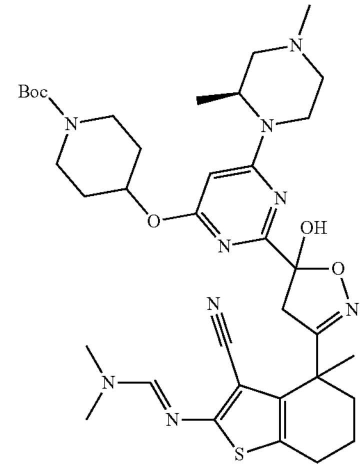 [SMILES: C[C@H]1CN(C)CCN1c1cc(OC2CCN(C(=O)OC(C)(C)C)CC2)nc(C2(O)CC(C3(C)CCCc4sc(/N=C/N(C)C)c(C#N)c43)=NO2)n1] | 1.63 | 722.00 | A |
| C-2i | 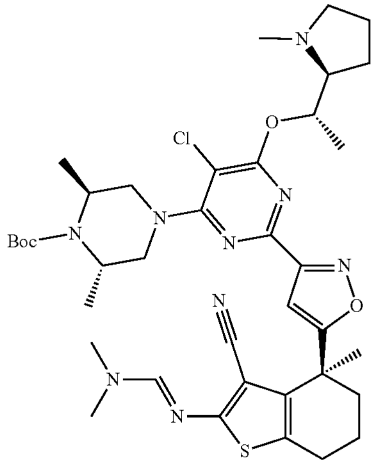 [SMILES: C[C@H](Oc1nc(-c2cc([C@@]3(C)CCCc4sc(/N=C/N(C)C)c(C#N)c43)on2)nc(N2C[C@H](C)N(C(=O)OC(C)(C)C)[C@@H](C)C2)c1Cl)[C@@H]1CCCN1C] | n.a. | n.a. | — |

Experimental Procedure for the Synthesis of C-4a

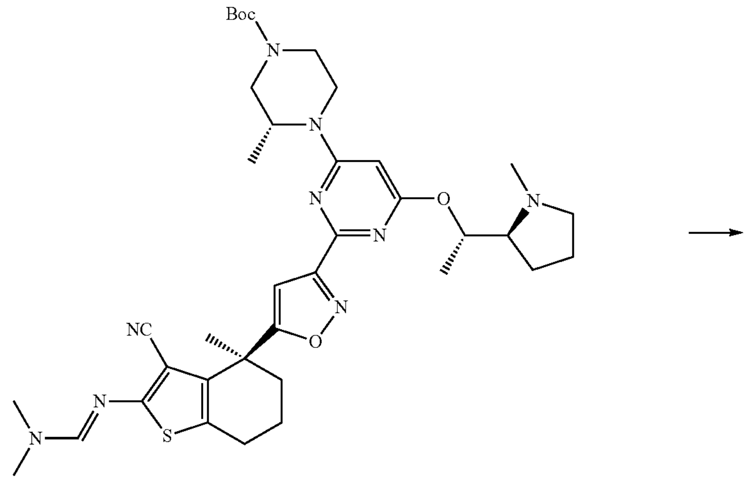

C-2a

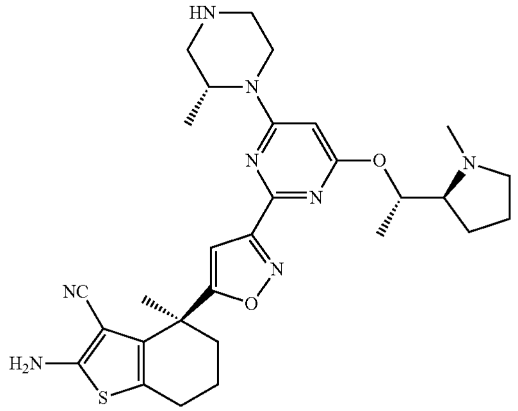

C-4a

To a solution of C-2a (286 mg, 0.398 mmol, 1.0 eq.) in THF (3 mL) is added an aqueous solution of HCl (1 mL, 2.00 mmol, 2 M) and the mixture is stirred at 65° C. for 1 h. Additional aqueous HCl (0.3 mL, 0.60 mmol, 2 M) is added to the mixture and stirring is continued for additional 3.5 h. The reaction is carefully neutralized and basified with saturated aqueous sodium bicarbonate solution and diluted with EtOAc and water. The phases are separated and the aqueous layer is extracted three times with EtOAc. The combined organic layer is concentrated under reduced pressure. The residue is taken up in acetonitrile and water and purified by basic reversed phase chromatography (gradient elution: 20% to 95% acetonitrile in water) to give the desired product C-4a.

The following intermediates C-4 (table 28) are available in an analogous manner starting from different intermediates C-2. The crude product C-4 is purified by chromatography if necessary.
TABLE 28
| # | structure | $t_{ret}$ [min] | $[M + H]^+$ | HPLC method |
|---|---|---|---|---|
| C-4a | 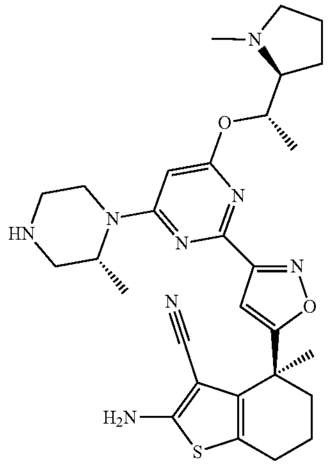 [SMILES: C[C@H](Oc1cc(N2CCNC[C@H]2C)nc(-c2cc([C@@]3(C)CCCc4sc(N)c(C#N)c43)on2)n1)[C@@H]1CCCN1C] | 1.32 | 563.00 | A |
| C-4b | 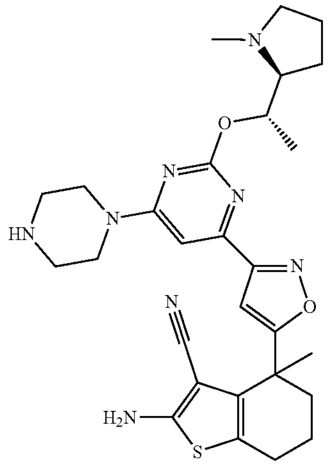 [SMILES: C[C@H](Oc1nc(-c2cc(C3(C)CCCc4sc(N)c(C#N)c43)on2)cc(N2CCNCC2)n1)[C@@H]1CCCN1C] | 0.603 | 549 | G |
| C-4c | 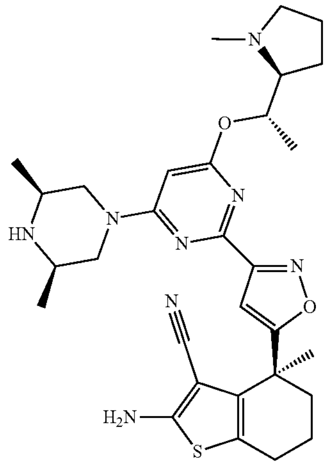 | 1.40 | 577.00 | A |

TABLE 28-continued
| # | structure | $t_{ret}$ [min] | $[M + H]^+$ | HPLC method |
|---|---|---|---|---|
| C-4d | 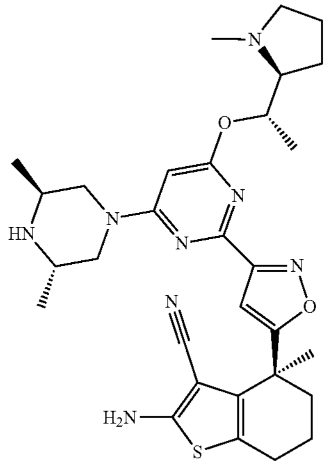 | 1.42 | 577.00 | A |
| C-4e | 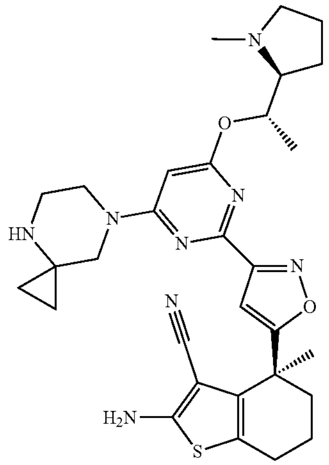 [SMILES: C[C@H](Oc1cc(N2CCNC3(CC3)C2)nc(-c2cc([C@@]3(C)CCCc4sc(N)c(C#N)c43)on2)n1)[C@@H]1CCCN1C] | 1.37 | 575.00 | A |
| C-4f | 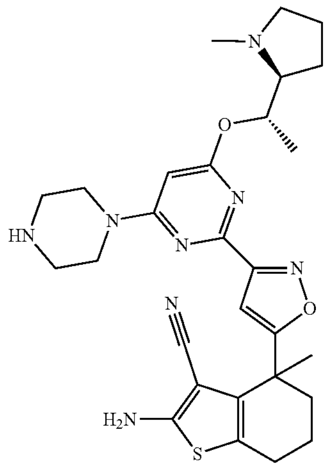 [SMILES: C[C@H](Oc1cc(N2CCNCC2)nc(-c2cc(C3(C)CCCc4sc(N)c(C#N)c43)on2)n1)[C@@H]1CCCN1C] | 1.53 | 549.00 | A |

TABLE 28-continued
| # | structure | $t_{ret}$ [min] | $[M + H]^+$ | HPLC method |
| --- | --- | --- | --- | --- |
| C-4g | 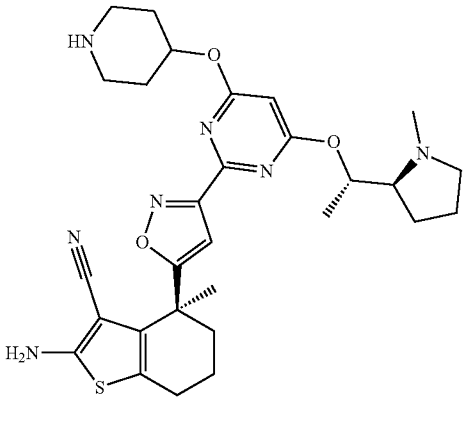 | 1.34 | 564.00 | A |
| C-4h | 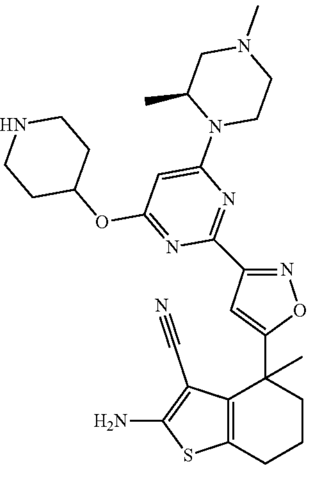 | 1.23 | 549.00 | A |
| C-4i | 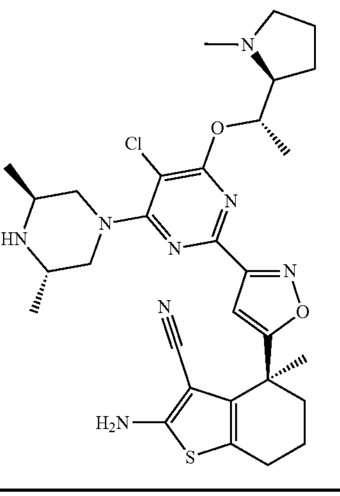 | 1.54 | 611.00 | A |

Experimental Procedure for the Synthesis of C-5a

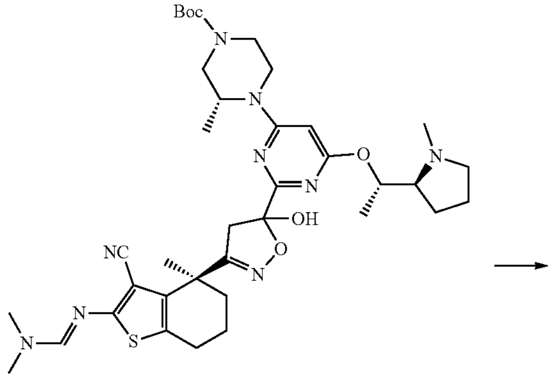

C-3a

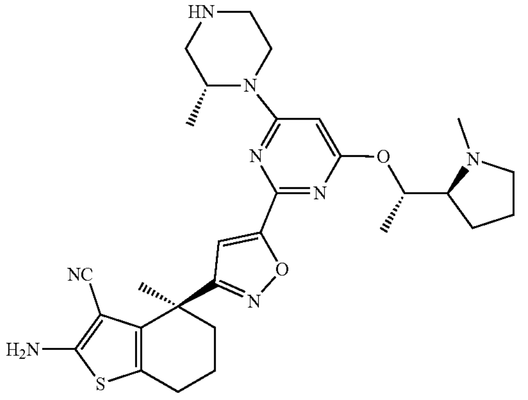

C-5a

To a solution of C-3a (65 mg, 0.09 mmol, 1.0 eq.) in THF (1 mL) is added an aqueous solution of HCl (135 mL, 0.54 mmol, 4 M) and the mixture is stirred at 65° C. for 75 min. The mixture is stirred at rt overnight and for 1 h at 65° C. The reaction is carefully neutralized and basified with saturated aqueous sodium bicarbonate solution and diluted with EtOAc and water. The phases are separated and the aqueous layer is extracted three times with EtOAc. The combined organic layer is concentrated under reduced pressure. The residue is taken up in acetonitrile and water and purified by basic reversed phase chromatography (gradient elution: 10% to 90% acetonitrile in water) to give the desired product C-5a.

(Note: In this one-step process under acidic conditions there is the formation of the aromatic isoxazole system, the cleavage of the Boc protecting group and the cleavage of the amidine protecting group, i.e. certain additional intermediates not depicted above are generated without isolation depending on the sequence of the sub-steps)

The following intermediates C-5 (table 29) are available in an analogous manner starting from different intermediates C-3. The crude product C-5 is purified by chromatography if necessary.

TABLE 29

| # | structure | $t_{ret}$ [min] | $[M + H]^+$ | HPLC method |
|---|---|---|---|---|
| C-5a | 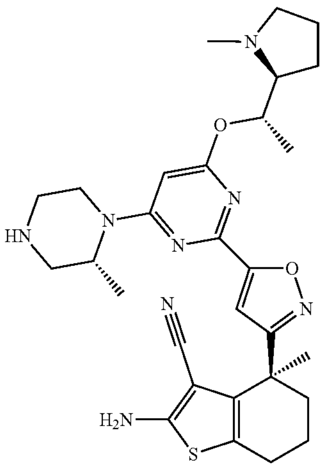 [SMILES: C[C@H](Oc1cc(N2CCNC[C@H]2C)nc(-c2cc([C@@]3(C)CCCc4sc(N)c(C#N)c43)no2)n1)[C@@H]1CCCN1C] | 1.35 | 563.00 | A |

TABLE 29-continued
| # | structure | $t_{ret}$ [min] | [M + H]+ | HPLC method |
|---|---|---|---|---|
| C-5b | 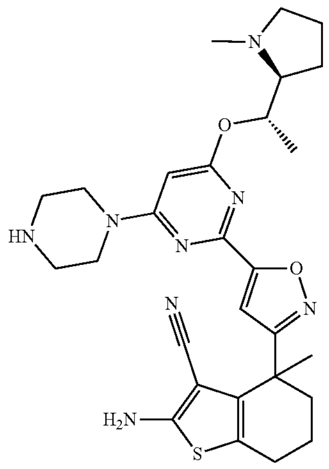 [SMILES: C[C@H](Oc1cc(N2CCNCC2)nc(-c2cc(C3(C)CCCc4sc(N)c(C#N)c43)no2)n1)[C@@H]1CCCN1C] | 1.54 | 549.00 | A |
| C-5c | 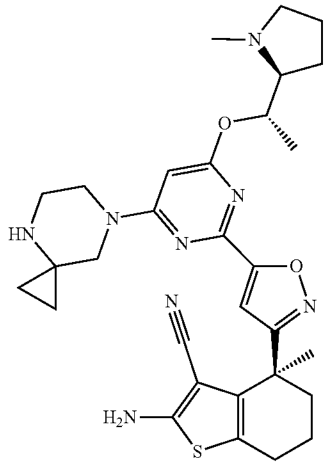 [SMILES: C[C@H](Oc1cc(N2CCNC3(CC3)C2)nc(-c2cc([C@@]3(C)CCCc4sc(N)c(C#N)c43)no2)n1)[C@@H]1CCCN1C] | 1.40 | 575.00 | A |
| C-5d | 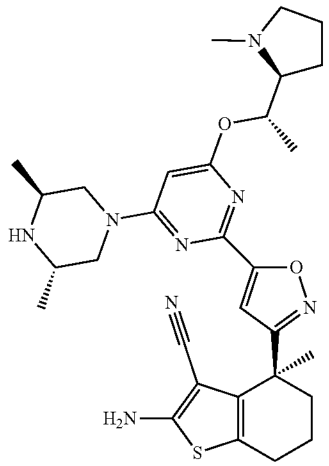 [SMILES: C[C@H](Oc1cc(N2C[C@H](C)N[C@@H](C)C2)nc(-c2cc([C@@]3(C)CCCc4sc(N)c(C#N)c43)no2)n1)[C@@H]1CCCN1C] | 1.45 | 577.00 | A |

TABLE 29-continued
| # | structure | $t_{ret}$ [min] | $[M + H]^+$ | HPLC method |
|---|---|---|---|---|
| C-5e | 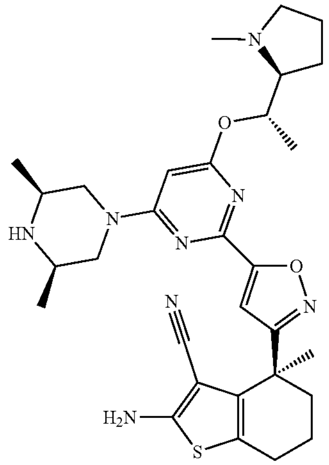 [SMILES: C[C@@H]1CN(c2cc(O[C@@H](C)[C@@H]3CCCN3C)nc(-c3cc([C@@]4(C)CCCc5sc(N)c(C#N)c54)no3)n2)C[C@H](C)N1] | 1.42 | 577.00 | A |
| C-5f | 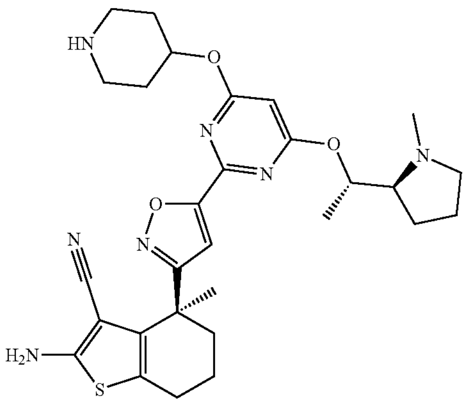 [SMILES: C[C@H](Oc1cc(OC2CCNCC2)nc(-c2cc([C@@]3(C)CCCc4sc(N)c(C#N)c43)no2)n1)[C@@H]1CCCN1C] | 1.35 | 564.00 | A |
| C-5g | 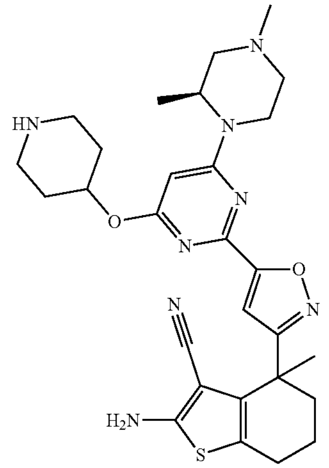 [SMILES: C[C@H]1CN(C)CCN1c1cc(OC2CCNCC2)nc(-c2cc(C3(C)CCCc4sc(N)c(C#N)c43)no2)n1] | 1.26 | 549.00 | A |

Experimental Procedure for the Synthesis of C-6a

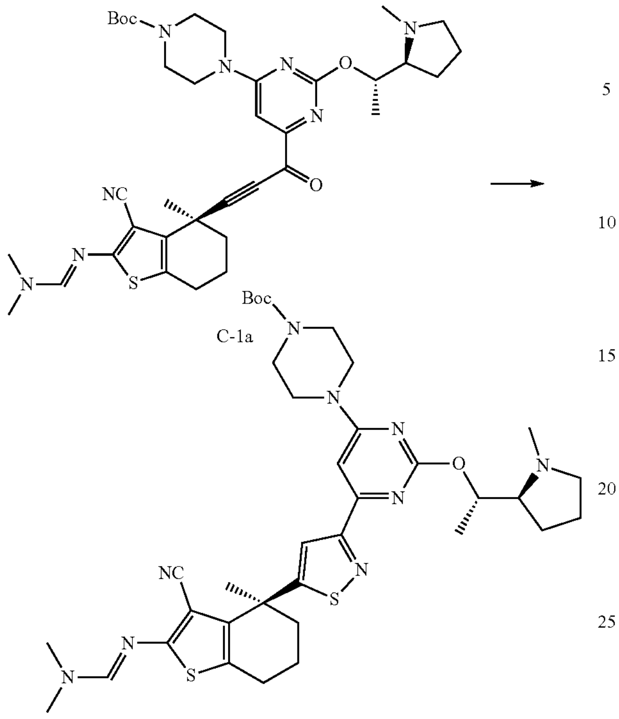

C-1a

C-6a

To a solution of hydroxylamine-O-sulfonic acid (52.5 mg, 0.47 mmol, 1.7 eq.) in MeOH (0.2 mL) is added a solution of C-1a (188 mg, 0.27, 1.0 eq.) in MeOH (1 mL) and the mixture is stirred for 5 h at rt. Sodium bicarbonate (25.2 mg, 0.30 mmol, 1.1 eq.) and sodium hydrogen sulfide (38.2 mg, 0.68 mmol, 2.5 eq.) are added to the reaction mixture and it is stirred at 50° C. for 1.5 h. The reaction mixture is diluted with water and EtOAc. The phases are separated and the aqueous layer is extracted three times with EtOAc. The combined organic layer is concentrated under reduced pressure. The residue is taken up in acetonitrile and water and purified by basic reversed phase chromatography (gradient elution: 35% to 98% acetonitrile in water) to give the desired product C-6a.

The following intermediates C-6 (table 30) are available in an analogous manner starting from different intermediates C-1. The crude products C-6 are purified by chromatography if necessary.

TABLE 30

| # | structure | $t_{ret}$ [min] | $[M + H]^+$ | HPLC method |
|---|---|---|---|---|
| C-6a | 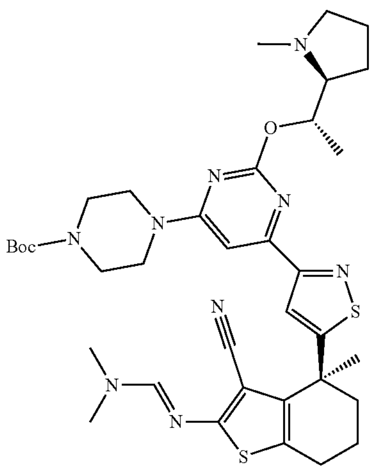 [SMILES: C[C@H](Oc1nc(-c2cc([C@@]3(C)CCCc4sc(/N=C/N(C)C)c(C#N)c43)sn2)cc(N2CCN(C(=O)OC(C)(C)C)CC2)n1)[C@@H]1CCCN1C] | 1.77 | 720.00 | A |

TABLE 30-continued
| # | structure | $t_{ret}$ [min] | $[M + H]^+$ | HPLC method |
|---|---|---|---|---|
| C-6b | 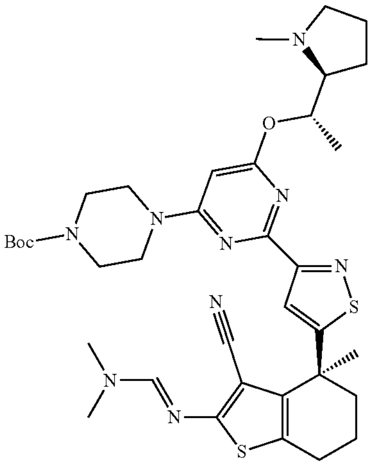 [SMILES: C[C@H](Oc1cc(N2CCN(C(=O)OC(C)(C)C)CC2)nc(-c2cc([C@@]3(C)CCCc4sc(/N=C/N(C)C)c(C#N)c43)sn2)n1)[C@@H]1CCCN1C] | 1.75 | 720.00 | A |
| C-6c | 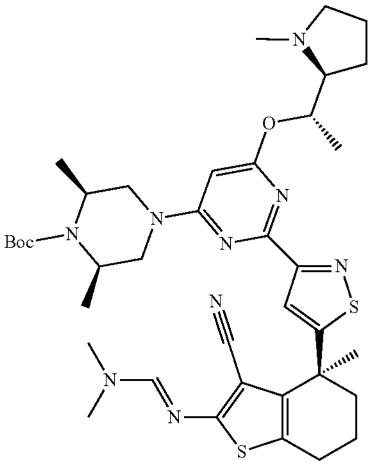 [SMILES: C[C@H](Oc1cc(N2C[C@@H](C)N(C(=O)OC(C)(C)C)[C@@H](C)C2)nc(-c2cc([C@@]3(C)CCCc4sc(/N=C/N(C)C)c(C#N)c43)sn2)n1)[C@@H]1CCCN1C] | 1.89 | 748.00 | A |
| C-6d | 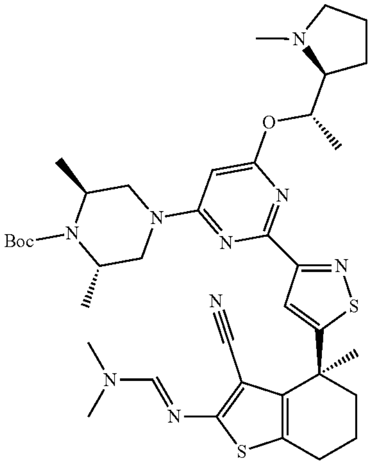 [SMILES: C[C@H](Oc1cc(N2C[C@H](C)N(C(=O)OC(C)(C)C)[C@@H](C)C2)nc(-c2cc([C@@]3(C)CCCc4sc(/N=C/N(C)C)c(C#N)c43)sn2)n1)[C@@H]1CCCN1C] | 1.87 | 748.00 | A |

TABLE 30-continued

| # | structure | $t_{ret}$ [min] | $[M + H]^+$ | HPLC method |
|---|---|---|---|---|
| C-6e | 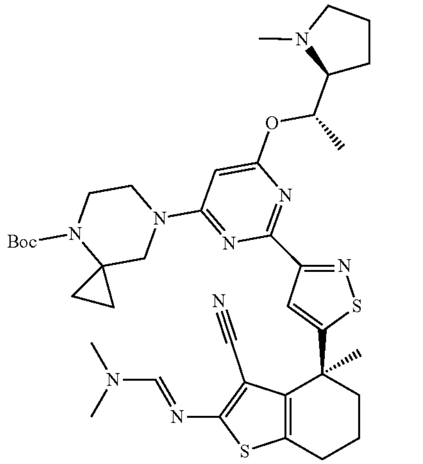 [SMILES: C[C@H](Oc1cc(N2CCN(C(=O)OC(C)(C)C)C3(CC3)C2)nc(-c2cc([C@@]3(C)CCCc4sc(/N=C/N(C)C)c(C#N)c43)sn2)n1)[C@@H]1CCCN1C] | 1.87 | 746.00 | A |
| C-6f | 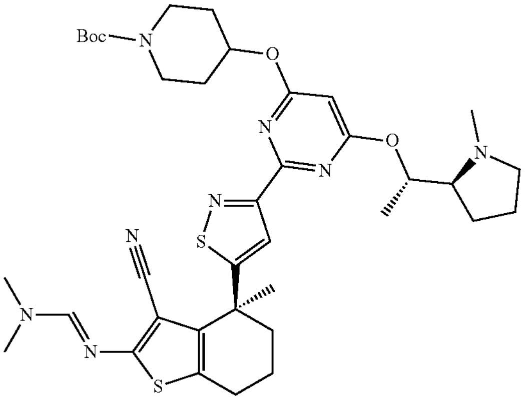 [SMILES: C[C@H](Oc1cc(OC2CCN(C(=O)OC(C)(C)C)CC2)nc(-c2cc([C@@]3(C)CCCc4sc(/N=C/N(C)C)c(C#N)c43)sn2)n1)[C@@H]1CCCN1C] | 1.86 | 735.00 | A |

Experimental Procedure for the Synthesis of C-7a

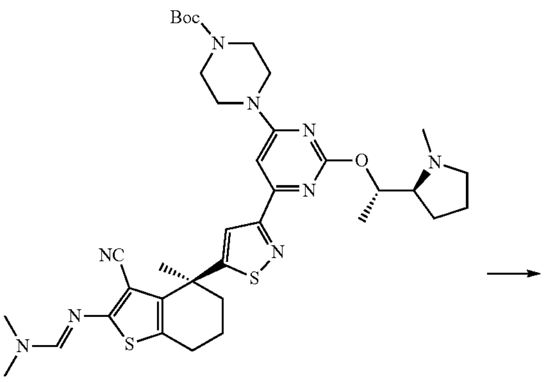

C-6a

-continued

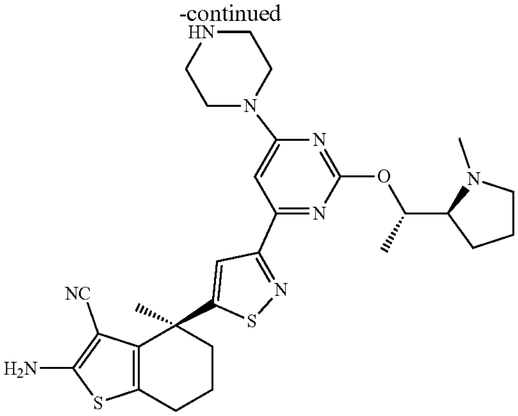

C-7a

To a solution of C-6a (69 mg, 0.096 mmol, 1.0 eq.) in THF (1.5 mL) is added an aqueous solution of HCl (0.500 mL, 1.00 mmol, 2 M) and the mixture is stirred at 65° C. for 3 h. The reaction is carefully neutralized and basified with saturated aqueous sodium bicarbonate solution and diluted with EtOAc and water. The phases are separated and the aqueous layer is extracted three times with EtOAc. The combined organic layer is concentrated under reduced pressure. The residue is taken up in acetonitrile and water and purified by basic reversed phase chromatography (gradient elution: 10% to 95% acetonitrile in water) to give the desired product C-7a.

The following intermediates C-7 (table 31) are available in an analogous manner starting from different intermediates C-6. The crude product C-7 is purified by chromatography if necessary.
TABLE 31
| # | structure | $t_{ret}$ [min] | $[M+H]^+$ | HPLC method |
| --- | --- | --- | --- | --- |
| C-7a | 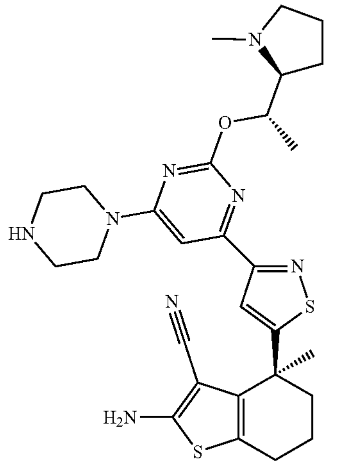 [SMILES: C[C@H](Oc1nc(-c2cc([C@@]3(C)CCCc4sc(N)c(C#N)c43)sn2)cc(N2CCNCC2)n1)[C@@H]1CCCN1C] | 1.28 | 565.00 | A |
| C-7b | 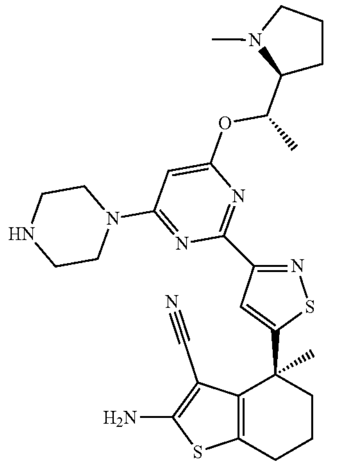 [SMILES: C[C@H](Oc1cc(N2CCNCC2)nc(-c2cc([C@@]3(C)CCCc4sc(N)c(C#N)c43)sn2)n1)[C@@H]1CCCN1C] | 1.29 | 565 | A |
| C-7c | 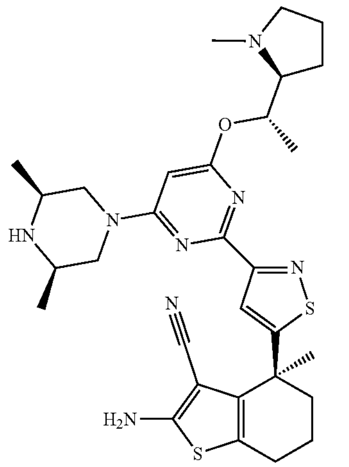 [SMILES: C[C@@H]1CN(c2cc(O[C@@H](C)[C@@H]3CCCN3C)nc(-c3cc([C@@]4(C)CCCc5sc(N)c(C#N)c54)sn3)n2)C[C@H](C)N1] | 1.42 | 593.00 | A |

TABLE 31-continued
| # | structure | $t_{ret}$ [min] | $[M + H]^+$ | HPLC method |
|---|---|---|---|---|
| C-7d | 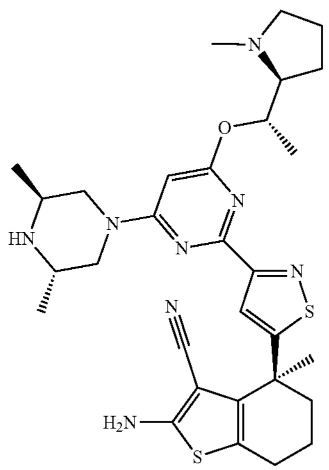 [SMILES: C[C@H](Oc1cc(N2C[C@H](C)N[C@@H](C)C2)nc(-c2cc([C@@]3(C)CCCc4sc(N)c(C#N)c43)sn2)n1)[C@@H]1CCCN1C] | 1.50 | 593.00 | A |
| C-7e | 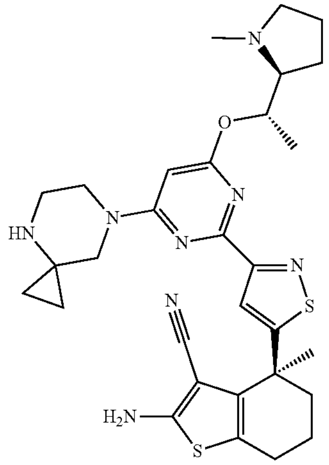 [SMILES: C[C@H](Oc1cc(N2CCNC3(CC3)C2)nc(-c2cc([C@@]3(C)CCCc4sc(N)c(C#N)c43)sn2)n1)[C@@H]1CCCN1C] | 1.41 | 591.00 | A |
| C-7f | 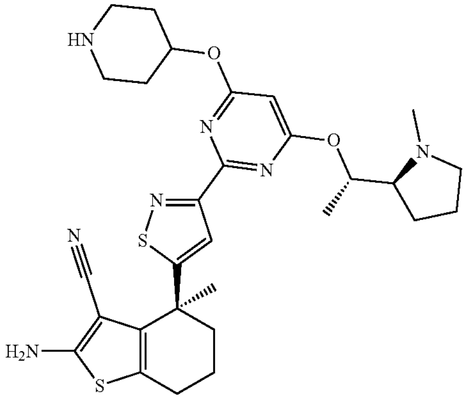 | 1.35 | 580.00 | A |

Synthesis of Final Compounds (I) According to the Invention:

Experimental Procedure for the Synthesis of Compound Ib-1

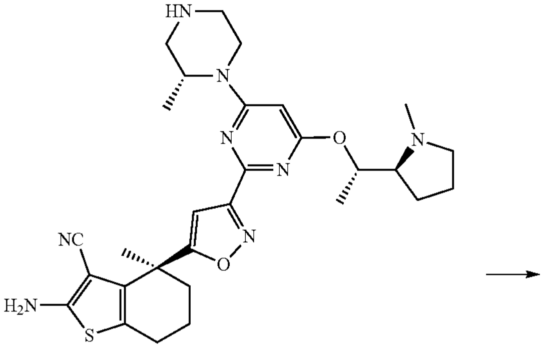

C-4a

-continued

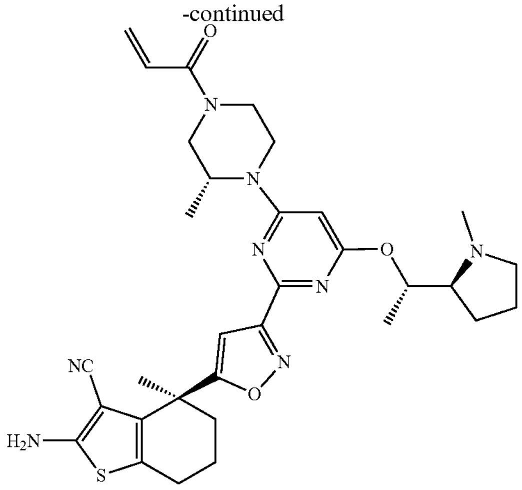

Ib-1

To a solution of potassium carbonate (22.1 mg, 0.16 mmol, 2.0 eq.) in acetone (0.3 mL) and water (70 μL) is added a freshly prepared solution of acryloyl chloride in acetone (120 μL, 0.12 mmol, 1 M, 1.5 eq.). The mixture is stirred for 5 min before a solution of intermediate C-4a (45 mg, 0.08 mmol, 1.0 eq.) in acetone (1 mL) is added and the reaction mixture is stirred for 10 min. After completion of the reaction the mixture is diluted with acetonitrile and water, filtered and purified by basic reversed phase chromatography (gradient elution: 10% to 98% acetonitrile in water) to give the desired compound Ib-1.

The following compounds Ib, Ic and Id (table 32) are available in an analogous manner starting from different intermediates C-4, C5 and C-7, respectively. The crude products Ib, Ic and Id are purified by chromatography if necessary.

TABLE 32

| # | structure | $t_{ret}$ [min] | $[M + H]^+$ | HPLC method | $IC_{50}$ G12C::SOS1 [nM] |
|---|---|---|---|---|---|
| Ib-1 | 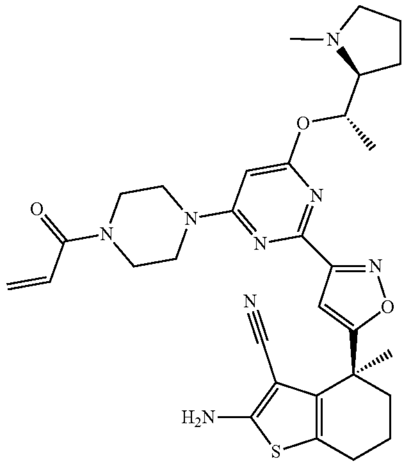 | 1.38 | 617 | A | 1.6 |

TABLE 32-continued
| # | structure | $t_{ret}$ [min] | $[M + H]^+$ | HPLC method | $IC_{50}$ G12C::SOS1 [nM] |
|---|---|---|---|---|---|
| Ib-2 | 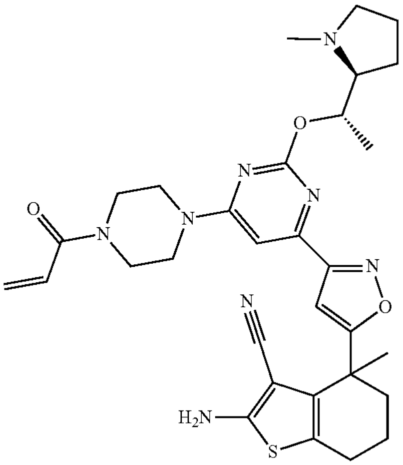 [SMILES: C=CC(=O)N1CCN(c2cc(-c3cc(C4(C)CCCc5sc(N)c(C#N)c54)on3)nc(O[C@@H](C)[C@@H]3CCCN3C)n2)CC1] | 1.37 | 603 | A | 2 |
| Ib-3 | 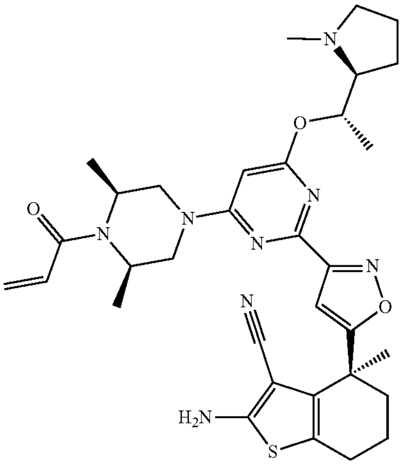 [SMILES: C=CC(=O)N1[C@H](C)CN(c2cc(O[C@@H](C)[C@@H]3CCCN3C)nc(-c3cc([C@@]4(C)CCCc5sc(N)c(C#N)c54)on3)n2)C[C@@H]1C] | 1.44 | 631 | A | 2 |
| Ib-4 | 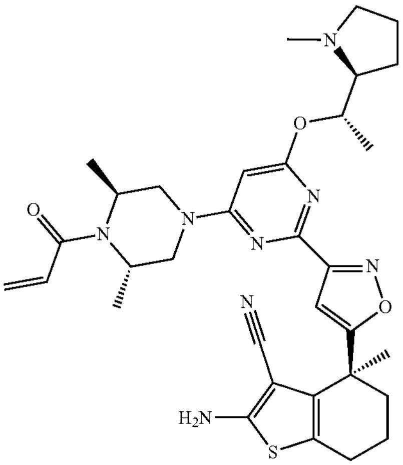 [SMILES: C=CC(=O)N1[C@@H](C)CN(c2cc(O[C@@H](C)[C@@H]3CCCN3C)nc(-c3cc([C@@]4(C)CCCc5sc(N)c(C#N)c54)on3)n2)C[C@@H]1C] | 1.43 | 631 | A | 1.6 |

TABLE 32-continued
| # | structure | $t_{ret}$ [min] | $[M + H]^+$ | HPLC method | $IC_{50}$ G12C::SOS1 [nM] |
|---|---|---|---|---|---|
| Ib-5 | 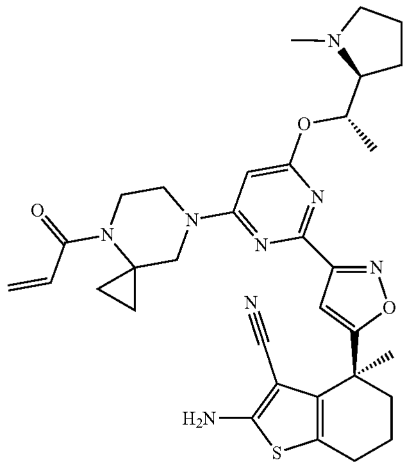 [SMILES: C=CC(=O)N1CCN(c2cc(O[C@@H](C)[C@@H]3CCCN3C)nc(-c3cc([C@@]4(C)CCCc5sc(N)c(C#N)c54)on3)n2)CC12CC2] | 1.44 | 629 | A | 3 |
| Ib-6 | 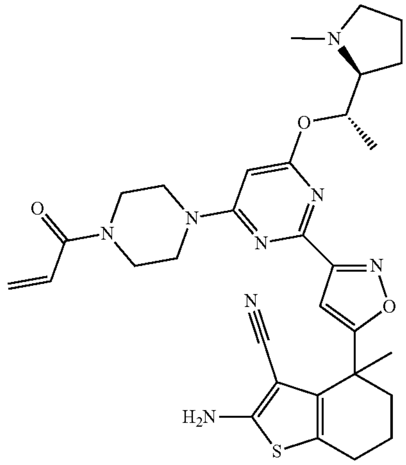 [SMILES: C=CC(=O)N1CCN(c2cc(O[C@@H](C)[C@@H]3CCCN3C)nc(-c3cc(C4(C)CCCc5sc(N)c(C#N)c54)on3)n2)CC1] | 1.38 | 603 | A | 3 |
| Ib-7 | 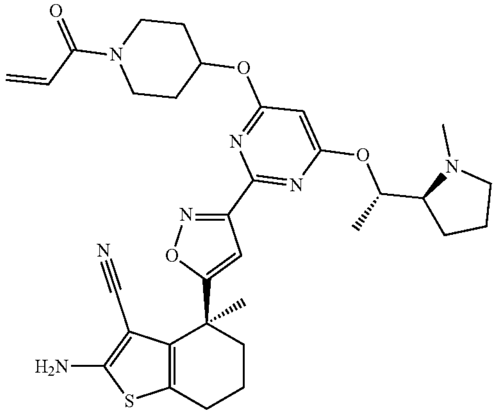 [SMILES: C=CC(=O)N1CCC(Oc2cc(O[C@@H](C)[C@@H]3CCCN3C)nc(-c3cc([C@@]4(C)CCCc5sc(N)c(C#N)c54)on3)n2)CC1] | 1.44 | 618 | A | 1.5 |

TABLE 32-continued
| # | structure | $t_{ret}$ [min] | [M + H]$^+$ | HPLC method | $IC_{50}$ G12C::SOS1 [nM] |
|---|---|---|---|---|---|
| Ib-8 | 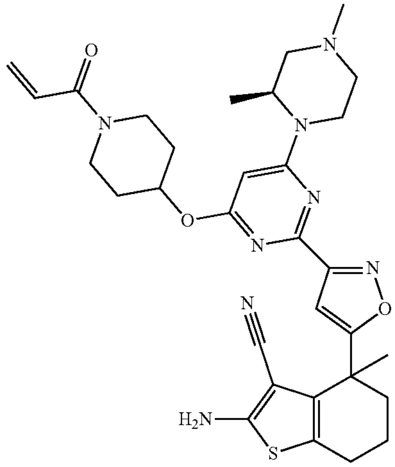 [SMILES: C=CC(=O)N1CCC(Oc2cc(N3CCN(C)C[C@@H]3C)nc(-c3cc(C4(C)CCCc5sc(N)c(C#N)c54)on3)n2)CC1] | 1.35 | 603 | A | 13 |
| Ib-9 | 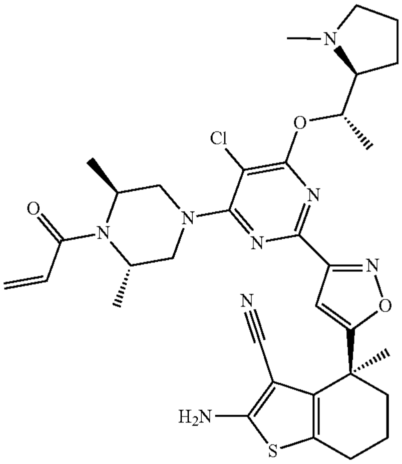 [SMILES: C=CC(=O)N1[C@@H](C)CN(c2nc(-c3cc([C@@]4(C)CCCc5sc(N)c(C#N)c54)on3)nc(O[C@@H](C)[C@@H]3CCCN3C)c2Cl)C[C@@H]1C] | 1.57 | 665 | A | 4 |
| Ic-1 | 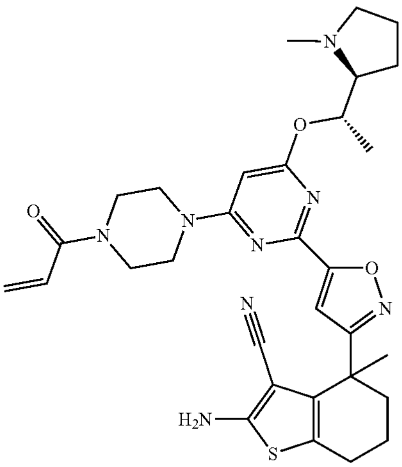 [SMILES: C=CC(=O)N1CCN(c2cc(O[C@@H](C)[C@@H]3CCCN3C)nc(-c3cc(C4(C)CCCc5sc(N)c(C#N)c54)no3)n2)CC1] | 1.41 | 603 | A | 3 |

TABLE 32-continued
| # | structure | $t_{ret}$ [min] | $[M + H]^+$ | HPLC method | $IC_{50}$ G12C::SOS1 [nM] |
|---|---|---|---|---|---|
| Ic-2 | 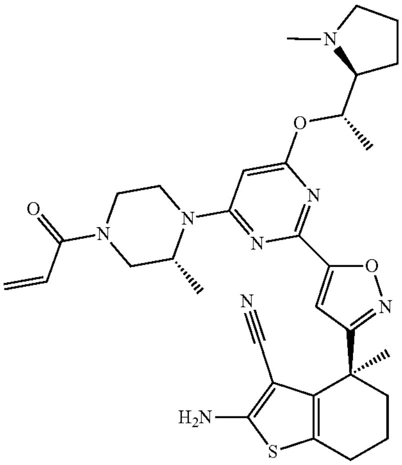 [SMILES: C=CC(=O)N1CCN(c2cc(O[C@@H](C)[C@@H]3CCCN3C)nc(-c3cc([C@@]4(C)CCCc5sc(N)c(C#N)c54)no3)n2)[C@H](C)C1] | 1.42 | 617 | A | 2 |
| Ic-3 | 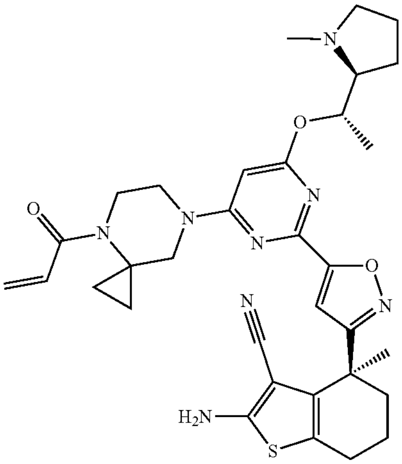 [SMILES: C=CC(=O)N1CCN(c2cc(O[C@@H](C)[C@@H]3CCCN3C)nc(-c3cc([C@@]4(C)CCCc5sc(N)c(C#N)c54)no3)n2)CC12CC2] | 1.47 | 629 | A | 3 |
| Ic-4 | 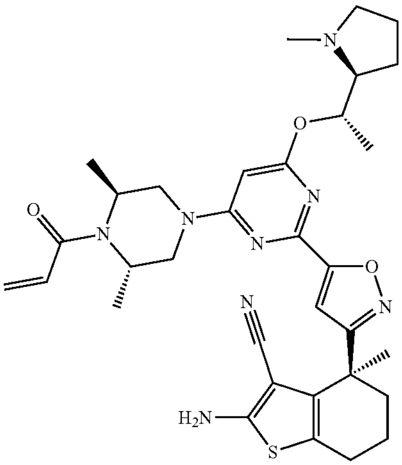 [SMILES: C=CC(=O)N1[C@@H](C)CN(c2cc(O[C@@H](C)[C@@H]3CCCN3C)nc(-c3cc([C@@]4(C)CCCc5sc(N)c(C#N)c54)no3)n2)C[C@@H]1C] | 1.46 | 631 | A | 1.9 |

TABLE 32-continued
| # | structure | $t_{ret}$ [min] | $[M + H]^+$ | HPLC method | $IC_{50}$ G12C::SOS1 [nM] |
|---|---|---|---|---|---|
| Ic-5 | 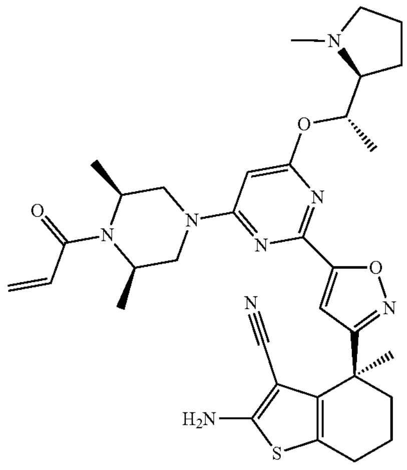 [SMILES: C=CC(=O)N1[C@H](C)CN(c2cc(O[C@@H](C)[C@@H]3CCCN3C)nc(-c3cc([C@@]4(C)CCCc5sc(N)c(C#N)c54)no3)n2)C[C@@H]1C] | 1.47 | 631 | A | 5 |
| Ic-6 | 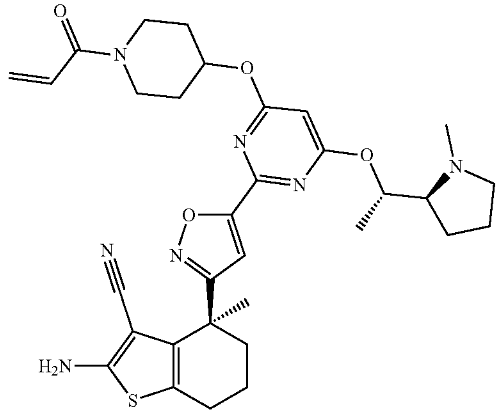 [SMILES: C=CC(=O)N1CCC(Oc2cc(O[C@@H](C)[C@@H]3CCCN3C)nc(-c3cc([C@@]4(C)CCCc5sc(N)c(C#N)c54)no3)n2)CC1] | 1.47 | 618 | A | 1.6 |
| Ic-7 | 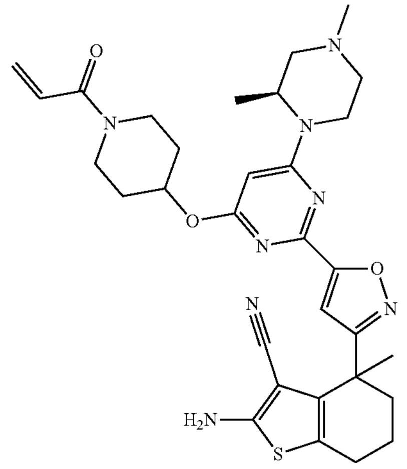 [SMILES: C=CC(=O)N1CCC(Oc2cc(N3CCN(C)C[C@@H]3C)nc(-c3cc(C4(C)CCCc5sc(N)c(C#N)c54)no3)n2)CC1] | 1.38 | 603 | A | 44 |

TABLE 32-continued
| # | structure | $t_{ret}$ [min] | $[M + H]^+$ | HPLC method | $IC_{50}$ G12C::SOS1 [nM] |
|---|---|---|---|---|---|
| Id-1 | 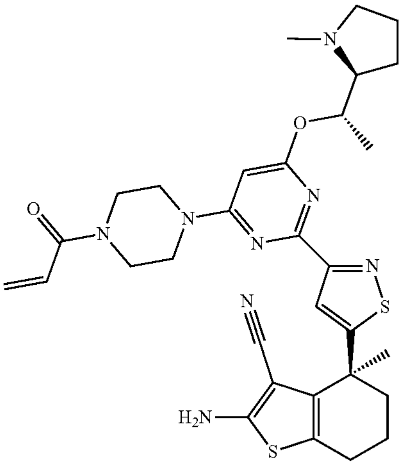 [SMILES: C=CC(=O)N1CCN(c2cc(O[C@@H](C)[C@@H]3CCCN3C)nc(-c3cc([C@@]4(C)CCCc5sc(N)c(C#N)c54)sn3)n2)CC1] | 1.36 | 619 | A | 1.6 |
| Id-2 | 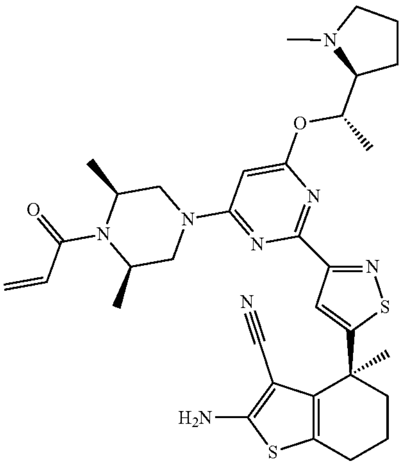 [SMILES: C=CC(=O)N1[C@H](C)CN(c2cc(O[C@@H](C)[C@@H]3CCCN3C)nc(-c3cc([C@@]4(C)CCCc5sc(N)c(C#N)c54)sn3)n2)C[C@@H]1C] | 1.47 | 647 | A | 1.6 |
| Id-3 | 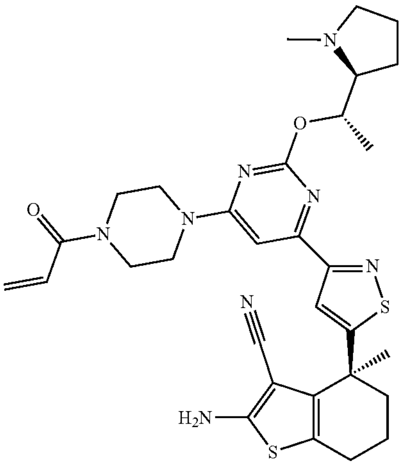 [SMILES: C=CC(=O)N1CCN(c2cc(-c3cc([C@@]4(C)CCCc5sc(N)c(C#N)c54)sn3)nc(O[C@@H](C)[C@@H]3CCCN3C)n2)CC1] | 1.36 | 619 | A | 1.7 |

TABLE 32-continued
| # | structure | $t_{ret}$ [min] | [M + H]$^+$ | HPLC method | $IC_{50}$ G12C::SOS1 [nM] |
|---|---|---|---|---|---|
| Id-4 | 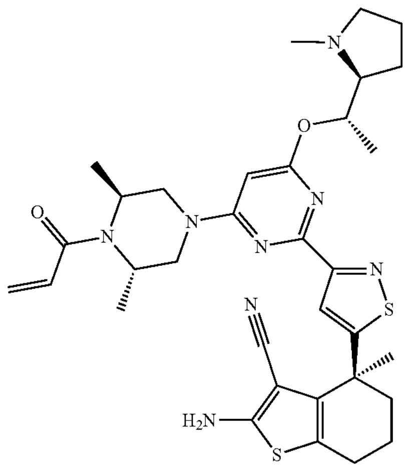 [SMILES: C=CC(=O)N1[C@@H](C)CN(c2cc(O[C@@H](C)[C@@H]3CCCN3C)nc(-c3cc([C@@]4(C)CCCc5sc(N)c(C#N)c54)sn3)n2)C[C@@H]1C] | 1.47 | 647 | A | 1.7 |
| Id-5 | 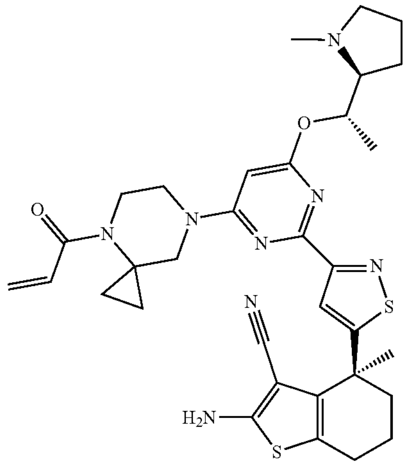 [SMILES: C=CC(=O)N1CCN(c2cc(O[C@@H](C)[C@@H]3CCCN3C)nc(-c3cc([C@@]4(C)CCCc5sc(N)c(C#N)c54)sn3)n2)CC12CC2] | 1.47 | 645 | A | 1.7 |
| Id-6 | 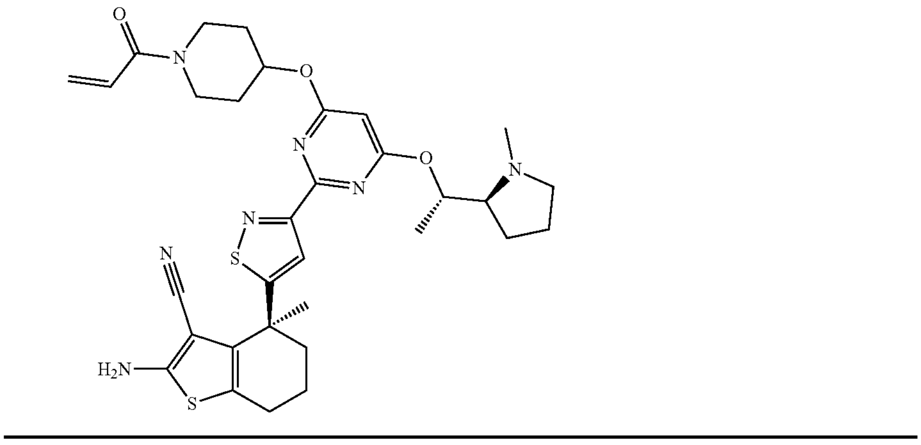 | 1.45 | 634 | A | 1.6 |

Experimental Procedure for the Synthesis of Compound Ib-10

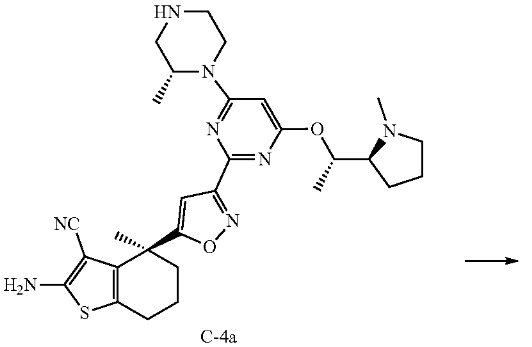

C-4a

-continued

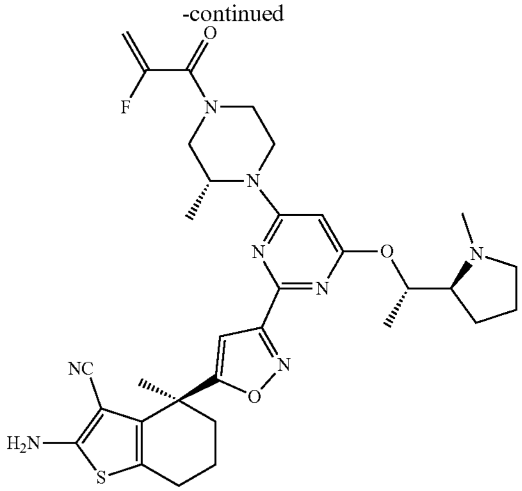

Ib-10

To a solution of 2-fluoroacrylic acid (7.5 mg, 0.083 mmol, 2.6 eq.) and HATU (30.4 mg, 0.08 mmol, 2.5 eq.) in DMF (0.5 mL) is added trimethylamine (27.7 μL, 0.19 mmol, 6.0 eq.). The mixture is stirred for 1 min at rt before a solution of intermediate C-4a (18 mg, 0.03 mmol, 1.0 eq.) in DMF (0.5 mL) is added. The reaction mixture is stirred for one additional minute. After completion of the reaction the mixture is diluted with acetonitrile and water, filtered and purified by basic reversed phase chromatography (gradient elution: 10% to 98% acetonitrile in water) to give the desired compound Ib-10.

The following additional compounds Ib, Ic and Id (table 33) are available in an analogous manner starting from different intermediates C-4, C5 and C-7. The crude products Ib, Ic and Id are purified by chromatography if necessary.

TABLE 33

| # | structure | $t_{ret}$ [min] | $[M + H]^+$ | HPLC method | $IC_{50}$ G12C::SOS1 [nM] |
|---|---|---|---|---|---|
| Ib-10 | 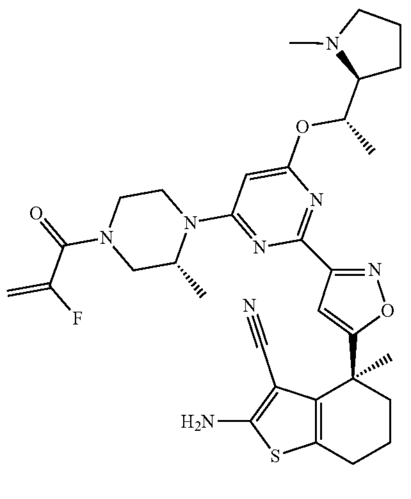 [SMILES: C=C(F)C(=O)N1CCN(c2cc(O[C@@H](C)[C@@H]3CCCN3C)nc(-c3cc([C@@]4(C)CCCc5sc(N)c(C#N)c54)on3)n2)[C@H](C)C1] | 1.49 | 635 | A | 13 |

TABLE 33-continued
| # | structure | $t_{ret}$ [min] | $[M + H]^+$ | HPLC method | $IC_{50}$ G12C::SOS1 [nM] |
|---|---|---|---|---|---|
| Ib-11 | 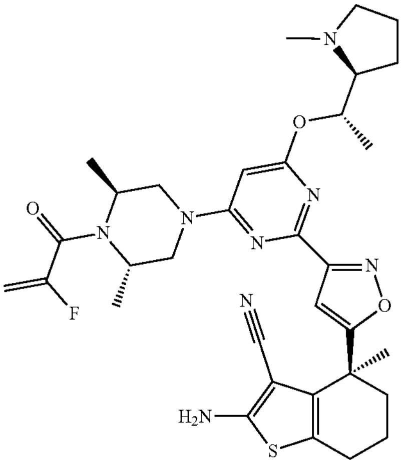 [SMILES: C=C(F)C(=O)N1[C@@H](C)CN(c2cc(O[C@@H](C)[C@@H]3CCCN3C)nc(-c3cc([C@@]4(C)CCCc5sc(N)c(C#N)c54)on3)n2)C[C@@H]1C] | 1.53 | 649 | A | 15 |
| Ib-12 | 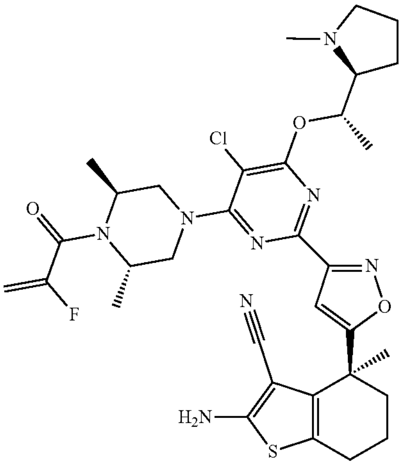 [SMILES: C=C(F)C(=O)N1[C@@H](C)CN(c2nc(-c3cc([C@@]4(C)CCCc5sc(N)c(C#N)c54)on3)nc(O[C@@H](C)[C@@H]3CCCN3C)c2Cl)C[C@@H]1C] | 1.66 | 683 | A | 74 |
| Ib-13 | 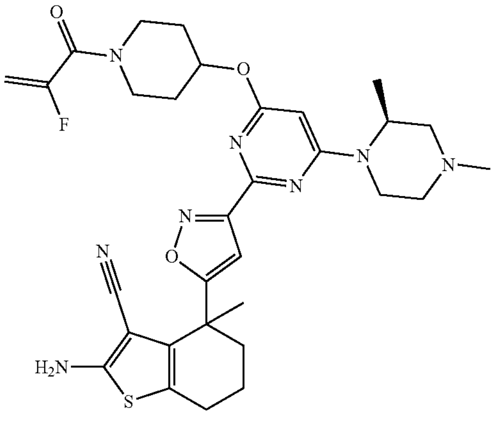 [SMILES: C=C(F)C(=O)N1CCC(Oc2cc(N3CCN(C)C[C@@H]3C)nc(-c3cc(C4(C)CCCc5sc(N)c(C#N)c54)on3)n2)CC1] | 1.42 | 621 | A | 278 |

TABLE 33-continued
| # | structure | $t_{ret}$ [min] | [M + H]$^+$ | HPLC method | $IC_{50}$ G12C::SOS1 [nM] |
|---|---|---|---|---|---|
| Ic-8 | 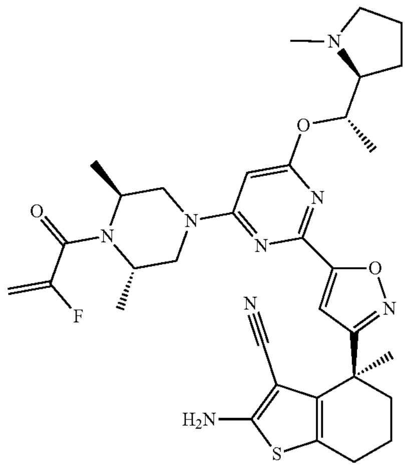 [SMILES: C=C(F)C(=O)N1[C@@H](C)CN(c2cc(O[C@@H](C)[C@@H]3CCCN3C)nc(-c3cc([C@@]4(C)CCCc5sc(N)c(C#N)c54)no3)n2)C[C@@H]1C] | 1.56 | 649 | A | 41 |
| Id-7 | 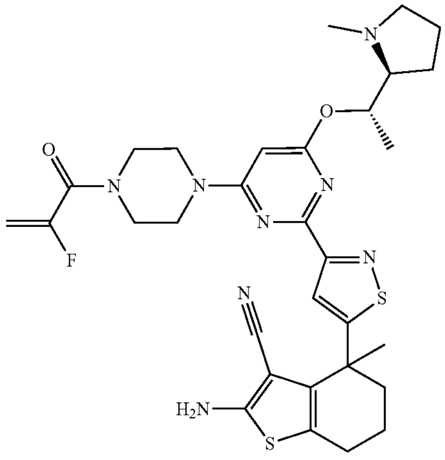 [SMILES: C=C(F)C(=O)N1CCN(c2cc(O[C@@H](C)[C@@H]3CCCN3C)nc(-c3cc(C4(C)CCCc5sc(N)c(C#N)c54)sn3)n2)CC1] | 1.49 | 637 | A | 5 |
| Id-8 | 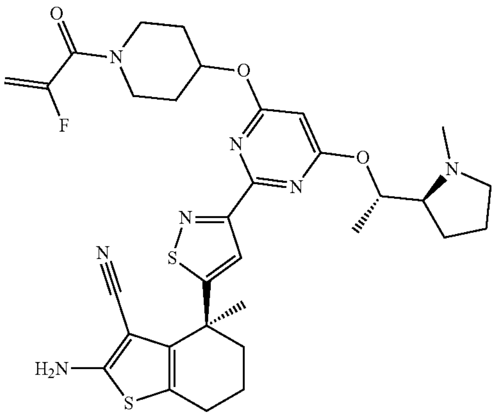 [SMILES: C=C(F)C(=O)N1CCC(Oc2cc(O[C@@H](C)[C@@H]3CCCN3C)nc(-c3cc([C@@]4(C)CCCc5sc(N)c(C#N)c54)sn3)n2)CC1] | 1.55 | 652 | A | 3 |

Experimental Procedure for the Synthesis of Compound Ib-14

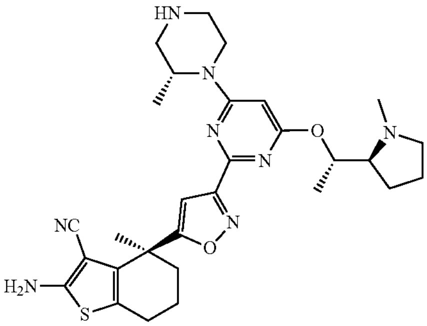

C-4a

-continued

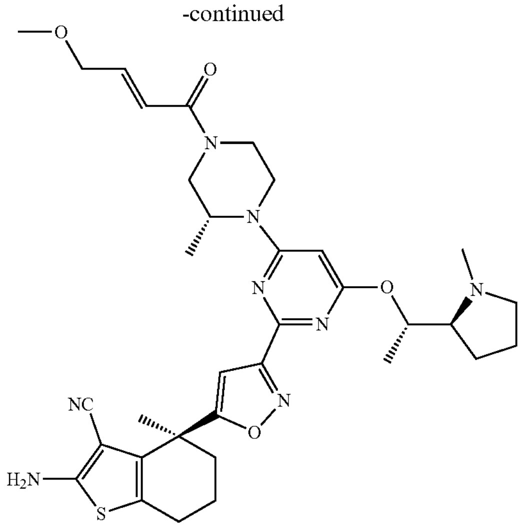

Ib-14

To a solution of 4-methoxy-2-enoic acid (10.8 mg, 0.09 mmol, 1.5 eq.) in anhydrous DMF (0.2 mL) is added DIPEA (54.2 μL, 0.31 mmol, 5 eq.) and HATU (26.0 mg, 0.07 mmol, 1.1 eq.) and the mixture is stirred for 10 min. A solution of intermediate C-4a (35.0 mg, 0.06 mmol, 1.0 eq.) in DMF (0.3 mL) is added and the reaction mixture is stirred for 10 min. After completion of the reaction the mixture is diluted with acetonitrile and water, filtered and purified by basic reversed phase chromatography (gradient elution: 10% to 95% acetonitrile in water) to give the desired compound Ib-14.

The following additional compounds Ib, Ic and Id (table 34) are available in an analogous manner starting from different intermediates C-4, C5 and C-7. The crude products Ib, Ic and Id are purified by chromatography if necessary.

TABLE 34

| # | structure | $t_{ret}$ [min] | [M + H]+ | HPLC method | $IC_{50}$ G12C::SOS1 [nM] |
|---|---|---|---|---|---|
| Ib-14 | 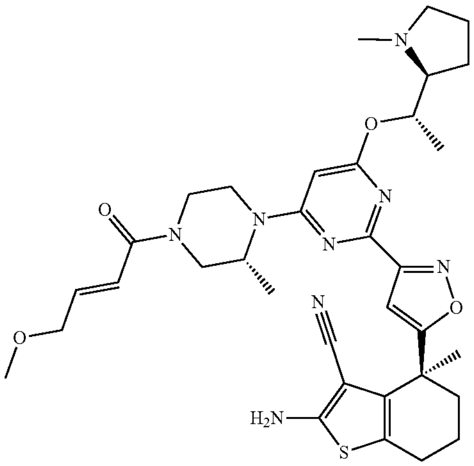 [SMILES: COC/C=C/C(=O)N1CCN(c2cc(O[C@@H](C)[C@@H]3CCCN3C)nc(-c3cc([C@@]4(C)CCCc5sc(N)c(C#N)c54)on3)n2)[C@H](C)C1] | 1.39 | 661 | A | 6 |

TABLE 34-continued
| # | structure | $t_{ret}$ [min] | $[M + H]^+$ | HPLC method | $IC_{50}$ G12C::SOS1 [nM] |
|---|---|---|---|---|---|
| Ib-15 | 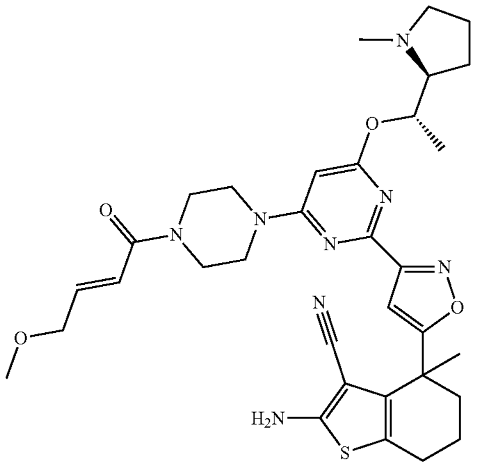 [SMILES: COC/C=C/C(=O)N1CCN(c2cc(O[C@@H](C)[C@@H]3CCCN3C)nc(-c3cc(C4(C)CCCc5sc(N)c(C#N)c54)on3)n2)CC1] | 1.40 | 647 | A | 17 |
| Ib-16 | 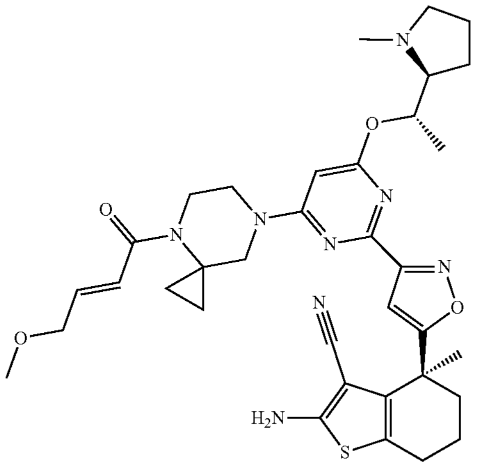 [SMILES: COC/C=C/C(=O)N1CCN(c2cc(O[C@@H](C)[C@@H]3CCCN3C)nc(-c3cc([C@@]4(C)CCCc5sc(N)c(C#N)c54)on3)n2)CC12CC2] | 1.47 | 673 | A | 42 |
| Ic-9 | 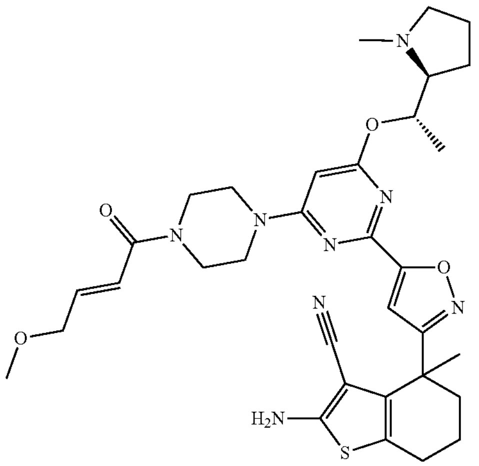 [SMILES: COC/C=C/C(=O)N1CCN(c2cc(O[C@@H](C)[C@@H]3CCCN3C)nc(-c3cc(C4(C)CCCc5sc(N)c(C#N)c54)no3)n2)CC1] | n.a. | n.a. | — | 29 |

TABLE 34-continued
| # | structure | $t_{ret}$ [min] | $[M + H]^+$ | HPLC method | $IC_{50}$ G12C::SOS1 [nM] |
|---|---|---|---|---|---|
| Id-9 | 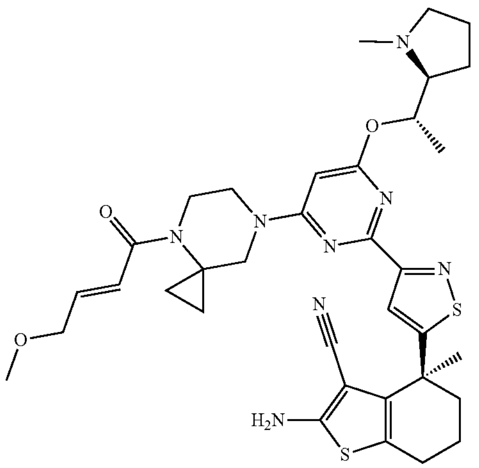 [SMILES: COC/C=C/C(=O)N1CCN(c2cc(O[C@@H](C)[C@@H]3CCCN3C)nc(-c3cc([C@@]4(C)CCCc5sc(N)c(C#N)c54)sn3)n2)CC12CC2] | 1.46 | 689 | A | 21 |

Scheme 8
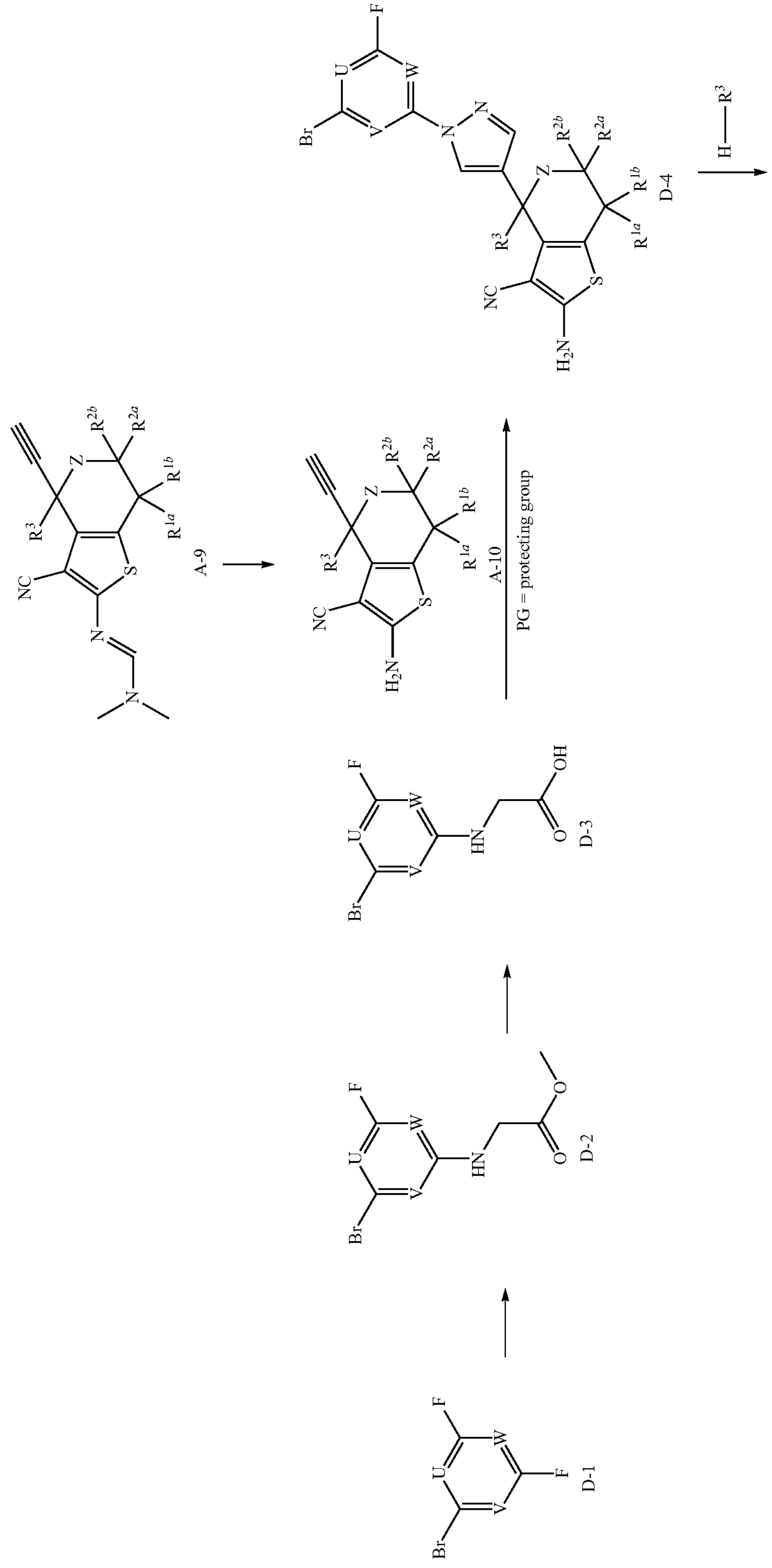
D-1 D-2 D-3 A-9 A-10 D-4

-continued
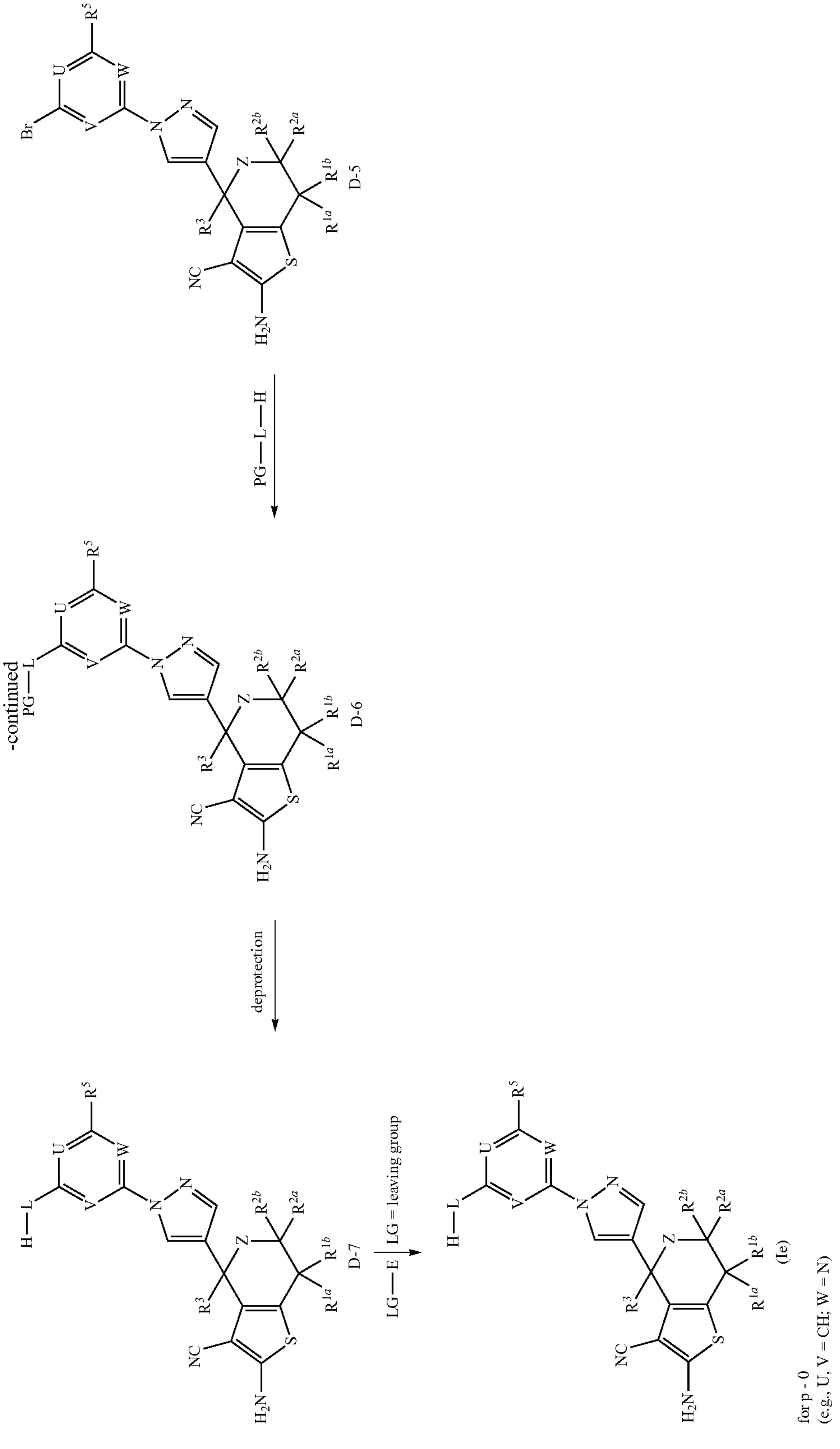
D-5
D-6
D-7
(Ie)
for p - 0
(e.g., U, V = CH; W = N)

Experimental Procedure for the Synthesis of D-2a

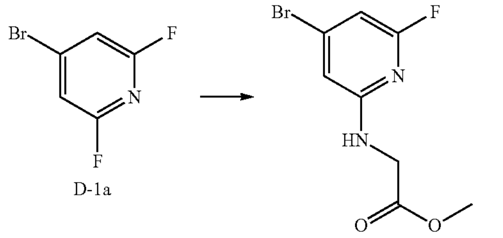

D-1a D-2a

DIPEA (1.58 mL, 9.18 mmol, 2.5 eq.) is added to a solution of D-1a (712.0 mg, 3.67 mmol) and methyl 2-aminoacetate hydrochloride (553.0 mg, 4.41 mmol, 1.2 eq.) in DMSO (10 mL) and the mixture is stirred in a closed vessel for 16 h at 100° C. After full conversion some drops of water are added to the reaction mixture and the product is isolated via basic reversed phase chromatography (gradient elution: 20% to 90% acetonitrile in water) yielding D-2a (HPLC method B; $t_{ret}$=0.58 min; $[M+H]^+$=263).

Experimental Procedure for the Synthesis of D-3a

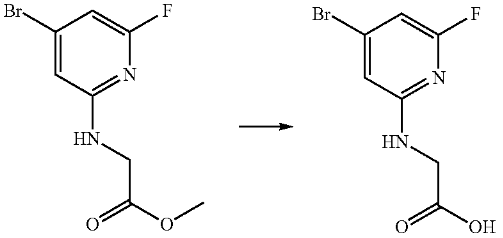

D-2a D-3a

D-2a (795.0 mg, 3.02 mmol) is dissolved in THF (15.0 mL), 1 M aqueous NaOH (4.53 mL, 4.53 mmol, 1.5 eq.) is added and the mixture is stirred for 1 h at rt. After full conversion, the reaction mixture is concentrated and the residue is acidified to pH 3 using 6 M aqueous HCl. The formed precipitate is collected by filtration, dissolved in DMSO and purified via acidic reversed phase chromatography (gradient elution: 10% to 70% acetonitrile in water) yielding D-3a. Acidic reversed phase chromatography (gradient elution: 10% to 70% acetonitrile in water) of the filtrate from the aqueous workup yields another product fraction (HPLC method C; $t_{ret}$=0.42 min; $[M+H]^+$=249).

Experimental Procedure for the Synthesis of D-4a

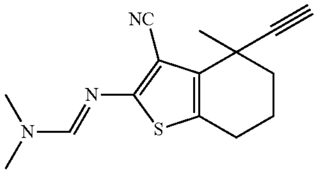

A-9b

-continued

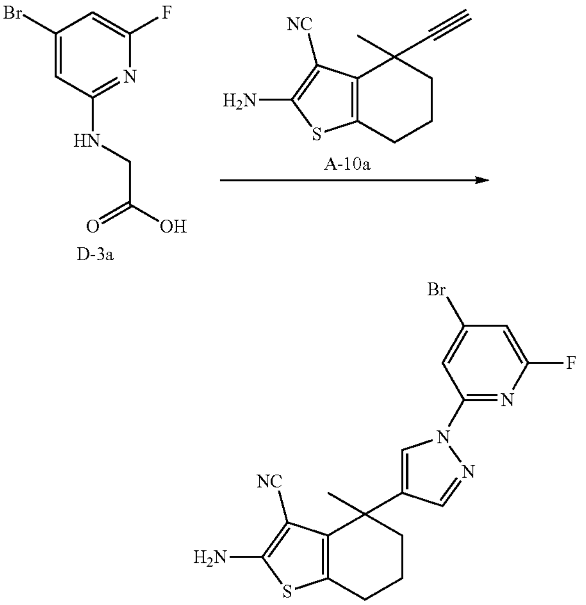

D-3a A-10a D-4a

D-3a (570.0 mg, 2.29 mmol) is treated with tert-butyl nitrite (298.4 µL, 2.52 mmol, 1.1 eq.) and stirred vigorously for 0.5 h at rt. Trifluoroacetic acid anhydride (795.4 µL, 5.72 mmol, 2.5 eq.) is added and the mixture is stirred for 0.5 h at rt. t-BuOH (13.0 mL), TEA (1903.6 µL, 13.73 mmol, 6.0 eq.), a solution of disodium 4,7-diphenyl-1,10-phenanthroline-3,8-disulfonate trihydrate (270.3 mg, 0.46 mmol, 0.20 eq.) in water (6.5 mL), a solution of copper (II) sulfate pentahydrate (114.30 mg, 0.46 mmol, 0.20 eq.) in water (6.5 mL), A-10a (495.08 mg, 2.29 mmol, 1.0 eq.), and sodium ascorbate (906.86 mg, 4.58 mmol, 2.0 eq.) are added and the mixture is stirred for 16 h at rt. After complete conversion the mixture is diluted with DCM and brine, the layers are separated and the aqueous phase is extracted with DCM. The organic layers are combined, dried, filtered, concentrated and the crude product is purified via basic reversed phase chromatography (gradient elution: 35% to 98% acetonitrile in water) yielding D-4a (HPLC method B; $t_{ret}$=0.87 min; $[M+H]^+$=432).

Experimental Procedure for the Synthesis of D-5a

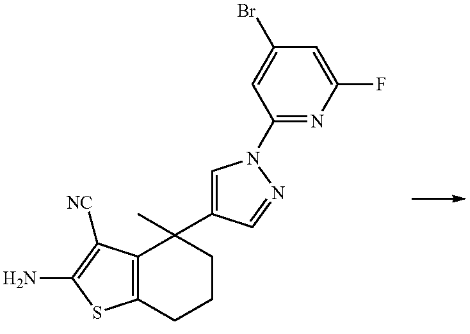

D-4a

-continued

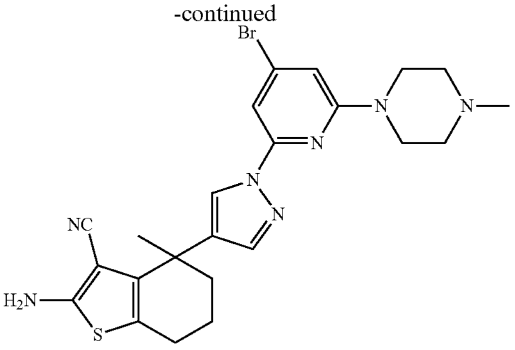

D-5a

D-4a (480.7 mg, 1.11 mmol) is treated with 1-methylpiperazine (616.7 μL, 5.56 mmol, 5.0 eq.) and DIPEA (286.96 μL, 1.67 mmol, 1.5 eq.) and the mixture is stirred for 0.5 h at rt and 16 h at 40° C. After complete conversion, water is added to the mixture and the resulting suspension is stirred for 15 min at rt. The precipitate is collected by filtration, washed with water and dried yielding D-5a which is used for the following step without further purification (HPLC method A; $t_{ret}$=1.46 min; $[M+H]^+$=512/514).

Experimental Procedure for the Synthesis of D-6a

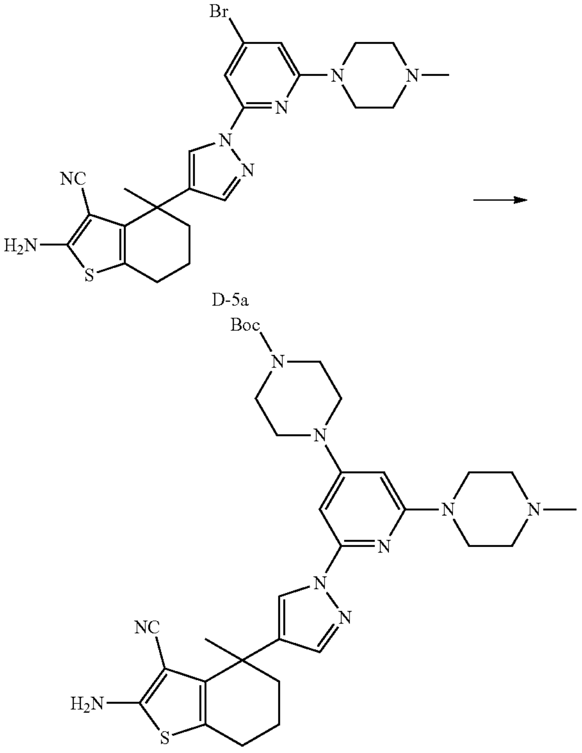

D-5a

D-6a

D-5a (518.0 mg, 1.01 mmol) is combined with tert-butyl piperazine-1-carboxylate (3.77 g, 20.22 mmol, 20.0 eq.) and DIPEA (695.6 μL, 4.04 mmol, 4.0 eq.) and the mixture is stirred for 6 days at 120° C. in a closed vessel. After complete conversion the mixture is diluted with DCM and brine, the layers are separated and the aqueous phase is extracted with DCM. The organic layers are combined, dried, filtered, and concentrated under reduced pressure yielding D-6a which is used for the following step without further purification (HPLC method B; $t_{ret}$=0.86 min; $[M+H]^+$=618).

Experimental Procedure for the Synthesis of D-7a

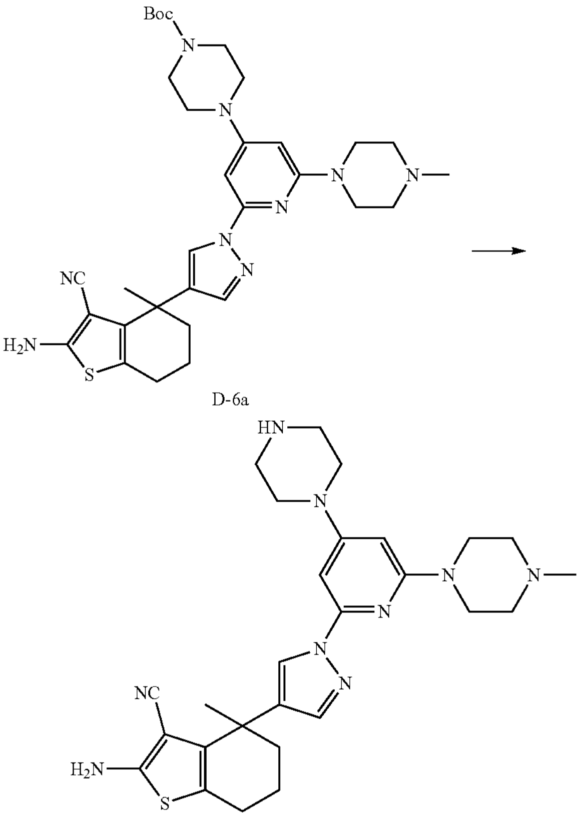

D-6a

D-7a

A mixture of D-6a (624.5 mg, 1.01 mmol) and dioxane (8 mL) is treated with HCl (4 N in dioxane, 5.05 mL, 20.22 mmol, 20.0 eq.) and stirred for 30 min at 70° C. followed by 20 min at 80° C. After complete conversion the mixture is concentrated under reduced pressure and the crude product is purified via basic reversed phase chromatography (gradient elution: 20% to 98% acetonitrile in water) yielding D-7a (HPLC method B; $t_{ret}$=0.62 min; $[M+H]^+$=518).

Experimental Procedure for the Synthesis of Ie-1

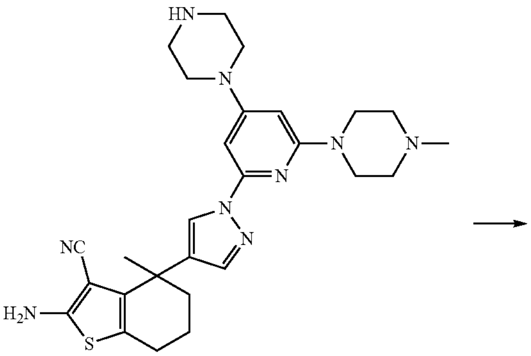

D-7a

-continued

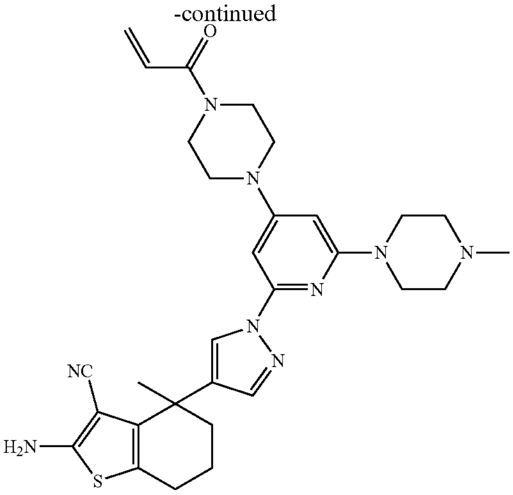

Ie-1

The synthesis is performed according to the procedure described for Ib-1 yielding Ie-1.

TABLE 35

| # | structure | $t_{ret}$ [min] | $[M + H]^+$ | HPLC method | $IC_{50}$ G12C::SOS1 [nM] |
|---|---|---|---|---|---|
| Ie-1 | 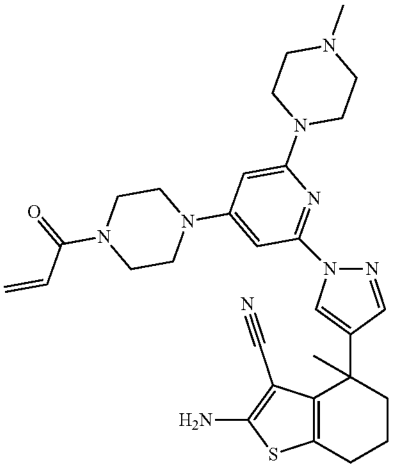 [SMILES: C=CC(=O)N1CCN(c2cc(N3CCN(C)CC3)nc(-n3cc(C4(C)CCCc5sc(N)c(C#N)c54)cn3)c2)CC1] | 1.26 | 572 | A | 280 |

The following Examples describe the biological activity of the compounds according to the invention, without restricting the invention to these Examples.

KRAS::SOS1 AlphaScreen Binding Assay

This assay can be used to examine the potency with which compounds according to the invention binding to KRAS G12C inhibit the protein-protein interaction between SOS1 and KRAS G12C. This inhibits the GEF functionality of SOS1 and locks KRAS G12C in its inactive, GDP-bound state. Low $IC_{50}$ values in this assay setting are indicative of strong inhibition of protein-protein interaction between SOS1 and KRAS:

Reagents:

GST-tagged SOS1 (564_1049_GST_TEV_ECO) produced in-house

GST-TEV-SOS1 (564-1049) is purchased from Viva Biotech Ltd.

The expression construct of KRAS G12C (amino acids 1-169 of reference sequence P01116-2 (uniprot), with additional mutations: C51S, C80L, and C118S) containing a C-terminal avi-tag was obtained by gene synthesis (GeneArt, Thermo Fisher) in donor vector (pDONR-221) and transferred by recombinant cloning into pDEST17 vector bearing an N-terminal His6-tag. The protein was expressed in *E. coli* and the purified protein was biotinylated with the *E. coli* biotin ligase (BirA) before usage.

GDP (Sigma Cat No G7127)

AlphaLISA Glutathione Acceptor Beads (PerkinElmer, Cat No AL109)

AlphaScreen Streptavidin Donor Beads (PerkinElmer Cat No 6760002)

Assay plates: Proxiplate-384 PLUS, white (PerkinElmer, Cat No 6008289)

Assay buffer:

1×PBS 0.1% BSA 0.05% Tween 20

KRAS::SOS1 GDP mix:

7.5 nM (final assay concentration) KRAS G12C, 10 UM (final assay concentration) GDP and 5 nM (final assay concentration) GST-SOS1 are mixed in assay buffer prior to use and kept at room temperature.

Bead Mix:

AlphaLISA Glutathione Acceptor Beads and AlphaScreen Streptavidin Donor Beads are mixed in assay buffer at a concentration of 10 μg/mL (final assay concentration) each prior to use and kept at room temperature.

Assay Protocol:

Compounds are diluted to a final start concentration of 100 UM and are tested in duplicate. Assay-ready plates (ARPs) are generated using an Access Labcyte Workstation with a Labcyte Echo 550 or 555 accoustic dispenser. For compound a start concentration of 100 μM, 150 nL of compound solution is transferred per well in 11 concentrations in duplicate with serial 1:5 dilutions.

The assay is run using a fully automated robotic system in a darkened room below 100 Lux. 10 μL of KRAS::SOS1 GDP mix is added into columns 1-24 to the 150 nL of compound solution (final dilution in the assay 1:100, final DMSO concentration 1%).

After 30 minutes incubation time 5 μL of bead mix is added into columns 1-23. Plates are kept at room temperature in a darkened incubator. After further 60 minutes incubation, the signal is measured using a PerkinElmer Envision HTS Multilabel Reader using the AlphaScreen specifications from PerkinElmer. Each plate contains the following controls:

diluted DMSO+KRAS::SOS1 GDP mix+bead mix diluted DMSO+KRAS::SOS1 GDP mix

Result Calculation:

$IC_{50}$ values are calculated and analyzed using a 4 parametric logistic model.

Tables of example compounds disclosed herein contain $IC_{50}$ values determined using the above assay.

Ba/F3 Cell Model Generation and Proliferation Assay

Ba/F3 cells were ordered from DSMZ (ACC300, Lot17) and grown in RPMI-1640 (ATCC 30-2001)+10% FCS+10 ng/ml IL-3 at 37° C. in 5% $CO_2$ atmosphere. Plasmids containing KRASG12 mutants were obtained from GeneScript. To generate KRASG12-dependent Ba/F3 models, Ba/F3 cells were transduced with retroviruses containing vectors that harbor KRASG12 isoforms. Platinum-E cells (Cell Biolabs) were used for retrovirus packaging. Retrovirus was added to Ba/F3 cells. To ensure infection, 4 μg/mL polybrene was added and cells were spinfected. Infection efficiency was confirmed by measuring GFP-positive cells using a cell analyzer. Cells with an infection efficiency of 10% to 20% were further cultivated and puromycin selection with 1 μg/mL was initiated. As a control, parental Ba/F3 cells were used to show selection status. Selection was considered successful when parental Ba/F3 cells cultures died. To evaluate the transforming potential of KRASG12 mutations, the growth medium was no longer supplemented with IL-3. Ba/F3 cells harboring the empty vector were used as a control. Approximately ten days before conducting the experiments, puromycin was left out.

For proliferation assays, Ba/F3 cells were seeded into 384-well plates at $1\times10^3$ cells/60 μL in growth media (RPMI-1640+10% FCS). Compounds were added using an Access Labcyte Workstation with a Labcyte Echo 550 or 555 acoustic dispenser. All treatments were performed in technical duplicates. The assay is run using a fully automated robotic system. Treated cells were incubated for 72 h at 37° C. with 5% $CO_2$. AlamarBlue™ (ThermoFisher), a viability stain, was added and fluorescence measured in the PerkinElmer Envision HTS Multilabel Reader. The raw data were imported into and analyzed with the Boehringer Ingelheim proprietary software MegaLab (curve fitting based on the program PRISM, GraphPad Inc.).

$IC_{50}$ values of representative compounds (I) according to the invention measured with this assay are presented in table 36.

Plasma Protein Binding (PPB)

Binding of test compound to plasma was determined using equilibrium dialysis (ED) and quantitative mass spectrometry interfaced with liquid chromatography (LC-MS). In brief, ED was performed with dialysis devices consisting of two chambers separated by a semipermeable membrane with a molecular weight cut-off of 5-10 kg/mol. One chamber was filled with commercially sourced plasma (mouse and human plasma, respectively) or serum (10% FCS in PBS) containing 1-10 μmol/L test compound and the other chamber was filled with phosphate-buffer saline (PBS) with or without dextran. The dialysis chamber was incubated for 3-5 hours at 37° C. After incubation, protein was precipitated from aliquots of each chamber and the concentration of test compound in the supernatant of the plasma-containing compartment ($c_{plasma}$) and of the buffer-containing compartment ($c_{buffer}$) was determined by LC-MS. The fraction of unbound test compound (not bound to plasma) ($f_u$) was calculated according to the following equation:

$$f_u\ [\%] = \frac{c_{buffer}}{c_{plasma}} \times 100$$

Data in table 36 shows that compounds of the invention measured in these assays have very good anti-proliferative potency against Ba/F3 cells bearing a G12C mutation, very often in the single-digit nanomolar range, even though they show high plasma protein binding to FCS used in this assay (i.e. they are in fact only present in free form for inhibition to a much lesser extent). This is why $IC_{50}$ values of this assay have been corrected by the plasma protein binding of the compounds in 10% FCS (fraction unbound ($f_u$), see last column in table 36). The data also shows that many compounds of the invention have a lower $IC_{50}$/higher potency (see uncorrected and especially corrected $IC_{50}$S) than the most advanced G12C inhibitors in the clinic, i.e. sotorasib and adagrasib, at a similar level of protein binding in human plasma. Such compounds might possibly achieve the same treatment efficacy at lower doses or allow for the achievement of a higher treatment efficacy at the same doses in humans. The same principle of correction can also be applied to the $IC_{50}$s of the proliferation assays described below (see results in table 37).

TABLE 36

| # | $IC_{50}$ Ba/F3 KRASG12C [nM] | PPB 10% FCS $f_u$ [%] | PPB mouse $f_u$ [%] | PPB human $f_u$ [%] | $IC_{50}$ Ba/F3 KRASG12C (corrected) [nM] |
|---|---|---|---|---|---|
| Ib-1 | 1.8 | 7.5 | 1.1 | 3.2 | 0.14 |
| Ib-3 | 3.9 | 7.8 | 0.4 | 1.8 | 0.30 |
| Ib-4 | 1.7 | 5.5 | 0.7 | 2.1 | 0.09 |
| Ib-5 | 3.8 | 5.8 | 0.4 | 1.9 | 0.22 |
| Ib-6 | 1.6 | 16.7 | 1.4 | 5.9 | 0.27 |
| Ib-7 | 0.2 | 12.7 | 0.7 | 1.8 | 0.03 |
| Ib-8 | 13.5 | 19.8 | 0.1 | 1.4 | 2.67 |
| Ib-9 | 2.9 | 2.6 | 0.1 | 0.2 | 0.08 |
| Ib-10 | 13.1 | 6.3 | 0.5 | 1.3 | 0.83 |
| Ib-11 | 12.6 | 4.5 | 0.3 | n.a. | 0.57 |
| Ib-12 | 67.9 | 1.6 | <0.04 | <0.052 | 1.09 |
| Ib-13 | 349.7 | 11.4 | <0.05 | 0.5 | 39.87 |
| Ib-14 | 16.0 | 6.6 | 1.0 | 1.6 | 1.06 |
| Ib-15 | 72.4 | 18.5 | 1.1 | 4.1 | 13.39 |
| Ib-16 | 123.8 | 4.4 | 0.2 | 2.0 | 5.45 |
| Ic-1 | 1.5 | n.a. | n.a. | n.a. | — |
| Ic-2 | 2.3 | n.a. | n.a. | n.a. | — |
| Ic-3 | 5.5 | 10.9 | n.a. | 2.8 | 0.60 |
| Ic-4 | 1.8 | 8.3 | 1.1 | 2.7 | 0.15 |
| Ic-5 | 6.7 | 14.8 | 0.3 | 2.0 | 0.99 |
| Ic-6 | 0.7 | 9.3 | <0.1 | n.a. | 0.07 |
| Ic-7 | 35.3 | 25.2 | 0.1 | 2.0 | 8.90 |
| Ic-8 | 35.6 | 7.8 | 0.3 | n.a. | 2.78 |
| Ic-9 | 87.0 | 25.9 | 0.8 | 4.3 | 22.53 |
| Id-1 | 0.4 | 47.6 | 2.1 | n.a. | 0.19 |
| Id-2 | 2.0 | 43.4 | 0.3 | 0.9 | 0.87 |
| Id-3 | <1.3 | n.a. | n.a. | n.a. | — |
| Id-4 | 1.3 | 37.1 | 0.5 | 1.4 | 0.48 |
| Id-5 | 3.2 | 33.8 | 0.3 | n.a. | 1.08 |
| Id-6 | 0.2 | 52.1 | 0.3 | n.a. | 0.10 |
| Id-7 | 5.4 | n.a. | n.a. | n.a. | — |
| Id-8 | 4.3 | 35.2 | <0.09 | 0.4 | 1.51 |
| Id-9 | 44.0 | 33.6 | 0.3 | n.a. | 14.78 |
| sotorasib | 43.7 | 77.4 | 9.4. | 2.7 | 33.82 |
| adagrasib | 6.6 | 43.0 | 0.4 | 1.4 | 2.84 |

Additional Proliferation Assays with G12C Mutant Cancer Cell Lines

SW 837 CTG Proliferation Assay (CRC)

SW837 cells (ATCC #CCL-235) were grown in cell culture flasks (175 $cm^2$) using L-15 10% FCS, 1% L-Glu, 1×NEAA and 1× Na-Pyrovat. Cultures were incubated at 37° C. and 0% $CO_2$ in a humidified atmosphere, with medium change or subcultivation 2-3 times a week. Materials used for the assay were CulturPlate-384, White Opaque 384-well Microplate, Sterile and Tissue Culture Treated (Perkin Elmer #6007680), Leibovitz L15 Medium and FBS #SH30071.03 (HyClone).

The proliferation assays started (day1) with seeding cells in flat bottom 384 well microtiter plates in 90 μL L-15 10% FCS, 1% L-Glu, 1×NEAA and 1× Na-Pyrovat at a density of 500 cells/well. Any other luminescence compatible plate format is possible. On day 2, 10 μL dilutions of the test compounds covering a concentration range between app. 0.1 and 10.000 nM were added to the cells. Cells were incubated for 5 days in a humidified, $CO_2$ controlled (no $CO_2$) incubator at 37° C. On day 7 100 μL of Cell Titer Glow reagent (Cell titer Glo Luminescent Cat. No. G7571, Promega) were added to each well and incubated for additional 10 min at room temperature (with agitation). Luminescence was measured on a Wallac Victor using standard luminescence read out. $IC_{50}$ values were calculated using standard Levenburg Marquard algorithms (GraphPad Prism).

$IC_{50}$ values of representative compounds (I) according to the invention measured with this assay are presented in table 37.

MiaPaCa-2 CTG Proliferation Assay (Pancreatic Cancer)

MiaPaCa-2 cells (ATCC® CRM-CRL-1420™) were grown in cell culture flasks (175 $cm^2$) using DMEM medium supplemented with 10% fetal bovine serum. Cultures were incubated at 37° C. and 5% $CO_2$ in a humidified atmosphere, with medium change or subcultivation 2-3 times a week. Materials used for the assay were CulturPlate-384, White Opaque 384-well microplate, Sterile and Tissue Culture Treated (Perkin Elmer #6007680), DMEM medium and FBS #SH30071.03 (HyClone).

The proliferation assays started (day1) with seeding cells in flat bottom 384 well microtiter plates in 90 μL DMEM medium supplemented with 10% FBS at a density of 500 cells/well. Any other luminescence compatible plate format is possible. On day 2, 10 μL dilutions of the test compounds covering a concentration range between app. 0.1 and 10.000 nM were added to the cells. Cells were incubated for 5 days in a humidified, incubator with 5% $CO_2$ at 37° C. On day 7 100 μl of Cell Titer Glow reagent (Cell titer Glo Luminescent Cat. No. G7571, Promega) were added to each well and incubated for additional 10 min at room temperature (with agitation). Luminescence was measured on a Wallac Victor using standard luminescence read out. $IC_{50}$ values were calculated using standard Levenburg Marquard algorithms (GraphPad Prism).

$IC_{50}$ values of representative compounds (I) according to the invention measured with this assay are presented in table 37.

NCI-H358 CTG Proliferation Assay (120 h) (NSCLC)

NCI-H358 cells (ATCC No. CRL-5807) were dispensed into white bottom opaque 96 well plates (Perkin Elmer cat no. 5680) at a density of 2000 cells per well in 100 μL RPMI-1640 ATCC-Formulation (Gibco #A10491)+10% FCS. Cells were incubated overnight at 37° C. in a humidified tissue culture incubator at 5% $CO_2$. Compounds (10 mM stock in DMSO) were added at logarithmic dose series using the HP Digital Dispenser D300 (Tecan), normalizing for added DMSO. For the TO time point measurement, untreated cells were analyzed at the time of compound addition. Plates were incubated for 120 hours, and cell viability was measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values were determined from viability measurements by non-linear regression using a four parameter model.

$IC_{50}$ values of representative compounds (I) according to the invention measured with this assay are presented in table 37.

NCI-H2122 CTG proliferation assay (120 h) (NSCLC)

The CTG assay is designed to measure quantitatively the proliferation of NCI-H2122 cells (ATCC CRL-5985), using the CellTiter Glow Assay Kit (Promega G7571). Cells are grown in RPMI medium (ATCC) supplemented with Fetal Calf Serum (Life Technologies, Gibco BRL, Cat. No. 10270-106). On "day 0" 1000 NCI-H2122 cells are seeded in 60 μL RPMI ATCC+10% FCS+Penstrep in a 384-well plate, flat bottom. Cells are then incubated in the plates at 37° C. in a $CO_2$ incubator overnight. On day 1, compounds are added with the ECHO acoustic liquid handler system (Beckman Coulter), including DMSO controls. Plates are incubated for 120 hours, and cell viability is measured using CellTiter-Glo luminescent cell viability reagent (Promega product code G7570). Viability (stated as percent of control) is defined as relative luminescence units RLU of each well divided by the RLU of cells in DMSO controls. $IC_{50}$ values are determined from viability measurements by non-linear regression using a four parameter model.

TABLE 37

| # | $IC_{50}$ SW837 [nM] | $IC_{50}$ MiaPACA2 [nM] | $IC_{50}$ NCl-H358 [nM] |
|---|---|---|---|
| Ib-1 | 0.67 | 22.58 | 1.87 |
| Ib-4 | 0.69 | 20.05 | 0.55 |
| Ib-5 | 15.84 | 28.01 | 9.68 |
| Ib-6 | <1 | 9.0 | 1.67 |
| Ib-10 | 14.88 | 56.80 | 40.56 |
| Ib-11 | 5.63 | 104.63 | 34.62 |
| Ib-14 | 11.34 | 35.96 | 19.05 |
| Ic-1 | 1.30 | 23.80 | 3.13 |
| Ic-2 | 3.67 | 9.01 | 4.75 |
| Ic-3 | 10.56 | 122.78 | 24.26 |
| Ic-4 | 1.62 | 6.87 | 2.49 |
| Ic-5 | 7.15 | 47.91 | 15.65 |
| Ic-7 | 44.69 | 331.87 | 76.79 |
| Ic-8 | 36.56 | 396.05 | 93.53 |
| Ic-9 | 124.21 | 331.91 | 169.23 |
| Id-1 | 0.20 | 2.25 | 0.44 |
| Id-2 | 1.09 | 21.32 | 2.57 |
| Id-4 | 0.68 | 15.31 | 1.09 |
| Id-5 | 0.80 | 26.88 | 5.98 |
| Id-6 | 0.35 | 13.78 | 0.93 |
| sotorasib | 17.0 | 49.0 | 21.0 |
| adagrasib | 13.0 | 28.0 | 10.0 |

ERK Phosphorylation Assay

ERK phosphorylation assays are used to examine the potency with which compounds inhibit the KRAS G12C-mediated signal transduction in a KRAS G12C mutant human cancer cell line in vitro. This demonstrates the molecular mode of action of compounds according to the invention by interfering with the RAS G12C protein signal transduction cascade. Low $IC_{50}$ values in this assay setting are indicative of high potency of the compounds according to the invention. It is observed that compounds according to the invention demonstrate an inhibitory effect on ERK phosphorylation in a KRAS G12C mutant human cancer cell line, thus confirming the molecular mode of action of the compounds on RAS G12C protein signal transduction.

ERK phosphorylation assays are performed using the following human cell lines:

NCI-H358 (ATCC (ATCC CRL-5807): human lung cancer with a KRAS G12C mutation (→assay 1) and NCI-H358_Cas9_SOS2, i.e. the same cell line, in which SOS2 was knocked (→assay 2). Vectors containing the designed DNA sequences for the production of gRNA for SOS2 protein knock-out were obtained from Sigma-Aldrich. To generate the NCI-H358 SOS2 knock-out cell line, NCI-H358 cells expressing Cas9 endonuclease were transfected with XtremeGene9 reagent and the correspondent plasmids. Transfection efficiency was confirmed by measuring GFP-positive cells using a cell analyzer. GFP positive cells were collected and further expanded. These GFP-positive cell pools were single-cell diluted and SOS2 knock-out clones were identified via Western-blot and genomic DNA sequencing analysis.

Materials Used for the Assay:

- RPMI-1640 Medium (ATCC® 30-2001™)
- Fetal Bovine Serum (FBS) from HyClone (SH30071.03)
- Non-essential amino acids from Thermo Fischer Scientific (11140035)
- Pyruvate from Thermo Fischer Scientific (11360039)
- Glutamax from Thermo Fischer Scientific (35050061)
- 384 plates from Greiner Bio-One (781182)
- Proxiplate™ 384 from PerkinElmer Inc. (6008280)
- AlphaLISA SureFire Ultra p-ERK1/2 (Thr202/Tyr204) Assay Kit (ALSU-PERK-A500)
- EGF from Sigma (E4127)
- Acceptor Mix: Protein A Acceptor Beads from PerkinElmer (6760137M)
- Donor Mix: AlphaScreen Streptavidin-coated Donor Beads from PerkinElmer (6760002)
- Trametinib
- Staurosporine from Sigma Aldrich (S6942)

Assay Setup:

Cells are seeded at 40,000 cells per well in/60 µL of RPMI with 10% FBS, non-essential amino acids, pyruvate and glutamax in Greiner TC 384 plates. The cells are incubated for 1 h at room temperature and then incubated overnight in an incubator at 37° C. and 5% $CO_2$ in a humidified atmosphere. 60 nL compound solution (10 mM DMSO stock solution) is then added using a Labcyte Echo 550 device. After a 1 h incubation in the aforementioned incubator the medium is removed after centrifugation and the cells lysed by addition of 20 µL of 1.6-fold lysis buffer from the AlphaLISA SureFire Ultra PERK1/2 (Thr202/Tyr204) Assay Kit with added protease inhibitors, 100 nM trametinib+100 nM staurosporine. After 20 minutes of incubation at room temperature with shaking, 6 µL of each lysate sample is transferred to a 384-well Proxiplate and analyzed for pERK (Thr202/Tyr204) with the AlphaLISA SureFire Ultra PERK1/2 (Thr202/Tyr204) Assay Kit. 3 µL Acceptor Mix and 3 µL Donor Mix are added under subdued light and incubated for 2 h at room temperature in the dark, before the signal is measured on a PerkinElmer Envision HTS Multilabel Reader. The raw data were imported into and analyzed with the Boehringer Ingelheim proprietary software MegaLab (curve fitting based on the program PRISM, GraphPad Inc.).

$IC_{50}$ values of representative compounds (I) according to the invention measured with this assay are presented in table 38 ($IC_{50}$s from assay 2 are marked with *, all others are from assay 1).

TABLE 38

| # | $IC_{50}$ H358 pERK [nM] |
|---|---|
| Ib-1 | 1.7* |
| Ib-10 | 32.8* |
| Ib-11 | 44.4* |
| Ib-12 | 829.8* |
| Ib-13 | 1136.4* |
| Ib-14 | 12.6* |
| Ib-15 | 32.7* |
| Ib-16 | 969.0* |
| Ib-2 | 3.1* |
| Ib-3 | 4.1* |
| Ib-4 | 2.4* |
| Ib-5 | 6.7* |
| Ib-6 | 2.0* |
| Ib-7 | 0.6* |
| Ib-8 | 12.7* |
| Ib-9 | 11.3* |
| Ic-1 | 1.6* |
| Ic-2 | 3.7* |
| Ic-3 | 12.3* |
| Ic-4 | 3.4* |
| Ic-5 | 13.1* |
| Ic-6 | 0.5* |
| Ic-7 | 56.8* |
| Ic-8 | 134.3* |
| Ic-9 | 46.2* |
| Id-1 | 0.7* |
| Id-2 | 5.4* |
| Id-3 | 1.1* |
| Id-4 | 2.2* |
| Id-5 | 3.1* |
| Id-6 | 1.1* |
| Id-7 | 20.5* |
| Id-8 | 16.1* |
| Id-9 | 58.9* |
| Ie-1 | 124.7 |

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodiumcarboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Tablets | per tablet |
|---|---|---|
| | active substance according to formula (I) | 25 mg |
| | lactose | 50 mg |
| | microcrystalline cellulose | 24 mg |
| | magnesium stearate | 1 mg |
| | | 100 mg |

The active substance, lactose and cellulose are mixed together. The mixture is screened, then either moistened with water, kneaded, wet-granulated and dried or dry-granulated or directly final blend with the magnesium stearate and compressed to tablets of suitable shape and size. When wet-granulated, additional lactose or cellulose and magnesium stearate is added and the mixture is compressed to produce tablets of suitable shape and size.

| D) | Ampoule | solution |
|---|---|---|
| | active substance according to formulae (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (II)

(II)

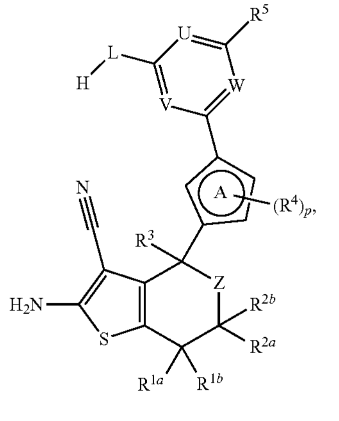

wherein $R^{1a}$ and $R^{1b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

$R^{2a}$ and $R^{2b}$ are both independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

and/or, optionally, one of $R^{1a}$ or $R^{1b}$ and one of $R^{2a}$ or $R^{2b}$ together with the carbon atoms they are attached form a cyclopropane ring;

Z is —$(CR^{6a}R^{6b})_n$—;

each $R^{6a}$ and $R^{6b}$ is independently selected from the group consisting of hydrogen, $C_{1-4}$alkyl, $C_{1-4}$haloalkyl, $C_{1-4}$alkoxy, $C_{1-4}$haloalkoxy, halogen, —$NH_2$, —NH($C_{1-4}$alkyl), —N($C_{1-4}$alkyl)$_2$, $C_{3-5}$cycloalkyl and 3-5 membered heterocyclyl;

n is selected from the group consisting 0, 1 and 2;

$R^3$ is selected from the group consisting of hydrogen, $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

ring A is a ring selected from the group consisting of pyrrole, furan, thiophene, imidazole, pyrazole, oxazole, isoxazole, thiazole, isothiazole and triazole;

each $R^4$, if present, is independently selected from the group consisting of $C_{1-6}$alkyl, $C_{1-6}$haloalkyl, $C_{1-6}$alkoxy, $C_{1-6}$haloalkoxy, cyano-$C_{1-6}$alkyl, halogen, —OH, —$NH_2$, —NH($C_{1-4}$alkyl), —N($C_{1-4}$alkyl)$_2$, —CN, $C_{3-5}$cycloalkyl and 3-5 membered heterocyclyl;

p is selected from the group consisting 0, 1, 2 and 3;

U is selected from the group consisting of nitrogen (═N—) and carbon substituted with $R^A$ (═C($R^A$)—);

V is selected from the group consisting of nitrogen (═N—) and carbon substituted with $R^B$ (═C($R^B$)—);

W is selected from the group consisting of nitrogen (—N—) and carbon substituted with $R^C$ (═C($R^C$)—);

$R^A$, $R^B$ and $R^C$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(═O)$NH_2$, —C(═O)NH($C_{1-4}$alkyl), —C(═O)N($C_{1-4}$alkyl)$_2$, —S—$C_{1-6}$alkyl, —S(═O)$_2$—$C_{1-6}$alkyl, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(═O)$NH_2$, —C(═O)NH($C_{1-4}$alkyl) and —C(═O)N($C_{1-4}$alkyl)$_2$;

$R^5$ is selected from the group consisting of $R^{a1}$ and $R^{b1}$;

$R^{a1}$ is selected from the group consisting of $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —CN, —C(═O)$R^{c1}$, —C(═O)$OR^{c1}$, —C(═O)$NR^{c1}R^{c1}$, —S(═O)$_2R^{c1}$, —S(═O)$_2NR^{c1}R^{c1}$, NHC(═O)$R^{c1}$, —$N(C_{1-4}alkyl)C(=O)R^{c1}$, —$NHS(=O)_2R^{c1}$, —$N(C_{1-4}alkyl)S(=O)_2R^{c1}$, —$NHC(=O)OR^{c1}$, —$N(C_{1-4}alkyl)C(=O)OR^{c1}$ and the bivalent substituent =O;

each $R^{c1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$NR^{e1}R^{e1}$, halogen, —CN, —$C(=O)R^{e1}$, —$C(=O)OR^{e1}$, —$C(=O)NR^{e1}R^{e1}$, —$S(=O)_2R^{e1}$, —$S(=O)_2NR^{e1}R^{e1}$, —$NHC(=O)R^{e1}$, —$N(C_{1-4}alkyl)C(=O)R^{e1}$, —$NHS(=O)_2R^{e1}$, —$N(C_{1-4}alkyl)S(=O)_2R^{e1}$, —$NHC(=O)OR^{e1}$, —$N(C_{1-4}alkyl)C(=O)OR^{e1}$ and the bivalent substituent =O;

each $R^{e1}$ is independently selected from the group consisting of hydrogen, $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkenyl, $C_{2-6}$alkynyl, $C_{3-10}$cycloalkyl, $C_{4-10}$cycloalkenyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl optionally substituted with one or more, identical or different $C_{1-4}$alkyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(=O)$C_{1-4}$alkyl, —$NH(C_{1-4}alkyl)$, —$N(C_{1-4}alkyl)_2$ and the bivalent substituent =O;

L is -$L^1$-$L^2$-$L^3$-, wherein $L^1$ is linked to the hydrogen (H) of residue H-L-;

$L^1$ is selected from the group consisting of a bond, —NH—, —$N(C_{1-4}alkyl)$-, —O—, —C(=O)—, —NH—C(=O)—, —$N(C_{1-4}alkyl)$-C(=O)—, —C(=O)—NH—, —C(=O)—$N(C_{1-4}alkyl)$-, —C(=O)—, $C_{1-6}$alkylen, $C_{3-7}$cycloalkylene, phenylene, 4-12 membered heterocyclylene and 5-10 membered heteroarylene;

$L^2$ is selected from the group consisting of $C_{1-6}$alkylen, $C_{3-7}$cycloalkylene, phenylene, 4-12 membered heterocyclylene and 5-10 membered heteroarylene;

$L^3$ is selected from the group consisting of a bond, —NH—, —$N(C_{1-4}alkyl)$-, —O—, —C(=O)—, —NH—C(=O)—, —$N(C_{1-4}alkyl)$-C(=O)—, —C(=O)—NH—, —C(=O)—$N(C_{1-4}alkyl)$-, —C(=O)—, $C_{1-6}$alkylen, $C_{3-7}$cycloalkylene, phenylene, 4-12 membered heterocyclylene and 5-10 membered heteroarylene;

wherein each $C_{1-6}$alkylen, $C_{3-7}$cycloalkylene, phenylene, 4-12 membered heterocyclylene and 5-10 membered heteroarylene in $L^1$, $L^2$ and $L^3$ is optionally and independently substituted with one or more, identical or different substituent(s) selected from the group consisting of $C_{2-6}$alkinyl, $C_{1-6}$haloalkyl, $C_{3-7}$cycloalkyl, phenyl, 5-6 membered heteroaryl, halogen, —OH, —CN, $C_{1-6}$alkoxy, —$NH_2$, —$NH(C_{1-4}alkyl)$, —$N(C_{1-4}alkyl)_2$, —C(=O)OH, —C(=O)—$OC_{1-6}$alkyl, —$C(=O)NH_2$, —$C(=O)NH(C_{1-4}alkyl)$, —$C(=O)N(C_{1-4}alkyl)_2$, the bivalent substituent =O and $C_{1-6}$alkyl optionally substituted with one or more, identical or different substituent(s) selected from the group consisting of halogen, —OH, —CN, $C_{1-4}$alkoxy, —$NH_2$, —$NH(C_{1-4}alkyl)$, —$N(C_{1-4}alkyl)_2$, —C(=O)OH, —C(=O)—$OC_{1-6}$alkyl, —$C(=O)NH_2$, —$C(=O)NH(C_{1-4}alkyl)$ and —$C(=O)N(C_{1-4}alkyl)_2$;

or a salt thereof.

2. The compound or salt according to claim 1 of the formula (II*)

(II*)

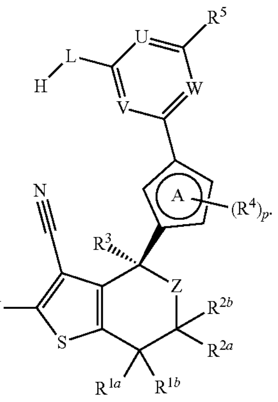

3. The compound or salt according to claim 1, wherein $R^{1a}$ and $R^{1b}$ are both independently selected from the group consisting of hydrogen and $C_{1-4}$alkyl;

$R^{2a}$ and $R^{2b}$ are both independently selected from the group consisting of hydrogen and halogen.

4. The compound or salt according to claim 1, wherein Z is —$CH_2$—.

5. The compound or salt according to claim 1, wherein $R^3$ is selected from the group consisting of hydrogen, $C_{1-4}$alkyl, $C_{1-4}$haloalkyl, $C_{1-4}$alkoxy, $C_{1-4}$haloalkoxy, cyano-$C_{1-4}$alkyl, halogen, —OH, —$NH_2$, —$NH(C_{1-4}alkyl)$, —$N(C_{1-4}alkyl)_2$ and —CN.

6. The compound or salt according to claim 1, wherein ring A is selected from the group consisting of

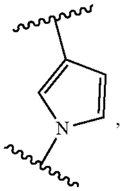 , 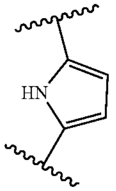 , 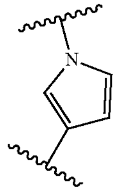 ,

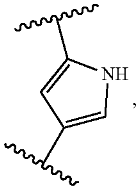 , 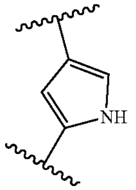 , 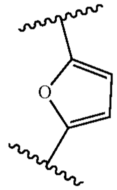 ,

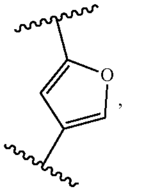 , 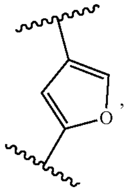 , 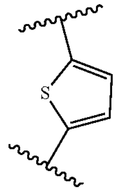 ,

-continued

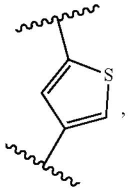
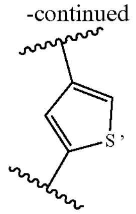
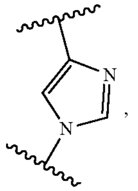
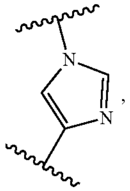
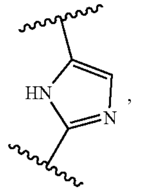
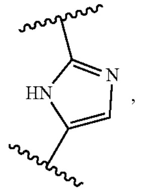
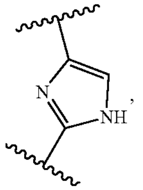
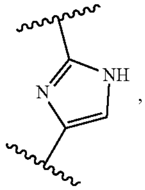
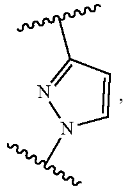
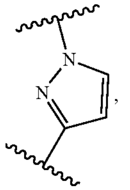
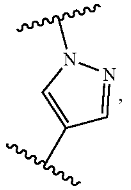
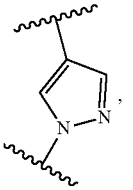
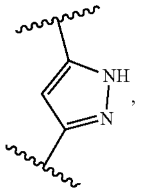
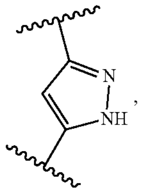
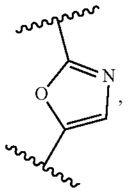
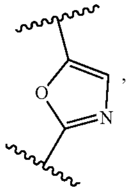
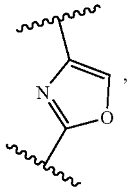
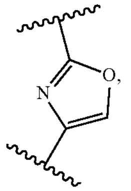
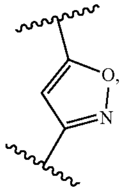
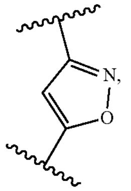
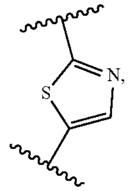
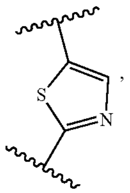
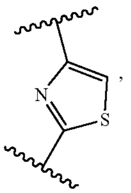
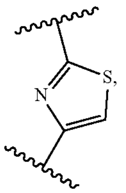
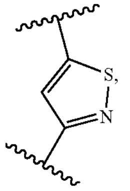
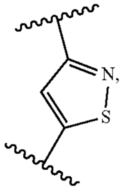
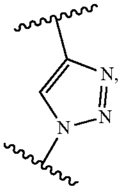

-continued

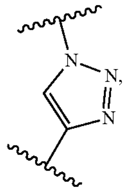
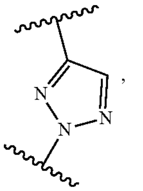
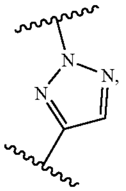
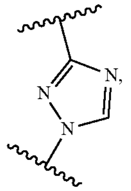
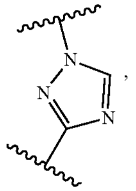
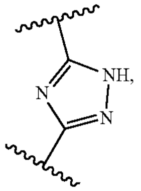
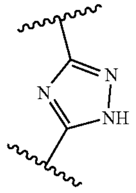
and
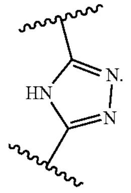

7. The compound or salt according to claim 1, wherein p is 0.

8. The compound or salt according to claim 1, wherein
U is carbon substituted with $R^A$ (=C($R^A$)—);
V is carbon substituted with $R^B$ (=C($R^B$)—);
W is nitrogen (=N—);
$R^A$ and $R^B$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

9. The compound or salt according to claim 1, wherein
U is carbon substituted with $R^A$ (=C($R^A$)—);
V is carbon substituted with $R^B$ (=C($R^B$)—);
W is carbon substituted with $R^C$(=C($R^C$)—);
$R^A$, $R^B$ and $R^C$ is each independently selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(=O)N($C_{1-4}$ alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(=O)$NH_2$, —C(=O)NH($C_{1-4}$alkyl) and —C(=O)N($C_{1-4}$alkyl)$_2$.

10. The compound or salt according to claim 1, wherein
U is nitrogen (=N—);
V is carbon substituted with $R^B$ (—C($R^B$)—);
W is nitrogen (=N—);
$R^B$ is selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(=O)$NH_2$, —C(=O)NH($C_{1-4}$alkyl), —C(═O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(═O)$NH_2$, —C(═O)NH($C_{1-4}$alkyl) and —C(═O)N($C_{1-4}$alkyl)$_2$.

11. The compound or salt according to claim 1, wherein U is carbon substituted with $R^A$ (═C($R^A$)—);

V is nitrogen (═N—);

W is nitrogen (═N—);

$R^A$ is selected from the group consisting of hydrogen, $C_{1-6}$haloalkyl, $C_{2-6}$alkynyl optionally substituted with $C_{3-5}$cycloalkyl, $C_{1-6}$alkoxy, $C_{1-6}$haloalkoxy, halogen, —CN, —OH, —$NH_2$, —NH($C_{1-4}$alkyl), —N($C_{1-4}$alkyl)$_2$, —C(═O)$NH_2$, —C(═O)NH($C_{1-4}$alkyl), —C(═O)N($C_{1-4}$alkyl)$_2$, $C_{3-5}$cycloalkyl, 3-5 membered heterocyclyl and $C_{1-6}$alkyl optionally substituted with a substituent selected from the group consisting of $C_{1-6}$alkoxy, —CN, —OH, —$NH_2$, —NH($C_{1-4}$alkyl), —N($C_{1-4}$alkyl)$_2$, —C(═O)$NH_2$, —C(═O)NH($C_{1-4}$alkyl) and —C(═O)N($C_{1-4}$alkyl)$_2$.

12. The compound or salt according to claim 1, wherein U is nitrogen (═N—);

V is nitrogen (═N—);

W is nitrogen (═N—).

13. The compound or salt according to claim 1, wherein $R^5$ is selected from the group consisting of $R^{a1}$ and $R^{b1}$;

$R^{a1}$ is selected from the group consisting of $C_{1-6}$alkyl, $C_{1-6}$haloalkyl, $C_{2-6}$alkynyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{2-6}$alkynyl, $C_{3-10}$cycloalkyl, 3-11 membered heterocyclyl, $C_{6-10}$aryl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —CN, —C(═O)$R^{c1}$, —C(═O)$OR^{c1}$, —C(═O)$NR^{c1}R^{c1}$, —S(═O)$_2R^{c1}$, —S(═O)$_2NR^{c1}R^{c1}$, —NHC(═O)$R^{c1}$, —N($C_{1-4}$alkyl)C(═O)$R^{c1}$ and the bivalent substituent ═O;

each $R^{c1}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$NR^{e1}R^{e1}$ halogen, —CN, —C(═O)$R^{e1}$, —C(═O)$NR^{e1}R^{e1}$ and the bivalent substituent ═O;

each $R^{e1}$ is independently selected from the group consisting of hydrogen, $C_{1-6}$alkyl, $C_{1-6}$haloalkyl, $C_{3-10}$cycloalkyl, 3-11 membered heterocyclyl, $C_{6-10}$aryl and 5-10 membered heteroaryl, wherein the $C_{1-6}$alkyl, $C_{1-6}$haloalkyl, $C_{3-10}$cycloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, $C_{3-10}$cycloalkyl, 3-11 membered heterocyclyl optionally substituted with one or more, identical or different $C_{1-4}$alkyl, $C_{6-10}$aryl, 5-10 membered heteroaryl, —OH, $C_{1-6}$alkoxy, $C_{1-4}$alkoxy-$C_{1-4}$alkyl, hydroxy-$C_{1-4}$alkyl, halogen, —CN, —$NH_2$, —C(═O)$C_{1-4}$alkyl, —NH($C_{1-4}$alkyl), —N($C_{1-4}$alkyl)$_2$ and the bivalent substituent ═O.

14. The compound or salt according to claim 1, wherein $R^5$ is $R^{a1}$;

$R^{a1}$ is selected from the group consisting of 3-11 membered heterocyclyl and 5-10 membered heteroaryl, wherein the 3-11 membered heterocyclyl and 5-10 membered heteroaryl are all optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —C(═O)$OR^{c1}$ and the bivalent substituent ═O;

each $R^{c1}$ is independently selected from the group consisting of hydrogen, $C_{1-6}$alkyl, $C_{1-6}$haloalkyl, $C_{3-10}$cycloalkyl and 3-11 membered heterocyclyl, wherein the $C_{1-6}$alkyl, $C_{1-6}$haloalkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of —$OR^{e1}$, —$NR^{e1}R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

15. The compound or salt according claim 14, wherein $R^5$ is $R^{a1}$ selected from the group consisting of

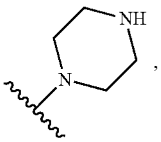,
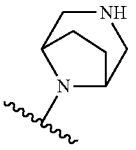,
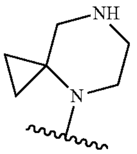,
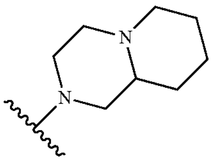,
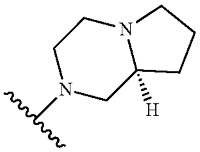,
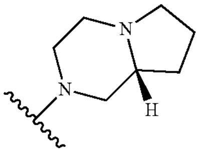,
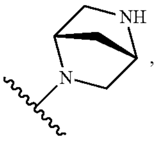,
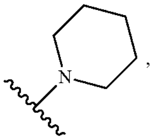,
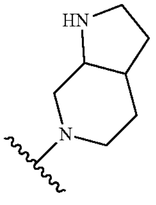,
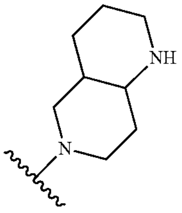,
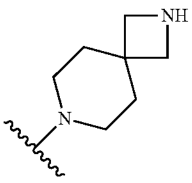, -continued

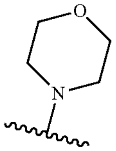, 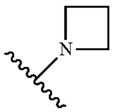, 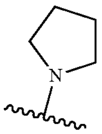,

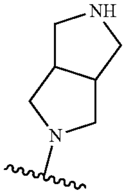, 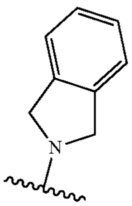,

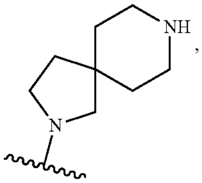, 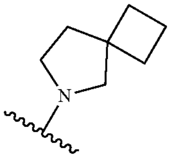,

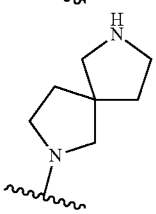, 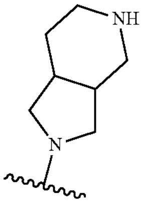,

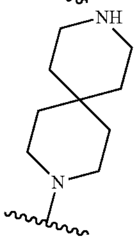, 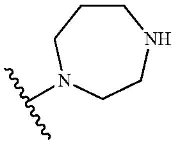 and

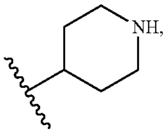

wherein each $R^{a1}$ is optionally substituted with one or more, identical or different $R^{b1}$ and/or $R^{c1}$;

each $R^{b1}$ is independently selected from the group consisting of —$OR^{c1}$, —$NR^{c1}R^{c1}$, halogen, —C(═O)$OR^{c1}$ and the bivalent substituent ═O;

each $R^{c1}$ is independently selected from the group consisting of hydrogen, $C_{1-6}$alkyl, $C_{1-6}$haloalkyl, $C_{3-10}$cycloalkyl and 3-11 membered heterocyclyl, wherein the $C_{1-6}$alkyl, $C_{1-6}$haloalkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of —$OR^{e1}$, —$NR^{e1}R^{e1}$ and halogen;

each $R^{e1}$ is independently selected from the group consisting of hydrogen, $C_{1-6}$alkyl, $C_{3-10}$cycloalkyl and 3-11 membered heterocyclyl, wherein the $C_{1-6}$alkyl, $C_{3-10}$cycloalkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

16. The compound or salt according to claim 1, wherein $R^5$ is $R^{b1}$;

$R^{b1}$ is independently selected from the group consisting of —$OR^{c1}$ and —$NR^{c1}R^{c1}$;

each $R^{c1}$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different $R^{d1}$ and/or $R^{e1}$;

each $R^{d1}$ is independently selected from the group consisting of —$OR^{e1}$, —$NR^{e1}R^{e1}$, halogen, —C(═O)$R^{e1}$ and —C(═O)$NR^{e1}R^{e1}$;

each $R^{e1}$ is independently selected from the group consisting of hydrogen, $C_{1-6}$alkyl, $C_{3-10}$cycloalkyl, 3-11 membered heterocyclyl, $C_{6-10}$aryl and 5-10 membered heteroaryl, wherein the $C_{1-6}$alkyl, $C_{3-10}$cycloalkyl, 3-11 membered heterocyclyl, $C_{6-10}$aryl and 5-10 membered heteroaryl are all optionally substituted with one or more, identical or different substituent(s) selected from the group consisting of $C_{1-6}$alkyl, $C_{1-6}$haloalkyl, 3-11 membered heterocyclyl optionally substituted with one or more, identical or different $C_{1-4}$alkyl, $C_{1-6}$alkoxy, halogen and the bivalent substituent ═O.

17. The compound or salt according to claim 16, wherein $R^5$ is $R^{b1}$;

$R^{b1}$ is —$OR^{c1}$;

each $R^{c1}$ is independently selected from the group consisting of $C_{1-6}$alkyl, $C_{3-10}$cycloalkyl, and 3-11 membered heterocyclyl, wherein the $C_{1-6}$alkyl, $C_{3-10}$cycloalkyl and 3-11 membered heterocyclyl are all optionally substituted with one or more, identical or different $R^{d1}$ and/or $R^{e1}$;

each $R^{d1}$ is independently selected from the group consisting of —$NR^{e1}R^{e1}$ and halogen;

each $R^{e1}$ is independently selected from the group consisting of hydrogen, $C_{1-6}$alkyl and 3-11 membered heterocyclyl, wherein the $C_{1-6}$alkyl and 3-11 membered heterocyclyl are all optionally substituted with one or more, identical or different substituent(s) selected from the group consisting of $C_{1-6}$alkyl and 3-11 membered heterocyclyl optionally substituted with one or more, identical or different $C_{1-4}$alkyl.

18. The compound or salt according to claim 1, wherein L is -$L^1$-$L^2$-$L^3$-, wherein $L^1$ is linked to E the hydrogen (H) of residue H-L-;

$L^1$ is selected from the group consisting of a bond, $C_{1-6}$alkylen and 4-12 membered heterocyclylene;

$L^2$ is selected from the group consisting of $C_{1-6}$alkylen, phenylene and 4-12 membered heterocyclylene;

$L^3$ is selected from the group consisting of a bond, —NH—, —N($C_{1-4}$alkyl)- and —O—;

wherein each $C_{1-6}$alkylen, phenylene and 4-12 membered heterocyclylene in $L^1$ and $L^2$ is optionally and independently substituted with one or more, identical or different substituent(s) selected from the group consisting of $C_{2-6}$alkinyl, $C_{1-6}$haloalkyl, $C_{3-7}$cycloalkyl, phenyl, 5-6 membered heteroaryl, halogen, —OH, —CN, $C_{1-6}$alkoxy, —$NH_2$, —NH($C_{1-4}$alkyl), —N($C_{1-4}$alkyl)$_2$, —C(═O)OH, —C(═O)—O$C_{1-6}$alkyl, —C(═O)$NH_2$, —C(═O)NH($C_{1-4}$alkyl), —C(═O)N($C_{1-4}$alkyl)$_2$, the bivalent substituent ═O and $C_{1-6}$alkyl optionally substituted with one or more, identical or different substituent(s) selected from the group consisting of halogen, —OH, —CN, —$NH_2$, $C_{1-4}$alkoxy, —NH($C_{1-4}$alkyl), —N($C_{1-4}$alkyl)$_2$, —C(═O)OH, —C(═O)—O$C_{1-6}$alkyl, —C(═O)$NH_2$, —C(═O)NH($C_{1-4}$alkyl) and —C(═O)N ($C_{1-4}$alkyl)$_2$.

19. The compound or salt according to claim 18, wherein

L is -$L^1$-$L^2$-$L^3$-, wherein $L^1$ is linked to the hydrogen (H) of residue H-L-;

$L^1$ is selected from the group consisting of a bond, $C_{1-6}$alkylen and 4-12 membered heterocyclylene;

$L^2$ is selected from the group consisting of $C_{1-6}$alkylen, phenylene and 4-12 membered heterocyclylene;

$L^3$ is selected from the group consisting of a bond, —NH—, —N($C_{1-4}$alkyl)- and —O—;

wherein each $C_{1-6}$alkylen, phenylene and 4-12 membered heterocyclylene in $L^1$ and $L^2$ is optionally and independently substituted with one or more, identical or different $C_{1-6}$alkyl.

20. A compound according to claim 1 selected from the group consisting of C-4a

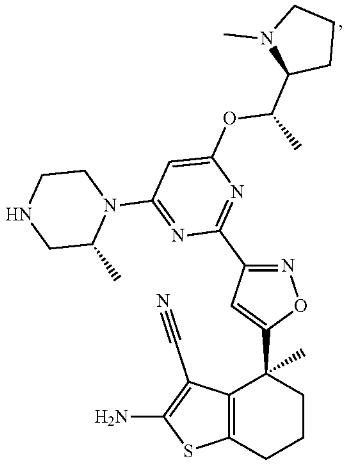

C-4b

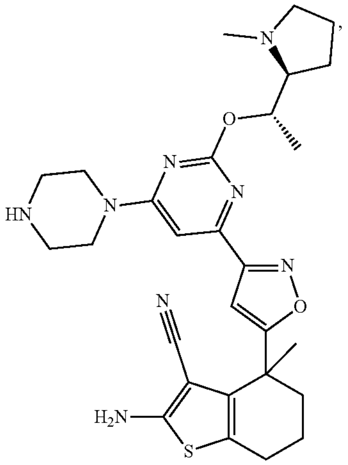

-continued

C-4c

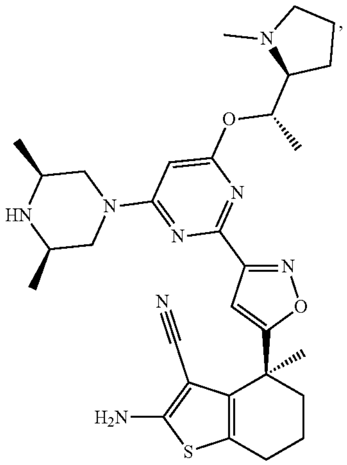

C-4d

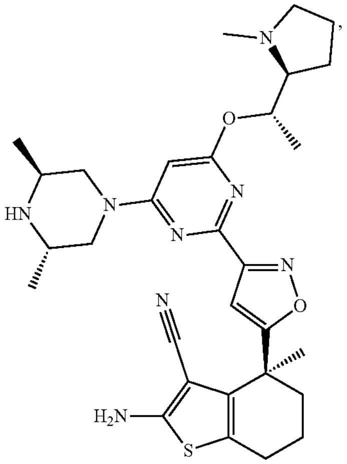

C-4e

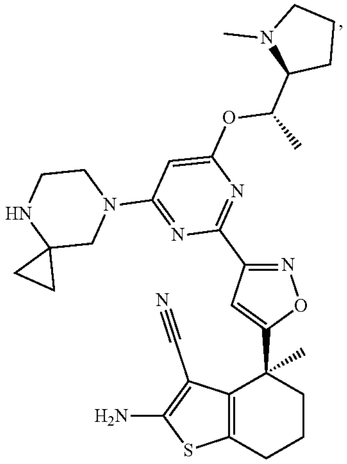

-continued
C-4f
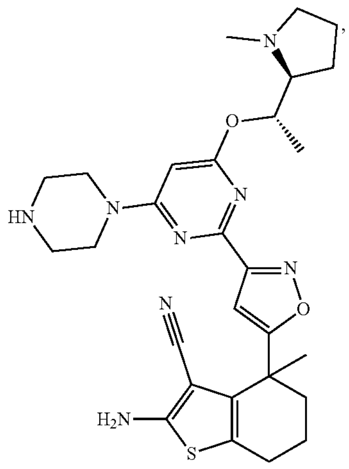
C-4g
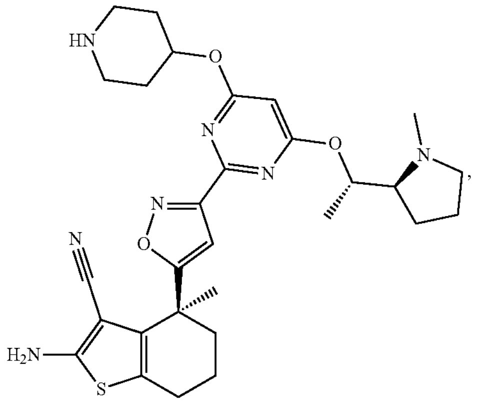
C-4h
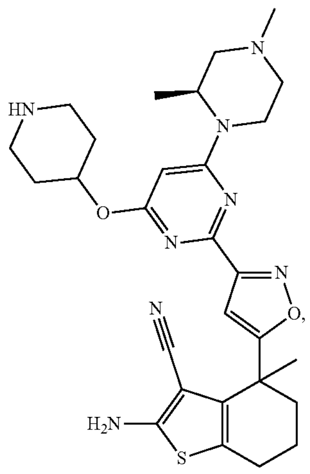
-continued
C-4i
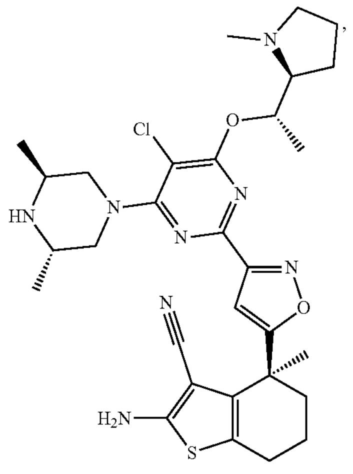
C-5a
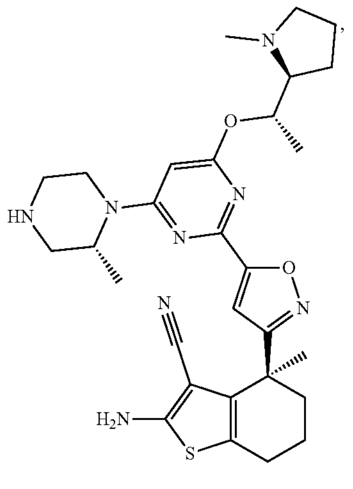
C-5b
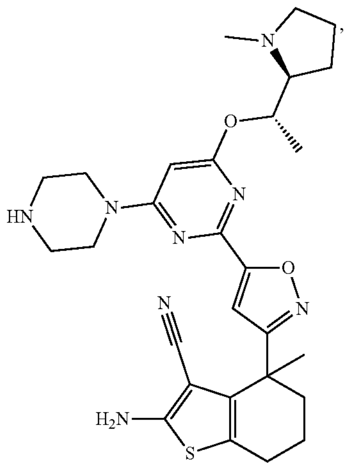

-continued
C-5c
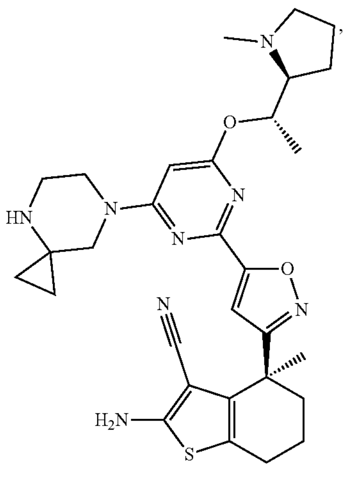
C-5d
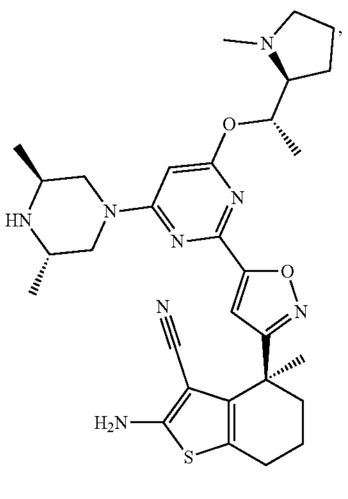
C-5e
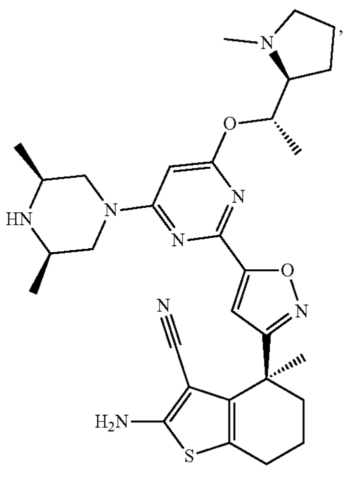
-continued
C-5f
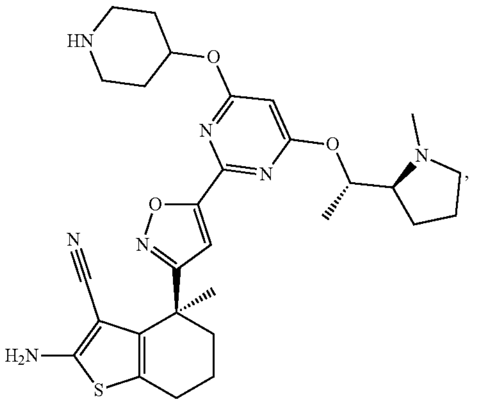
C-5g
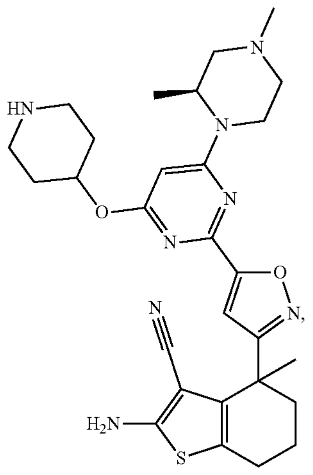
C-7a
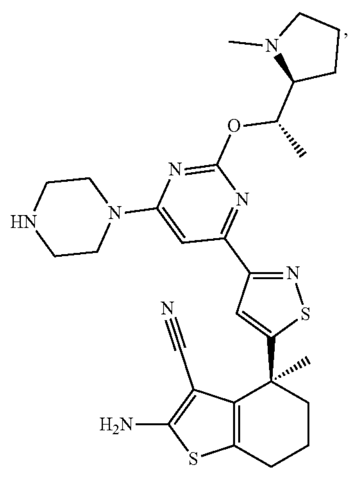

-continued
C-7b
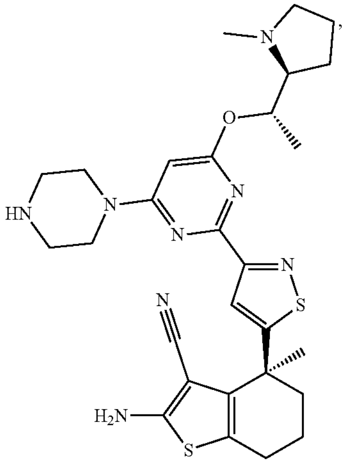
C-7c
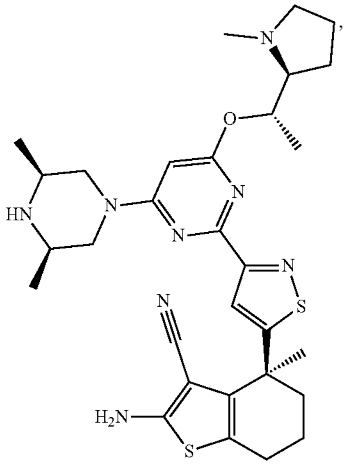
C-7d
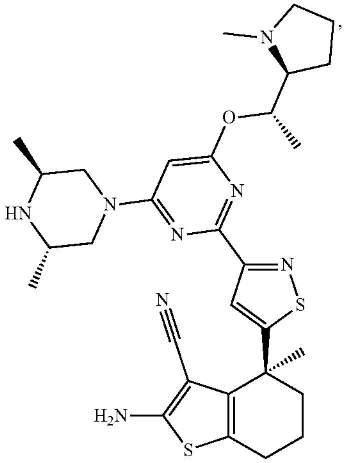
-continued
C-7e
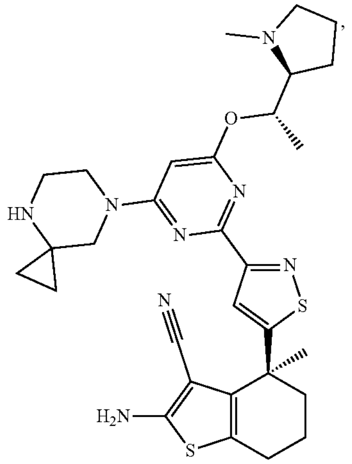
C-7f
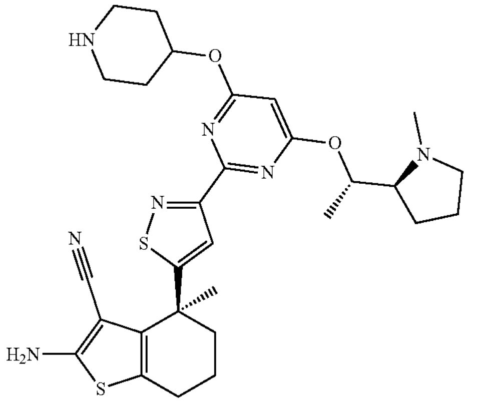
and
D-7a
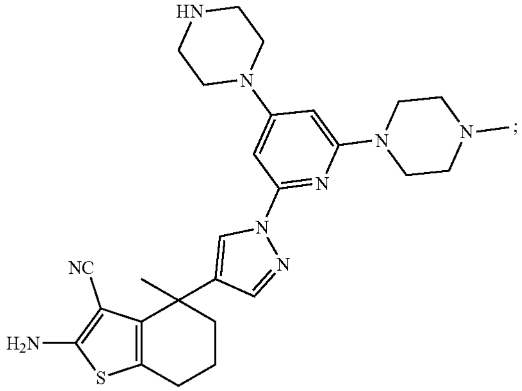
or a salt thereof.
* * * * *